(12) United States Patent
Parrag et al.

(10) Patent No.: US 10,632,075 B2
(45) Date of Patent: *Apr. 28, 2020

(54) GLASS FORMULATIONS AND USES THEREOF

(71) Applicant: Ripple Therapeutics Corporation, Toronto (CA)

(72) Inventors: Ian Charles Parrag, Mississauga (CA); Matthew Alexander John Statham, Milton (CA); Kyle Battiston, Toronto (CA); Dimitra Louka, Toronto (CA); Hans Christian Fischer, Toronto (CA); J. Paul Santerre, Toronto (CA); Wendy Alison Naimark, Toronto (CA)

(73) Assignee: Ripple Therapeutics Corporation, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/396,135

(22) Filed: Apr. 26, 2019

(65) Prior Publication Data

US 2019/0275167 A1 Sep. 12, 2019

Related U.S. Application Data

(63) Continuation of application No. PCT/CA2019/050135, filed on Feb. 1, 2019.

(60) Provisional application No. 62/758,234, filed on Nov. 9, 2018, provisional application No. 62/627,608, filed on Feb. 7, 2018, provisional application No. 62/625,460, filed on Feb. 2, 2018.

(51) Int. Cl.

| A61K 9/16 | (2006.01) |
|---|---|
| A61K 47/55 | (2017.01) |
| A61K 47/69 | (2017.01) |
| A61P 29/00 | (2006.01) |
| A61K 9/00 | (2006.01) |
| A61K 9/70 | (2006.01) |
| A61K 9/51 | (2006.01) |
| A61K 31/573 | (2006.01) |
| A61K 9/50 | (2006.01) |
| A61K 47/54 | (2017.01) |

(52) U.S. Cl.
CPC ............ *A61K 9/167* (2013.01); *A61K 9/0048* (2013.01); *A61K 9/0051* (2013.01); *A61K 9/0092* (2013.01); *A61K 9/1682* (2013.01); *A61K 9/50* (2013.01); *A61K 9/5089* (2013.01); *A61K 9/51* (2013.01); *A61K 9/5192* (2013.01); *A61K 9/7007* (2013.01); *A61K 31/573* (2013.01); *A61K 47/55* (2017.08); *A61K 47/6921* (2017.08); *A61K 47/6953* (2017.08); *A61P 29/00* (2018.01)

(58) Field of Classification Search
None
See application file for complete search history.

(56) References Cited

U.S. PATENT DOCUMENTS

| 3,663,579 A | 5/1972 | Stache et al. |
|---|---|---|
| 4,024,871 A | 5/1977 | Stephenson |
| 4,532,316 A | 7/1985 | Henn |
| 4,833,215 A | 5/1989 | Jedlinski et al. |
| 4,916,193 A | 4/1990 | Tang et al. |
| 5,013,841 A | 5/1991 | Matsumoto et al. |
| 5,217,493 A | 6/1993 | Raad et al. |
| 5,250,524 A | 10/1993 | Kramer et al. |
| 5,321,099 A | 6/1994 | Goldwasser et al. |
| 5,387,598 A | 2/1995 | Rossignol |
| 5,512,558 A | 4/1996 | Enhsen et al. |
| 5,578,621 A | 11/1996 | Rossignol |
| 5,798,115 A | 8/1998 | Santerre et al. |
| 5,856,348 A | 1/1999 | Rossignol |
| 5,859,038 A | 1/1999 | Rossignol |
| 5,886,013 A | 3/1999 | Rossignol |
| 5,965,590 A | 10/1999 | Rossignol |
| 5,968,961 A | 10/1999 | Rossignol |
| 6,020,353 A | 2/2000 | Rossignol |
| 6,051,576 A | 4/2000 | Ashton et al. |
| 6,096,525 A | 8/2000 | Patnaik |
| 6,117,894 A | 9/2000 | Rossignol |
| 6,127,507 A | 10/2000 | Santerre |
| 6,299,604 B1 | 10/2001 | Ragheb et al. |
| 6,344,035 B1 | 2/2002 | Chudzik et al. |
| 6,429,300 B1 | 8/2002 | Kurz et al. |
| 6,602,915 B2 | 8/2003 | Uhrich |
| 6,689,350 B2 | 2/2004 | Uhrich |
| 6,703,037 B1 | 3/2004 | Hubbell et al. |
| 6,770,725 B2 | 8/2004 | Santerre |
| 8,349,309 B2 | 1/2013 | Santerre et al. |

(Continued)

FOREIGN PATENT DOCUMENTS

| CA | 2461099 A1 | 4/2003 |
|---|---|---|
| CA | 2467321 A1 | 11/2005 |

(Continued)

OTHER PUBLICATIONS

"Step-growth polymerization," <http://en.wikipedia.org/wiki/Step-growth_polymerization>, retrieved on Jan. 12, 2012 (11 pages).

Bach et al., "Retention of antibacterial activity and bacterial colonization of antiseptic-bonded central venous catheters," J Antimicrob Chemother. 37:315-22 (1996).

Blondeau, "Fluoroquinolones: mechanism of action, classification, and development of resistance," Surv Ophthalmol. 49(Suppl. 2):S73-8 (2004).

*The Merck Index: An Encyclopedia of Chemicals, Drugs and Biologicals,* 14th Edition. O'Neil et al. (eds.), Merck & Co., Inc.: Whitehouse Station, NJ, 1306-7 (2006).

Burger, Isosterism and bioisosterism in drug design. *Progress in Drug Research,* vol. 37. Ernst Jucker (ed.), 287-328 (1991) (43 pages).

(Continued)

*Primary Examiner* — Jeffrey T. Palenik

(74) *Attorney, Agent, or Firm* — Clark & Elbing LLP

(57) ABSTRACT

The disclosure features pharmaceutical compositions formed from prodrug dimers for the extended delivery of a drug and for the treatment of a disease or condition.

29 Claims, 38 Drawing Sheets

(56) References Cited

U.S. PATENT DOCUMENTS

| | | | | |
|---|---|---|---|---|
| 8,968,626 | B2* | 3/2015 | Pham | D01D 5/0069 264/172.15 |
| 9,056,048 | B2 | 6/2015 | Diamond et al. | |
| 2003/0035787 | A1 | 2/2003 | Uhrich | |
| 2003/0039689 | A1 | 2/2003 | Chen et al. | |
| 2003/0118528 | A1 | 6/2003 | Walters et al. | |
| 2003/0158598 | A1 | 8/2003 | Ashton et al. | |
| 2003/0203030 | A1* | 10/2003 | Ashton | A61K 9/0019 424/484 |
| 2004/0087664 | A1 | 5/2004 | Marcus et al. | |
| 2004/0180036 | A1 | 9/2004 | Ashton et al. | |
| 2005/0008695 | A1 | 1/2005 | Ashton et al. | |
| 2005/0031577 | A1 | 2/2005 | Uhrich | |
| 2005/0070470 | A1 | 3/2005 | Coy et al. | |
| 2005/0159609 | A1 | 7/2005 | King et al. | |
| 2005/0220839 | A1 | 10/2005 | DeWitt et al. | |
| 2005/0255079 | A1 | 11/2005 | Santerre et al. | |
| 2010/0062974 | A1 | 3/2010 | LaRonde et al. | |
| 2013/0289223 | A1 | 10/2013 | Santerre et al. | |
| 2014/0256696 | A1 | 9/2014 | Sinha et al. | |
| 2016/0038651 | A1 | 2/2016 | Santerre et al. | |
| 2019/0247311 | A1 | 8/2019 | Parrag et al. | |

FOREIGN PATENT DOCUMENTS

| | | | | |
|---|---|---|---|---|
| CA | 2571320 | A1 | 11/2005 | |
| CN | 1968715 | B | 12/2010 | |
| JP | H07501470 | A | 2/1995 | |
| JP | H0924093 | A | 1/1997 | |
| JP | 2000-501318 | A | 2/2000 | |
| JP | 2007-537168 | A | 12/2007 | |
| WO | WO-95/11907 | A1 | 5/1995 | |
| WO | WO-95/20567 | A1 | 8/1995 | |
| WO | WO-95/28393 | A1 | 10/1995 | |
| WO | WO-97/29778 | A2 | 8/1997 | |
| WO | WO-98/07458 | A1 | 2/1998 | |
| WO | WO-98/50035 | A1 | 11/1998 | |
| WO | WO-99/06430 | A1 | 2/1999 | |
| WO | WO-99/12990 | A1 | 3/1999 | |
| WO | WO-02/09768 | A2 | 2/2002 | |
| WO | WO-03/028527 | A2 | 4/2003 | |
| WO | WO-03/040104 | A1 | 5/2003 | |
| WO | WO-2004/016214 | A2 | 2/2004 | |
| WO | WO-2005/110485 | A1 | 11/2005 | |
| WO | WO 2011/120044 | A1* | 9/2011 | A61K 31/58 |
| WO | WO-2014/139033 | A1 | 9/2014 | |
| WO | WO-2017/083794 | A1 | 5/2017 | |

OTHER PUBLICATIONS

Cheng et al., "Intravitreal sustained-release dexamethasone device in the treatment of experimental uveitis," Invest Ophthalmol Vis Sci. 36(2):442-53 (1995).
Chirife et al., "In vitro antibacterial activity of concentrated polyethylene glycol 400 solutions," Antimicrob Agents Chemother. 24(3):409-12 (1983).
Coessens et al., "Synthesis and in vitro stability of macromolecular prodrugs of norfloxacin," J Cont Release. 47:283-91 (1997).
DiTizio et al., "A liposomal hydrogel for the prevention of bacterial adhesion to catheters," Biomaterials. 19(20):1877-84 (1998).
Extended European Search Report for European Application No. 17206101.2, dated Jun. 6, 2018 (8 pages).
Extended European Search Report for European Patent Application No. 14764271.4, dated Oct. 24, 2016 (7 pages).
Final Rejection for Japanese Application No. 2015-561873, dated May 8, 2018 (8 pages).
First Office Action for Chinese Patent Application No. 201480027630.6, dated Mar. 14, 2017 (15 pages) (English language translation provided).
Ghosh, "Studies directed towards polymeric quinolone antibiotics—synthesis of potential monomers from nalidixic acid," Polymeric Mat Sci Engin. 59:790-3 (1988).

Ghosh, Monomers and Polymers from Nalidixic Acid- Synthesis, Characterization, and Hydrolysis Study. *Progress in Biomedical Polymers*. C.G. Gebelein and R.L. Dunn (eds.), Plenum Press, 335-45 (1990).
International Patent Application No. PCT/CA2019/050133. Interface Biologics, Inc., "Ocular Insert," filed Feb. 1, 2019 (116 pages).
International Patent Application No. PCT/CA2019/050135. Interface Biologics, Inc., "Glass Formulations and Uses Thereof," filed Feb. 1, 2019 (181 pages).
International Patent Application No. PCT/CA2019/050136. Interface Biologics, Inc., "Dexamethsone Prodrug Compositions and Uses Thereof," filed Feb. 1, 2019 (87 pages).
International Preliminary Report on Patentability for International Application No. PCT/CA2014/050284, dated Sep. 15, 2015 (8 pages).
International Search Report and Written Opinion for International Application No. PCT/CA2019/050133, dated Apr. 29, 2019 (16 pages).
International Search Report and Written Opinion for International Application No. PCT/CA2019/050135, dated Apr. 29, 2019 (12 pages).
International Search Report and Written Opinion for International Application No. PCT/CA2019/050136, dated Apr. 29, 2019 (11 pages).
International Search Report and Written Opinion for International Patent Application No. PCT/CA2014/050284, dated Jun. 2, 2014 (13 pages).
Kanra et al., "The short-term efficacy and safety of dexamethasone implant in a difficult-to-treat patient population with persistent diabetic macular edema," Ret Vit. 26(3):221-7 (2017) (8 pages).
Kerns et al., "Piperazinyl-linked fluoroquinolone dimers possessing potent antibacterial activity against drug-resistant strains of *Staphylococcus aureus*," Bioorg Med Chem Lett. 13(10):1745-9 (2003).
Li et al., "Dimeric and Oligomeric Steroids," Chem Rev. 97(1):283-304 (1997).
Michael et al., "Enhanced RNA binding of dimerized aminoglycosides," Bioorg Med Chem. 7(7):1361-71 (1999).
Modak et al., "A New Method for the Direct Incorporation of Antibiotic in Prosthetic Vascular Grafts," Surg Gynecol Obstet. 164:143-147 (1987).
Nathan et al., "Copolymers of Lysine and Polyethylene Glycol: A New Family of Functionalized Drug Carriers," Bioconjug Chem. 4:54-62 (1993).
Nishida et al., "Studies on synthesis of antibacterial agent (NM441). I. Kinetics and mechanism of the reaction of 4-(bromomethyl)-5-methyl-1,3-dioxol-2-one with 1-substituted piperazine (NM394)," Bull Chem Soc Jpn. 67:1419-26 (1994).
Nosova et al., "Synthesis of new fluorinated derivatives of quinolinecarboxylic acids," Chem Heterocycl Compd. 38(8):922-8 (2002).
Notice of Reasons for Rejection for Japanese Patent Application No. 2015-561873, dated Sep. 19, 2017 (7 Pages) (English language translation provided).
Odian, Introduction. *Principles of Polymerization*; Fourth Edition. Wiley-Interscience, 6-9 (2004) (7 pages).
Paryzek et al., "A new approach to steroid dimers and macrocycles by the reaction of 3-chlorocarbonyl derivatives of bile acids with O,O-, N,N-, and S,S-dinucleophiles," Tetrahedron Lett. 53(46):6212-5 (2012).
Patani et al., "Bioisosterism: A Rational Approach in Drug Design," Chem Rev. 96(8):3147-76 (1996).
Ren et al., "Macromolecular prodrug of dexamethasone prevents particle-induced peri-implant osteolysis with reduced systemic side effects," available in PMC Feb. 10, 2015, published in final edited form as: J Control Release. 175:1-9 (2014) (24 pages).
Roseeuw et al., "Polymeric prodrugs of antibiotics with improved efficiency," J Mater Sci Mater Med. 10:743-6 (1999).
Woo et al., "Biological characterization of a novel biodegradable antimicrobial polymer synthesized with fluoroquinolones," J Biomed Mater Res. 59(1):35-45 (2002).
Woo et al., "Synthesis and characterization of a novel biodegradable antimicrobial polymer," Biomaterials. 21(12):1235-46 (2000).

(56) References Cited

OTHER PUBLICATIONS

Xue et al., "New dimeric cholesteryl-based A(LS)2 gelators with remarkable gelling abilities: organogel formation at room temperature," J Colloid Interface Sci. 361(2):556-64 (2011).
Yang, et al., "Utilization of quinolone drugs as monomers: characterization of the synthesis reaction products for poly(norfloxacin diisocyanatododecane polycaprolactone)," Biomacromolecules. 2(1):134-41 (2001).
Office Action for U.S. Appl. No. 16/396,135, dated Jul. 3, 2019 (14 pages).
Response to Non-Final Office Action for U.S. Appl. No. 16/396,400, dated Sep. 24, 2019 (9 pages).

* cited by examiner

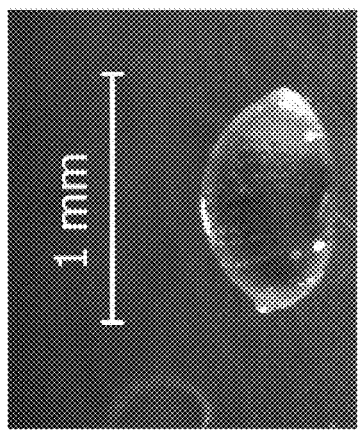
FIG. 2A
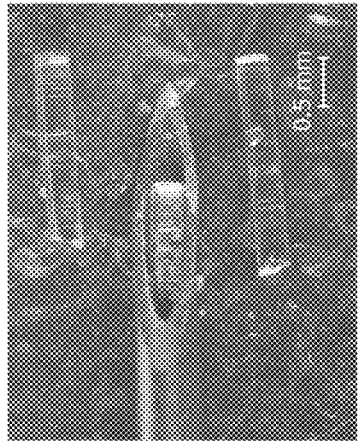
FIG. 2B  FIG. 2C
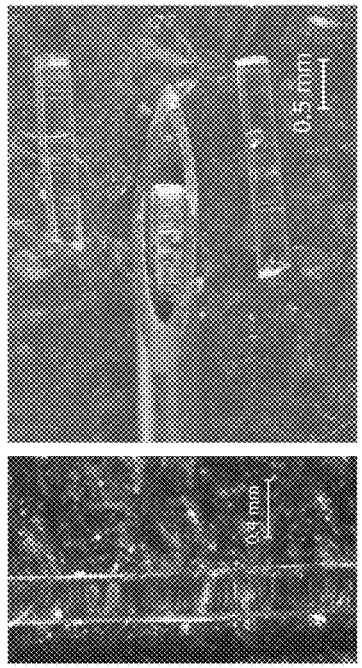
FIG. 2D
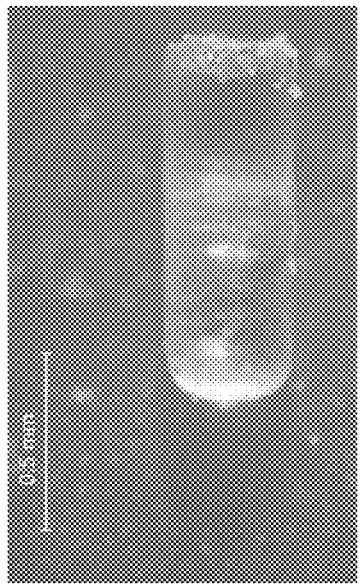
FIG. 2E
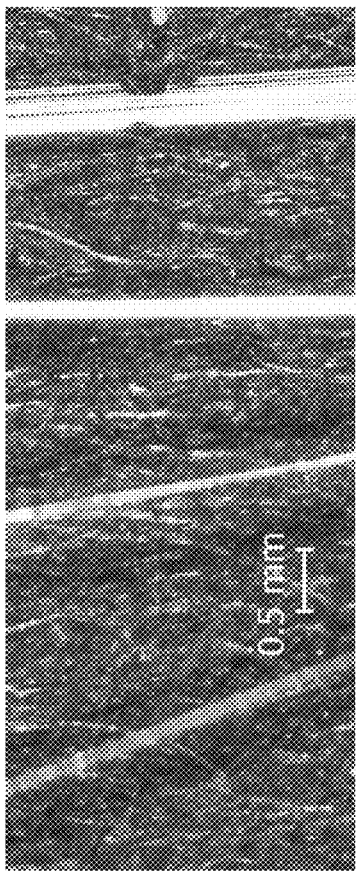

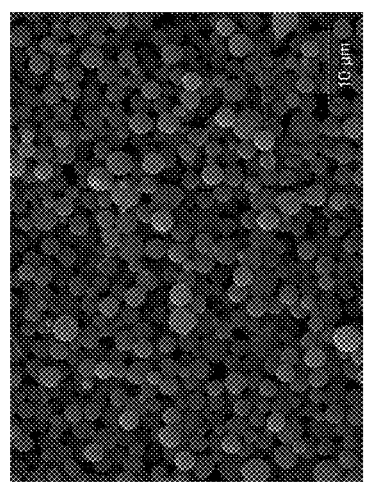
FIG. 3I
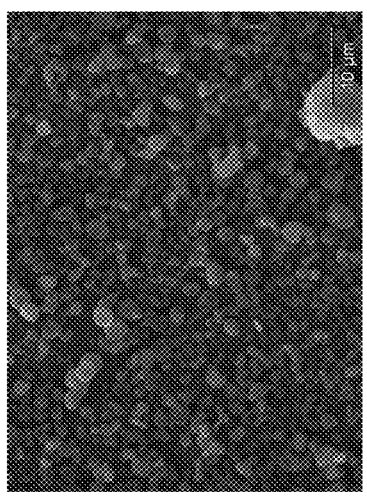
FIG. 3H
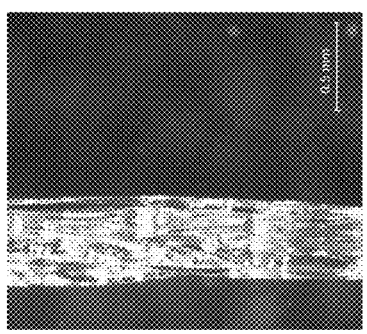
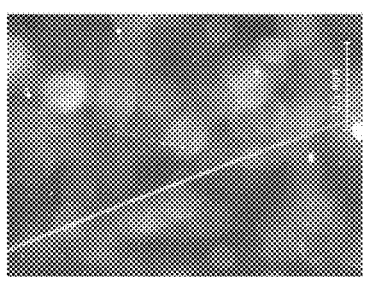
FIG. 3G
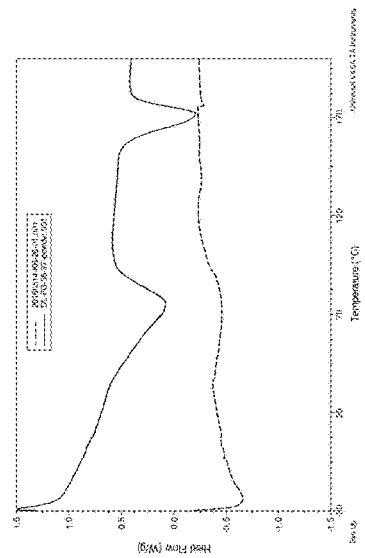
FIG. 3K
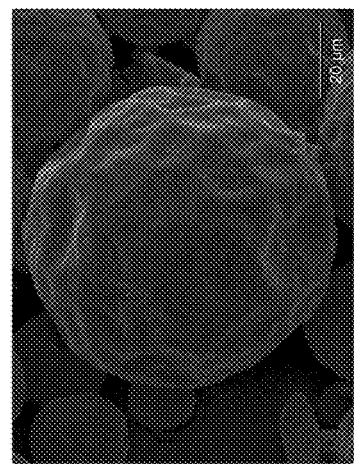
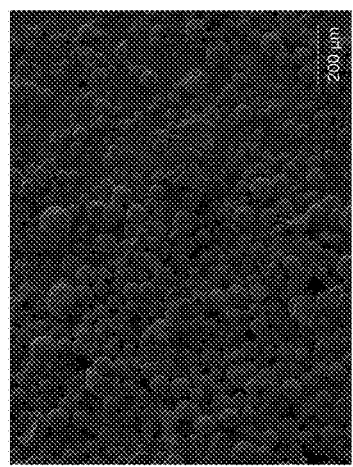
FIG. 3J

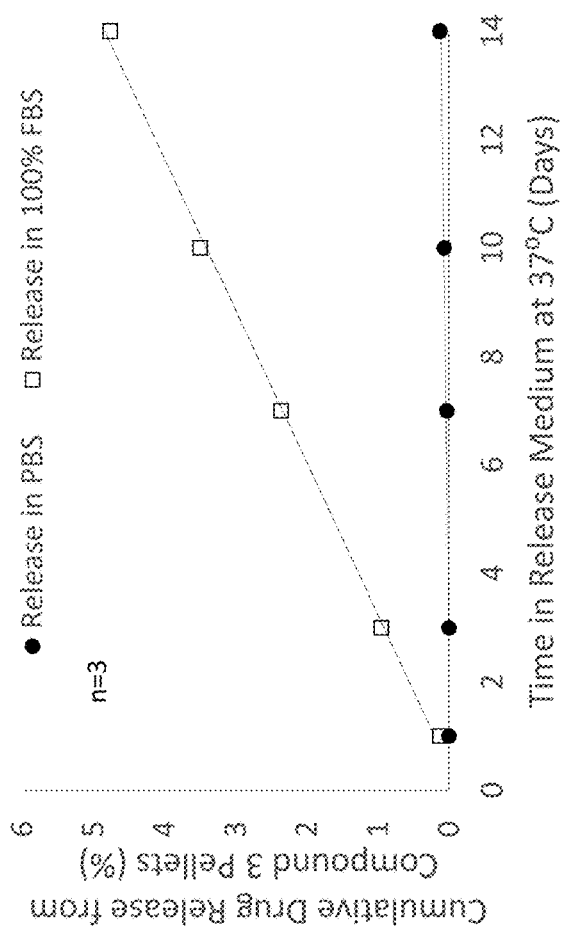
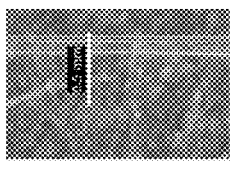
FIG. 10D
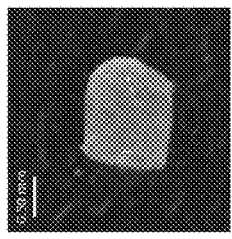
FIG. 10C
FIG. 10B
FIG. 10E
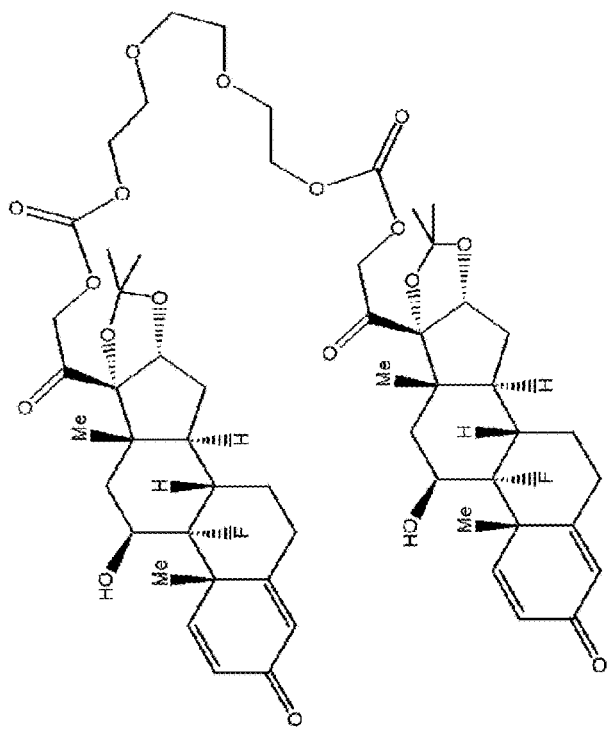
FIG. 10A

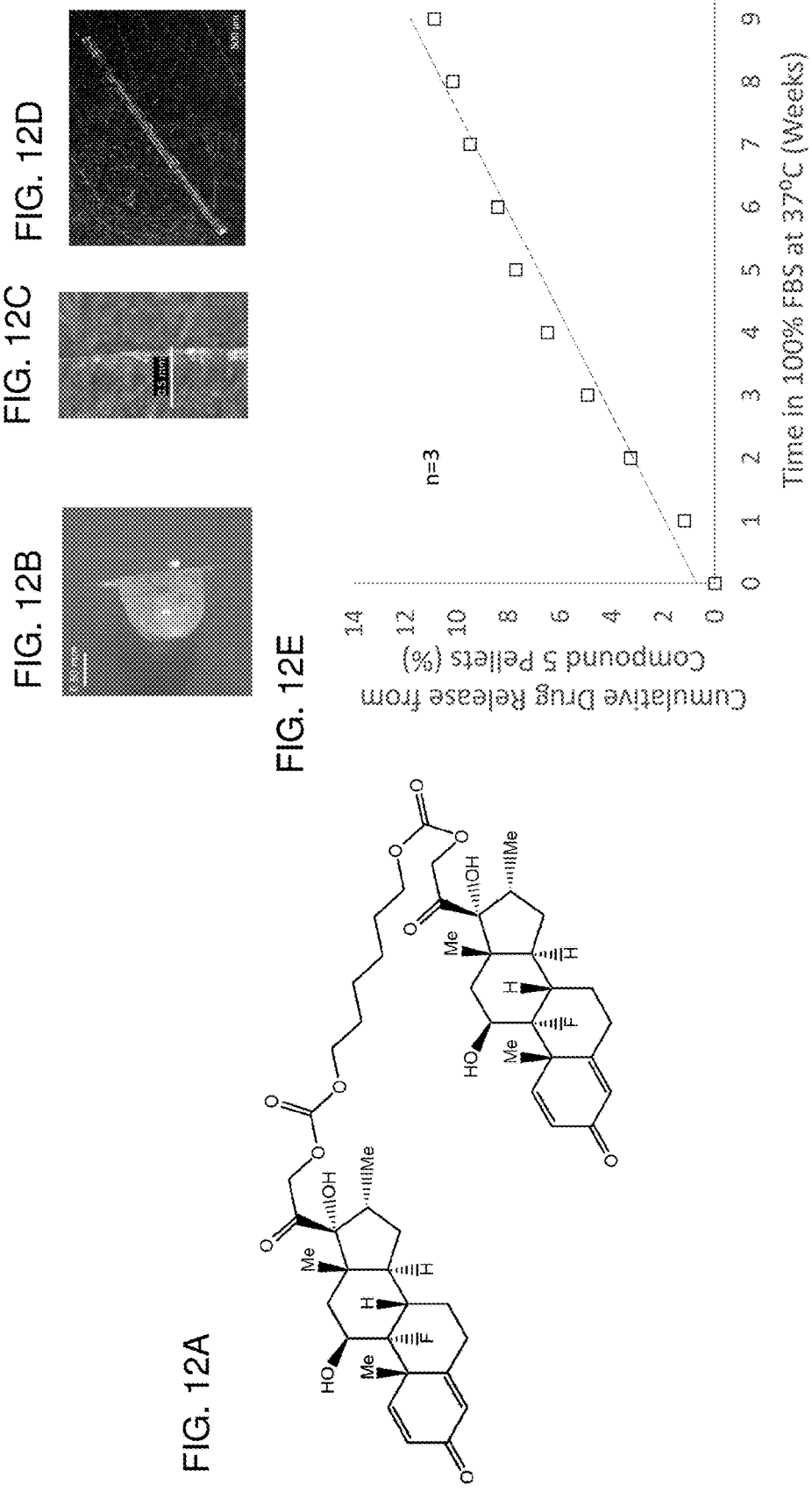

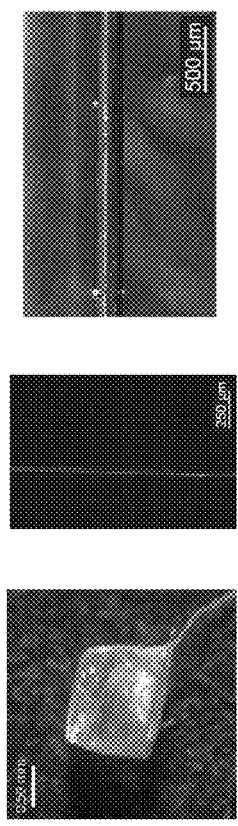
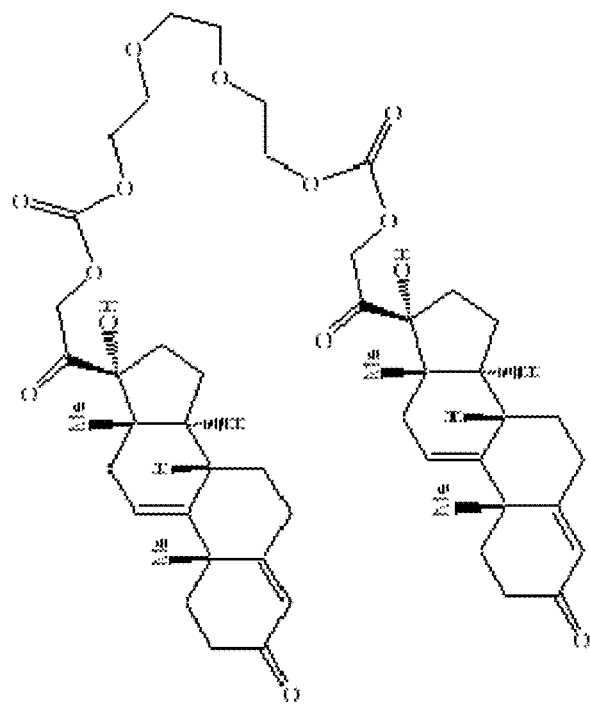
FIG. 14D
FIG. 14C
FIG. 14B
FIG. 14E
FIG. 14A

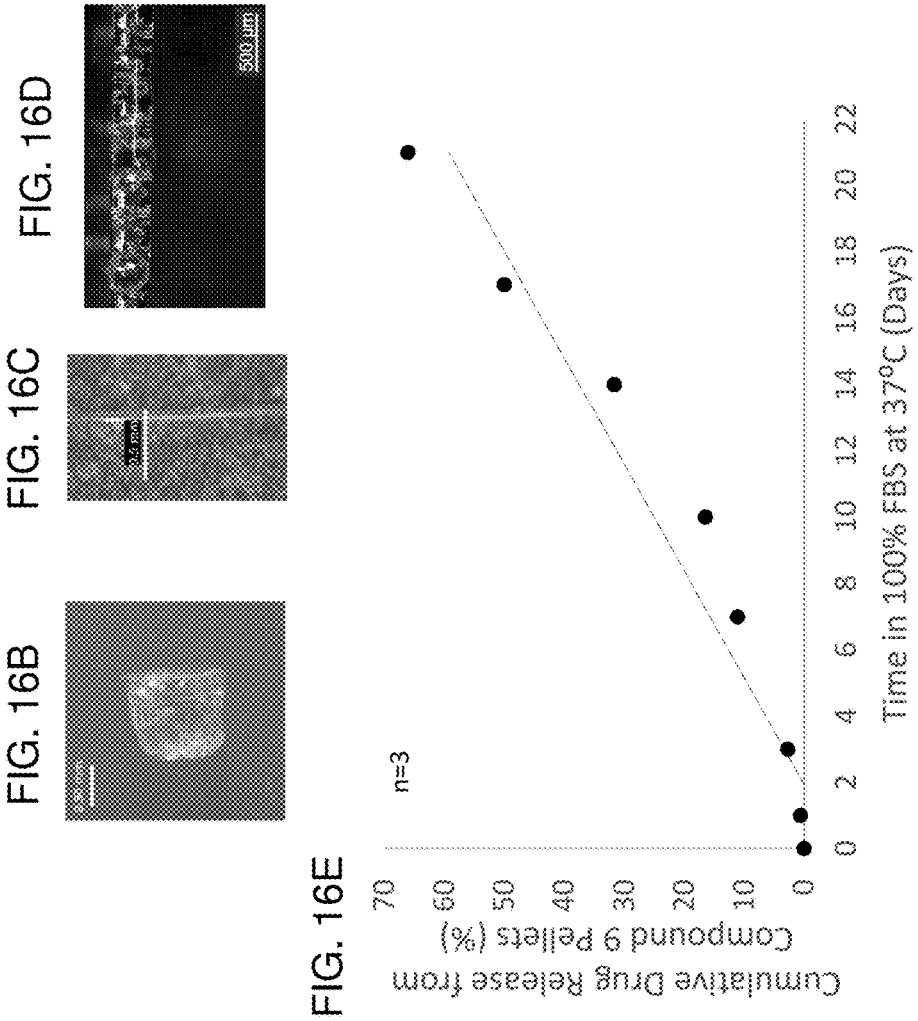

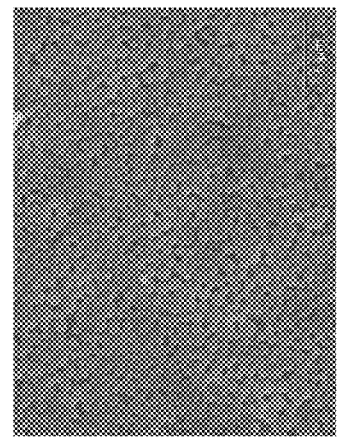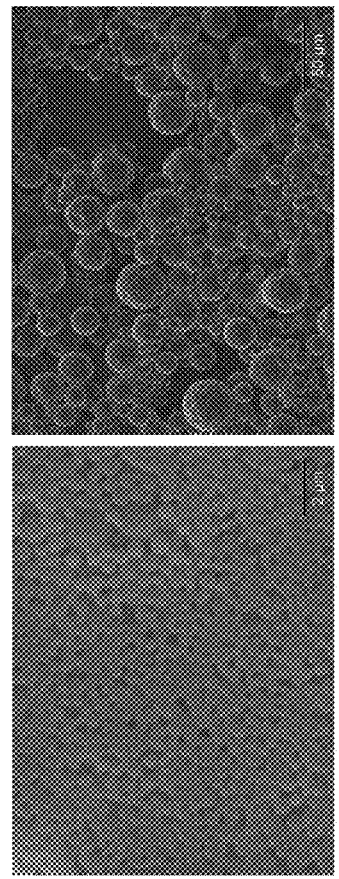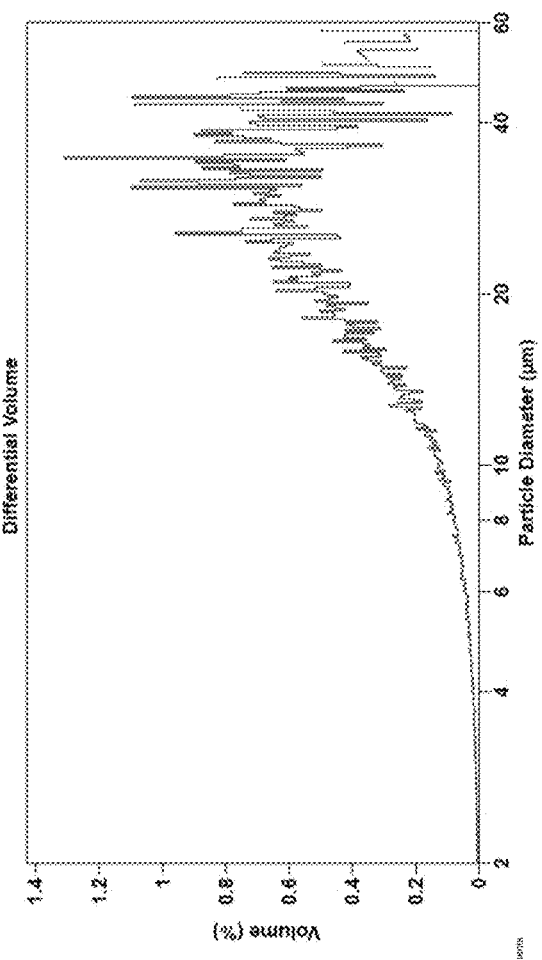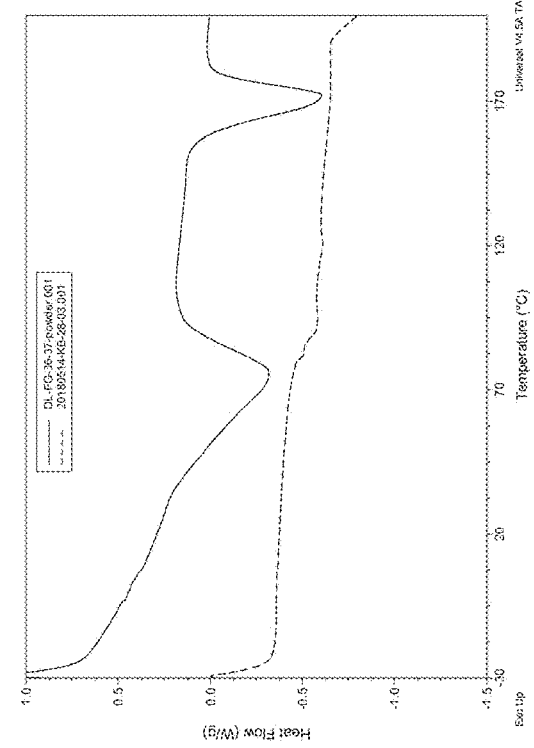
FIG. 18A  FIG. 18B  FIG. 18C  FIG. 18D  FIG. 18E  FIG. 18F

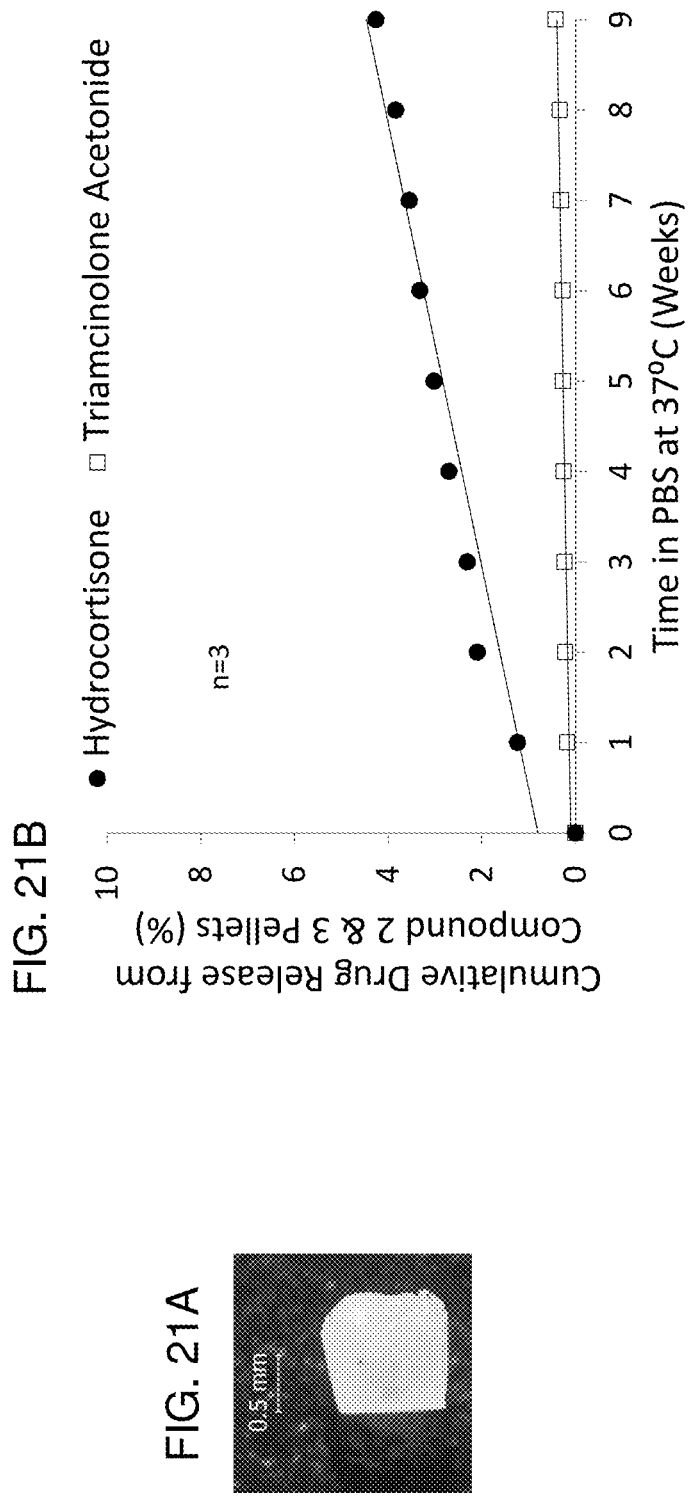

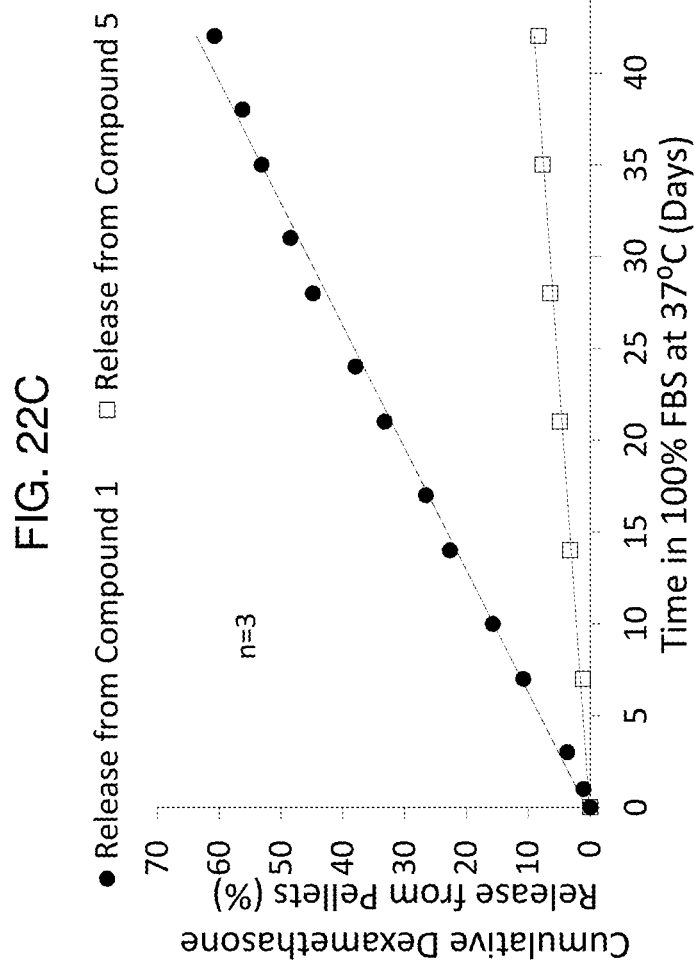

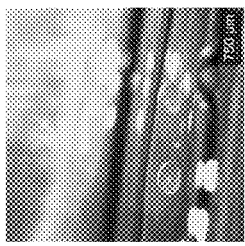
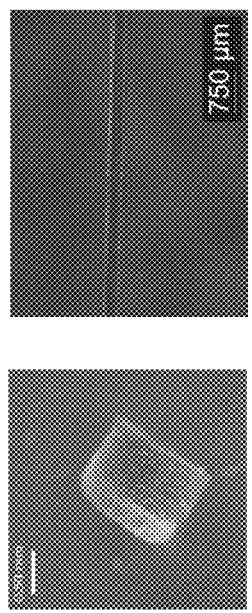
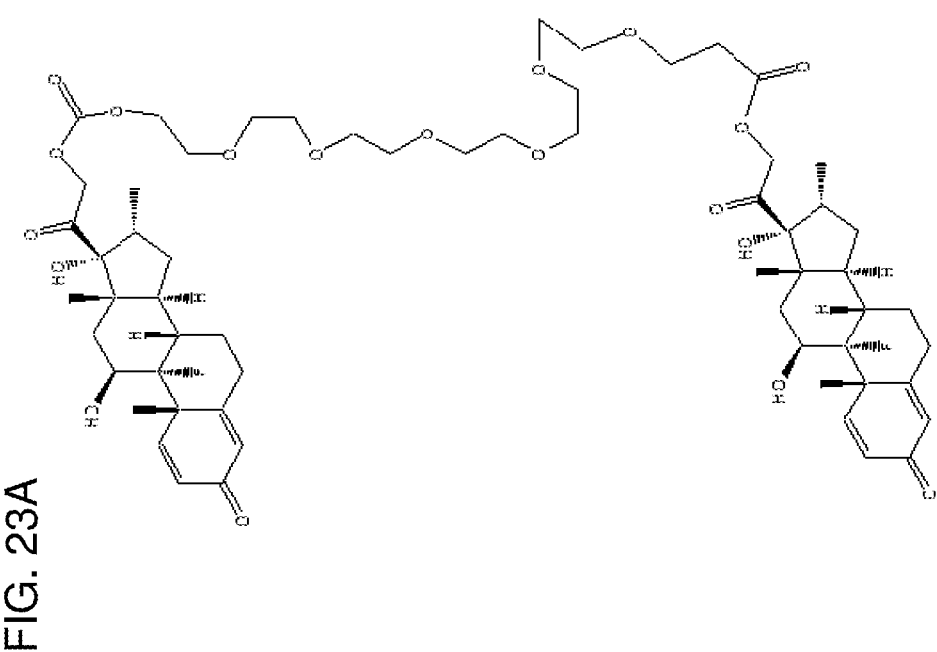

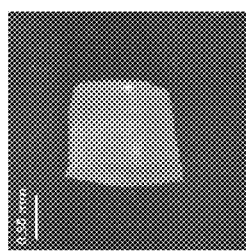
FIG. 27C
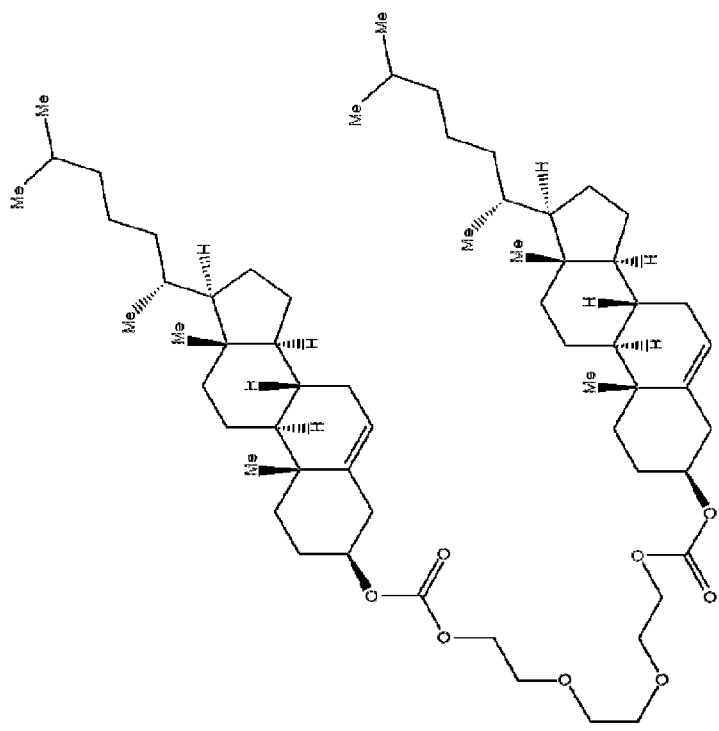
FIG. 27B
FIG. 27A

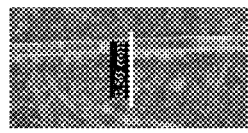
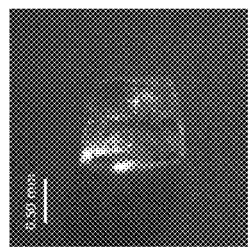
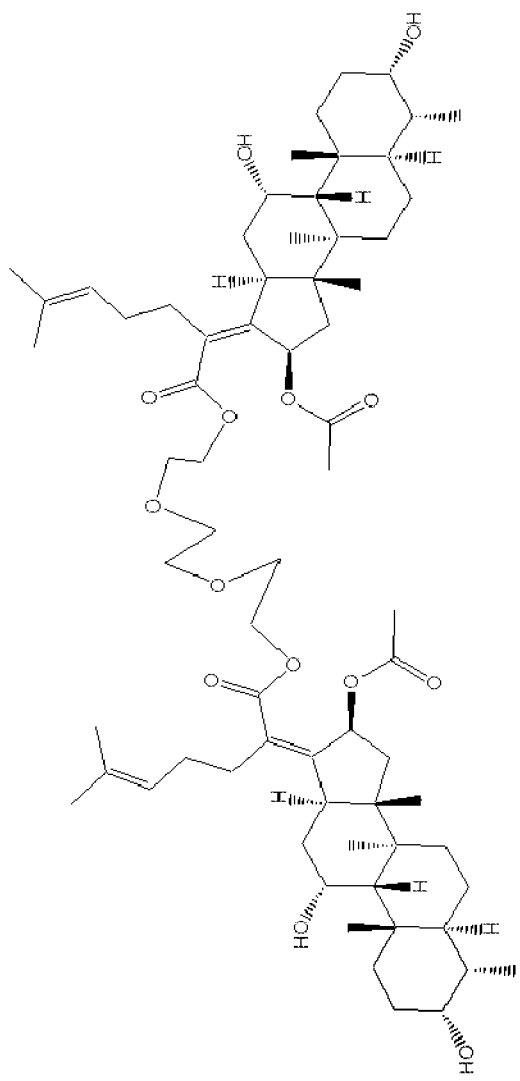
FIG. 28A
FIG. 28B
FIG. 28C

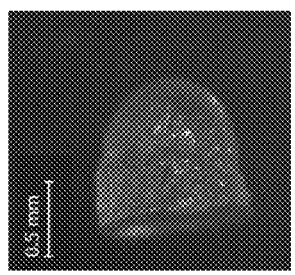
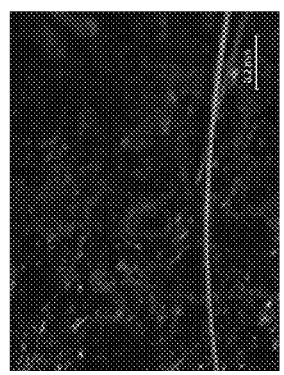
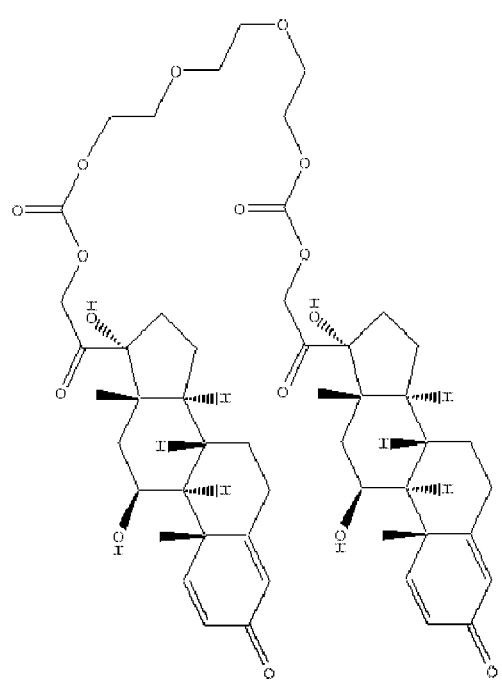
FIG. 30A
FIG. 30B
FIG. 30C

GLASS FORMULATIONS AND USES THEREOF

BACKGROUND OF THE DISCLOSURE

Steroids are useful drugs in a variety of medical fields, for example in ophthalmology, oncology, laryngology, endocrinology and metabolic diseases, rheumatology, urology, neurology, cardiology, dental medicine, dermatology, otology, post-surgical medicine, orthopedics, pain management, and gynecology.

SUMMARY OF THE DISCLOSURE

The disclosure features steroid dimers and articles formed from the steroid dimers. The articles of the disclosure can be machined, molded, emulsion-processed, electrospun, electrosprayed, blow molded, fiber spun (e.g., wet spun, dry spun, melt spun, heat spun, or gel spun), or extruded to form a fiber, fiber mesh, woven fabric, non-woven fabric, pellet, cylinder, microparticle (e.g., a microbead), nanoparticle (e.g., a nanobead), or any other type shaped article from which the prodrug steroid dimer is released in a controlled fashion.

In a first aspect, the disclosure provides an article including a compound of formula (A-VIII):

$$D1\text{-}L\text{-}D2 \tag{A-VIII}$$

or a pharmaceutically acceptable salt thereof, wherein (i) each of D1 and D2 is, independently, a radical formed from a steroid; and L is a linker covalently linking D1 to D2, (ii) at least 90% (w/w) of the article is the compound of formula (A-VIII), (iii) the article is free of controlled release excipient, and (iv) D1 and D2 is released from the article at 37° C. in 100% bovine serum or at 37° C. in PBS at a rate such that $t_{10}$ is greater than or equal to $\frac{1}{10}$ of $t_{50}$.

In another aspect, the disclosure features an article including a compound of formula (A-VIII):

$$D1\text{-}L\text{-}D2 \tag{A-VIII}$$

or a pharmaceutically acceptable salt thereof, wherein (i) each of D1 and D2 is, independently, a radical formed from a steroid; and L is a linker covalently linking D1 to D2, (ii) at least 90% (w/w) of the article is the compound of formula (A-VIII), (iii) the article is a fiber, fiber mesh, woven fabric, non-woven fabric, pellet, cylinder, hollow tube, microparticle, nanoparticle, or shaped article, and (iv) the article is free of controlled release excipient.

In some embodiments, the compound, D1, or D2 are released from the article through surface erosion.

In another aspect, the disclosure features an article formed from a compound of formula (A-VIII):

$$D1\text{-}L\text{-}D2 \tag{A-VIII}$$

or a pharmaceutically acceptable salt thereof, in which the article is prepared by a process including the steps of: (a) heating the compound, or a pharmaceutically acceptable salt thereof, to form a melt; and (b) cooling the melt to form the composition, in which each of D1 and D2 is, independently, a radical formed from a steroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

The disclosure further features an article including a compound of formula (A-VIII):

$$D1\text{-}L\text{-}D2 \tag{A-VIII}$$

or a pharmaceutically acceptable salt thereof, in which the article is formed by a process including the steps of: (a) heating the compound, or a pharmaceutically acceptable salt thereof, to form a melt; and (b) injection molding the melt to form the article, in which each of D1 and D2 is, independently, a radical formed from a steroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

The disclosure also features an article including a compound of formula (A-VIII):

$$D1\text{-}L\text{-}D2 \tag{A-VIII}$$

or a pharmaceutically acceptable salt thereof, in which the article is formed by a process including the steps of: (a) heating the compound, or a pharmaceutically acceptable salt thereof, to form a melt; and (b) blow molding the melt to form the article, in which each of D1 and D2 is, independently, a radical formed from a steroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

The disclosure features an article including a compound of formula (A-VIII):

$$D1\text{-}L\text{-}D2 \tag{A-VIII}$$

or a pharmaceutically acceptable salt thereof, in which the article is formed by a process including the steps of: (a) dissolving the compound, or a pharmaceutically acceptable salt thereof, to form a solution; and (b) evaporating the solvent to form the article (e.g., free formed to form a film, from a mold to form a shaped article, or from a spinneret to form a fiber), in which each of D1 and D2 is, independently, a radical formed from a steroid; and L is a linker covalently linking D1 to D2. In particular embodiments, step (b) includes solvent casting to form a film or a fiber. In particular embodiments, the article is free of controlled release excipient, free of a crystallization inhibiting excipient, free of a mechanical integrity enhancing excipient, and/or free of a binding excipient; or the article optionally has a glassy state.

The disclosure also features an article including a compound of formula (A-VIII):

$$D1\text{-}L\text{-}D2 \tag{A-VIII}$$

or a pharmaceutically acceptable salt thereof, in which the article is formed by a process including the steps of: (a) dissolving the compound, or a pharmaceutically acceptable salt thereof, to form a solution; and (b) electrospinning or electrospraying the solution to form the article, in which each of D1 and D2 is, independently, a radical formed from a steroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

The disclosure further features an article including a compound of formula (A-VIII):

$$D1\text{-}L\text{-}D2 \tag{A-VIII}$$

or a pharmaceutically acceptable salt thereof, in which the article is formed by a process including the steps of: (a) heating the compound, or a pharmaceutically acceptable salt thereof, to form a melt; and (b) electrospinning or electrospraying the melt to form the article, in which each of D1 and D2 is, independently, a radical formed from a steroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

The disclosure features an article including a compound of formula (A-VIII):

$$D1-L-D2 \quad \text{(A-VIII)}$$

or a pharmaceutically acceptable salt thereof, in which the article is formed by a process including the steps of: (a) heating the compound, or a pharmaceutically acceptable salt thereof, to form a melt; (b) extruding the melt to form the article, in which each of D1 and D2 is, independently, a radical formed from a steroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

In some embodiments of the articles of the disclosure, the compound is processed as described herein (e.g., melt processed or solvent processed) to form a glassy state solid. The glassy state solid is subsequently heated above its glass transition temperature, Tg, and heat processed (e.g., molded, blow molded, heat spun, electrospun, electrosprayed, or extruded to form a shaped article (e.g., a fiber, fiber mesh, woven fabric, non-woven fabric, pellet, cylinder, microparticle (e.g., a microbead), or nanoparticle (e.g., a nanobead), or another shaped article). In other embodiments, microparticles are prepared by melting the compound to form glassy state pellets or other shaped forms, crushing the glassy state articles into rough or irregular-shaped particles, filtering particles through sieves, and heating the particles above the Tg to round them into smoother spherical particles.

In an embodiment of any of the above articles, L has a molecular weight of from 80 to 800 Da, e.g., 80 to 100 Da, 80 to 200 Da, 80 to 300 Da, 80 to 400 Da, 80 to 500 Da, 80 to 600 Da, or 80 to 700 Da. In another embodiment of any of the above articles, L is covalently linked to D1 and to D2 via one or more ester, carbonate, carbonate ester, or anhydride linkages. In particular embodiments, L is covalently linked to D1 and to D2 via one or more carbonate linkages.

In a particular embodiment of any of the above articles, L includes the radical —C(O)—(R$^A$)—C(O)— or —O—(R$^A$)—O—; R$^A$ is a radical of a polyol and includes at least one free hydroxyl group or R$^A$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$—, or —(CH$_2$CH(CH$_3$)O)$_s$CH$_2$CH(CH$_3$)—; and q, r, and s are integers from 1 to 10 (e.g., 1 to 10, 1 to 5, or 5 to 10).

The disclosure features an article formed from a compound of the disclosure.

In an embodiment of any of the above articles, each of D1 and D2 is an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid. In a particular embodiment of any of the above articles, the compound is further described by one of formulas (II)-(LXXV), described herein. In another embodiment of any of the above articles, each of D1 and D2 is, independently, described by any one of formulas (I-a) to (I-vvv), described herein.

In the articles of the disclosure, D1 and D2 can be formed from the same steroid, or D1 and D2 can be formed from different steroids.

In a particular embodiment of any of the above articles, the article includes a mixture of two or more compounds of formula (A-VIII).

In certain embodiments, at least 70% (w/w) of the article is a compound of formula (A-VIII), e.g., at least 75% (w/w), at least 80% (w/w), at least 85% (w/w), at least 90% (w/w), at least 95% (w/w), or at least 99% (w/w).

In another embodiment of any of the above articles, the compound is released from the article through surface erosion. In certain embodiments of any of the above articles, the surface erosion releases less than 20% (e.g., less than 18%, 15%, 12%, 10%, or 5%) of D1 or D2 (as a percentage of the total drug, D1 or D2, present in the article in prodrug form) at 37° C. in 100% bovine serum over 5 days, 6 days, 7 days, 8 days, 9 days, 10 days, or 12 days (e.g., less than 10% of D1 or D2 at 37° C. in 100% bovine serum over 5 days). In other embodiments of any of the above articles, the surface erosion releases less than 2.0% (e.g., less than 1.8%, 1.5%, 1.2%, 1.0%, or 0.5%) of D1 or D2 (as a percentage of the total drug, D1 or D2, present in the article in prodrug form) at 37° C. in PBS over 5 days, 7 days, 10 days, or 14 days (e.g., less than 2% of D1 or D2 at 37° C. in PBS over 5 days). In still other embodiments of any of the above articles, the surface erosion releases greater than 20% (e.g., greater than 22%, 24%, 26%, 28%, or 30%) of D1 or D2 (as a percentage of the total drug, D1 or D2, present in the article in prodrug form) at 37° C. in 100% bovine serum over not fewer than 6 days, 8 days, 10 days, or 12 days (e.g., greater than 24% of D1 or D2 at 37° C. in 100% bovine serum over 10 days). In other embodiments of any of the above articles, the surface erosion releases greater than 5.0% (e.g., greater than 6.0%, 8.0%, 10%, 12%, or 15%) of D1 or D2 (as a percentage of the total drug, D1 or D2, present in the article in prodrug form) at 37° C. in PBS over not fewer than 6 days, 8 days, 10 days, or 12 days (e.g., greater than 5% of D1 or D2 at 37° C. in PBS over 10 days). The compound (D1 and/or D2) can be released from the article at a rate such that $t_{10}$ is greater than or equal to $\frac{1}{10}$ of $t_{50}$.

In still another embodiment of any of the above articles, the article further includes from 0.1% to 10% (e.g., from 0.1 to 5%, from 0.1 to 2%, from 0.5 to 2%, from 1 to 10%) (w/w) of one or more additives, in which the one or more additives are plasticizers (e.g., glycerol, triacetin, isopropyl alcohol, ethanol, or ethylene glycol), antioxidants (e.g., ascorbic acid, vitamin E, sodium metabisulfite, butylated hydroxytoluene, p-hydroxybenxyl alcohol, or butylated hydroxy anisole), binders (e.g., polyvinyl pyrrolidone, carboxymethyl cellulose, hydroxypropyl cellulose, or hydroxypropyl methyl cellulose), lubricants, radio-opaque agents, and mixtures thereof.

In still another embodiment of any of the above articles, the article is a fiber, fiber mesh, woven fabric, non-woven fabric, pellet, cylinder, microparticle (e.g., a microbead), nanoparticle (e.g., a nanobead), or another shaped article. For example, the article is a milled microbead or nanobead.

In other embodiments, the article is in the form of glassy state fibers having a mean diameter of from about 0.01 to 1 mm, e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm. In some embodiments, a mean length of the fiber can range from about 20 mm to 20 meters, e.g., 20 to 100 mm, 75 to 300 mm, 100 mm to 1 meter, 0.5 meters to 6 meters, or 1.0 meters to 20 meters.

In certain embodiments, the article is in the form of glassy state pellets having a mean diameter of from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm.

In some embodiments, the article is in the form of glassy state cylinders of from about 0.5 to 20 mm in length, e.g., about to 0.5 to 1 mm, about 0.5 to 2 mm, about 0.5 to 4 mm, about 0.5 to 6 mm, about 0.5 to 8 mm, about 0.5 to 10 mm, about 0.5 to 12 mm, about 0.5 to 14 mm, about 0.5 to 16 mm, or about 0.5 to 18 mm. In some embodiments, the article is in the form of glassy state cylinders of from about 0.1 to 1 mm diameter, e.g., about 0.1 to 0.2 mm, about 0.1 to 0.3 mm, about 0.1 to 0.4 mm, about 0.2 to 0.5 mm, about 0.1 to 0.6 mm, about 0.1 to 0.7 mm, about 0.1 to 0.8 mm, or about 0.1 to 0.9 mm. In some embodiments, the mean diameter of the cylinder is in the range of about 0.01 to 1 mm and the mean length of the cylinder is about 0.1 mm to 4.0 mm. In some embodiments, the length of the cylinder is about 0.5 to 10 mm, or about 1 to 10 mm.

In some embodiments, the article is mechanically stable. For example, the article is resistant to breaking under deformation.

In other embodiments, the article is in the form of glassy state microparticles, e.g., microbeads, having a mean diameter of from about 1 to 1000 µm, e.g., about 10 to 1000 µm, about 100 to 1000 µm, about 200 to 1000 µm, about 500 to 1000 µm, about 700 to 1000 µm, or about 900 to 1000 µm.

In certain embodiments, the article is in the form of glassy state nanoparticles, e.g., nanobeads, having a mean diameter of from about 0.01 to 1 µm, e.g., about 0.05 to 1 µm, about 0.1 to 1 µm, about 0.2 to 1 µm, about 0.3 to 1 µm, about 0.4 to 1 µm, about 0.5 to 1 µm, about 0.6 to 1 µm, about 0.7 to 1 µm, about 0.8 to 1 µm, or about 0.9 to 1 µm.

The disclosure features a fiber formed from a compound of the disclosure (e.g., a compound described by one of formulas (II)-(LXXV), described herein, or a steroid dimer in which each of D1 and D2 is, independently, described by any one of formulas (I-a) to (I-ii), described herein). In particular embodiments, the fiber is free of controlled release excipient, free of a crystallization inhibiting excipient, free of a mechanical integrity enhancing excipient, and/or free of a binding excipient.

The disclosure further features a fiber formed from a compound of formula (A-VIII):

D1-L-D2 (A-VIII)

or a pharmaceutically acceptable salt thereof, in which the fiber is prepared by a process including the steps of: (a) dissolving the compound, or a pharmaceutically acceptable salt thereof, in a solvent to form a solution; and (b) electrospinning, dry spinning, wet spinning or gel spinning the solution to form the fiber, in which each of D1 and D2 is, independently, a radical formed from a steroid; and L is a linker covalently linking D1 to D2. In particular embodiments, the fiber is free of controlled release excipient, free of a crystallization inhibiting excipient, free of a mechanical integrity enhancing excipient, and/or free of a binding excipient; or the fiber optionally has a glassy state.

The disclosure further features a fiber formed from a compound of formula (A-VIII):

D1-L-D2 (A-VIII)

or a pharmaceutically acceptable salt thereof, in which the fiber is prepared by a process including the steps of: (a) heating the compound, or a pharmaceutically acceptable salt thereof, to form a melt; and (b) extruding the melt to form the fiber (i.e., melt spinning), each of D1 and D2 is, independently, a radical formed from a steroid; and L is a linker covalently linking D1 to D2. In particular embodiments, the fiber is free of controlled release excipient, free of a crystallization inhibiting excipient, free of a mechanical integrity enhancing excipient, and/or free of a binding excipient; or the fiber optionally has a glassy state.

The disclosure features a fiber formed from a compound of formula (A-VIII):

D1-L-D2 (A-VIII)

or a pharmaceutically acceptable salt thereof, in which the fiber is prepared by a process including the steps of: (a) heating the compound, or a pharmaceutically acceptable salt thereof, to form a melt; and (b) electrospinning the melt to form the fiber, in which each of D1 and D2 is, independently, a radical formed from a steroid; and L is a linker covalently linking D1 to D2. In particular embodiments, the fiber is free of controlled release excipient, free of a crystallization inhibiting excipient, free of a mechanical integrity enhancing excipient, and/or free of a binding excipient; or the fiber optionally has a glassy state.

In an embodiment of any of the above fibers, L has a molecular weight of from 80 to 800 Da, e.g., 80 to 100 Da, 80 to 200 Da, 80 to 300 Da, 80 to 400 Da, 80 to 500 Da, 80 to 600 Da, or 80 to 700 Da. In another embodiment of any of the above fibers, L is covalently linked to D1 and to D2 via one or more ester, carbonate, carbonate ester, or anhydride linkages. In particular embodiments, L is covalently linked to D1 and to D2 via one or more carbonate linkages.

In a particular embodiment of any of the above fibers, L includes the radical —C(O)—($R^4$)—C(O)— or —O—($R^4$)—O—; $R^4$ is a radical of a polyol and includes at least one free hydroxyl group or $R^4$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$—, or —(CH$_2$CH(CH$_3$)O)$_s$CH$_2$CH(CH$_3$)—; and q, r, and s are integers from 1 to 10 (e.g., 1 to 10, 1 to 5, or 5 to 10).

In an embodiment of any of the above fibers, each of D1 and D2 is an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid. In a particular embodiment of any of the above fibers, the compound is further described by one of formulas (II)-(LXXV), described herein. In another embodiment of any of the above fibers, each of D1 and D2 is, independently, described by any one of formulas (I-a) to (I-vvv), described herein.

In the fibers of the disclosure, D1 and D2 can be formed from the same steroid, or D1 and D2 can be formed from different steroids.

In a particular embodiment of any of the above fibers, the fiber includes a mixture of two or more compounds of formula (A-VIII).

In certain embodiments, at least 70% (w/w) of the fiber is a compound of formula (A-VIII), e.g., at least 75% (w/w), at least 80% (w/w), at least 85% (w/w), at least 90% (w/w), at least 95% (w/w), or at least 99% (w/w).

In another embodiment of any of the above fibers, the compound is released from the fiber through surface erosion. In certain embodiments of any of the above fibers, the surface erosion releases less than 20% (e.g., less than 18%, 15%, 12%, 10%, or 5%) of D1 or D2 (as a percentage of the total drug, D1 or D2, present in the fiber in prodrug form) at 37° C. in 100% bovine serum over 5 days, 6 days, 7 days, 8 days, 9 days, 10 days, or 12 days (e.g., less than 10% of D1 or D2 at 37° C. in 100% bovine serum over 5 days). In other embodiments of any of the above fibers, the surface erosion releases less than 2.0% (e.g., less than 1.8%, 1.5%, 1.2%, 1.0%, or 0.5%) of D1 or D2 (as a percentage of the total drug, D1 or D2, present in the fiber in prodrug form) at 37° C. in PBS over 5 days, 7 days, 10 days, or 14 days (e.g., less than 2% of D1 or D2 at 37° C. in PBS over 5 days). In still other embodiments of any of the above fibers, the surface erosion releases greater than 20% (e.g., greater than 22%, 24%, 26%, 28%, or 30%) of D1 or D2 (as a percentage of the total drug, D1 or D2, present in the fiber in prodrug form) at 37° C. in 100% bovine serum over not fewer than 6 days, 8 days, 10 days, or 12 days (e.g., greater than 24% of D1 or D2 at 37° C. in 100% bovine serum over 10 days). In other embodiments of any of the above fibers, the surface erosion releases greater than 5.0% (e.g., greater than 6.0%, 8.0%, 10%, 12%, or 15%) of D1 or D2 (as a percentage of the total drug, D1 or D2, present in the fiber in prodrug form) at 37° C. in PBS over not fewer than 6 days, 8 days, 10 days, or 12 days (e.g., greater than 5% of D1 or D2 at 37° C. in PBS over 10 days). In other embodiments, the compound (D1 and/or D2) is released from the fiber at a rate such that $t_{10}$ is greater than or equal to $\frac{1}{10}$ of $t_{50}$.

In still another embodiment of any of the above fibers, the fiber further includes from 0.1% to 10% (e.g., from 0.1 to 5%, from 0.1 to 2%, from 0.5 to 2%, from 1 to 10%) (w/w) of one or more additives, in which the one or more additives are plasticizers (e.g., glycerol, triacetin, isopropyl alcohol, ethanol, or ethylene glycol), antioxidants (e.g., ascorbic acid, vitamin E, sodium metabisulfite, butylated hydroxytoluene, p-hydroxybenxyl alcohol, or butylated hydroxy anisole), binders (e.g., polyvinyl pyrrolidone, carboxymethyl cellulose, hydroxypropyl cellulose, or hydroxypropyl methyl cellulose), lubricants, radio-opaque agents, and mixtures thereof.

The disclosure features (i) a fiber mesh formed from a fiber of the disclosure; a woven fabric formed from a fiber of the disclosure; and non-woven fabric formed from a fiber of the disclosure. The fiber mesh, woven fabric, and non-woven fabric can be formed from the fibers using methods known in the art. In particular embodiments, the fiber mesh is free of controlled release excipient, free of a crystallization inhibiting excipient, free of a mechanical integrity enhancing excipient, and/or free of a binding excipient; or the fiber mesh optionally has a glassy state.

In another aspect, the disclosure features a glassy state composition formed from a compound of the disclosure (e.g., a compound described by one of formulas (II)-(LXXV), described herein, or a steroid dimer in which each of D1 and D2 is, independently, described by any one of formulas (I-a) to (I-vvv), described herein). In particular embodiments, the glassy state composition is free of controlled release excipient, free of a crystallization inhibiting excipient, free of a mechanical integrity enhancing excipient, and/or free of a binding excipient.

In another aspect, the disclosure further features a glassy state composition formed from a compound of formula (A-VIII):

$$D1-L-D2 \qquad (A\text{-}VIII)$$

or a pharmaceutically acceptable salt thereof, in which the glassy state composition is prepared by a process including the steps of: (a) heating the compound, or a pharmaceutically acceptable salt thereof, to form a melt; and (b) cooling the melt to form the composition, in which each of D1 and D2 is, independently, a radical formed from a steroid; and L is a linker covalently linking D1 to D2. In particular embodiments, the glassy state composition is free of controlled release excipient, free of a crystallization inhibiting excipient, free of a mechanical integrity enhancing excipient, and/or free of a binding excipient.

In an embodiment of any of the above glassy state compositions, L has a molecular weight of from 80 to 800 Da, e.g., 80 to 100 Da, 80 to 200 Da, 80 to 300 Da, 80 to 400 Da, 80 to 500 Da, 80 to 600 Da, or 80 to 700 Da. In another embodiment of any of the above glassy state compositions, L is covalently linked to D1 and to D2 via one or more ester, carbonate, carbonate ester, or anhydride linkages. In particular embodiments, L is covalently linked to D1 and to D2 via one or more carbonate linkages.

In a particular embodiment of any of the above glassy state compositions, L includes the radical —C(O)—($R^4$)—C(O)— or —O—($R^4$)—O—; $R^4$ is a radical of a polyol and includes at least one free hydroxyl group or $R^4$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—; and q, r, and s are integers from 1 to 10 (e.g., 1 to 10, 1 to 5, or 5 to 10).

In an embodiment of any of the above glassy state compositions, each of D1 and D2 is an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid. In a particular embodiment of any of the above glassy state compositions, the compound is further described by one of formulas (II)-(LXXV), described herein. In another embodiment of any of the above glassy state compositions, each of D1 and D2 is, independently, described by any one of formulas (I-a) to (I-vvv), described herein.

In the glassy state compositions of the disclosure, D1 and D2 can be formed from the same steroid, or D1 and D2 can be formed from different steroids.

In a particular embodiment of any of the above glassy state compositions, the glassy state composition includes a mixture of two or more compounds of formula (A-VIII).

In certain embodiments, at least 70% (w/w) of the glassy state composition is a compound of formula (A-VIII), e.g., at least 75% (w/w), at least 80% (w/w), at least 85% (w/w), at least 90% (w/w), at least 95% (w/w), or at least 99% (w/w).

In another embodiment of any of the above glassy state compositions, the compound is released from the glassy state composition through surface erosion. In certain embodiments of any of the above glassy state compositions, the surface erosion releases less than 20% (e.g., less than 18%, 15%, 12%, 10%, or 5%) of D1 or D2 (as a percentage of the total drug, D1 or D2, present in the glassy state composition in prodrug form) at 37° C. in 100% bovine serum over 5 days, 6 days, 7 days, 8 days, 9 days, 10 days, or 12 days (e.g., less than 10% of D1 or D2 at 37° C. in 100% bovine serum over 5 days). In other embodiments of any of the above glassy state compositions, the surface erosion releases less than 2.0% (e.g., less than 1.8%, 1.5%, 1.2%, 1.0%, or 0.5%) of D1 or D2 (as a percentage of the total drug, D1 or D2, present in the glassy state composition in prodrug form) at 37° C. in PBS over 5 days, 7 days, 10 days, or 14 days (e.g., less than 2% of D1 or D2 at 37° C. in PBS over 5 days). In still other embodiments of any of the above glassy state compositions, the surface erosion releases greater than 20% (e.g., greater than 22%, 24%, 26%, 28%, or 30%) of D1 or D2 (as a percentage of the total drug, D1 or D2, present in the glassy state composition in prodrug form) at 37° C. in 100% bovine serum over not fewer than 6 days, 8 days, 10 days, or 12 days (e.g., greater than 24% of D1 or D2 at 37° C. in 100% bovine serum over 10 days). In other embodiments of any of the above articles, the surface erosion releases greater than 5.0% (e.g., greater than 6.0%, 8.0%, 10%, 12%, or 15%) of D1 or D2 (as a percentage of the total drug, D1 or D2, present in the glassy state composition in prodrug form) at 37° C. in PBS over not fewer than 6 days, 8 days, 10 days, or 12 days (e.g., greater than 5% of D1 or D2 at 37° C. in PBS over 10 days). In other embodiments, the compound (D1 and/or D2) is released from the glassy state composition at a rate such that $t_{10}$ is greater than or equal to $\frac{1}{10}$ of $t_{50}$.

In still another embodiment of any of the above glassy state compositions, the glassy state composition further includes from 0.1% to 10% (e.g., from 0.1 to 5%, from 0.1 to 2%, from 0.5 to 2%, from 1 to 10%) (w/w) of one or more additives, in which the one or more additives are plasticizers (e.g., glycerol, triacetin, isopropyl alcohol, ethanol, or ethylene glycol), antioxidants (e.g., ascorbic acid, vitamin E, sodium metabisulfite, butylated hydroxytoluene, p-hydroxybenzyl alcohol, or butylated hydroxy anisole), binders (e.g., polyvinyl pyrrolidone, carboxymethyl cellulose, hydroxypropyl cellulose, or hydroxypropyl methyl cellulose), lubricants, radio-opaque agents, and mixtures thereof.

In particular embodiments of any of the above glassy state compositions, the glassy state composition is machined, molded, emulsion-processed, electrospun, electrosprayed, blow molded, or extruded.

In other embodiments of any of the above glassy state compositions, the glassy state composition is a fiber, fiber mesh, woven fabric, non-woven fabric, pellet, cylinder, microparticle (e.g., a microbead), nanoparticle (e.g., a nanobead), or another shaped article. For example, the glassy state composition is a shaped article in the form of: (i) fibers having a mean diameter of from about 0.01 to 1 mm; (ii) pellets having a mean diameter of from about 0.2 to 5 mm; (iii) cylinders of from about 0.5 to 20 mm in length and from about 0.01 to 1 mm in diameter; (iv) microbeads, having a mean diameter of from about 1 to 1000 µm; or (v) nanobeads, having a mean diameter of from about 0.01 to 1 µm. The glassy state composition can be in the shape of a cylinder, a cube, a sheet, a star, a toroid, a pyramid, a sphere, an irregular polygon, or a regular polygon.

In another aspect, the disclosure features a substrate including a coating formed from a compound of formula (A-VIII):

$$D1\text{-}L\text{-}D2 \qquad \text{(A-VIII)}.$$

In particular embodiments, the coating is free of controlled release excipient, free of a crystallization inhibiting excipient, free of a mechanical integrity enhancing excipient, and/or free of a binding excipient; or the coating optionally has a glassy state.

In an embodiment of any of the above coatings, L has a molecular weight of from 80 to 800 Da.

In a particular embodiment of any of the above coatings, L is covalently linked to D1 and to D2 via one or more ester, carbonate, carbonate ester, or anhydride linkages. In particular embodiments, L is covalently linked to D1 and to D2 via one or more carbonate linkages.

In certain embodiments, each of D1 and D2 are an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid.

In another embodiment of any of the above coatings, the compound is further described by one of formulas (II)-(LXXV).

In still another embodiment of any of the above coatings, D1 and D2 are formed from the same steroid, or D1 and D2 are formed from different steroids.

In particular embodiments of any of the above coatings, the coating includes a mixture of two or more compounds of formula (A-VIII).

In other embodiments of any of the above coatings, at least 70% (w/w) of the coating is a compound of formula (A-VIII).

In other embodiments of any of the above coatings, at least 90% (w/w) of the coating is the compound.

In an embodiment of any of the above coatings, the compound, D1, or D2 are released from the coating through surface erosion.

In certain embodiments of any of the above coatings, the surface erosion releases less than 20% (e.g., less than 18%, 15%, 12%, 10%, or 5%) of D1 or D2 (as a percentage of the total drug, D1 or D2, present in the coating in prodrug form) at 37° C. in 100% bovine serum over 5 days, 6 days, 7 days, 8 days, 9 days, 10 days, or 12 days (e.g., less than 10% of D1 or D2 at 37° C. in 100% bovine serum over 5 days). In other embodiments of any of the above coatings, the surface erosion releases less than 2.0% (e.g., less than 1.8%, 1.5%, 1.2%, 1.0%, or 0.5%) of D1 or D2 (as a percentage of the total drug, D1 or D2, present in the coating in prodrug form) at 37° C. in PBS over 5 days, 7 days, 10 days, or 14 days (e.g., less than 2% of D1 or D2 at 37° C. in PBS over 5 days). In still other embodiments of any of the above coatings, the surface erosion releases greater than 20% (e.g., greater than 22%, 24%, 26%, 28%, or 30%) of D1 or D2 (as a percentage of the total drug, D1 or D2, present in the coating in prodrug form) at 37° C. in 100% bovine serum over not fewer than 6 days, 8 days, 10 days, or 12 days (e.g., greater than 24% of D1 or D2 at 37° C. in 100% bovine serum over 10 days). In other embodiments of any of the above coatings, the surface erosion releases greater than 5.0% (e.g., greater than 6.0%, 8.0%, 10%, 12%, or 15%) of D1 or D2 (as a percentage of the total drug, D1 or D2, present in the coating in prodrug form) at 37° C. in PBS over not fewer than 6 days, 8 days, 10 days, or 12 days (e.g., greater than 5% of D1 or D2 at 37° C. in PBS over 10 days). In other embodiments, the compound (D1 and/or D2) is released from the coating at a rate such that $t_{10}$ is greater than or equal to $\frac{1}{10}$ of $t_{50}$.

In certain embodiments, the article further includes from 0.1% to 10% (w/w) of one or more additives, in which the one or more additives are plasticizers, antioxidants, binders, lubricants, radio-opaque agents, and mixtures thereof.

In particular embodiments of any of the above coatings, the substrate includes a coating formed from a compound of the disclosure.

In other embodiments of any of the above coatings, at least 70% (w/w) of the coating is the compound.

In an embodiment of any of the above coatings, at least 90% (w/w) of the coating is the compound.

In an embodiment of any of the above coatings, the coating has a glassy state and is formed from a compound of the disclosure.

The disclosure further features a coating having a glassy state formed from a compound of the disclosure.

The disclosure features an implantable medical device including a coating of the disclosure, in which the coating resides on the surface of the implantable medical device.

In an aspect, the disclosure features a compound described by the formula (A-I):

D1-O-L-O-D2    a(A-I), or a pharmaceutically acceptable salt thereof, in which each of D1-O and D2-O is, independently, a radical formed from a steroid; L is —C(O)—OC(O)—($R^B$)—C(O)O—C(O)—; and $R^B$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, in which the steroid is an anabolic steroid, an androgenic steroid, a progestin steroid, an estrogen steroid, a cancer treatment steroid, an antibiotic steroid, a glucocorticoid steroid, a benign steroid, or a corticosteroid.

In a related aspect, the disclosure features a compound described by the formula (A-III):

D1-O-L-O-D2    (A-II), or a pharmaceutically acceptable salt thereof, in which each of D1-O and D2-O is, independently, a radical formed from a steroid; L is —C(O)O—($R^A$)—OC(O)—; in which O—($R^A$)—O is a radical of a polyol and includes at least one free hydroxyl group, in which the steroid is an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, or a corticosteroid.

In another aspect, the disclosure features a compound described by the formula (A-III):

D1-O-L-O-D2    (A-III), or a pharmaceutically acceptable salt thereof, in which each of D1-O and D2-O is, independently, a radical formed from a steroid; L is —C(O)O—($R^A$)—OC(O)—, —C(O)—($R^B$)—C(O)—, or —C(O)—OC(O)—($R^B$)—C(O)O—C(O)—; $R^A$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10, and each $R^B$ is independently $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, in which the steroid is an anabolic steroid, an androgenic steroid, a progestin steroid, an estrogen steroid, a cancer treatment steroid, an antibiotic steroid, a glucocorticoid steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, or a benign steroid.

In a related aspect, the disclosure features a compound described by the formula (A-IV):

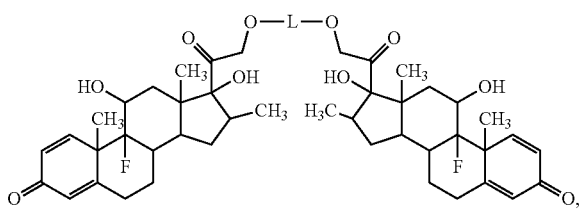

(A-IV)

or a pharmaceutically acceptable salt thereof, in which L is —C(O)O—($R^A$)—OC(O)—; $R^A$ includes $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10.

In an embodiment of any of the above aspects, O—($R^A$)—O is a radical of a polyol formed from a cyclitol (e.g., bornesitol, conduritol, inositol, ononitol, pinitol, pinpollitol, quebrachitol, quinic acid, shikimic acid, valienol, or viscumitol), a sugar alcohol (e.g., sorbitol, mannitol, xylitol, maltitol, lactitol, erythritol, isomalt), or glycerin. In particular embodiments, the linker L is formed from a polyol and includes 1, 2, 3, or 4 hydroxyl groups. In another embodiment, O—($R^A$)—O is a radical formed from an alkane diol (e.g., a $C_{1-10}$ diol), diethylene glycol, triethylene glycol, tetraethylene glycol, or pentaethylene glycol.

In an embodiment of the above aspects, each of D1-O and D2-O is, independently, described by any one of formulas (I-a) to (I-sss), described herein. For example, at least one of D1-O and D2-O is formed from: (i) an anabolic steroid including from androisoxazole, androstenediol, bolandiol, bolasterone, clostebol, ethylestrenol, formyldienolone, 4-hydroxy-19-nortestosterone, methandriol, methenolone, methyltrienolone, nandrolone, norbolethone, oxymesterone, stenbolone, and trenbolone; (ii) an androgenic steroid including boldenone, fluoxymesterone, mestanolone, mesterolone, methandrostenolone, 17-methyltestosterone, 17-α-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate tiomesterone dehydroepiandrosterone (DHEA), androstenedione, androstenediol, androsterone, dihydrotestosterone (DHT), and androstanolone; (iii) a progestin steroid including norethisterone, norethisterone acetate, gestodene, levonorgestrel, allylestrenol, anagestone, desogestrel, dimethisterone, dydrogesterone, ethisterone, ethynodiol, ethynodiol diacetate, etonogestrel, gestodene, ethinylestradiol, haloprogesterone, 17-hydroxy-16-methylene-progesterone, 17 alpha-hydroxyprogesterone, lynestrenol, medroxyprogesterone, melengestrol, norethindrone, norethynodrel, norgesterone, gestonorone, norethisterone, norgestimate, norgestrel, levonorgestrel, norgestrienone, norvinisterone, pentagestrone, MENT (7-methyl-19-testosterone); norelgestromin, and trimigestone drospirenone, tibolone, and megestrol; (iv) an estrogen steroid including estrogen, eguilenin, equilin, 17β-estradiol, estradiol benzoate, estriol, ethinyl estradiol, mestranol, moxestrol, mytatrienediol, quinestradiol, and quinestrol; (v) a glucocorticoid including medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, loprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6α-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol; (vi) a steroid including abiraterone, cyproterone acetate, dutasteride, enzalutamide, finasteride, galeterone, fusidic acid, cholesterol, 11-deoxycortisol, 11-deoxycorticosterone, pregnenolone, cholic acid, chenodeoxycholic acid, ursodeoxycholic acid, obeticholic acid, tetrahydrocortisone, tetrahydrodeoxycortisol, tetrahydrocorticosterone, 5α-dihydrocorticosterone, and 5α-dihydropregesterone; (vii) an anti-angiogenic steroid or an intraocular pressure (IOP) lowering steroid including anecortave acetate, anecortave, 11-epicortisol, 17α-hydroxyprogesterone, tetrahydrocortexolone, and tetrahydrocortisol; (viii) a cholic acid-related bile acid steroid including deoxycholic acid, apocholic acid, dehydrocholic acid, glycochenodeoxycholic acid, glycocholic acid, glycodeoxycholic acid, hyodeoxycholic acid, lithocholic acid, α-muricholic acid, β-muricholic acid, γ-muricholic acid, w-muricholic acid, taurochenodeoxycholic acid, taurocholic acid, taurodeoxycholic acid, taurolithocholic acid, and tauroursodeoxycholic acid; (ix) a neurosteroid including alphaxalone, alphadolone, hydroxydione, minaxolone, tetrahydrodeoxycorticosterone, allopregnanolone, pregnanolone, ganoxolone, 3α-androstanediol, epipregnanolone, isopregnanolone, and 24(S)-hydroxycholesterol; (x) other steroid including flugestone, prebediolone, chlormadinone acetate, medrogestone, and segesterone acetate; (xi) a pheromone including androstadienol, androstadienone, androstenol, androstenone, estratetraenol, 5-dehydroprogesterone, 6-dehydro-retroprogesterone, allopregnanolone, and hydroxyprogesterone caproate; (xii) a steroid metabolite including tetrahydrotriamcinolone, cortienic acid, 11-dehydrocorticosterone, 11β-hydroxypregnenolone, ketoprogesterone, 17-hydroxypregnenolone, 17,21-dihydroxypregnenolone, 18-hydroxycorticosterone, deoxycortisone, 21-hydroxypregnenolone, and progesterone; or (xiii) a progestin including allopregnone-3α,20α-diol, allopregnone-3β,20β-diol, allopregnane-3β,21-diol-11,20-dione, allopregnane-3β,17α-diol-20-one, 3,20-allopregnanedione,3β, 11β,17α,20β,21-pentol, allopregnane-3β,17α,20β,21-tetrol, allopregnane-3α,11β,17α,21-tetrol-20-one, allopregnane-3β,11β,17α,21-tetrol-20-one, allopregnane-3β,17α,20β-triol, allopregnane-3β,17α,21-triol-11,20-dione, allopregnane-3β,11β,21-triol-20-one, allopregnane-3β,17α,21-triol-20-one, allopregnane-3α-ol-20-one, allopregnane-3β-ol-20-one, pregnanediol, 3,20-pregnanedione, 4-pregnene-20,21-diol-3,11-dione, 4-pregnene-11β,17α,20β,21-tetrol-3-one, 4-pregnene-17α,20β,21-triol-3,11-dione, 4-pregnene-17α,20β,21-triol-3-one, and pregnenolone.

In a related aspect, the disclosure features a compound described by the formula (A-VI):

D1-C(O)-L-C(O)-D2         (A-VI), or a pharmaceutically acceptable salt thereof, in which each of D1-C(O) and D2-C(O) is, independently, a radical formed from a steroid; L is —O—($R^A$)—O— or —OC(O)—O—($R^A$)—O—C(O)O—; $R^A$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; and n, m, and p are integers from 1 to 10.

In an embodiment of the compounds of formula (A-VI), O—($R^A$)—O is a radical of a polyol formed from a cyclitol (e.g., bornesitol, conduritol, inositol, ononitol, pinitol, pinpollitol, quebrachitol, quinic acid, shikimic acid, valienol, or viscumitol), a sugar alcohol (e.g., sorbitol, mannitol, xylitol, maltitol, lactitol, erythritol, isomalt), or glycerin. In particular embodiments, the linker L is formed from a polyol and includes 1, 2, 3, or 4 hydroxyl groups. In another embodiment, O—($R^A$)—O is a radical formed from an alkane diol (e.g., a $C_{1-10}$ diol), diethylene glycol, triethylene glycol, tetraethylene glycol, or pentaethylene glycol.

The disclosure further features a compound described by the formula (A-VII):

D1-C(O)-L-C(O)-D2         (A-VII), or a pharmaceutically acceptable salt thereof, in which each of D1-C(O) and D2-C(O) is, independently, a radical formed from a steroid; L is —O—C(O)—O—($R^A$)—O—C(O)—O—; and $R^A$ is $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms.

In particular embodiments of the compounds of formulas (A-VI) and (A-VII), at least one of D1-C(O) and D2-C(O) is formed from fusidic acid, cholic acid, chenodeoxycholic acid, ursodeoxycholic acid, or obeticholic acid.

In an embodiment of any of the above compounds: (i) each of D1-O and D2-O are formed from the same steroid, (ii) each of D1-C(O) and D2-C(O) are formed from the same steroid, (iii) each of D1-O and D2-O are formed from different steroids, or (iv) each of D1-C(O) and D2-C(O) are formed from different steroids.

In a particular embodiment of any of the above compounds, $R^4$ is a $C_{1-10}$ alkylene.

In still another embodiment of any of the above compounds upon hydrolysis D1 and D2 form corticosteroids including alclometasone, beclomethasone, betamethasone, betamethasone valerate, budesonide, chloroprednisone, cloprednol, corticosterone, cortisone, desonide, desoximerasone, dexamethasone, diflorasone, diflucortolone, enoxolone, flucloronide, flumethasone, flunisolide, fluocinolone acetonide, fluocortolone, fluprednisolone, flurandrenolide, halometasone, hydrocortisone, hydrocortisone butyrate, meprednisone, methylprednicolone, paramethasone, prednisolone, prednisone, prednival, prednylidene, triamcinolone, and triamcinolone acetonide.

In another embodiment of any of the above compounds, the compound is further described by one of formulas (II)-(LXXV), described herein.

In still another embodiment of any of the above compounds, $R^4$ is —$(CH_2CH_2O)_qCH_2CH_2$—, q is an integer of 1 to 10, and upon hydrolysis each of D1 and D2, independently, form dexamethasone, triamcinolone, betamethasone, prednisolone, prednisone, fluocinolone, fluocinolone acetonide, mometosone, mometosone furoate, anecoratve, hydrocortisone, triamcinolone acetonide, abiraterone, fusidic acid, or cholesterol.

Articles of the disclosure can be formed by the steps of (a) heating a compound of formula (A-VIII) above its melting point (e.g., depending upon the compound, heating to 110-145° C., 130-185° C., 150-215° C., or 180-240° C.) to form a melt, and (b) cooling the melt to form an article. The article can be shaped during step (a), prior to cooling, by pressing the melt into a mold, by extruding the melt from an orifice (e.g., to form a cylinder or another shape), or by forming droplets of the melt and allowing the droplets to cool into glassy state droplets. Fibers can be formed by spinning (e.g. melt spinning, heat spinning, or electrospinning), or pulling the melt (e.g., with tweezers) at different rates to yield glassy state fibers of different diameters.

Alternatively, articles of the disclosure can be formed by the steps of (a) dissolving a compound of formula (A-VIII) in a volatile organic solvent (e.g., acetone, methanol, dichloromethane, tetrahydrofuran, chloroform, or mixtures thereof) to form a solution, and (b) removing the organic solvent to form an article. The article can be shaped during step (b), prior to completely removing the organic solvent, by electrospraying, electrospinning, or fiber spinning the solution. For example, a 50:50 v/v mixture of dichloromethane/tetrahydrofuran at 100% wt/v solution of the compound can be loaded at a rate of 0.5 mL/h and electrospun onto a cylindrical mandrel rotating at 1150 rpm, forming aligned glassy state fibers. Fibers can be also formed by wet, dry, or gel spinning to form glassy state fibers of different diameters. Microparticles can be prepared by electrospraying a solution containing the compound at a concentration of about 20% to 40% w/v or 25% to 50% w/v of the solution. Nanoparticles can be prepared by electrospraying a solution containing the compound at a concentration of about 3% to 15% w/v or 5% to 18% w/v of the solution. Alternatively, a shaped article can be formed by placing the solution in a mold and evaporating the volatile organic solvent to form a shaped article.

The disclosure features a method for forming an article including a compound of formula (A-VIII):

$$D1-L-D2 \qquad (A\text{-}VIII)$$

or a pharmaceutically acceptable salt thereof, wherein each of D1 and D2 is, independently, a radical formed from a steroid; and L is a linker covalently linking D1 to D2, and wherein the article is formed by a process including the steps of: (a) heating the compound, or a pharmaceutically acceptable salt thereof, to form a melt; (b) cooling the melt to form a glassy state composition; and (c) heating the glassy state composition to a temperature above the glass transition temperature of the glassy state composition and shaping the glassy state composition to form a shaped article. Step (c) can include extruding, molding, blow molding, heat spinning, electrospinning, or electrospraying the glassy state composition to form the shaped article. In particular embodiments, the method forms an article that is free of controlled release excipient, free of a crystallization inhibiting excipient, of a mechanical integrity enhancing excipient, and/or free of a binding excipient; or the method forms an article that optionally has a glassy state.

In a related aspect, the disclosure features a method of forming an article including a compound of formula (A-VIII):

$$D1-L-D2 \qquad (A\text{-}VIII)$$

or a pharmaceutically acceptable salt thereof, wherein each of D1 and D2 is, independently, a radical formed from a steroid; and L is a linker covalently linking D1 to D2, and wherein the article is formed by a process including the steps of: (a) dissolving the compound, or a pharmaceutically acceptable salt thereof, in a solvent to form a solution; (b) evaporating the solvent to form a glassy state composition; and (c) heating the glassy state composition to a temperature above the glass transition temperature of the glassy state composition and shaping the glassy state composition to form a shaped article. Step (c) can include extruding, molding, blow molding, heat spinning, electrospinning, or electrospraying the glassy state composition to form the shaped article. In particular embodiments, the method forms an article that is free of controlled release excipient, free of a crystallization inhibiting excipient, free of a mechanical integrity enhancing excipient, and/or free of a binding excipient; or the method forms an article that optionally has a glassy state.

In a further aspect, the disclosure features a method of forming an article comprising a compound of formula (A-VIII):

$$D1-L-D2 \qquad (A\text{-}VIII)$$

or a pharmaceutically acceptable salt thereof, wherein each of D1 and D2 is, independently, a radical formed from a steroid; and L is a linker covalently linking D1 to D2, and wherein the article is formed by a process comprising the steps of: (a) dissolving the compound, or a pharmaceutically acceptable salt thereof, in a solvent to form a solution; (b) electrospraying the solution to form a glassy state composition; and (c) heating the glassy state composition to a temperature above the glass transition temperature of the glassy state composition and shaping the glassy state composition to form a coating. In particular embodiments, the method forms an article that is free of controlled release excipient, free of a crystallization inhibiting excipient, free of a mechanical integrity enhancing excipient, and/or free of a binding excipient; or the method forms an article that optionally has a glassy state.

In some embodiments of the methods of the disclosure, the compound is processed as described herein (e.g., melt processed or solvent processed) to form a glassy state solid. The glassy state solid is subsequently heated above its glass transition temperature, Tg, and molded or extruded to form a shaped article (e.g., a fiber, fiber mesh, woven fabric, non-woven fabric, pellet, cylinder, microparticle (e.g., a microbead), or nanoparticle (e.g., a nanobead), or another shaped article). In other embodiments, microparticles are prepared by melting the compound to form glassy state pellets or other shaped forms, crushing the glassy state articles into rough or irregular-shaped particles, filtering particles through sieves, and heating the particles above the Tg to round them into smoother spherical particles.

In some embodiments of the methods and compositions of the disclosure, the article is free of controlled release excipient.

In particular embodiments of the methods and compositions of the disclosure, the article is free of a crystallization inhibiting excipient In certain embodiments of the methods and compositions of the disclosure, the article is free of a mechanical integrity enhancing excipient.

In yet further embodiments of the methods and compositions of the disclosure, the article is free of a binding excipient.

In another aspect, the disclosure features Compound 3. The disclosure further features a pharmaceutical composition comprising Compound 3 and a pharmaceutically acceptable excipient.

In another aspect, the disclosure features Compound 17. The disclosure further features a pharmaceutical composition comprising Compound 17 and a pharmaceutically acceptable excipient.

Definitions

The term "free of controlled release polymer," as used herein, refers to the absence of an amount of a polymeric material of greater than 10 KDa in the articles of the disclosure that is sufficient to delay or slow the release of the steroid dimer from the article in comparison to the release profile observed for an otherwise identical article containing none of the polymeric material, where the release profile is measured at 37° C. in 100% fetal bovine serum (FBS).

The term "free of a crystallization inhibiting excipient," as used herein, refers to the absence of an amount of an excipient in the articles of the disclosure that is sufficient to reduce the amount of crystalline steroid dimer in the article in comparison to the amount of crystalline steroid dimer observed in an otherwise identical article containing none of the excipient. The level of crystallinity can be measured using DSC or XRD. In particular embodiments, the articles of the disclosure are free of a crystallization inhibiting excipient that is a polymeric material of greater than 10 KDa.

The term "free of a mechanical integrity enhancing excipient," as used herein, refers to the absence of an amount of an excipient in the articles of the disclosure that is sufficient to increase the mechanical integrity of the article in comparison to the mechanical integrity of an otherwise identical article containing none of the excipient. The mechanical integrity of an article can be tested using a 3- or 4-point mechanical bend test (ASTM C1684-18) on the formulation with or without the excipient with the article in the shape of a rod either in the dry state (prior to drug release) or after 15-30% drug release. For articles with a rectangular shape, the mechanical integrity can be tested using a 3-point mechanical bend test (ASTM D790-17) or 4-point mechanical bend test (ASTM D6272) on the formulation with or without excipient either in the dry state (prior to drug release) or after 15-30% drug release. A reduction in mechanical integrity causes the articles to break apart sooner, increasing the total surface area of the quantity of articles, and resulting in a more rapid release profile, where the release profile is measured at 37° C. in 100% FBS. In particular embodiments, the articles of the disclosure are free of a mechanical integrity enhancing excipient that is a polymeric material of greater than 10 KDa.

The term "free of a binding excipient," as used herein, refers to the absence of an amount of an excipient in the articles of the disclosure that is sufficient to delay or slow the release of the steroid dimer from the article in comparison to the release profile observed for an otherwise identical article containing none of the binding excipient, where the release profile is measured at 37° C. in 100% FBS.

The term "anti-angiogenic steroid" refers to a steroid that halts the process of developing new blood vessels (i.e., angiogenesis). Examples of anti-angiogenic steroids include anecortave acetate, anecortave, 11-epicortisol, 17α-hydroxyprogesterone, tetrahydrocortexolone, and tetrahydrocortisol.

The term "benign steroid" as used herein, refers to low glucocorticoid activity and low mineralcorticoid activity. Benign steroids include, without limitation, cholesterol, bile acids (such as cholic acid), and phytosterols (such as beta-sitosterol). Exemplary benign steroids include cholesterol, 11-deoxycortisol, 11-deoxycorticosterone, pregnenolone, cholic acid, chenodeoxycholic acid, ursodeoxycholic acid, obeticholic acid, tetrahydrocortisone, tetrahydrodeoxycortisol, tetrahydrocorticosterone, 5α-dihydrocorticosterone, and 5α-dihydropregesterone.

The term "cholesterol-derivative" refers to steroids that are derived from cholesterol. Examples of cholesterol-derivatives are 22R-hydroxycholesterol, and 20α-22R-dihydroxycholesterol.

The term "cholic acid-related bile acid steroid" refers to a steroid that is derived from cholic acid. Examples of cholic acid-related bile acid steroids are deoxycholic acid, apocholic acid, dehydrocholic acid, glycochenodeoxycholic acid, glycocholic acid, glycodeoxycholic acid, hyodeoxycholic acid, lithocholic acid, α-muricholic acid, β-muricholic acid, γ-muricholic acid, ω-muricholic acid, taurochenodeoxycholic acid, taurocholic acid, taurodeoxycholic acid, taurolithocholic acid, and tauroursodeoxycholic acid.

The term "cylinder," as used herein, refers to the shape of the pharmaceutical compositions of the disclosure that has parallel sides and a circular or oval cross section, or a shaped cross section (e.g., a star shaped cross section). A mean diameter of the cylinder can range from about 0.01 to 1 mm diameter, e.g., about 0.01 to 0.2 mm, about 0.1 to 0.3 mm, about 0.1 to 0.4 mm, about 0.2 to 0.5 mm, about 0.1 to 0.6 mm, about 0.1 to 0.7 mm, about 0.1 to 0.8 mm, or about 0.1 to 0.9 mm. A mean length of the cylinder can range from about 0.05 to 20 mm, e.g., about 0.05 to 1 mm, about 0.5 to 2 mm, about 0.5 to 4 mm, about 0.5 to 6 mm, about 0.5 to 8 mm, about 0.5 to 10 mm, about 0.5 to 12 mm, about 0.5 to 14 mm, about 0.5 to 16 mm, or about 0.5 to 18 mm. In some embodiments, the mean diameter of the cylinder is in the range of about 0.01 to 1 mm and the mean length of the cylinder is about 0.1 mm to 4.0 mm. In some embodiments, the mean length of the cylinder is about 0.5 to 10 mm, or about 1 to 10 mm.

The term "fiber," as used herein, refers to the shape of the pharmaceutical compositions of the disclosure that is elongated or threadlike. A mean diameter of the fiber can range from about 0.01 to 1 mm, e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm. A mean length of the fiber can range from about 20 to 20,000 mm, e.g., about 20 to 1000 mm, about 20 to 2,000 mm, about 100 to 2,000 mm, about 100 to 5,000 mm, about 1,000 to 8,000 mm, about 2,000 to 8,000 mm, about 2,000 to 10,000 mm, about 2,000 to 12,000 mm, about 2,000 to 15,000 mm, or about 5,000 to 18,000 mm.

The term "fiber mesh," as used herein refers to a web or a net in having many attached or woven fibers. The fiber mesh can have aligned and unaligned morphologies.

The term "glassy state," as used herein, refers to an amorphous solid including greater than 70%, 80%, 90%, 95%, 98%, or 99% (w/w) of one or more drug dimers of the disclosure and exhibiting a glass transition temperature in the range of from 38 to 150° C. In the glassy state, as measured by DSC or XRD, the level of crystallinity is low, ranging from 0-15%, e.g., 0-1%, 0-3%, 0-5%, 0-7%, 0-9%, 0-10%, or 0-13%. Glass formulations of the disclosure can be formed using heat processing or solvent processing one or more drug dimers.

The term "intraocular pressure (IOP) lowering steroid" refers to a steroid that lowers the intraocular pressure. Examples of intraocular pressure (IOP) lowering steroids are anecortave acetate, anecortave, 11-epicortisol, 17α-hydroxyprogesterone, tetrahydrocortexolone, and tetrahydrocortisol.

The term "microparticle," as used herein, refers to the shape of the pharmaceutical compositions of the disclosure, which can be regularly or irregularly shaped. A mean diameter of the microparticle can range from about 1 to 1000 µm, e.g., about 10 to 1000 µm, about 100 to 1000 µm, about 200 to 1000 µm, about 500 to 1000 µm, about 700 to 1000 µm, or about 900 to 1000 µm. As used herein, a "microbead" refers to a microparticle that is spherical.

The term "nanoparticle," as used herein, refers to the shape of the pharmaceutical compositions of the disclosure, which can be regularly or irregularly shaped. A mean diameter of the nanoparticle can range from about 0.01 to 1 µm, e.g., about 0.05 to 1 µm, about 0.1 to 1 µm, about 0.2 to 1 µm, about 0.3 to 1 µm, about 0.4 to 1 µm, about 0.5 to 1 µm, about 0.6 to 1 µm, about 0.7 to 1 µm, about 0.8 to 1 µm, or about 0.9 to 1 µm. As used herein, a "nanobead" refers to a nanoparticle that is spherical.

The term "neurosteroid" refers to an endogenous or exogenous steroid that rapidly alters neuronal excitability through interaction with ligand-gated ion channels and other cell surface receptors. Exemplary neurosteroids are alphaxalone, alphadolone, hydroxydione, minaxolone, tetrahydrodeoxycorticosterone, allopregnanolone, pregnanolone, ganoxolone, 3α-androstanediol, epipregnanolone, isopregnanolone, and 24(S)-hydroxycholesterol.

The term "non-woven fabric," as used herein, refers to a web structure bonded together by entangling fibers.

The term "other steroid" refers to a compound that has a steroid-based structure. Examples of the steroids are flugestone, prebediolone, chlormadinone acetate, medrogestone, and segesterone acetate.

The term "pellet," as used herein, refers to the shape of the pharmaceutical compositions of the disclosure that is rounded, spherical, or cylindrical, or a combination thereof. A mean diameter of the pellet can range from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm.

The term "pharmaceutically acceptable salt" as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in J. Pharm. Sci. 66:1-19, 1977. The salts can be prepared in situ during the final isolation and purification of the compounds of the disclosure or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, carbonate, chloride, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pheromone" refers to a steroid hormone. Examples of pheromones are androstadienol, androstadienone, androstenol, androstenone, estratetraenol, 5-dehydroprogesterone, 6-dehydro-retroprogesterone, allopregnanolone, and hydroxyprogesterone caproate.

The term "steroid metabolite" refers to a product of metabolism of a steroid. Examples of steroid metabolites are tetrahydrotriamcinolone, cortienic acid, 11-dehydrocorticosterone, 1β-hydroxypregnenolone, ketoprogesterone, 17-hydroxypregnenolone, 17,21-dihydroxypregnenolone, 18-hydroxycorticosterone, deoxycortisone, 21-hydroxypregnenolone, and progesterone.

The term "progestin" refers to a natural or synthetic steroid hormone. Examples of progestins are allopregnone-3α,20α-diol, allopregnone-3β,20β-diol, allopregnane-3β,21-diol-11,20-dione, allopregnane-3β,17α-diol-20-one, 3,20-allopregnanedione, 3β,11β,17α,20β,21-pentol, allopregnane-3β,17α,20β,21-tetrol, allopregnane-3α,11β,17α,21-tetrol-20-one, allopregnane-3β,11β,17α,21-tetrol-20-one, allopregnane-3β,17α,20β-triol, allopregnane-3β,17α,21-triol-11,20-dione, allopregnane-3β,11β,21-triol-20-one, allopregnane-3β,17α,21-triol-20-one, allopregnane-3α-ol-20-one, allopregnane-3β-ol-20-one, pregnanediol, 3,20-pregnanedione, 4-pregnene-20,21-diol-3,11-dione, 4-pregnene-11β,17α,20β,21-tetrol-3-one, 4-pregnene-17α,20β,21-triol-3,11-dione, 4-pregnene-17α,20β,21-triol-3-one, and pregnenolone.

The term "surface erosion," as used herein refers to a process of a gradual disintegration of the pharmaceutical compositions of the disclosure and release of a free drug from the drug dimer. Surface erosion can be tailored to achieve desired drug release rates. Surface erosion can depend on the drug composition of the drug dimer, and can be modulated by the cleavage of drug-linker bond through hydrolysis and/or enzymatic degradation. The rate of surface erosion and release of a given drug from a drug dimer may also depend on the quantity of the loaded drug dimer as a percent of the final drug dimer formulation, article size (e.g. dimensions), solubility of drug dimer (e.g., through selection of appropriate drug and/or linker), and/or surface area of the article. For example, surface erosion mechanism of drug release allows drug delivery articles to be tailored with specific physical features (dimensions, diameters, surface areas, total mass, etc.) to achieve desired drug release rates, and drug release may be designed to be initiated within minutes or hours, and may continue to occur over days, weeks, months, or years.

As used herein, "$t_{50}$" is the time at which 50% of the releasable drug has been released from an article of the disclosure. Time $t_{10}$ is, correspondingly, the time at which 10% of the releasable drug has been released from an article of the disclosure. When the release curve is perfectly linear, $t_{10}$ =⅕ of $t_{50}$. When there is an initial burst of released drug, $t_{10}$ is much less than ⅕ of $t_{50}$. In the compositions and methods of the disclosure $t_{10}$ can be equal to or greater than 1/10 of $t_{50}$. Drug release from an article or compound of the disclosure can be measured at 37° C. in 100% bovine serum, or at 37° C. in PBS, as described in Example 1.

The term "woven fabric," as used herein, refers to pharmaceutical compositions that resemble materials that are formed by weaving of fibers.

Chemical Definitions

By "acyl" is meant a chemical moiety with the formula —C(O)R', where R' is selected from the group consisting of $C_{1-10}$ alkyl, $C_{2-20}$ alkene, heteroalkyl, $C_{2-20}$ alkyne, $C_{5-10}$ aryl, and cyclic system. Examples of acyl groups include, without limitation, acetyl, propanoyl, butanoyl, pentanoyl, and tetrahydrofuran-2-oyl.

By "aliphatic" is meant a non-aromatic chemical moiety of hydrocarbons. Aliphatics may be cyclic, straight, or branched chains, and may be saturated or unsaturated, and may have single, double, or triple bonds.

By "alkoxy" is meant a chemical substituent of the formula —OR, wherein R is an alkyl group. By "aryloxy" is meant a chemical substituent of the formula —OR, wherein R is a $C_{5-10}$ aryl group.

As used herein, the terms "alkylene," "alkenylene," "alkynylene," and the prefix "alk" refer to divalent groups having a specified size, typically $C_{1-10}$ or $C_{1-20}$ for the saturated groups (e.g., alkylene or alk) and $C_{2-20}$ or $C_{2-20}$ for the unsaturated groups (e.g., alkenylene or alkynylene). They include straight-chain, branched-chain, and cyclic forms as well as combinations of these, containing only C and H when unsubstituted. Because they are divalent, they can link together two parts of a molecule. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a $C_1$ alkylene that is substituted by =O, for example.

By "alkylthio" is meant a chemical substituent of the formula —SR, wherein R is an alkyl group.

By "arylthio" is meant a chemical substituent of the formula —SR, wherein R is a $C_{5-10}$ aryl group.

By "$C_{1-20}$ alkyl" is meant a branched or unbranched saturated hydrocarbon group, having 1 to 20 carbon atoms, inclusive. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "$C_{2-20}$ alkene" is meant a branched or unbranched hydrocarbon group containing one or more double bonds, desirably having from 2 to 10 carbon atoms. A $C_{2-20}$ alkene may optionally include monocyclic, bicyclic, or tricyclic rings, in which each ring desirably has five or six members. The $C_{2-20}$ alkene group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "$C_{2-20}$ alkyne" is meant a branched or unbranched hydrocarbon group containing one or more triple bonds, desirably having from 2 to 10 carbon atoms. A $C_{2-20}$ alkyne may optionally include monocyclic, bicyclic, or tricyclic rings, in which each ring desirably has five or six members. The $C_{2-20}$ alkyne group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "carbonate ester" is meant a linkage group having the formula —C(O)O—C(O)—O—.

By "carboxyalkyl" is meant a chemical moiety with the formula —(R)—COOH, wherein R is an alkyl group.

By "cyclic acetal" is meant a ring structure including two oxygen atoms separated by a carbon atom which is optionally substituted (e.g., 1,3-dioxolane). Exemplary substituents include, without limitation, alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, quaternary amino, phosphodiester, phosphoramidate, phosphate, phosphonate, phosphonate ester, sulfonate, sulfate, sulfhydryl, phenol, amidine, guanidine, and imidazole groups.

The term "cyclic system" refers to a compound that contains one or more covalently closed ring structures, in which the atoms forming the backbone of the ring are composed of any combination of the following: carbon, oxygen, nitrogen, sulfur, and phosphorous. The cyclic system may be substituted or unsubstituted. Exemplary substituents include, without limitation, alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

By "fluoroalkyl" is meant an alkyl group that is substituted with a fluorine.

By "heteroalkyl" is meant a branched or unbranched alkyl group in which one or more methylenes (—CH$_2$—) are replaced by nitrogen, oxygen, sulfur, carbonyl, thiocarbonyl, phosphoryl, or sulfonyl moieties. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "hydroxyalkyl" is meant a chemical moiety with the formula —(R)—OH, wherein R is an alkyl group.

BRIEF DESCRIPTION OF THE DRAWINGS

FIG. 2A to FIG. 2E are a series of images showing Compound 1 (Dex-TEG-Dex) processed into different glassy state forms by multiple processing methods from the melt state.

FIG. 3A to FIG. 3K are a series of images showing Compound 1 (Dex-TEG-Dex) processed into different glassy state forms by multiple processing methods from the solution state.

FIG. 10A to FIG. 10E are a series of images and a graph showing Compound 3 (Triamcinolone Acetonide-Triethylene Glycol-Triamcinolone Acetonide, TA-TEG-TA) formed into heat-molded pellets, fibers, and extruded cylinders, as well as drug release over time.

FIG. 12A to FIG. 12E are a series of images and a graph showing Compound 5 (Dexamethasone-Hexane-Dexamethasone, Dex-HEX-Dex) formed into heat-molded pellets, fibers, and extruded cylinders, as well as drug release over time.

FIG. 14A to FIG. 14E are an image and a graph showing Compound 7 (Anecortave-Triethylene Glycol-Anecortave, Anec-TEG-Anec) formed into heat-molded pellets and drug release over time.

FIG. 16A to FIG. 16E are a series of images and a graph showing Compound 9 (Fusidic Acid-Triethylene Glycol-Fusidic Acid (carbonate ester), FA-TEG-FA (CE)) formed into heat-molded pellets and fibers, as well as drug release over time.

FIG. 18A to FIG. 18G are a series of images and graphs showing nano- and micro-particle formation of Compounds 3 and 5 and cumulative drug release for Compound 3 over time.

FIG. 21A and FIG. 21B are an image and a graph showing a mixture of Compounds 2 and 3 formed into heat-molded pellets and drug release over time.

FIG. 22A to FIG. 22C are a series of graphs showing hydrocortisone release from heat-molded pellets formed from Compounds 2, 4, 6, or 1 & 2 over time (FIG. 22A), dexamethasone release from heat-molded pellets formed form Compounds 1, 4, or 1 & 2 over time (FIG. 22B), or dexamethasone release from heat-molded pellets formed from Compounds 1 and 5 over time (FIG. 22C).

FIG. 23A to FIG. 23D are a series of images and a graph showing Compound 11 (Dexamethasone-Heptaethylene Glycol-Dexamethasone, Dex-EG7-Dex) formed into heat-molded pellets and extruded cylinders, and the extruded cylinders after two weeks in PBS at 37° C.

FIG. 27A to FIG. 27C are a series of images showing Compound 14 (Cholesterol-Triethylene Glycol-Cholesterol, CHS-TEG-CHS) formed into heat-molded pellets and fibers.

FIG. 28A to FIG. 28C are a series of images showing Compound 15 (Fusidic Acid-Triethylene Glycol-Fusidic Acid (ester), FA-TEG-FA (E)) formed into heat-molded pellets and fibers.

FIG. 30A to FIG. 30C are a series of images showing Compound 17 (Prednisolone-Triethylene Glycol-Prednisolone, Pred-TEG-Pred) formed into heat-molded pellets and fibers.

DETAILED DESCRIPTION

Figure 1C:
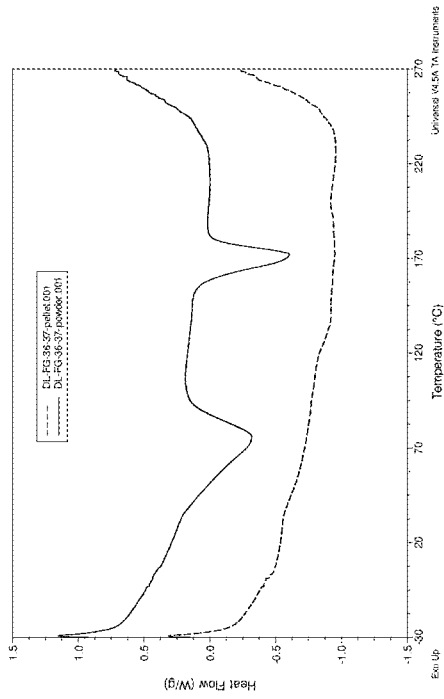
FIG. 1A to FIG. 1F are a series of images and a graph showing Compound 1 (dexamethasone-triethylene glycol-dexamethasone, Dex-TEG-Dex) formed into pellets in the glassy state and drug release through surface erosion from an intact pellet.

While the clinical importance of sustained drug release delivery systems to maintain therapeutic concentration of drugs for extended periods of time (e.g., days to weeks, to months or even years) has been well acknowledged for decades, there has been a limited number of successfully commercialized products on the market to date. It is recognized in this disclosure that to develop successful sustained drug delivery systems, technical difficulties must be overcome ranging from drug degradation during formulation process; lack of controlled release, including unwanted burst or incomplete release associated with diffusion or bulk erosion mechanisms of drug release; low encapsulation efficiency; and formulation complexity.

For locally administered sustained release delivery systems, it is recognized in this disclosure that additional challenges can arise where the mass balance of the carrier or matrix for the drug hinders drug loading, or where the carriers and matrices produce unwanted effects (i.e., such as local inflammation).

It is recognized in this disclosure that there is an unmet need for a sustained release drug system that is formulated to release a drug via a surface erosion process in the absence or with a minimal amount of carrier and/or excipient agents, at a rate-controlled manner over an extended period of time (e.g., days to weeks, to months or even years), where the system contains predominantly drug and minimizes side effects associated with the use of carriers or matrices.

This disclosure describes prodrug dimers that can be in a crystallizable form and have unique properties that allow them to be processed as viscous fluids from a melt or solution, in order yield shaped articles where most of the material is in a glassy state. The shaped articles may be held together by secondary (e.g., non-crystalline) interactions and have the ability to release their prodrug/drug elements from these shaped forms upon surface mediated degradation/dissolution. This may provide a controlled rate of drug release over days, weeks, months, or years, due to unique interactions between the molecules that exist in a mostly amorphous state while holding the shaped form intact as the surface erodes. This disclosure may alter the need for a carrier matrix to provide shape and form to a drug delivery depot or device, and therefore, may mitigate the issues of phase separation of drug from the matrix, and incompatible processing conditions between the formulations' components. Further, such materials can minimize inflammatory responses because the drugs/prodrugs undergoing surface erosion from the shaped article can be released in the biological environment in a non-particulate (e.g., non-crystalline) form and, when formed from anti-inflammatory steroids, can have inherent anti-inflammatory activity from the drugs being released from the prodrug shaped form.

The compounds of the disclosure can be designed for the controlled and sustained release of a steroid drug from the prodrug dimer used to make the shaped article. The release rate from an article of the disclosure can be controlled through several engineerable design parameters, including: 1) selection of the steroid drug; 2) selection of the functional group of the drug for conjugatation (e.g., if multiple exist); 3) selection of the linker; 4) selection of the linkage group (i.e., esters, carbonates, carbonate esters, or anhydrides); 5) selection of the surface area of the shaped article; and 6) selection of the drug loading in the shaped article (e.g., by adding traditional pharmaceutical excipients or mixing other steroid dimers as excipients when making the shaped article). This disclosure can also be applied to the controlled release of two or more steroid drugs through the use of heterodimers (i.e., different steroid drugs on the two ends of the linkers), or by forming shaped articles with mixtures of two or more steroid homodimers, steroid heterodimers, or a mixture of both steroid homodimers and steroid heterodimers. Articles formed from the compounds of the disclosure can yield sustained and uniform release of the steroid compounds, without exhibiting any burst release (e.g., $t_{10}$ can be equal to or greater than $\frac{1}{10}$ of $t_{50}$) and without reliance upon degradable matrices, which can cause undesirable local side effects (such as inflammation). The high drug loading that can be present in the articles of the disclosure are suitable for producing locally effective concentrations of a steroid drug for periods of days to weeks to months or even years.

The disclosure features compounds of formula (A-VIII) and articles formed from compounds of formula (A-VIII):

$$D1-L-D2 \qquad (A\text{-}VIII)$$

or a pharmaceutically acceptable salt thereof, wherein each of D1 and D2 is, independently, a radical formed from a steroid; and L is a linker covalently linking D1 to D2. Each of D1 and D2 can be, independently, selected from an anabolic steroid, an androgenic steroid, a progestin steroid, an estrogen steroid, a cancer treatment steroid, an antibiotic steroid, a glucocorticoid steroid, a benign steroid, or a corticosteroid. L can be covalently linked to D1 and to D2 via one or more ester, carbonate, carbonate ester, or anhydride linkages. Ester, carbonate, carbonate ester, or anhydride linkages formed from a functional group on D1 and D2 can be selected from, e.g., hydroxyl or carboxy. For example, L can include the radical —C(O)—(R$^A$)—C(O)—, —C(O)—OC(O)—(R$^A$)—C(O)O—C(O)—, or —O—(R$^A$)—O—, where R$^A$ is a radical of a polyol and includes at least one free hydroxyl group or R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—, and q, r, and s are integers from 1 to 10 (e.g., 1 to 10, 1 to 5, or 5 to 10). The articles of the disclosure can be machined, molded, emulsion-processed, electrospun, electrosprayed, blow molded, dry spun, heat spun, melt spun, gel spun, or extruded to form a fiber, fiber mesh, woven fabric, non-woven fabric, pellet, cylinder, microparticle (e.g., a microbead), nanoparticle (e.g., a nanobead), or another shaped article.

The compound can be further described by the formula (A-III):

$$D1\text{-}O\text{-}L\text{-}O\text{-}D2 \qquad (A\text{-}II),$$

or a pharmaceutically acceptable salt thereof, wherein each of D1-O and D2-O is, independently, a radical formed from a steroid.

In some embodiments, each of D1-O and D2-O is, independently, described by any one of formulas (I-a) to (I-sss):

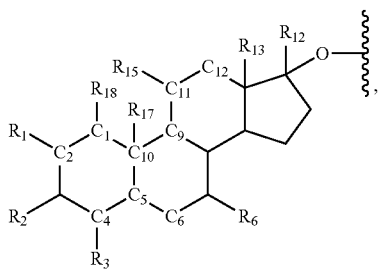

(I-a)

where the bond between $C_1$ and $C_2$, $C_4$ and $C_5$, $C_5$ and $C_6$, $C_9$ and $C_{10}$, and $C_{11}$ and $C_{12}$ is a single or a double bond; $R_1$ represents H, $CH_3$, or HC(O); $R_2$ represents =O, OH, or H; or $R_1$ and $R_2$ taken together with carbons to which they are attached form an isoxazole; $R_3$ represents H, a halogen atom, or OH; $R_6$ represents H or $CH_3$; $R_{12}$ represents H, $CH_3$, or $CH_3CH_2$; $R_{13}$ represents $CH_3$ or $CH_3CH_2$; $R_{15}$ represents H or OH; $R_{17}$ represents H or $CH_3$; and $R_{18}$ represents H or $CH_3$;

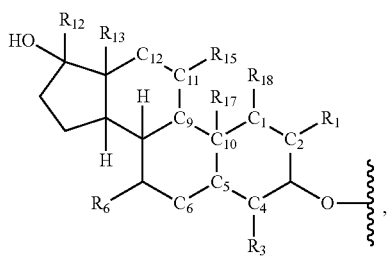

(I-b)

where the bond between $C_1$ and $C_2$, $C_4$ and $C_5$, $C_5$ and $C_6$, $C_9$ and $C_{10}$, and $C_{11}$ and $C_{12}$ is a single or a double bond; $R_1$ represents H, $CH_3$, or HC(O); $R_3$ represents H, a halogen atom, or OH; $R_6$ represents H or $CH_3$; $R_{12}$ represents H, $CH_3$, or $CH_3CH_2$; $R_{13}$ represents $CH_3$ or $CH_3CH_2$; $R_{15}$ represents H or OH; $R_{17}$ represents H or $CH_3$; and $R_{18}$ represents H or $CH_3$;

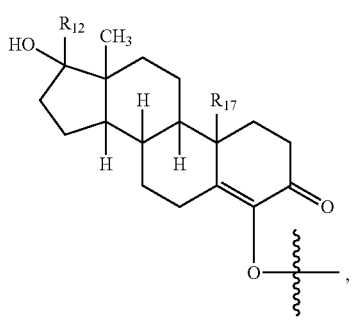

(I-c)

where $R_{12}$ represents H or $CH_3$; and $R_{17}$ represents H or $CH_3$;

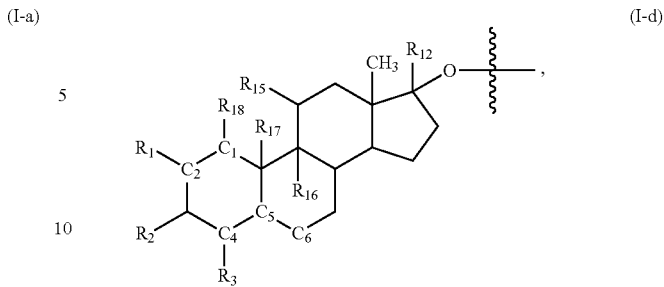

(I-d)

where the bond between $C_1$ and $C_2$, $C_4$ and $C_5$, and $C_5$ and $C_6$ is a single or a double bond; $C_2$ is O, C or $CH_2$; $R_1$ represents H, —CHOH, or is absent; $R_2$ represents =O or OH; or $R_1$ and $R_2$ taken together with carbons to which they are attached form a pyrazole; $R_3$ represents H or OH; $R_{12}$ represents H, $CH_3$, optionally substituted alkynylene, $C_{1-6}$ alkoxy, or $CH_3CH_2$; $R_{15}$ represents H or OH; $R_{16}$ represents H or a halogen atom; $R_{17}$ represents H or $CH_3$; and $R_{18}$ represents H or $CH_3$;

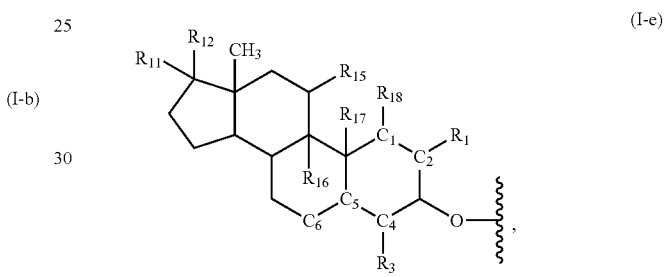

(I-e)

where the bond between $C_1$ and $C_2$, $C_4$ and $C_5$, and $C_5$ and $C_6$ is a single or a double bond; $C_2$ is O, C or $CH_2$; $R_1$ represents H, —CHOH, or is absent; $R_3$ represents H or OH; $R_{11}$ represents H, OH, $CH_3$, optionally substituted alkynylene, $CH_3CH_2$, =O, —OC(O)$CH_2CH_3$, or is absent; $R_{12}$ represents H, OH, $CH_3$, optionally substituted alkynylene, $CH_3CH_2$, =O, —OC(O)$CH_2CH_3$, or is absent; $R_{15}$ represents H or OH; $R_{16}$ represents H or a halogen atom; $R_{17}$ represents H or $CH_3$; and $R_{18}$ represents H or $CH_3$;

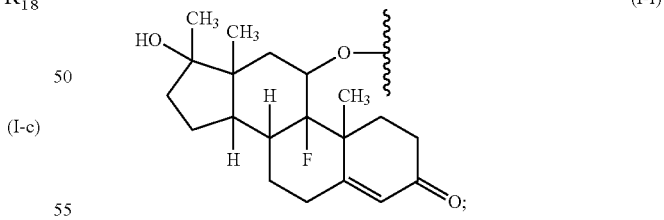

(I-f)

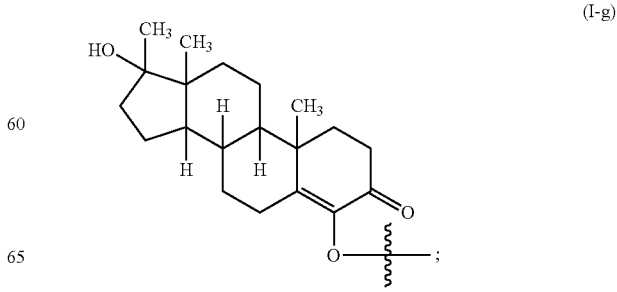

(I-g)

-continued

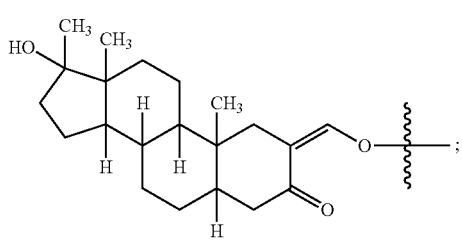
(I-h)

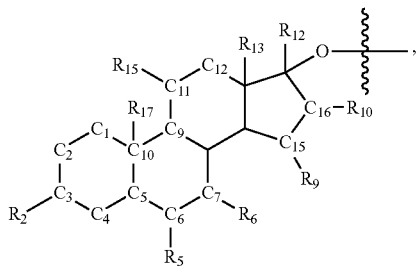
(I-i)

where the bond between $C_1$ and $C_{10}$, $C_2$ and $C_3$, $C_3$ and $C_4$, $C_4$ and $C_5$, $C_5$ and $C_6$, $C_6$ and $C_7$, $C_5$ and $C_{10}$, $C_9$ and $C_{10}$, $C_{11}$ and $C_{12}$, $C_{15}$ and $C_{16}$ is a single or a double bond; $R_2$ represents H, =O, OH, =NOH, or $C_{1-6}$ alkoxy; $R_5$ represents H, $CH_3$, or a halogen atom; $R_6$ represents H or $CH_3$; or $R_5$ and $R_6$ taken together with carbons to which they are attached form a cyclopropane; $R_9$ is H; $R_{10}$ is H or =$CH_2$; or $R_9$ and $R_{10}$ taken together with carbons to which they are attached form a cyclopropane; $R_{12}$ represents H, optionally substituted alkynylene, —$CH_2CH$=$CH_2$, $CH_3$, —C(O)$CH_3$, or —CH=$CH_2$; $R_{13}$ represents $CH_3$ or $CH_2CH_3$; $R_{15}$ represents H or =$CH_2$; and $R_{17}$ represents H, $CH_3$, or is absent;

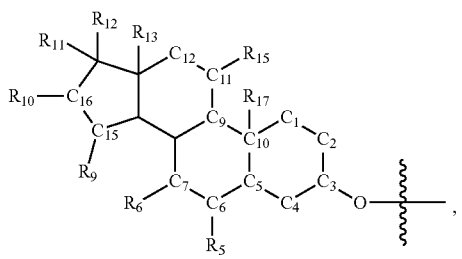
(I-j)

where the bond between $C_1$ and $C_{10}$, $C_2$ and $C_3$, $C_4$ and $C_5$, $C_6$ and $C_7$, $C_9$ and $C_{10}$, $C_9$ and $C_{10}$, $C_{11}$ and $C_{12}$, $C_{15}$ and $C_{16}$ is a single or a double bond; $R_5$ represents H, $CH_3$, or a halogen atom; $R_6$ represents H or $CH_3$; or $R_5$ and $R_6$ taken together with carbons to which they are attached form a cyclopropane; $R_9$ is H; $R_{10}$ is H or =$CH_2$; or $R_9$ and $R_{10}$ taken together with carbons to which they are attached form a cyclopropane; $R^{11}$ represents H, OH, optionally substituted alkynylene, —C(O)$CH_3$, —$CH_2CH$=$CH_2$, a halogen atom, —CH=$CH_2$, —OC(O)$CH_3$, $CH_3$, —C(O)C(OH)$CH_3$; $R_{12}$ represents H, OH, optionally substituted alkynylene, —C(O)$CH_3$, —$CH_2CH$=$CH_2$, a halogen atom, —CH=$CH_2$, —OC(O)$CH_3$, $CH_3$, —C(O)C(OH)$CH_3$; or $R_{11}$ and $R_{12}$ together with carbon to which they are attached form a lactone; $R_{13}$ represents $CH_3$ or $CH_2CH_3$; $R_{15}$ represents H or =$CH_2$; and $R_{17}$ represents H, $CH_3$, or is absent;

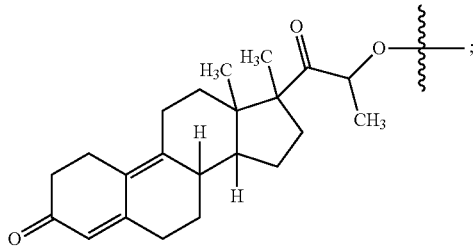
(I-k)

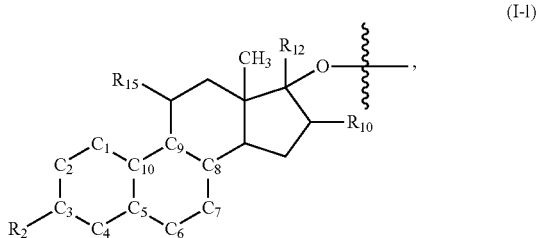
(I-l)

where the bond between $C_1$ and $C_2$, $C_1$ and $C_{10}$, $C_2$ and $C_3$, $C_3$ and $C_4$, $C_4$ and $C_5$, $C_6$ and $C_7$, $C_5$ and $C_{10}$, $C_7$ and $C_8$, and $C_8$ and $C_9$ is a single or a double bond; $R_2$ represents OH, —OC(O)Ph, or $C_{1-6}$ alkoxy; $R_{10}$ represents H or OH; $R_{12}$ represents H, optionally substituted alkynylene; and $R_{15}$ represents H or $C_{1-6}$ alkoxy;

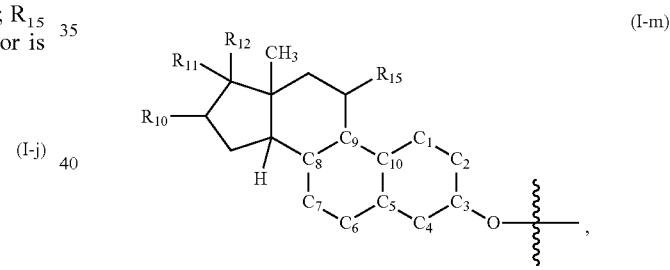
(I-m)

where the bond between $C_1$ and $C_2$, $C_1$ and $C_{10}$, $C_2$ and $C_3$, $C_3$ and $C_4$, $C_4$ and $C_5$, $C_6$ and $C_7$, $C_8$ and $C_{10}$, $C_7$ and $C_8$, and $C_8$ and $C_9$ is a single or a double bond; $R_{10}$ represents H or OH; $R_{11}$ represents H, OH, optionally substituted alkynylene, =O, or is absent; $R_{12}$ represents H, OH, optionally substituted alkynylene, =O, or is absent; and $R_{15}$ represents H or $C_{1-6}$ alkoxy;

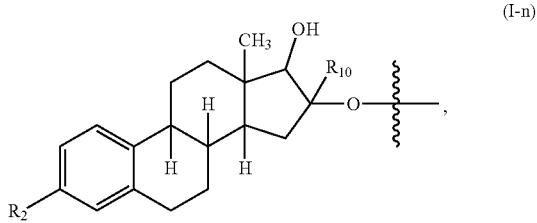
(I-n)

where $R_2$ represents OH or $C_{1-6}$ alkoxy; and $R_{10}$ represents H or $CH_3$;

(I-o)

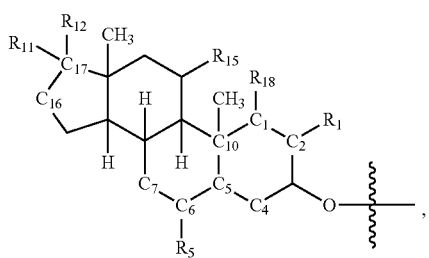

where the bond between $C_1$ and $C_2$, $C_4$ and $C_5$, $C_5$ and $C_6$, $C_6$ and $C_7$, and $C_{16}$ and $C_{17}$ is a single or a double bond; $C_4$ is NH, CH, or $CH_2$; $R_1$ represents H; $R_5$ represents H or a halogen atom; $R_{11}$ represents H, optionally substituted heteroaryl, —C(O)$C_{1-6}$ alkyl, —C(O)O$C_{1-6}$ alkyl, or —C(O)NHR, where R is optionally substituted alkyl or aryl; $R_{12}$ represents H, optionally substituted heteroaryl, —C(O)$C_{1-6}$ alkyl, —C(O)O$C_{1-6}$ alkyl, or —C(O)NHR, where R is optionally substituted alkyl or aryl; and $R_{11}$ represents H; or $R_1$ and $R_{11}$ taken together with carbons to which they are attached form a cyclopropane;

(I-p)

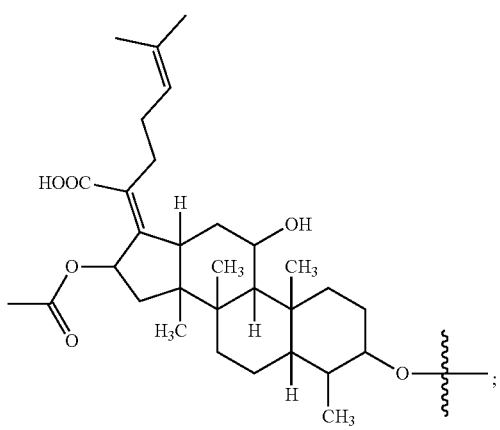

(I-q)

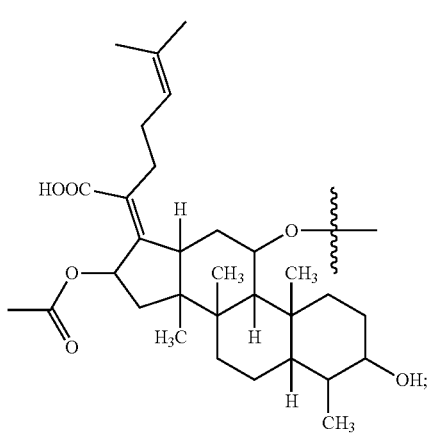

(I-r)

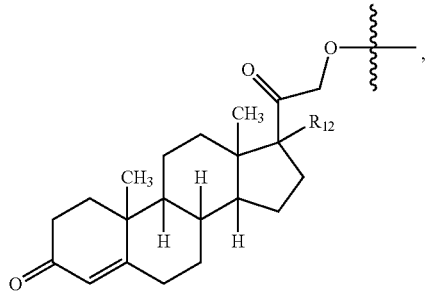

where $R_{12}$ is H or OH;

(I-s)

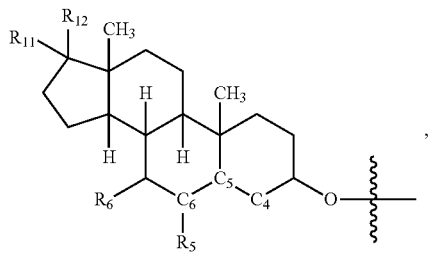

where the bond between $C_4$ and $C_5$, and $C_5$ and $C_6$ is a single or a double bond; $R_5$ represents H or $C_{1-6}$ alkyl; $R_6$ represents H or OH; $R_{11}$ represents H, OH, —C(O)$C_{1-6}$ alkyl, —C(O)$CH_2$OH, or —CH($CH_3$)$CH_2CH_2$C(O)OH; and $R_{12}$ represents H, OH, —C(O)$C_{1-6}$ alkyl, —C(O)$CH_2$OH, or —CH($CH_3$)$CH_2CH_2$C(O)OH;

(I-t)

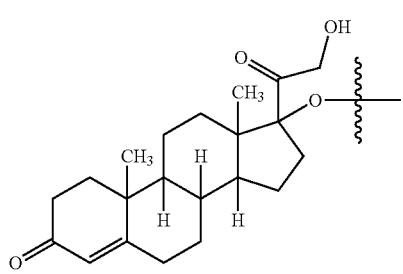

(I-u)

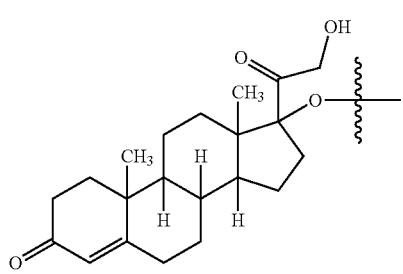

where $R_5$ represents H or $CH_2CH_3$; and $R_{14}$ represents H or OH;

(I-v)

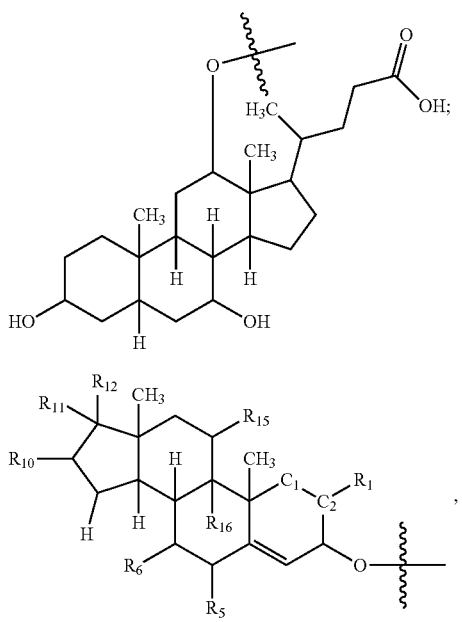

(I-w)

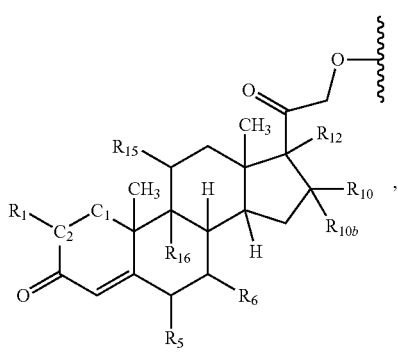

where the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or $=CH_2$; $R_{11}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{11}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; $R_{15}$ represents H, OH, $=O$, or a halogen atom; and $R_{16}$ represents H or a halogen atom;

(I-x)

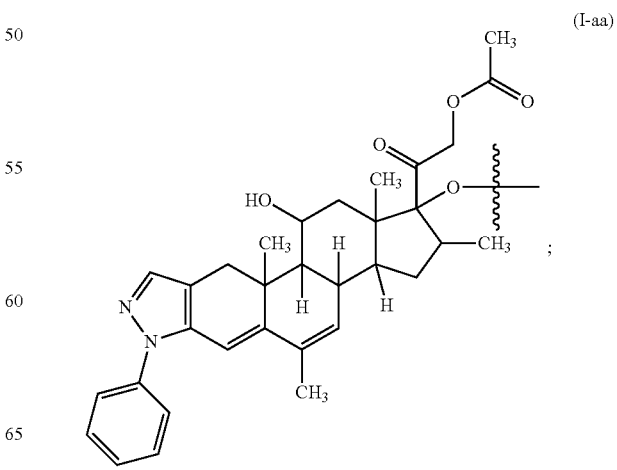

where the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or $=CH_2$; $R_{10b}$ represents H, $C_{1-6}$ alkyl, OH, $=CH_2$, or be absent; $R_{12}$ represents H, OH, optionally substituted —C(O)$C_{1-6}$ alkyl, —C(O)CH$_2$OC(O)$C_{1-6}$ alkyl, optionally substituted —OC(O)$C_{1-6}$ alkyl, or —OC(O)Ph; or $R_{10}$ and $R_{11}$ taken together with carbons to which they are attached form an optionally substituted cyclic acetal or optionally substituted heterocyclyl; $R_{15}$ represents H, OH, $=O$, or a halogen atom; and $R_{16}$ represents H or a halogen atom;

(I-y)

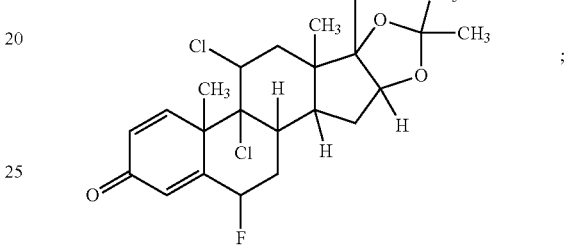

(I-z)

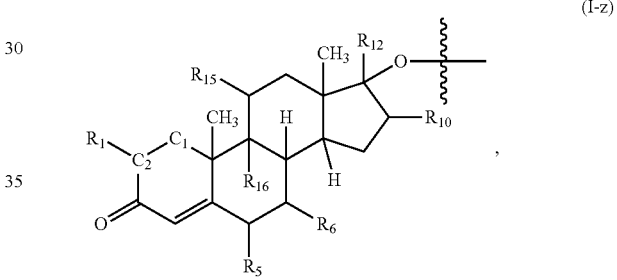

where the bond between $C_1$ and $C_2$ is a single or a double bond; $R_1$ represents H or a halogen atom; $R_5$ represents H, a halogen atom, or CH$_3$; $R_6$ represents H, a halogen atom; $R_{10}$ represents H, OH, CH$_3$, or $=CH_2$; $R_{12}$ represents optionally substituted —C(O)$C_{1-6}$ alkyl, —C(O)CH$_2$OC(O)$C_{1-6}$ alkyl, or —C(O)SCH$_2$F; $R_{15}$ represents OH or $=O$; and $R_{16}$ represents H or a halogen atom;

(I-aa)

(I-bb)

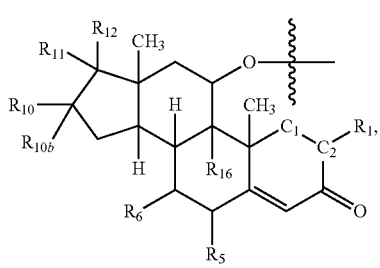

where $R_5$ represents H or a halogen atom; $R_{15}$ represents a halogen atom or OH; and $R_{16}$ represents H or a halogen atom;

(I-ee)

where the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =$CH_2$; $R_{10b}$ represents H, $C_{1-6}$ alkyl, OH, or =$CH_2$, or is absent; $R_{11}$ represents H, OH, $C_{1-6}$ alkyl, optionally substituted —C(O)$C_{1-6}$ alkyl, —C(O)$CH_2$OC(O)$C_{1-6}$ alkyl, optionally substituted —OC(O)$C_{1-6}$ alkyl, —OC(O)Ph, —OC(O)heterocyclyl, —$CH_2$C(O)$CH_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{11}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O)$CH_2$OC(O)$C_{1-6}$ alkyl, optionally substituted —OC(O)$C_{1-6}$ alkyl, —OC(O)Ph, —OC(O)heterocyclyl, —$CH_2$C(O)$CH_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; and $R_{16}$ represents H or a halogen atom;

(I-ff)

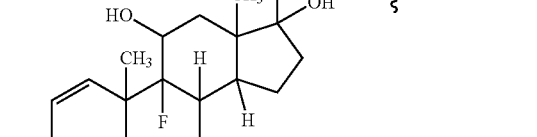

(I-cc)

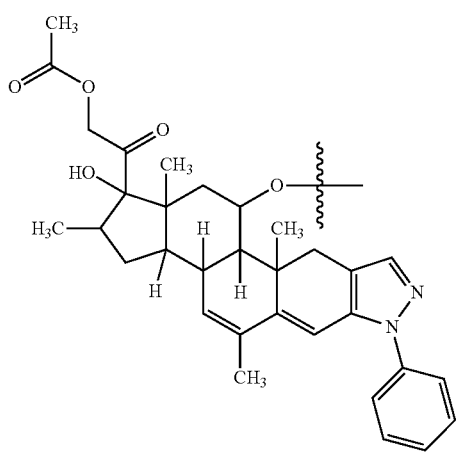

(I-gg)

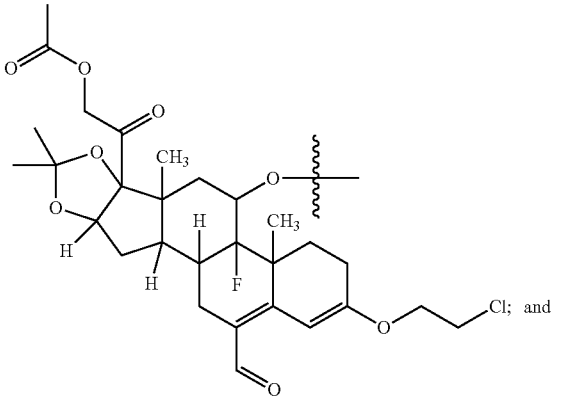

where the bond between $C_1$ and $C_2$ is a double or a single bond; $R_{16}$ represents H or a halogen atom; $R_5$ represents H, $CH_3$, or a halogen atom; $R_{12}$ represents H or a halogen atom; $R_{15}$ represents =O or OH; $R_{12}$ and $R_{10}$ each, independently, represent —H, $C_{1-10}$ alkyl, —OH, —O-acyl, or $R_{12}$ and $R_{10}$ combine to form a cyclic acetal of formula (XVIII-a) where:

(I-dd)

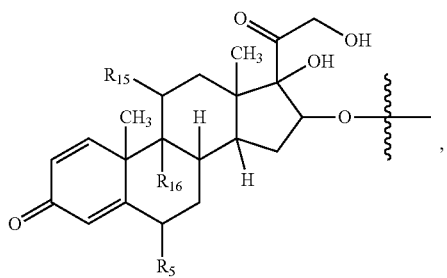

(I-gga)

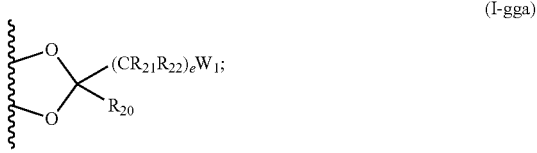

e is an integer from 0 to 6; $R_{20}$, $R_{21}$, and $R_{22}$ each, independently, represent H or $C_{1-10}$ alkyl; and $W_1$ represents H or $CH_3$;

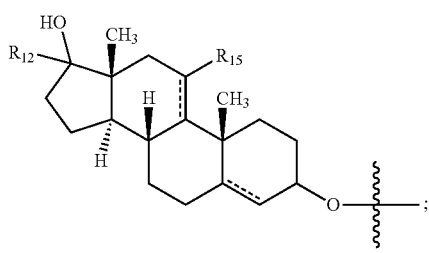 (I-jj)

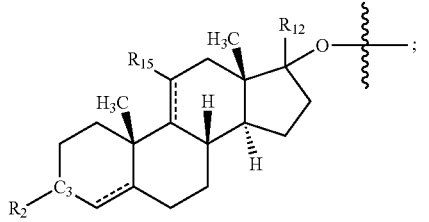 (I-kk)

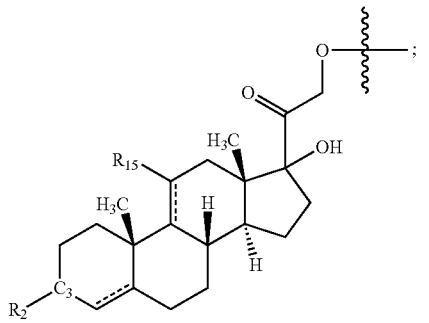 (I-ll)

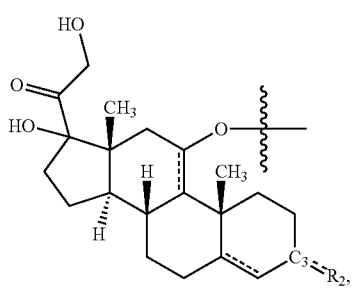 (I-mm)

where the bond between $C_3$ and $R_2$ is a single or a double bond; $R_2$ represents OH or =O; $R_{12}$ represents —C(=O)CH$_2$OC(=O)CH$_3$, —C(=O)CH$_2$OH, or —C(=O)CH$_3$; $R_{15}$ represents H or OH;

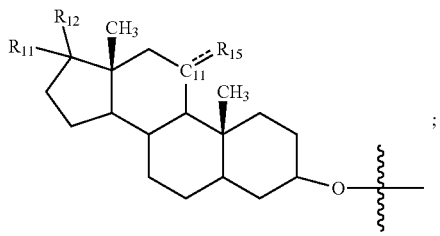 (I-nn)

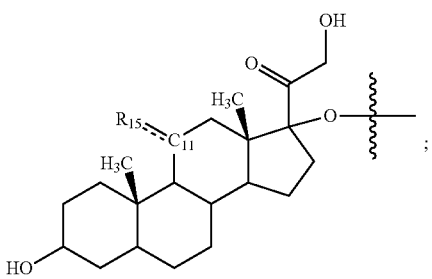 (I-oo)

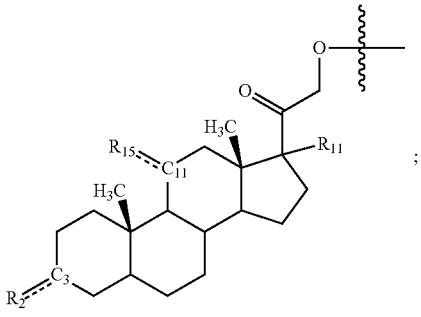 (I-pp)

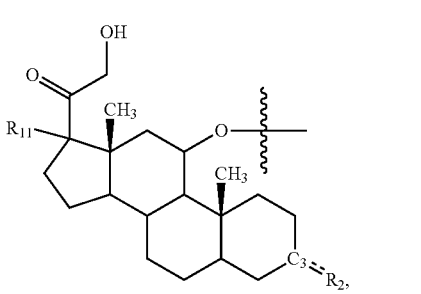 (I-qq)

where the bond between $C_3$ and $R_2$, and $C_{11}$ and $R_5$ is a single or a double bond; $R_2$ represents OH or =O; $R_{11}$ represents H, OH, —C(=O)CH$_2$OH, or —C(=O)CH$_3$; $R_{12}$ represents H, OH, —C(=O)CH$_2$OH, or —C(=O)CH$_3$; $R_{15}$ represents H, =O, or OH;

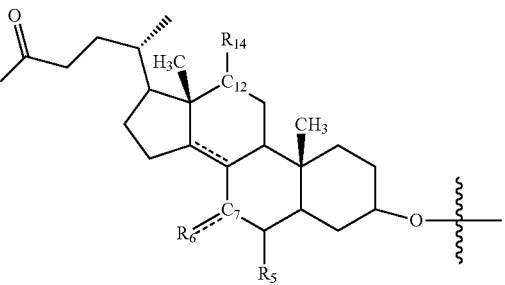 (I-rr)

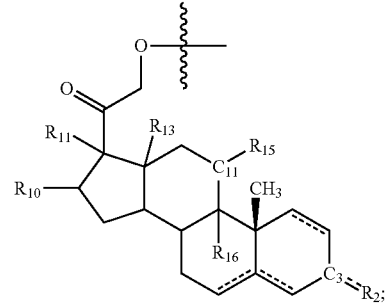
(I-xx)

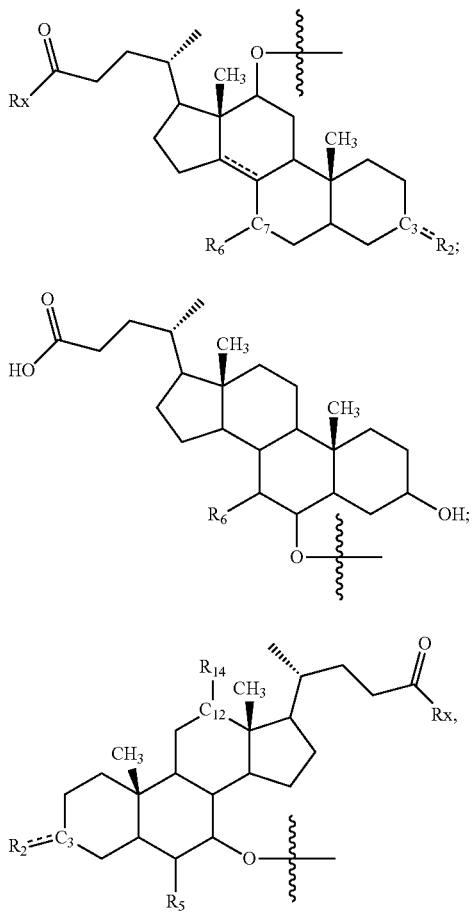
(I-ss)

(I-tt)

(I-uu)

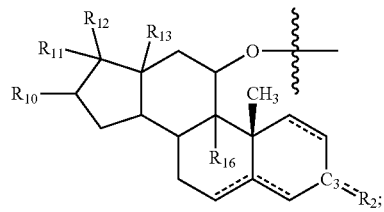
(I-yy)

where the bond between $C_3$ and $R_2$, $C_7$ and $R_6$, and $C_{12}$ and $R_{14}$ is a single or a double bond; Rx represents OH, —NHCH$_2$C(=O)OH, or —NHCH$_2$CH$_2$SO$_2$OH; $R_2$ represents OH or =O; $R_5$ represents H or OH; $R_6$ represents H, =O, or OH; $R_{14}$ represents H, =O, or OH;

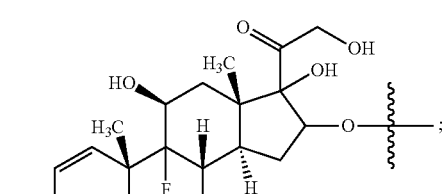
(I-zz)

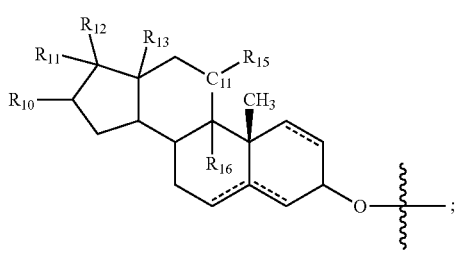
(I-vv)

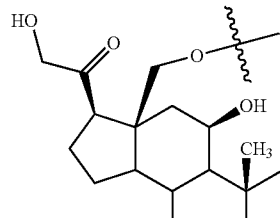
(I-aaa)

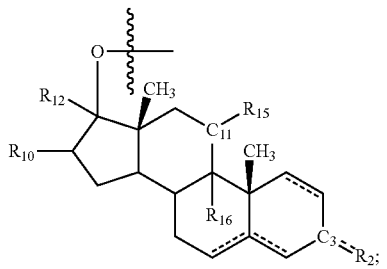
(I-ww)

where the bond between $C_3$ and $R_2$, and $C_{11}$ and $R_{15}$ is a single or a double bond; $R_2$ represents OH or =O; $R_{10}$ represents H or OH; $R_{11}$ represents H, OH, —C(=O)CH$_2$OH, —C(=O)OH, —C(=O)CH$_2$OH, or —C(=O)CH$_3$; $R_{12}$ represents H, OH, —C(=O)CH$_2$OH, —C(=O)OH, —C(=O)CH$_2$OH, or —C(=O)CH$_3$; $R_{13}$ represents —CH$_2$OH or —CH$_3$; $R_{15}$ represents H, OH, or =O; $R_{16}$ represents H or F;

(I-bbb)
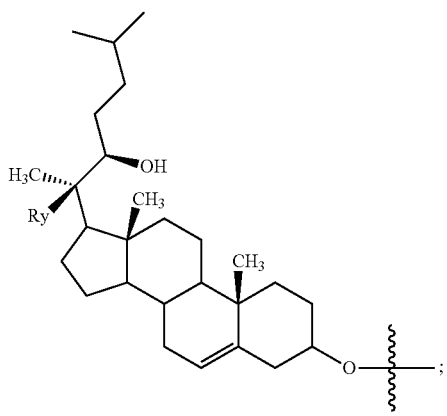
(I-ccc)
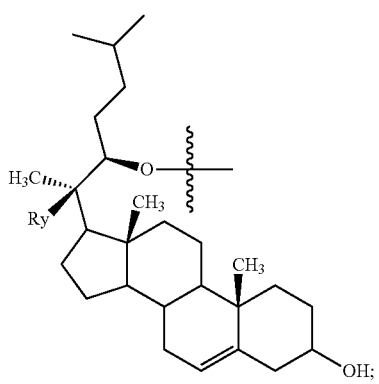
(I-ddd)
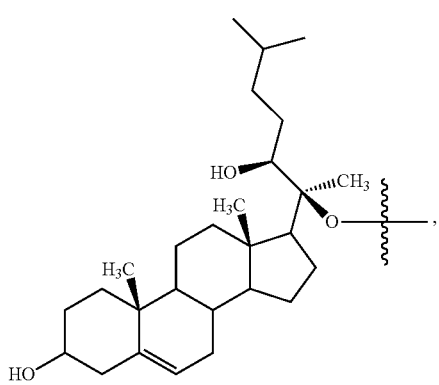
where Ry represents H or OH;
(I-eee)
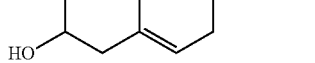
(I-fff)
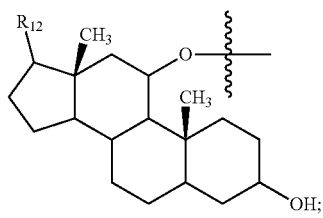
(I-ggg)
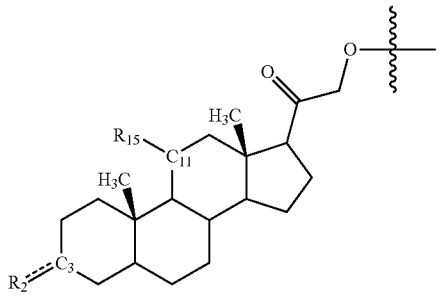
(I-hhh)
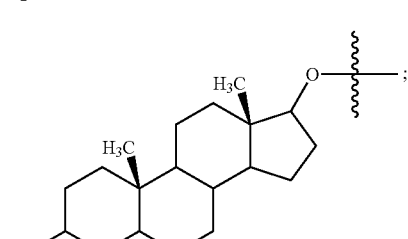
(I-iii)
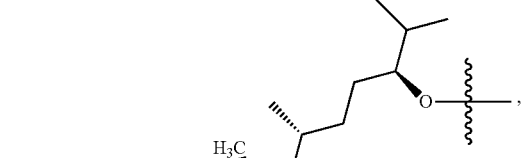
where the bond between $C_3$ and $R_2$, and $C_{11}$ and $R_{15}$ is a single or a double bond; Rz represents H or —$CH_3$; $R_1$ represents H or —$OCH_2CH_3$; $R_2$ represents OH or =O; $R_{12}$ represents —OH, —C(=O)$CH_3$, —C(=O)$CH_2$OH, or —CH($CH_3$)($CH_2$)$_2$CH(OH)CH($CH_3$)$_2$; $R_{15}$ represents H, —N($CH_3$)$_2$, or =O;
(I-jjj)
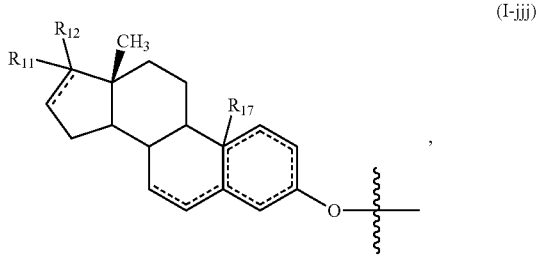

where the bond between $C_3$ and $R_2$ is a single or a double bond; $R_2$ represents OH or =O; $R_{11}$ represents H, —C(=O)CH$_3$, —OC(=O)(CH$_2$)$_4$CH$_3$, or is absent; $R_{12}$ represents H, —C(=O)CH$_3$, —OC(=O)(CH$_2$)$_4$CH$_3$, or is absent; $R_{17}$ represents CH$_3$ or is absent;

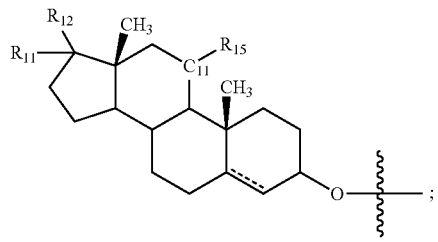

(I-kkk)

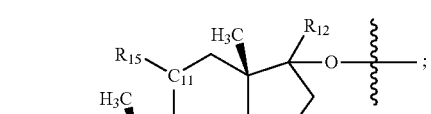

(I-lll)

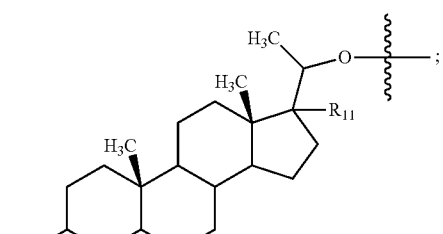

(I-mmm)

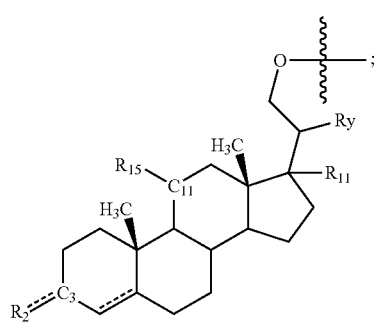

(I-nnn)

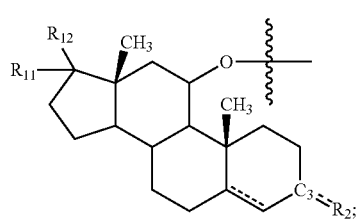

(I-ooo)

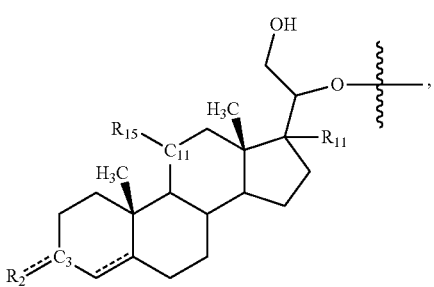

(I-ppp)

where the bond between $C_3$ and $R_2$, and $C_{11}$ and $R_{15}$ is a single or a double bond; Ry represents OH or =O; $R_2$ represents OH or =O; $R_{11}$ represents H, OH, —CH(OH)CH$_3$, —C(=O)CH$_2$OH, —C(=O)CH$_3$, or —CH(OH)CH$_2$OH; $R_{12}$ represents H, OH, —CH(OH)CH$_3$, —C(=O)CH$_2$OH, —C(=O)CH$_3$, or —CH(OH)CH$_2$OH; $R_{15}$ represents H, =O, or OH;

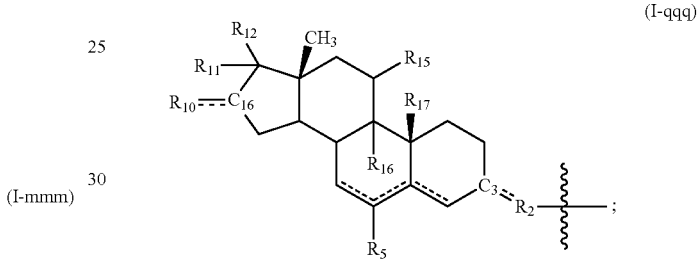

(I-qqq)

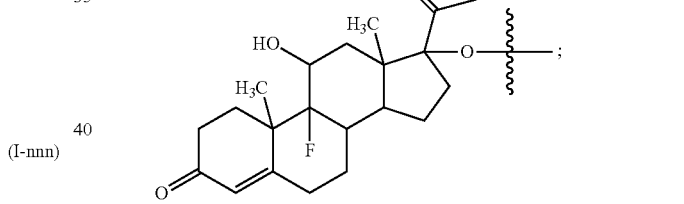

(I-rrr)

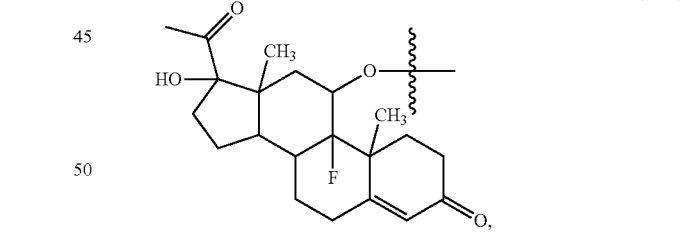

(I-sss)

where the bond between $C_3$ and $R_2$, and $C_{16}$ and $R_{10}$ is a single or a double bond; $R_2$ represents OH or =O; $R_5$ represents H, Cl, or —CH$_3$; $R_{10}$ represents H or =CH$_2$; $R_{11}$ represents H, OH, —CH$_3$, —C(=O)CH$_3$, —C(=O)CH$_2$OC(=O)CH$_3$, or —OC(=O)CH$_3$; $R_{12}$ represents H, OH, —CH$_3$, —C(=O)CH$_3$, —C(=O)CH$_2$OC(=O)CH$_3$, or —OC(=O)CH$_3$; $R_{15}$ represents H or OH; $R_{16}$ represents F or H; $R_{17}$ represents H or —CH$_3$.

In another embodiment, the compound is described by the formula (A-VII):

$$\text{D1-C(O)-L-C(O)-D2} \quad \text{(A-VII)},$$

or a pharmaceutically acceptable salt thereof, wherein each of D1-C(O) and D2-C(O) is, independently, a radical formed from a steroid; L is —O—C(O)—O—(R$^A$)—O—C(O)—O—; and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. Each of D1-C(O) and D2-C(O) can, independently, be formed, for example, from fusidic acid, cholic acid, chenodeoxycholic acid, ursodeoxycholic acid, or obeticholic acid. In the drug dimers of formula (A-VII), D1-C(O)— and D2-C(O)— can further be described, for example, by formulas (I-hh), (I-ii), (I-ttt), (I-uuu), and (I-vvv) below.

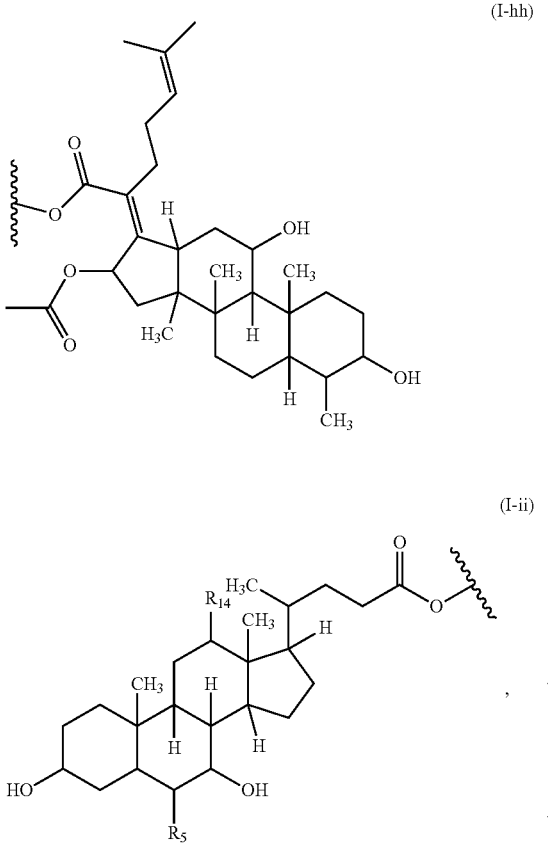

(I-hh)

(I-ii)

where R$_5$ represents H or C$_{1-6}$ alkyl, R$_{14}$ represents H or OH;

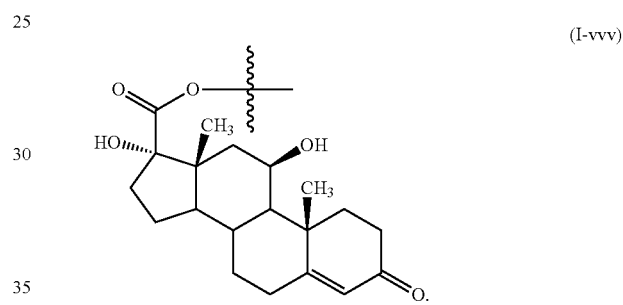

(I-ttt)

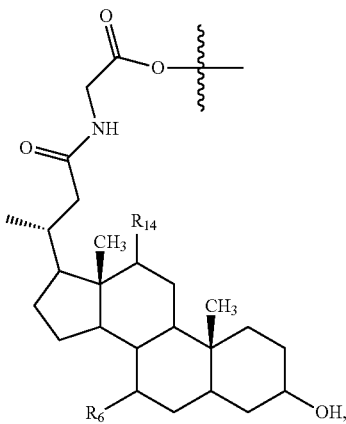

(I-uuu)

where the bond between C$_3$ and R$_2$, C$_7$ and R$_6$, and C$_{12}$ and R$_{14}$ is a single or a double bond; R$_2$ represents OH or =O; R$_5$ represents H or OH; R$_6$ represents H, =O, or OH; R$_{14}$ represents H, =O, or OH;

(I-vvv)

Drug dimers useful in the methods and compositions of the disclosure include homodimers and heterodimers. Steroids, including anabolic steroids, androgenic steroids, progestin steroids, estrogen steroids, cancer treatment steroids, antibiotic steroids, glucocorticoid steroids, benign steroids, corticosteroids, anti-angiogenic steroids, intraocular pressure (IOP) lowering steroids, cholic acid-related bile acid steroids, steroid metabolites, cholesterol-derivatives, neurosteroids, pheromones, progestins, or other steroids, can be used in drug dimers. Examples of anabolic steroids include androisoxazole, androstenediol, bolandiol, bolasterone, clostebol, ethylestrenol, formyldienolone, 4-hydroxy-19-nortestosterone, methandriol, methenolone, methyltrienolone, nandrolone, norbolethone, oxymesterone, stenbolone, and trenbolone. Androgenic steroids are, for example, boldenone, fluoxymesterone, mestanolone, mesterolone, methandrostenolone, 17-methyltestosterone, 17-α-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate tiomesterone dehydroepiandrosterone (DHEA), androstenedione, androstenediol, androsterone, dihydrotestosterone (DHT), androstanolone, and derivatives thereof. Exemplary progestin steroids are norethisterone, norethisterone acetate, gestodene, levonorgestrel, allylestrenol, anagestone, desogestrel, dimethisterone, dydrogesterone, ethisterone, ethynodiol, ethynodiol diacetate, etonogestrel, gestodene, ethinylestradiol, haloprogesterone, 17-hydroxy-16-methylene-progesterone, 17 alpha-hydroxyprogesterone, lynestrenol, medroxyprogesterone, melengestrol, norethindrone, norethynodrel, norgesterone, gestonorone, norethisterone, norgestimate, norgestrel, levonorgestrel, norgestrienone, norvinisterone, pentagestrone, MENT (7-methyl-19-testosterone); norelgestromin, and trimigestone drospirenone, tibolone, megestrol, and derivatives thereof. Examples of estrogen steroid are estrogen, eguilenin, equilin, 17β-estradiol, estradiol benzoate, estriol, ethinyl estradiol, mestranol, moxestrol, mytatrienediol, quinestradiol, and quinestrol. Steroids used in cancer treatment are, for example, abiraterone, cyproterone acetate, dutasteride, enzalutamide, finasteride, and galeterone. Exemplary antibiotic steroid is fusidic acid. Glucocorticoids include, for example, medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, loprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6α-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol. Exemplary benign steroids are cholesterol, 11-deoxycortisol, 11-deoxycorticosterone, pregnenolone, cholic acid, chenodeoxycholic acid, ursodeoxycholic acid, obeticholic acid, tetrahydrocortisone, tetrahydrodeoxycortisol, tetrahydrocorticosterone, 5α-dihydrocorticosterone, and 5α-dihydropregesterone. Exemplary anti-angiogenic steroids or intraocular pressure (IOP) lowering steroids are anecortave acetate, anecortave, 11-epicortisol, 17α-hydroxyprogesterone, tetrahydrocortexolone, and tetrahydrocortisol. Exemplary cholic acid-related bile acid steroids are deoxycholic acid, apocholic acid, dehydrocholic acid, glycochenodeoxycholic acid, glycocholic acid, glycodeoxycholic acid, hyodeoxycholic acid, lithocholic acid, α-muricholic acid, β-muricholic acid, γ-muricholic acid, ω-muricholic acid, taurochenodeoxycholic acid, taurocholic acid, taurodeoxycholic acid, taurolithocholic acid, and tauroursodeoxycholic acid. Exemplary neurosteroids are alphaxalone, alphadolone, hydroxydione, minaxolone, tetrahydrodeoxycorticosterone, allopregnanolone, pregnanolone, ganoxolone, 3α-androstanediol, epipregnanolone, isopregnanolone, and 24(S)-hydroxycholesterol. Exemplary other steroids are flugestone, prebediolone, chlormadinone acetate, medrogestone, and segesterone acetate. Exemplary pheromones are androstadienol, androstadienone, androstenol, androstenone, estratetraenol, 5-dehydroprogesterone, 6-dehydro-retroprogesterone, allopregnanolone, and hydroxyprogesterone caproate. Exemplary steroid metabolites are tetrahydrotriamcinolone, cortienic acid, 11-dehydrocorticosterone, 11β-hydroxypregnenolone, ketoprogesterone, 17-hydroxypregnenolone, 17,21-dihydroxypregnenolone, 18-hydroxycorticosterone, deoxycortisone, 21-hydroxypregnenolone, and progesterone. Exemplary progestins are allopregnone-3α,20α-diol, allopregnone-3β,20β-diol, allopregnane-3β,21-diol-11,20-dione, allopregnane-3,17α-diol-20-one, 3,20-allopregnanedione,3β,11β,17α,20β,21-pentol, allopregnane-3β,17α,20β, 21-tetrol, allopregnane-3α,11β,17α,21-tetrol-20-one, allopregnane-3β,11β,17α,21-tetrol-20-one, allopregnane-3β,17α,20β-triol, allopregnane-3β,17α,21-triol-11,20-dione, allopregnane-3β,1β,21-triol-20-one, allopregnane-3β, 17α,21-triol-20-one, allopregnane-3α-ol-20-one, allopregnane-3β-ol-20-one, pregnanediol, 3,20-pregnanedione, 4-pregnene-20,21-diol-3,11-dione, 4-pregnene-11β, 17α,20β,21-tetrol-3-one, 4-pregnene-17α,20β,21-triol-3, 11-dione, 4-pregnene-17α,20β,21-triol-3-one, and pregnenolone.

The drug dimers useful in making the articles of the disclosure can have any of formulas (A-I)-(LXXV), described herein.

Steroid Homodimers

The disclosure features homodimers of the formula (I):

$$D1-L-D2 \qquad (A\text{-}VIII)$$

or a pharmaceutically acceptable salt thereof, wherein D1 and D2 are radicals formed from the same steroid. L can be covalently linked to D1 and to D2 via one or more ester, carbonate, carbonate ester, or anhydride linkages. Ester, carbonate, carbonate ester, or anhydride linkages formed from a functional group on D1 and D2 can be selected from, e.g., hydroxyl or carboxy. For example, L can include the radical —C(O)—($R^4$)—C(O)—, —C(O)—OC(O)—($R^4$)—C(O)O—C(O)—, or —O—($R^4$)—O—, where $R^4$ is a radical of a polyol and includes at least one free hydroxyl group or $R^4$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—, and q, r, and s are integers from 1 to 10 (e.g., 1 to 10, 1 to 5, or 5 to 10). The homodimer can be further described by one of formulas (II)-(LXXV), below.

In some embodiments, the steroid is an anabolic steroid and the drug dimer is further described by the formula (II):

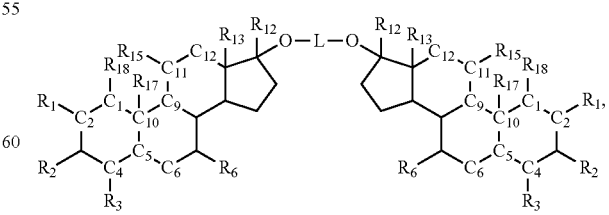

(II)

wherein the bond between $C_1$ and $C_2$, $C_4$ and $C_5$, $C_5$ and $C_6$, $C_9$ and $C_{10}$, and $C_{11}$ and $C_{12}$ is a single or a double bond; $R_1$ represents H, CH$_3$, or HC(O); $R_2$ represents =O, OH, or H;

or $R_1$ and $R_2$ taken together with carbons to which they are attached form an isoxazole; $R_3$ represents H, a halogen atom, or OH; $R_6$ represents H or $CH_3$; $R_{12}$ represents H, $CH_3$, or $CH_3CH_2$; $R_{13}$ represents $CH_3$ or $CH_3CH_2$; $R_{15}$ represents H or OH; $R_{17}$ represents H or $CH_3$; $R_{18}$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (II) can be formed from an anabolic steroid selected from the group consisting of androisoxazole, androstenediol, bolandiol, bolasterone, clostebol, ethylestrenol, formyldienonone, 4-hydroxy-19-nortestosterone, methandriol, methenolone, methyltrienolone, nandrolone, norbolethone, oxymesterone, stenbolone, and trenbolone.

In certain embodiments, the steroid is an anabolic steroid and the drug dimer is further described by the formula (III):

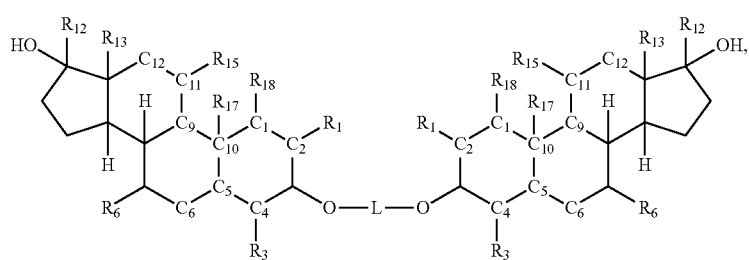

(III)

wherein the bond between $C_1$ and $C_2$, $C_4$ and $C_5$, $C_5$ and $C_6$, $C_9$ and $C_{10}$, and $C_{11}$ and $C_{12}$ is a single or a double bond; $R_1$ represents H, $CH_3$, or HC(O); $R_3$ represents H, a halogen atom, or OH; $R_6$ represents H or $CH_3$; $R_{12}$ represents H, $CH_3$, or $CH_3CH_2$; $R_{13}$ represents $CH_3$ or $CH_3CH_2$; $R_{15}$ represents H or OH; $R_{17}$ represents H or $CH_3$; $R_{18}$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (III) can be formed from an anabolic steroid selected from the group consisting of androstenediol, bolandiol, bolasterone, clostebol, formyldienonone, 4-hydroxy-19-nortestosterone, methandriol, methenolone, methyltrienolone, nandrolone, norbolethone, oxymesterone, stenbolone, and trenbolone.

In particular embodiments, the steroid is an anabolic steroid and the drug dimer is further described by the formula (IV):

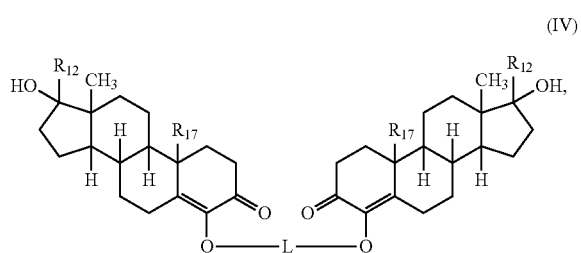

(IV)

wherein $R_{12}$ represents H or $CH_3$; $R_{17}$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_2$-alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (IV) can be formed from an anabolic steroid selected from 4-hydroxy-19-nortestosterone or oxymesterone.

In certain embodiments, the steroid is an androgenic steroid and the drug dimer is further described by the formula (V):

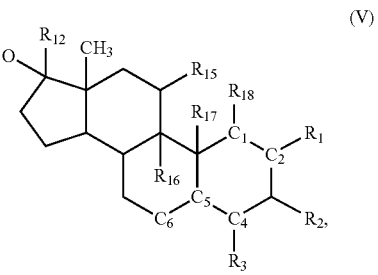

(V)

wherein the bond between $C_1$ and $C_2$, $C_4$ and $C_5$, and $C_5$ and $C_6$ is a single or a double bond; $C_2$ is O, C or $CH_2$; $R_1$ represents H, —CHOH, or is absent; $R_2$ represents =O or OH; or $R_1$ and $R_2$ taken together with carbons to which they are attached form a pyrazole; $R_3$ represents H or OH; $R_{12}$ represents H, $CH_3$, optionally substituted alkynylene, $C_{1-6}$ alkoxy, or $CH_3CH_2$; $R_1$ represents H or OH; $R_{16}$ represents H or a halogen atom; $R_{17}$ represents H or $CH_3$; $R_{18}$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (V) can be formed from an androgenic steroid selected from the group consisting of boldenone, fluoxymesterone, mestanolone, mesterolone, methandrostenolone, 17-methyltestosterone, 17-α-methyltestosterone 3-cyclopentyl enol ether, norethandrolone, normethandrone, oxandrolone, oxymesterone, oxymetholone, prasterone, stanlolone, stanozolol, testosterone, testosterone enanthate tiomesterone dehydroepiandrosterone (DHEA), androstenedione, androstenediol, androsterone, and dihydrotestosterone (DHT).

In particular embodiments, the steroid is an androgenic steroid and the drug dimer is further described by the formula (VI):

wherein the bond between $C_1$ and $C_2$, $C_4$ and $C_5$, and $C_5$ and $C_6$ is a single or a double bond; $C_2$ is O, C or $CH_2$; $R_1$ represents H, —CHOH, or is absent; $R_3$ represents H or OH; $R_{11}$ represents H, OH, $CH_3$, optionally substituted alkynylene, $CH_3CH_2$, =O, —OC(O)$CH_2CH_3$, or is absent; $R_{12}$ represents H, OH, $CH_3$, optionally substituted alkynylene, $CH_3CH_2$, =O, —OC(O)$CH_2CH_3$, or is absent; $R_{15}$ represents H or OH; $R_{16}$ represents H or a halogen atom; $R_{17}$ represents H or $CH_3$; $R_{18}$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms.

The drug dimer of formula (VI) can be formed from an androgenic steroid selected from the group consisting of boldenone, fluoxymesterone, mestanolone, mesterolone, methandrolone, 17-methyltestosterone, norethandrolone, normethandrone, oxandrolone, oxymesterone, oxymetholone, prasterone, stanlolone, testosterone, testosterone proprionate, testosterone enanthate tiomesterone dehydroepiandrosterone (DHEA), androstenedione, androstenediol, androsterone, and dihydrotestosterone (DHT).

In certain embodiments, the steroid is an androgenic steroid and the drug dimer is further described by formula (VII):

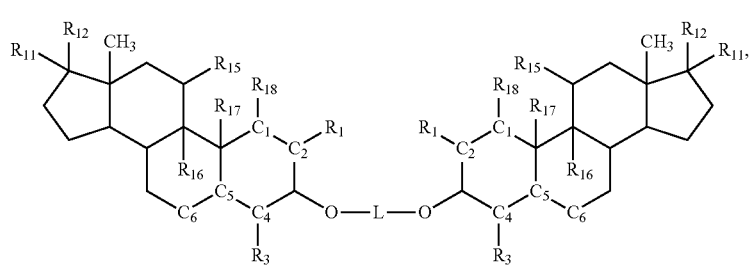

(VI)

(VII)

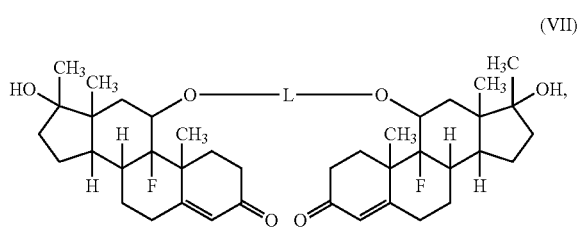

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (VII) can be formed from the androgenic steroid fluoxymesterone.

In particular embodiments, the steroid is an androgenic steroid and the drug dimer is further described by the formula (VIII):

(VIII)

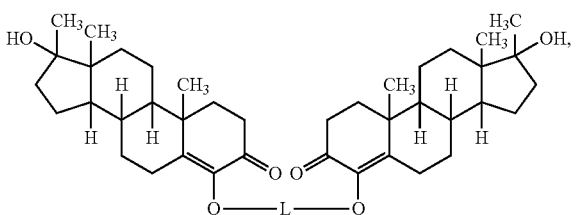

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (VIII) can be formed from the androgenic steroid oxymesterone.

In some embodiments, the steroid is an androgenic steroid and the drug dimer is further described by the formula (IX):

(IX)

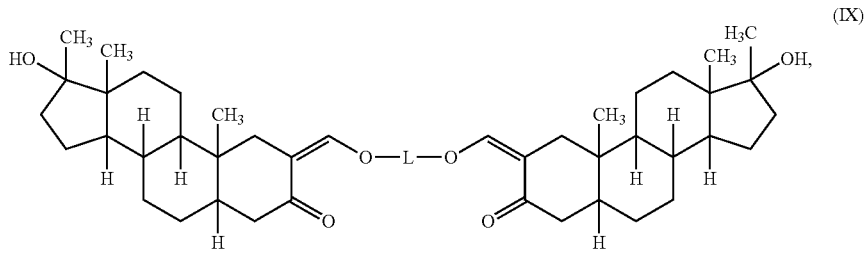

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (IX) can be formed from the androgenic steroid oxymetholone.

In particular embodiments, the steroid is a progestin steroid and the drug dimer is further described by the formula (X):

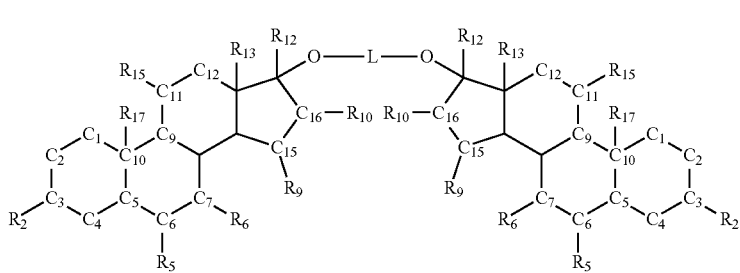

(X)

wherein the bond between $C_1$ and $C_{10}$, $C_2$ and $C_3$, $C_3$ and $C_4$, $C_4$ and $C_5$, $C_5$ and $C_6$, $C_6$ and $C_7$, $C_5$ and $C_{10}$, $C_9$ and $C_{10}$, $C_{11}$ and $C_{12}$, $C_{15}$ and $C_{16}$ is a single or a double bond; $R_2$ represents H, =O, OH, —NOH, or $C_{1-6}$ alkoxy; $R_5$ represents H, $CH_3$, or a halogen atom; $R_6$ represents H or $CH_3$; or $R_5$ and $R_6$ taken together with carbons to which they are attached form a cyclopropane; $R_9$ is H; $R_{10}$ is H or =$CH_2$; or $R_9$ and $R_{10}$ taken together with carbons to which they are attached form a cyclopropane; $R_{12}$ represents H, optionally substituted alkynylene, —$CH_2CH$=$CH_2$, $CH_3$, —C(O)$CH_3$, or —CH=$CH_2$; $R_{13}$ represents $CH_3$ or $CH_2CH_3$; $R_{15}$ represents H or =$CH_2$; $R_{17}$ represents H, $CH_3$, or is absent; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (X) can be formed from a progestin steroid selected from the group consisting of norethisterone, gestodene, levonorgestrel, allylestrenol, anagestone, desogestrel, dimethisterone, dydrogesterone, ethisterone, ethynodiol, etonogestrel, gestodene, ethinylestradiol, 17-hydroxy-16-methylene-progesterone, 17 alpha-hydroxyprogesterone, lynestrenol, medroxyprogesterone, melengestrol, norethindrone, norethynodrel, norgesterone, gestonorone, norethisterone, norgestrel, levonorgestrel, norgestrienone, pentagestrone, 7-methyl-19-testosterone (MENT), norelgestromin, tibolone, and megestrol.

In certain embodiments, the steroid is a progestin steroid and the drug dimer is further described by the formula (XI):

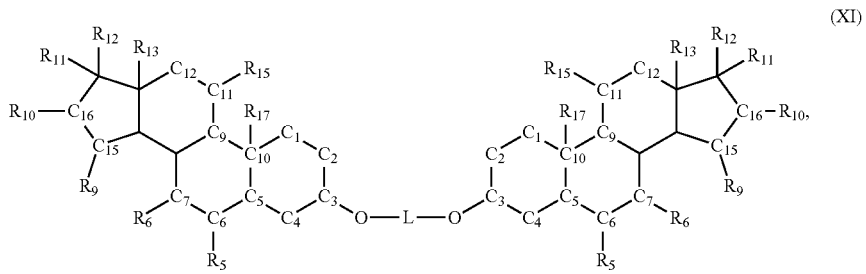

(XI)

wherein the bond between $C_1$ and $C_{10}$, $C_2$ and $C_3$, $C_4$ and $C_5$, $C_6$ and $C_7$, $C_5$ and $C_{10}$, $C_9$ and $C_{10}$, $C_{11}$ and $C_{12}$, $C_{15}$ and $C_{16}$ is a single or a double bond; $R_5$ represents H, $CH_3$, or a halogen atom; $R_6$ represents H or $CH_3$; or $R_5$ and $R_6$ taken together with carbons to which they are attached form a cyclopropane; $R_9$ is H; $R_{10}$ is H or =$CH_2$; or $R_9$ and $R_{10}$ taken together with carbons to which they are attached form a cyclopropane; $R^{11}$ represents H, OH, optionally substituted alkynylene, —C(O)$CH_3$, —$CH_2CH$=$CH_2$, a halogen atom, —CH=$CH_2$, —OC(O)$CH_3$, $CH_3$, —C(O)C(OH)$CH_3$; $R_{12}$ represents H, OH, optionally substituted alkynylene, —C(O)$CH_3$, —$CH_2CH$=$CH_2$, a halogen atom, —CH=$CH_2$, —OC(O)$CH_3$, $CH_3$, —C(O)C(OH)$CH_3$; or $R_{11}$ and $R_{12}$ together with carbon to which they are attached form a lactone; $R_{13}$ represents $CH_3$ or $CH_2CH_3$; $R_{15}$ represents H or =$CH_2$; $R_{17}$ represents H, $CH_3$, or is absent; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XI) can be formed from a progestin steroid selected from the group consisting of norethisterone, norethisterone acetate, gestodene, levonorgestrel, dimethisterone, dydrogesterone, ethisterone, ethynodiol, etonogestrel, gestodene, ethinylestradiol, haloprogesterone, 17-hydroxy-16-methylene-progesterone, 17 alpha-hydroxy-progesterone, medroxyprogesterone, melengestrol, norethindrone, norethynodrel, norgesterone, gestonorone, norethisterone, norgestimate, norgestrel, levonorgestrel, norgestrienone, 7-methyl-19-testosterone (MENT), norelgestromin, trimigestone, drospirenone, tibolone, and megestrol.

In some embodiments, the steroid is a progestin steroid and the drug dimer is further described by the formula (XII):

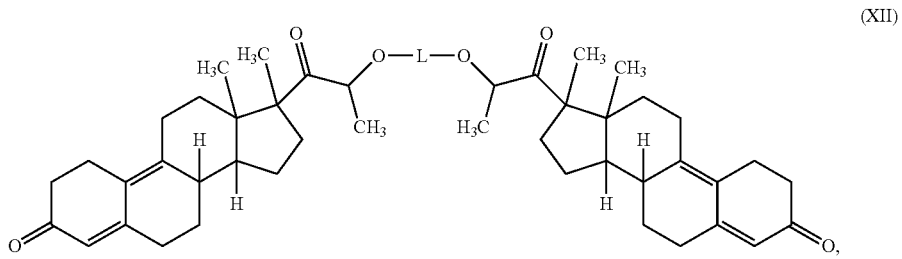
(XII)

Wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XII) can be formed from the progestin steroid trimigestone.

In particular embodiments, the steroid is an estrogen steroid and the drug dimer is further described by the formula (XIII):

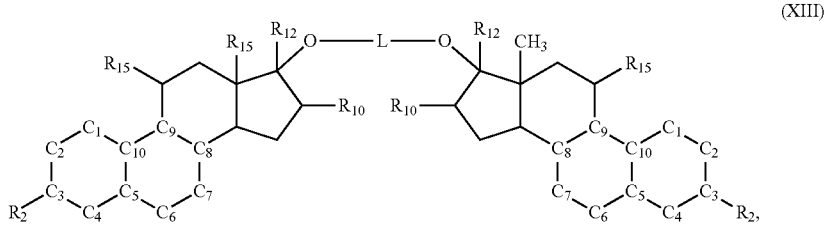
(XIII)

wherein the bond between $C_1$ and $C_2$, $C_1$ and $C_{10}$, $C_2$ and $C_3$, $C_3$ and $C_4$, $C_4$ and $C_5$, $C_6$ and $C_7$, $C_8$ and $C_{10}$, $C_7$ and $C_8$, and $C_8$ and $C_9$ is a single or a double bond; $R_2$ represents OH, —OC(O)Ph, or $C_{1-6}$ alkoxy; $R_{10}$ represents H or OH; $R_{12}$ represents H, optionally substituted alkynylene; $R_{15}$ represents H or $C_{1-6}$ alkoxy; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XIII) can be formed from an estrogen steroid selected from the group consisting of estrogen, eguilenin, equilin, 17β-estradiol, estradiol benzoate, estriol, ethinyl estradiol, mestranol, moxestrol, mytatrienediol, quinestradiol, and quinestrol.

In some embodiments, the steroid is an estrogen steroid and the drug dimer is further described by the formula (XIV):

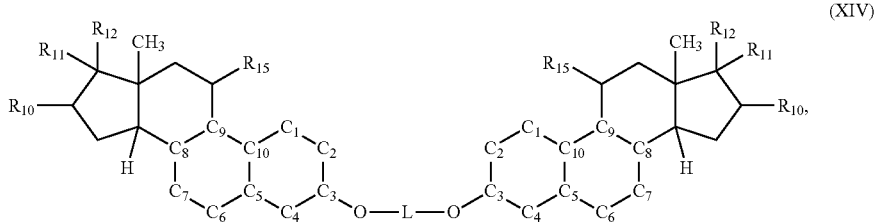

(XIV)

wherein the bond between $C_1$ and $C_2$, $C_1$ and $C_{10}$, $C_2$ and $C_3$, $C_3$ and $C_4$, $C_4$ and $C_5$, $C_6$ and $C_7$, $C_8$ and $C_{10}$, $C_7$ and $C_8$, and $C_8$ and $C_9$ is a single or a double bond; $R_{10}$ represents H or OH; $R_{11}$ represents H, OH, optionally substituted alkynylene, =O, or is absent; $R_{12}$ represents H, OH, optionally substituted alkynylene, =O, or is absent; $R_{15}$ represents H or $C_{1-6}$ alkoxy; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2H_2CHHCH_2H_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XIV) can be formed from an estrogen steroid selected from the group consisting of estrogen, eguilenin, equilin, 17β-estradiol, estriol, ethinyl estradiol, and moxestrol.

In some embodiments, the steroid is an estrogen steroid and the drug dimer is further described by the formula (XV):

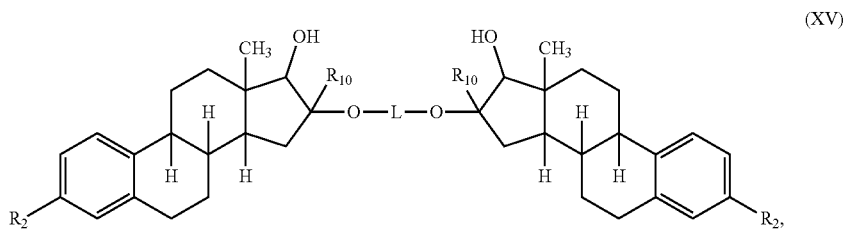

(XV)

wherein $R_2$ represents OH or $C_{1-6}$ alkoxy; $R_{10}$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XV) can be formed from an estrogen steroid selected from the group consisting of estriol, mytatrienediol, and quinestradiol.

In particular embodiments, the steroid is a cancer treatment steroid and the drug dimer is further described by the formula (XVI):

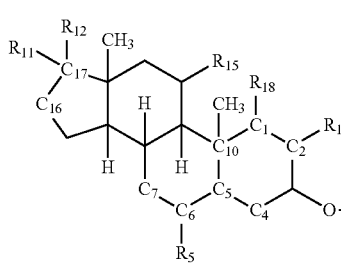
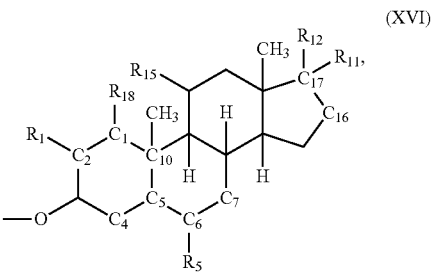

(XVI)

wherein the bond between $C_1$ and $C_2$, $C_4$ and $C_5$, $C_5$ and $C_6$, $C_6$ and $C_7$, and $C_{16}$ and $C_{17}$ is a single or a double bond; $C_4$ is NH, CH, or $CH_2$; $R_1$ represents H; $R_5$ represents H or a halogen atom; $R_{11}$ represents H, optionally substituted heteroaryl, —C(O)$C_{1-6}$ alkyl, —C(O)O$C_{1-6}$ alkyl, or —C(O)NHR, wherein R is optionally substituted alkyl or aryl; $R_{12}$ represents H, optionally substituted heteroaryl, —C(O)$C_{1-6}$ alkyl, —C(O)O$C_{1-6}$ alkyl, or —C(O)NHR, wherein R is optionally substituted alkyl or aryl; $R_{18}$ represents H; or $R_1$ and $R_{18}$ taken together with carbons to which they are attached form a cyclopropane; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2$O)$_n$$CH_2CH_2$O—, —O($CH_2CH_2CH_2CH_2$O)$_m$$CH_2CH_2CH_2CH_2$O—, or —O($CH_2CH(CH_3)$O)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XVI) can be formed from a cancer treatment steroid selected from the group consisting of abiraterone, cyproterone acetate, dutasteride, finasteride, and galeterone.

In some embodiments, the steroid is an antibiotic steroid and the drug dimer is further described by the formula (XVII):

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2$O)$_n$$CH_2CH_2$O—, —O($CH_2CH_2CH_2CH_2$O)$_m$$CH_2CH_2CH_2CH_2$O—, or —O($CH_2CH(CH_3)$O)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XVII) can be formed from the steroid antibiotic fusidic acid.

In particular embodiments, the steroid is an antibiotic steroid and the drug dimer is further described by the formula (XVIII):

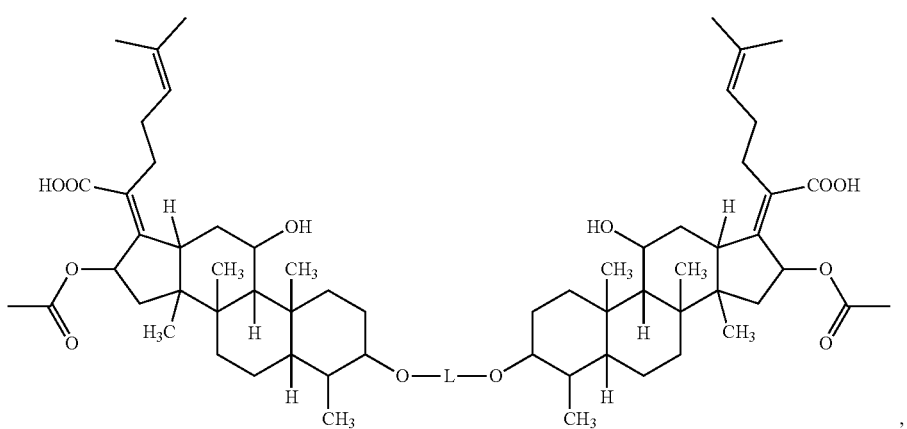

(XVII)

(XVIII)

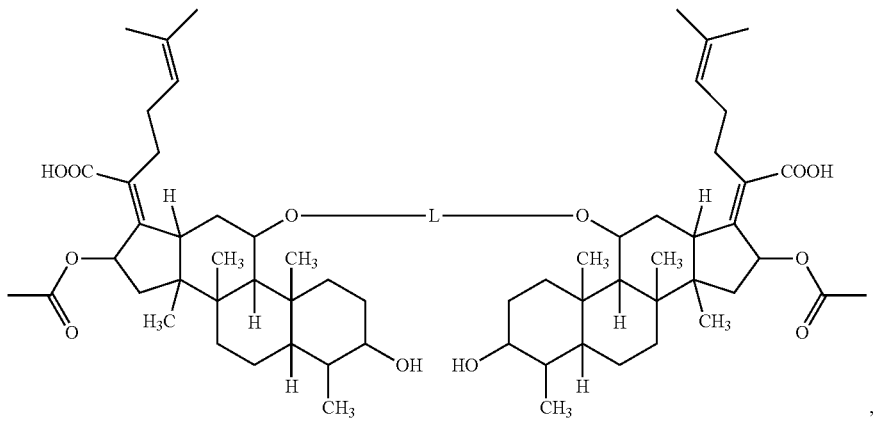

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XVIII) can be formed from the steroid antibiotic fusidic acid.

In some embodiments, the steroid is a benign steroid and the drug dimer is further described by the formula (XIX):

(XIX)

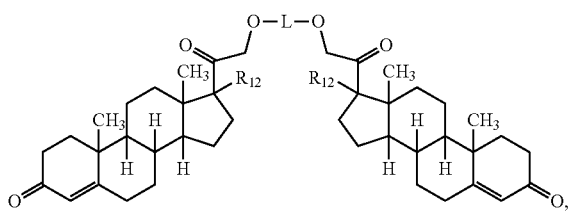

wherein R$_{12}$ is H or OH; L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched C$_{2-20}$ alkenylene, a linear or branched C$_{2-20}$ alkynylene, a C$_{5-10}$ arylene, a cyclic system of 3 to 10 atoms. The drug dimer of formula (XIX) can be formed from a benign steroid selected from 11-deoxycortisol and 11-deoxycorticosterone.

In particular embodiments, the steroid is a benign steroid and the drug dimer is further described by the formula (XX):

(XX)

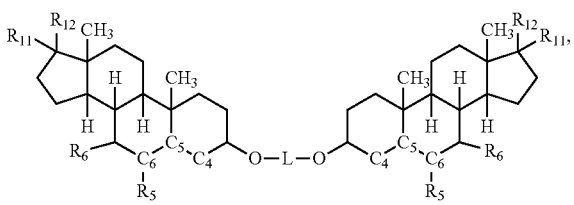

wherein the bond between C$_4$ and C$_5$, and C$_5$ and C$_6$ is a single or a double bond; R$_5$ represents H or C$_{1-6}$ alkyl; R$_6$ represents H or OH; R$_{11}$ represents H, OH, —C(O)C$_{1-6}$ alkyl, —C(O)CH$_2$OH, or —CH(CH$_3$)CH$_2$CH$_2$C(O)OH; R$_{12}$ represents H, OH, —C(O)C$_{1-6}$ alkyl, —C(O)CH$_2$OH, or —CH(CH$_3$)CH$_2$CH$_2$C(O)OH; L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XX) can be formed from a benign steroid selected from the group consisting of cholesterol, 11-deoxycortisol, 11-deoxycorticosterone, pregnenolone, cholic acid, chenodeoxycholic acid, ursodeoxycholic acid, and obeticholic acid.

In some embodiments, the steroid is a benign steroid and the drug dimer is further described by the formula (XXI):

(XXI)

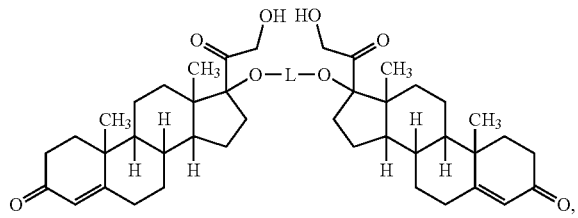

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XXI) can be formed from a benign steroid including 11-deoxycortisol.

In particular embodiments, the steroid is a benign steroid and the drug dimer is further described by the formula (XXII):

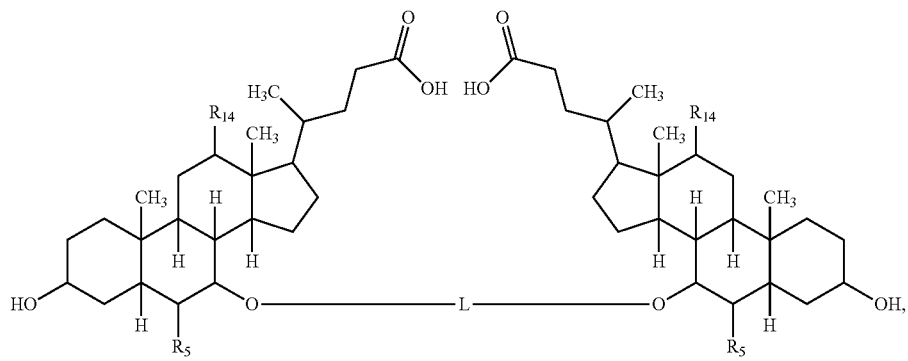

(XXII)

wherein R$_5$ represents H or CH$_2$CH$_3$; R$_{14}$ represents H or OH; L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XXII) can be formed from a benign steroid selected from the group consisting of cholic acid, chenodeoxycholic acid, ursodeoxycholic acid, and obeticholic acid.

In some embodiments, the steroid is a benign steroid and the drug dimer is further described by the formula (XXIII):

(XXIII)

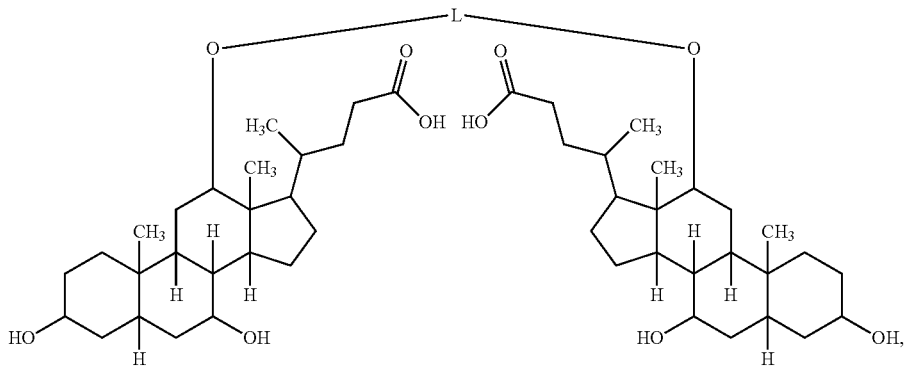

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXIII) can be formed from the benign steroid cholic acid.

In particular embodiments, the steroid is a glucocorticoid steroid and the drug dimer is further described by the formula (XXIV):

(XXIV)

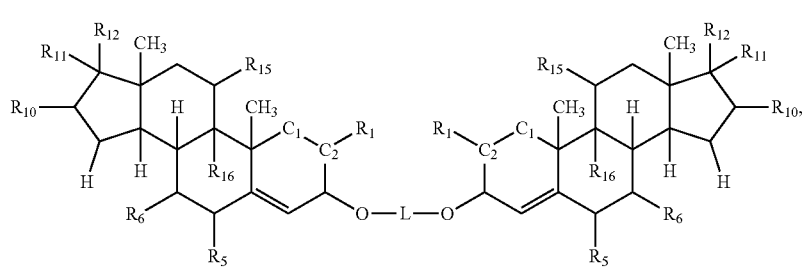

wherein the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =$CH_2$; $R_{11}$ represents H, OH, $C_{1-6}$ alkyl, optionally substituted —C(O)$C_{1-6}$ alkyl, —C(O)$CH_2OC(O)C_{1-6}$ alkyl, optionally substituted —OC(O)$C_{1-6}$ alkyl, —OC(O)Ph, —OC(O)heterocyclyl, —$CH_2C(O)CH_2OH$, —C(O)C(O)OH, —C(O)C(O)OC$_{1-6}$ alkyl, —C(O)SCH$_2$F, or —OC(O)OC$_{1-6}$ alkyl; or $R_{10}$ and $R_{11}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O)$CH_2OC(O)C_{1-6}$ alkyl, optionally substituted —OC(O)$C_{1-6}$ alkyl, —OC(O)Ph, —OC(O)heterocyclyl, —$CH_2C(O)$ $CH_2OH$, —C(O)C(O)OH, —C(O)C(O)OC$_{1-6}$ alkyl, —C(O)SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; $R_{15}$ represents H, OH, =O, or a halogen atom; $R_{16}$ represents H or a halogen atom; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXIV) can be formed from a glucocorticoid steroid selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cortisol, cortisone, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, halcinonide, halometasone, hydrocortisone, hydrocortisone acetate, hydrocortisone aceponate, hydrocortisone buteprate, hydrocortisone butyrate, loteprednol, meprednisone, 6α-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol.

In some embodiments, the steroid is a glucocorticoid steroid and the drug dimer is further described by the formula (XXV):

arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$)$_m$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXV) can be formed from a glucocorticoid steroid selected from the group consisting of alclometasone, beclometasone, betamethasone, betamethasone benzoate, betamethasone valerate, budesonide, cortisol, cortisone, desonide, desoximetasone, desoxycortone,

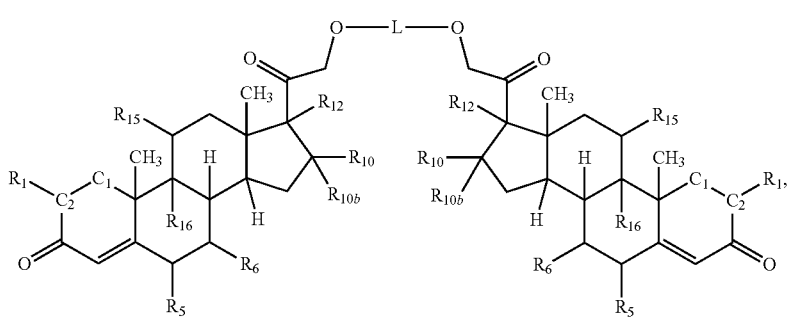

(XXV)

wherein the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =CH$_2$; $R_{10b}$ represents H, $C_{1-6}$ alkyl, OH, =CH$_2$, or be absent; $R_{12}$ represents H, OH, optionally substituted —C(O)$C_{1-6}$ alkyl, —C(O)CH$_2$OC(O)$C_{1-6}$ alkyl, optionally substituted —OC(O)$C_{1-6}$ alkyl, or —OC(O)Ph; or $R_{10}$ and $R_{11}$ taken together with carbons to which they are attached form an optionally substituted cyclic acetal or optionally substituted heterocyclyl; $R_{15}$ represents H, OH, =O, or a halogen atom; $R_{16}$ represents H or a halogen atom; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ desoxymethasone, dexamethasone, diflorasone, diflucortolone, difluorocortolone, fluclorolone, fluclorolone acetonide, fludroxycortide, flumetasone, flumethasone, flunisolide, flunisolide, fluocinolone, fluocinolone acetonide, fluocortolone, fluorocortisone, fluprednidene, fluprednisolone, halometasone, hydrocortisone, hydrocortisone butyrate, meprednisone, 6α-methylprednisolone, methylprednisolone, paramethasone, prednisolone, prednisone, prednylidene, triamcinolone, and triamcinolone acetonide.

In particular embodiments, the steroid is a glucocorticoid steroid and the drug dimer is further described by the formula (XXVI):

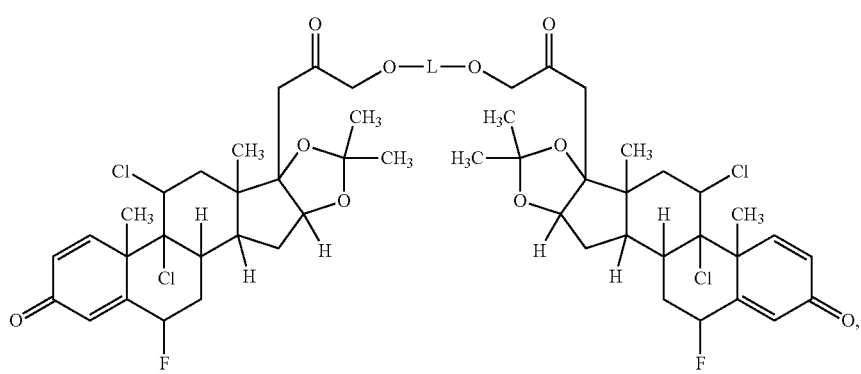

(XXVI)

wherein L is —C(O)O—($R^A$)—OC(O)—, —C(O)—OC(O)—($R^A$)—C(O)O—C(O)—, or —C(O)—($R^B$)—C(O)

O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXVI) can be formed from the glucocorticoid steroid fluclorolone acetonide.

In some embodiments, the steroid is a glucocorticoid steroid and the drug dimer is further described by the formula (XXVII):

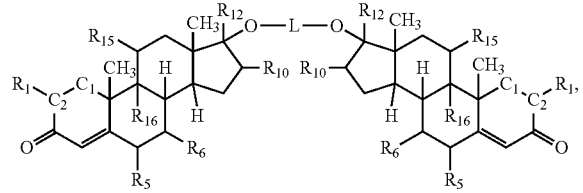

(XXVII)

wherein the bond between $C_1$ and $C_2$ is a single or a double bond; $R_1$ represents H or a halogen atom; $R_5$ represents H, a halogen atom, or $CH_3$; $R_6$ represents H, a halogen atom; $R_{10}$ represents H, OH, $CH_3$, or =$CH_2$; $R_{12}$ represents optionally substituted —C(O)$C_{1-6}$ alkyl, —C(O)$CH_2$OC(O)$C_{1-6}$ alkyl, or —C(O)$SCH_2F$; $R_{15}$ represents OH or =O; $R_{16}$ represents H or a halogen atom; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXVII) can be formed from a glucocorticoid steroid selected from the group consisting of alclometasone, beclometasone, betamethasone, clobetasol, clobetasone, cortisol, cortisone, dexamethasone, diflorasone, fluclorolone, flumetasone, flumethasone, flumethasone pivalate, fluocinolone, fluorocortisone, fluorometholone, fluperolone, fluprednidene, fluprednidene acetate, fluprednisolone, fluticasone, halometasone, hydrocortisone, hydrocortisone acetate, hydrocortisone butyrate, meprednisone, 6α-methylprednisolone, methylprednisolone, methylprednisolone acetate, mometasone, paramethasone, prednisolone, prednisone, prednylidene, tixocortol, triamcinolone, and ulobetasol.

In particular embodiments, the steroid is a glucocorticoid steroid and the drug dimer is further described by the formula (XXVIII):

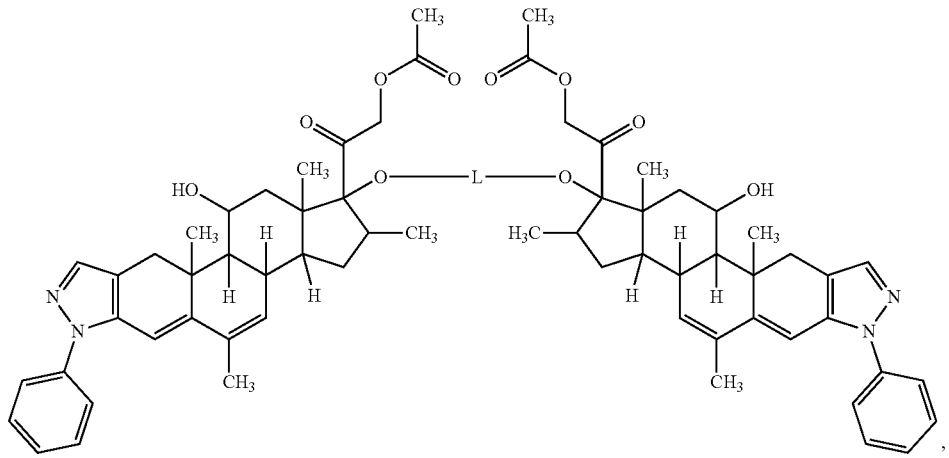

(XXVIII)

1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXVIII) can be formed from the glucocorticoid steroid cortivazol.

In some embodiments, the steroid is a glucocorticoid steroid and the drug dimer is further described by the formula (XXIX):

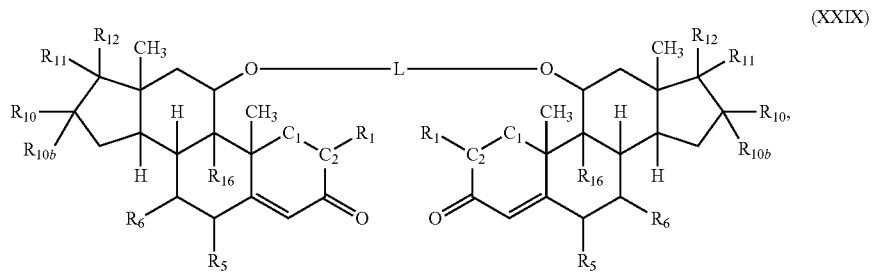

(XXIX)

wherein the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =CH$_2$; $R_{10b}$ represents H, $C_{1-6}$ alkyl, OH, or =CH$_2$, or is absent; $R_{11}$ represents H, OH, $C_{1-6}$ alkyl, optionally substituted —C(O) $C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O) OC$_{1-6}$ alkyl, —C(O)SCH$_2$F, or —OC(O)OC$_{1-6}$ alkyl; or $R_{10}$ and $R_{11}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O) CH$_2$OC(O)$C_{1-6}$ alkyl, optionally substituted —OC(O)$C_{1-6}$ alkyl, —OC(O)Ph, —OC(O)heterocyclyl, —CH$_2$C(O) CH$_2$OH, —C(O)C(O)OH, —C(O)C(O)OC$_{1-6}$ alkyl, —C(O) SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; $R_{16}$ represents H or a halogen atom; L is —C(O)O—(R$^A$)—OC(O)—, —C(O)—OC(O)—(R$^A$)—C (O)O—C(O)—, or —C(O)—(R$^B$)—C(O)O—(R$^A$)—OC (O)—(R$^B$)—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O, —O(CH$_2$CH$_2$CH$_2$CH$_2$O)$_m$ CH$_2$CH$_2$CH$_2$CH$_2$O—, or —O(CH$_2$CH(CH$_3$)O)$_p$CH$_2$CH (CH$_3$)O—; n, m, and p are integers from 1 to 10; and each R$^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXIX) can be formed from a glucocorticoid steroid selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cortisol, cortisone, cortivazol, deflazacort, desonide, desoximetasone, desoxymethasone, dexamethasone, diflorasone, diflorasone diacetate, diflucortolone, diflucortolone valerate, difluorocortolone, difluprednate, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6α-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol.

In particular embodiments, the steroid is a glucocorticoid steroid and the drug dimer is further described by the formula (XXX):

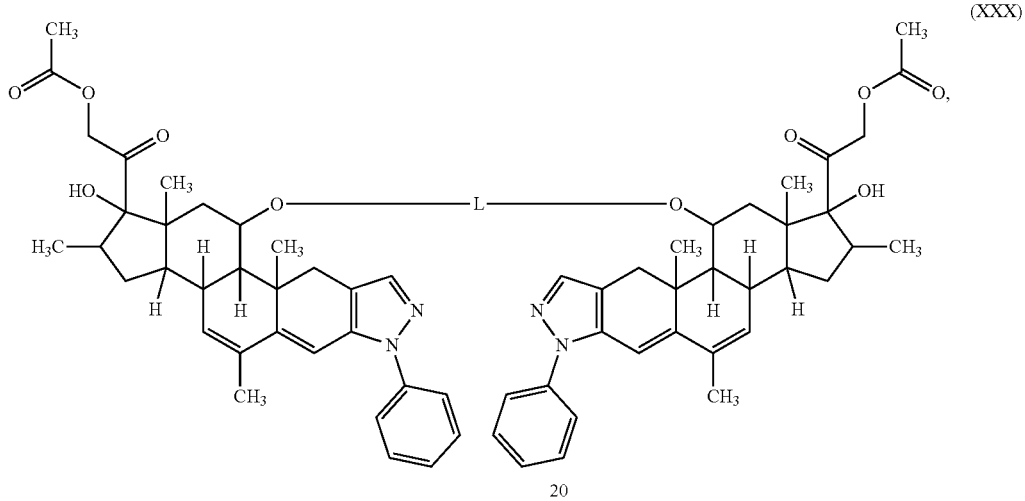

Wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XXX) can be formed from the glucocorticoid steroid cortivazol.

In some embodiments, the steroid is a glucocorticoid steroid and the drug dimer is further described by the formula (XXXI):

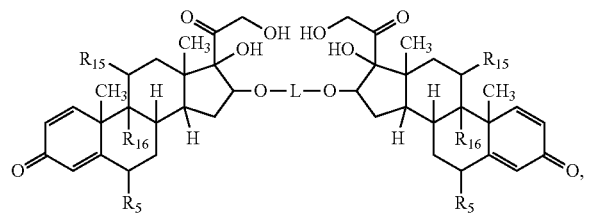

(XXXI)

wherein R$_5$ represents H or a halogen atom; R$_{15}$ represents a halogen atom or OH; R$_{16}$ represents H or a halogen atom; L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XXXI) can be formed from a glucocorticoid steroid selected from the group consisting of fluclorolone, fluocinolone, and triamcinolone.

In particular embodiments, the steroid is a glucocorticoid steroid and the drug dimer is further described by the formula (XXXII):

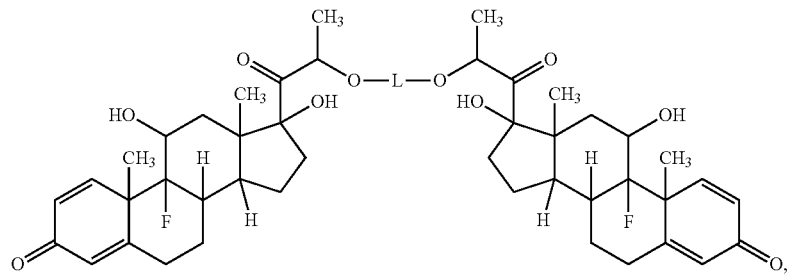

(XXXII)

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XXXII) can be formed from fluperolone.

In some embodiments, the steroid is a glucocorticoid steroid and the drug dimer is further described by the formula (XXXIII):

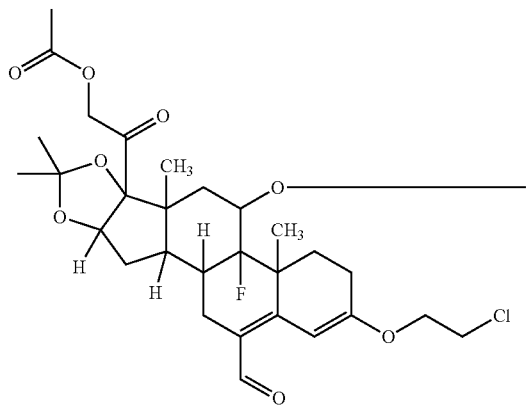
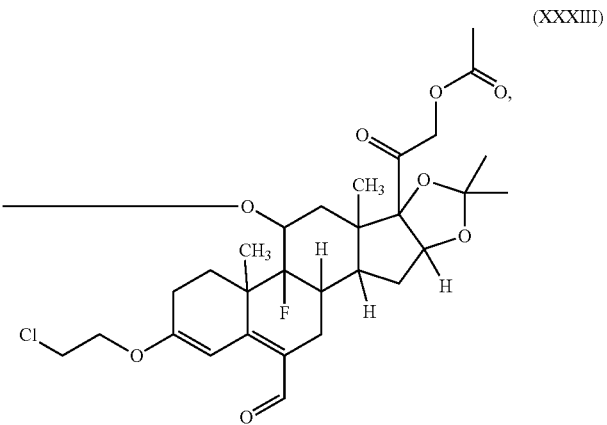

(XXXIII)

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{2-20}$ arylene, a cyclic system of 3 to 10 atoms. The drug dimer of formula (XXXIII) can be formed from formocortal.

In particular embodiments, the steroid is a corticosteroid and the drug dimer is further described by the formula (XXXIV):

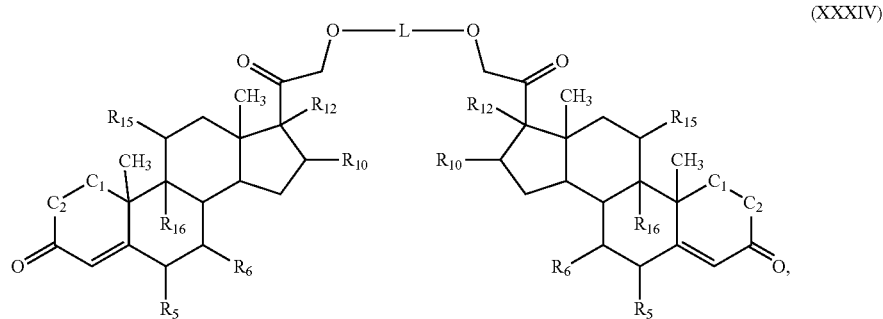

(XXXIV)

wherein the bond between $C_1$ and $C_2$ is a double or a single bond; $R_{16}$ represents H or a halogen atom; $R_5$ represents H, $CH_3$, or a halogen atom; $R_{12}$ represents H or a halogen atom; $R_{15}$ represents =O or OH; $R_{12}$ and $R_{10}$ each, independently, represent —H, $C_{1-10}$ alkyl, —OH, —O-acyl, or $R_{12}$ and $R_{10}$ combine to form a cyclic acetal of formula (XVIII-a) wherein:

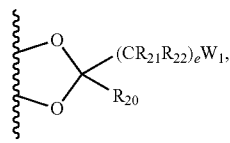

(XXXIV-a)

e is an integer from 0 to 6; $R_{20}$, $R_{21}$, and $R_{22}$ each, independently, represent H or $C_{1-10}$ alkyl; $W_1$ represents H or $CH_3$; L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXXIV) can be formed from a corticosteroid selected from the group consisting of alclometasone, beclomethasone, betamethasone, betamethasone valerate, budesonide, chloroprednisone, clopredenol, corticosterone, cortisone, desonide, desoximerasone, dexamethasone, diflorasone, diflucortolone, enoxolone, flucloronide, flumethasone, flunisolide, fluocinolone acetonide, fluocortolone, fluprednisolone, flurandrenolide, halometasone, hydrocortisone, hydrocortisone butyrate, meprednisone, methylprednicolone, paramethasone, prednisolone, prednisone, predni-val, prednylidene, triamcinolone, and triamcinolone acetonide.

In any of the above formulas (II)—(XXXIV), O—($R^A$)—O can be a radical of a polyol formed from a cyclitol, and sugar alcohol, or glycerin; or O—($R^A$)—O can be a radical formed from an alkane diol (e.g., a $C_{1-10}$ alkane diol), diethylene glycol, triethylene glycol, tetraethylene glycol, or pentaethylene glycol.

In particular embodiments, the steroid is a corticosteroid and the drug dimer is further described by the formula (XXXV):

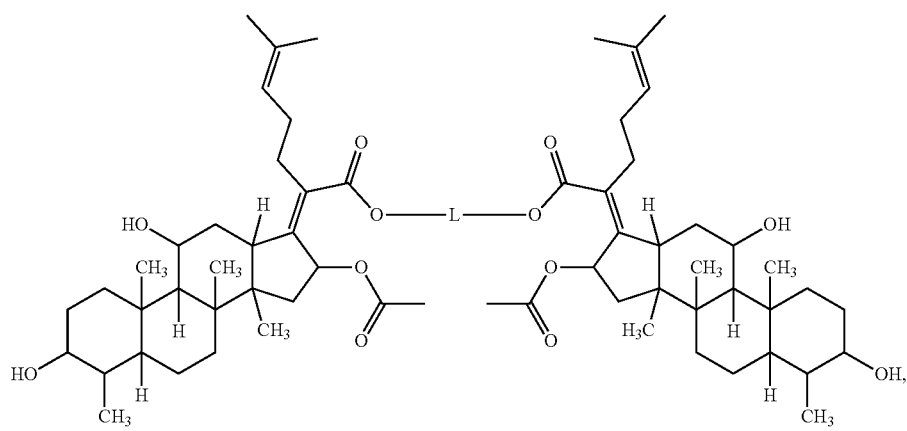

(XXXV)

wherein L is —C(O)—($R^A$)—C(O)—, —($R^A$)—, or —C(O)—O—($R^A$)—O—C(O)— and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms; or L is —O—($R^A$)—O— and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from —O($CH_2CH_2O$)$_n$$CH_2CH_2O$—, —O($CH_2CH_2CH_2CH_2O$)$_m$$CH_2CH_2CH_2CH_2O$—, and —O($CH_2CH(CH_3)O$)$_p$$CH_2CH(CH_3)O$—; and n, m, and p are integers from 1 to 10. The drug dimer of formula (XXXV) can be formed from fusidic acid.

In particular embodiments, the steroid is a corticosteroid and the drug dimer is further described by the formula (XXXVI):

(XXXVI)

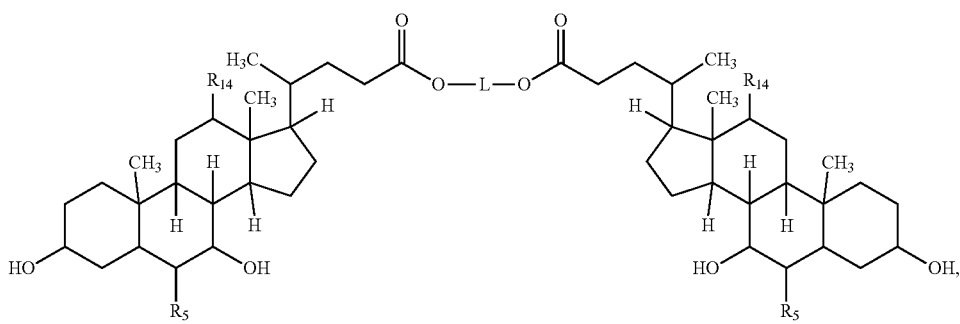

wherein $R_5$ represents H or $C_{1-6}$ alkyl; $R_{14}$ represents H or OH; and L is —C(O)—($R^A$)—C(O)—, —($R^A$)—, or —C(O)—O—($R^A$)—O—C(O)— and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms; or L is —O—($R^A$)—O— and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, and —O(CH$_2$CH(CH$_3$)O)$_p$CH$_2$CH(CH$_3$)O—; and n, m, and p are integers from 1 to 10. The drug dimer of formula (XXXVI) can be formed from chenodeoxycholic acid, ursodeoxycholic acid, or obeticholic acid.

In particular embodiments, the steroid is an anti-angiogenic steroid or an intraocular pressure (IOP) lowering steroid, and the drug dimer is further described by the formula (XXXVII):

(XXXVII)

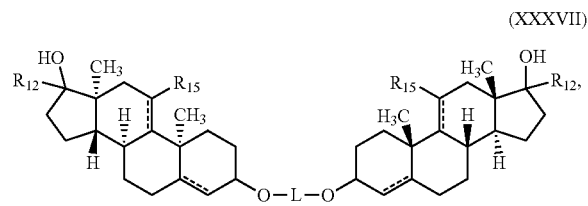

wherein $R_{12}$ represents —C(=O)CH$_2$OC(=O)CH$_3$, —C(=O)CH$_2$OH, or —C(=O)CH$_3$; $R_{15}$ represents H or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXXVII) can be formed from anecortave acetate, anecortave, 11-epicortisol, 17α-hydroxyprogesterone, tetrahydrocortexolone, or tetrahydrocortisol.

In particular embodiments, the steroid is an anti-angiogenic steroid or an intraocular pressure (IOP) lowering steroid, and the drug dimer is further described by the formula (XXXVIII):

(XXXVIII)

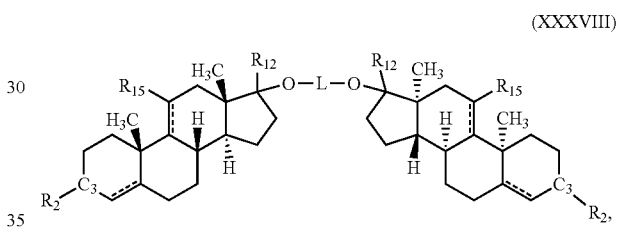

wherein the bond between $C_3$ and $R_2$ is a single or a double bond; $R_2$ represents OH or =O; $R_{12}$ represents —C(=O)CH$_2$OC(=O)CH$_3$, —C(=O)CH$_2$OH, or —C(=O)CH$_3$, $R_{15}$ represents H or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXXVIII) can be formed from anecortave acetate, anecortave, 11-epicortisol, 17α-hydroxyprogesterone, tetrahydrocortexolone, or tetrahydrocortisol.

In particular embodiments, the steroid is an anti-angiogenic steroid or an intraocular pressure (IOP) lowering steroid, and the drug dimer is further described by the formula (XXXIX):

(XXXIX)

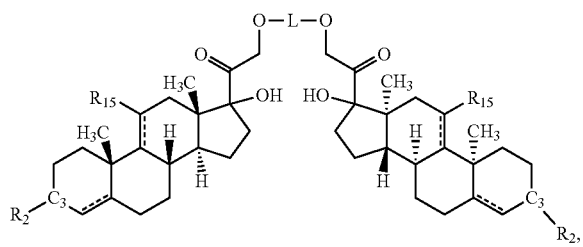

wherein the bond between $C_3$ and $R_2$ is a single or a double bond; $R_2$ represents OH or =O; $R_{15}$ represents H or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XXXIX) can be formed from anecortave, 11-epicortisol, tetrahydrocortexolone, or tetrahydrocortisol.

In particular embodiments, the steroid is an anti-angiogenic steroid or an intraocular pressure (IOP) lowering steroid, and the drug dimer is further described by the formula (XL):

(XL)

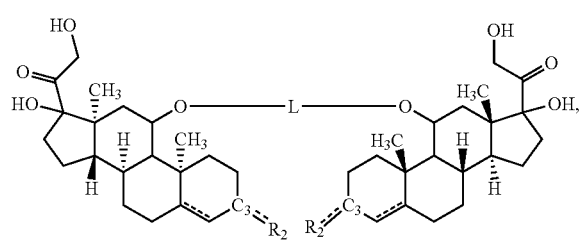

wherein the bond between $C_3$ and $R_2$ is a single or a double bond; $R_2$ represents OH or =O; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XL) can be formed from 11-epicortisol or tetrahydrocortisol.

In particular embodiments, the steroid is a benign steroid and the drug dimer is further described by the formula (XLI):

(XLI)

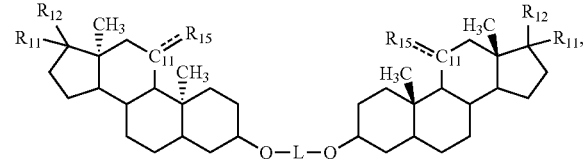

wherein the bond between $C_{11}$ and $R_{15}$ is a single or a double bond; $R_{11}$ represents H, OH, —C(=O)CH$_2$OH, or —C(=O)CH$_3$; $R_{12}$ represents H, OH, —C(=O)CH$_2$OH, or —C(=O)CH$_3$; $R_{15}$ represents H, =O, or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLI) can be formed from tetrahydrocortisone, tetrahydrodeoxycortisol, tetrahydrocorticosterone, 5α-dihydrocorticosterone, or 5α-dihydropregesterone.

In particular embodiments, the steroid is a benign steroid and the drug dimer is further described by the formula (XLII):

(XLII)

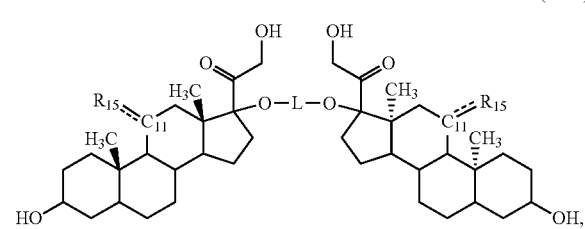

wherein the bond between $C_{11}$ and $R_{15}$ is a single or a double bond; $R_{15}$ represents H or =O; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$O—, or —O(CH$_2$CH(CH$_3$)O)$_p$CH$_2$CH (CH₃)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLII) can be formed from tetrahydrocortisone, or tetrahydrodeoxycortisol.

In particular embodiments, the steroid is a benign steroid and the drug dimer is further described by the formula (XLIII):

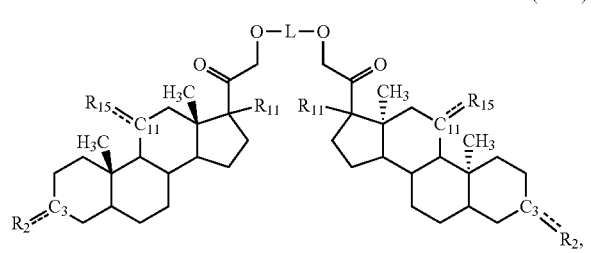

(XLIII)

wherein the bond between $C_3$ and $R_2$, and $C_{11}$ and $R_{15}$ is a single or a double bond; $R_2$ represents OH or =O; $R_{11}$ represents H, or OH; $R_{15}$ represents H, =O, or OH; and L is —C(O)O—$(R^A)$—OC(O)—, —C(O)—OC(O)—$(R^A)$—C(O)O—C(O)—, or —C(O)—$(R^B)$—C(O)O—$(R^A)$—OC(O)—$(R^B)$—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—$(R^A)$—O is a radical of a polyol and includes at least one free hydroxyl group or O—$(R^A)$—O is selected from: —O(CH₂CH₂O)$_n$CH₂CH₂O—, —O(CH₂CH₂CH₂CH₂O)$_m$CH₂CH₂CH₂CH₂O—, or —O(CH₂CH(CH₃)O)$_p$CH₂CH(CH₃)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLIII) can be formed from tetrahydrocortisone, tetrahydrodeoxycortisol, tetrahydrocorticosterone, or 5α-dihydrocorticosterone.

In particular embodiments, the steroid is a benign steroid and the drug dimer is further described by the formula (XLIV):

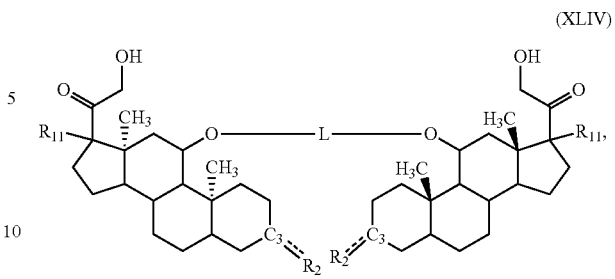

(XLIV)

wherein the bond between $C_3$ and $R_2$ is a single or a double bond; $R_2$ represents OH or =O; $R_{11}$ represents H or OH; and L is —C(O)O—$(R^A)$—OC(O)—, —C(O)—OC(O)—$(R^A)$—C(O)O—C(O)—, or —C(O)—$(R^B)$—C(O)O—$(R^A)$—OC(O)—$(R^B)$—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—$(R^A)$—O is a radical of a polyol and includes at least one free hydroxyl group or O—$(R^A)$—O is selected from: —O(CH₂CH₂O)$_n$CH₂CH₂O—, —O(CH₂CH₂CH₂CH₂O)$_m$CH₂CH₂CH₂CH₂O—, or —O(CH₂CH(CH₃)O)$_p$CH₂CH(CH₃)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLIV) can be formed from tetrahydrocortisone, tetrahydrocorticosterone, or 5α-dihydrocorticosterone.

In particular embodiments, the steroid is a cholic acid-related bile acid steroid and the drug dimer is further described by the formula (XLV):

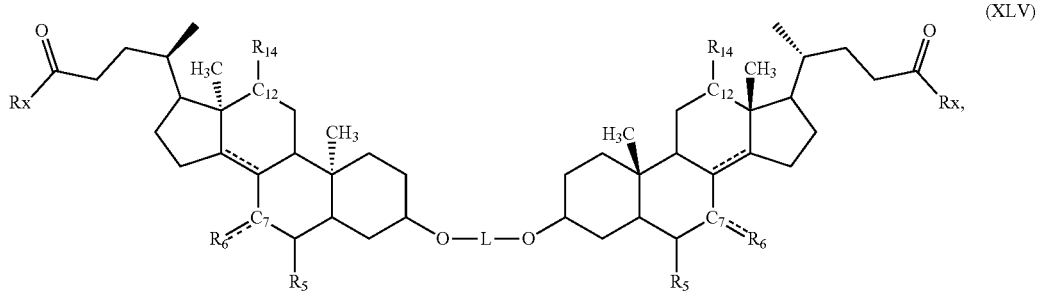

(XLV)

wherein the bond between $C_7$ and $R_6$, and $C_{12}$ and $R_{14}$ is a single or a double bond; Rx represents OH, —NHCH₂C(=O)OH, or —NHCH₂CH₂SO₂OH; $R_2$ represents OH or =O; $R_5$ represents H or OH; $R_6$ represents H, =O, or OH; $R_{14}$ represents H, =O, or OH; and L is —C(O)O—$(R^A)$—OC(O)—, —C(O)—OC(O)—$(R^A)$—C(O)O—C(O)—, or —C(O)—$(R^B)$—C(O)O—$(R^A)$—OC(O)—$(R^B)$—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—$(R^A)$—O is a radical of a polyol and includes at least one free hydroxyl group or O—$(R^A)$—O is selected from: —O(CH₂CH₂O)$_n$CH₂CH₂O—, —O(CH₂CH₂CH₂CH₂O)$_m$CH₂CH₂CH₂CH₂O—, or —O(CH₂CH(CH₃)O)$_p$CH₂CH(CH₃)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLV) can be formed from deoxycholic acid, apocholic acid, dehydrocholic acid, glycochenodeoxycholic acid, glycocholic acid, glycodeoxycholic acid, hyodeoxycholic acid, lithocholic acid, α-muricholic acid, β-muricholic acid, γ-muricholic acid, ω-muricholic acid, taurochenodeoxycholic acid, taurocholic acid, taurodeoxycholic acid, taurolithocholic acid, or tauroursodeoxycholic acid.

In particular embodiments, the steroid is a cholic acid-related bile acid steroid and the drug dimer is further described by the formula (XLVI):

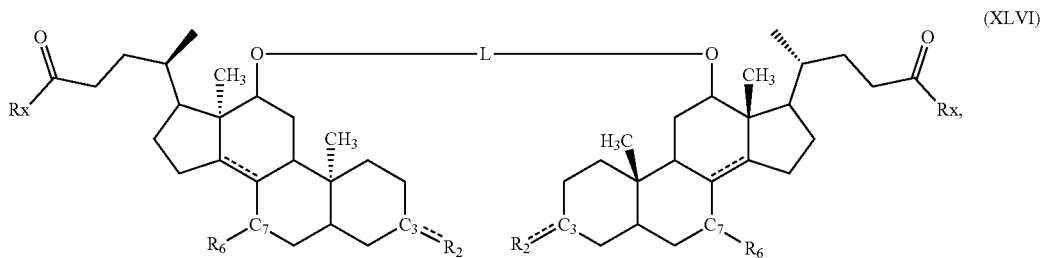

wherein the bond between $C_3$ and $R_2$, and $C_7$ and $R_6$ is a single or a double bond; Rx represents OH, —NHCH$_2$C(=O)OH, or —NHCH$_2$CH$_2$SO$_2$OH; $R_2$ represents OH or =O; $R_6$ represents H, =O, or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLVI) can be formed from deoxycholic acid, apocholic acid, dehydrocholic acid, glycocholic acid, glycodeoxycholic acid, taurocholic acid, or taurodeoxycholic acid.

In particular embodiments, the steroid is a cholic acid-related bile acid steroid and the drug dimer is further described by the formula (XLVII):

wherein $R_6$ represents H or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (XLVII) can be formed from hyodeoxycholic acid, α-muricholic acid, β-muricholic acid, γ-muricholic acid, or ω-muricholic acid.

In particular embodiments, the steroid is a cholic acid-related bile acid steroid and the drug dimer is further described by the formula (XLVIII):

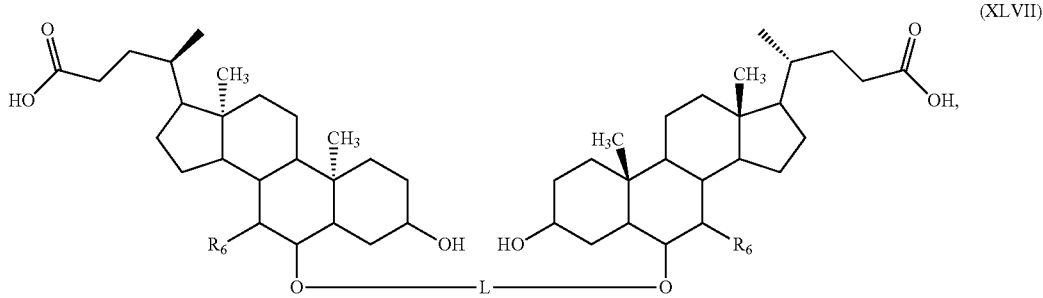

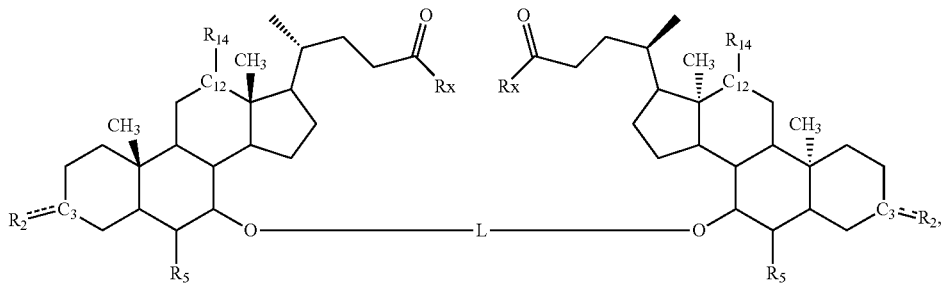
(XLVIII)

wherein the bond between $C_3$ and $R_2$, and $C_{12}$ and $R_{14}$ is a single or a double bond; Rx represents OH, —NHCH$_2$C(=O)OH, or —NHCH$_2$CH$_2$SO$_2$OH; $R_2$ represents OH or =O; $R_5$ represents H or OH; $R_{14}$ represents H, =O, or OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (XLVIII) can be formed from dehydrocholic acid, glycochenodeoxycholic acid, glycocholic acid, α-muricholic acid, β-muricholic acid, γ-muricholic acid, w-muricholic acid, taurochenodeoxycholic acid, taurocholic acid, or tauroursodeoxycholic acid.

In particular embodiments, the steroid is a cholic acid-related bile acid steroid and the drug dimer is further described by the formula (XLIX):

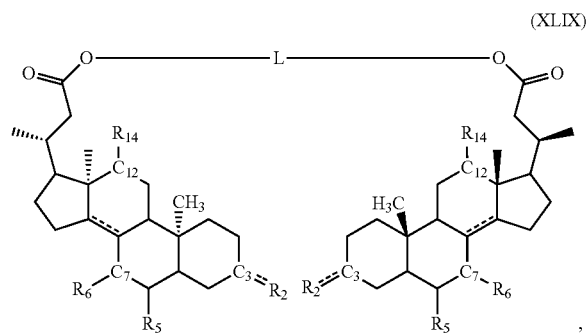
(XLIX)

wherein the bond between $C_3$ and $R_2$, $C_7$ and $R_6$, and $C_{12}$ and $R_{14}$ is a single or a double bond; $R_2$ represents OH or =O; $R_5$ represents H or OH; $R_6$ represents H, =O, or OH; $R_{14}$ represents H, =O, or OH; and L is —C(O)—(R$^A$)—C(O)—, —(R$^A$)—, or —C(O)—O—(R$^A$)—O—C(O)— and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms; or L is —O—(R$^A$)—O— and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, and —O(CH$_2$CH(CH$_3$)O)$_p$CH$_2$CH(CH$_3$)O—; and n, m, and p are integers from 1 to 10. The drug dimer of formula (XLIX) can be formed from deoxycholic acid, apocholic acid, dehydrocholic acid, hyodeoxycholic acid, lithocholic acid, α-muricholic acid, β-muricholic acid, γ-muricholic acid, or ω-muricholic acid.

In particular embodiments, the steroid is a cholic acid-related bile acid steroid and the drug dimer is further described by the formula (L):

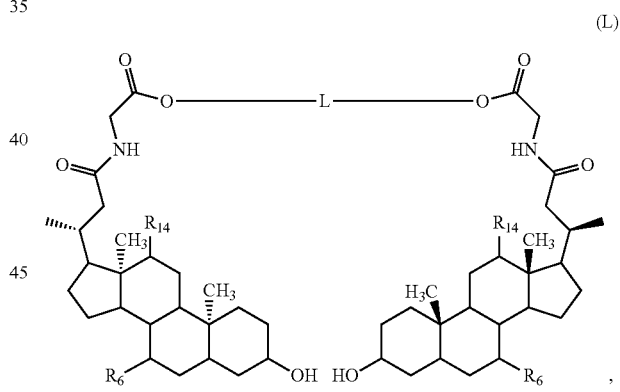
(L)

wherein $R_6$ represents H or OH; $R_{14}$ represents H or OH; and L is —C(O)—(R$^A$)—C(O)—, —(R$^A$)—, or —C(O)—O—(R$^A$)—O—C(O)— and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms; or L is —O—(R$^A$)—O— and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, and —O(CH$_2$CH(CH$_3$)O)$_p$CH$_2$CH(CH$_3$)O—; and n, m, and p are integers from 1 to 10. The drug dimer of formula (L) can be formed from glycochenodeoxycholic acid, glycocholic acid, or glycodeoxycholic acid.

In particular embodiments, the steroid is a steroid metabolite and the drug dimer is further described by the formula (LI):

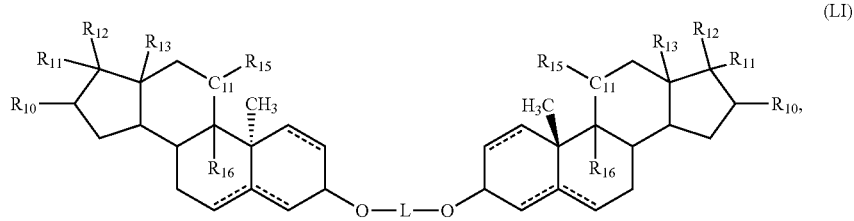

wherein the bond between $C_{11}$ and $R_{15}$ is a single or a double bond; $R_2$ represents OH or =O; $R_{10}$ represents H or OH; $R_{11}$ represents H, OH, —C(=O)CH$_2$OH, —C(=O)OH, —C(=O)CH$_2$OH, or —C(=O)CH$_3$; $R_{12}$ represents H, OH, —C(=O)CH$_2$OH, —C(=O)OH, —C(=O)CH$_2$OH, or —C(=O)CH$_3$; $R_{13}$ represents —CH$_2$OH or —CH$_3$; $R_{15}$ represents H, OH, or =O; $R_{16}$ represents H or F; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LI) can be formed from tetrahydrotriamcinolone, cortienic acid, 11-dehydrocorticosterone, 11β-hydroxypregnenolone, ketoprogesterone, 17-hydroxypregnenolone, 17,21-dihydroxypregnenolone, 18-hydroxycorticosterone, deoxycortisone, 21-hydroxypregnenolone, or progesterone.

In particular embodiments, the steroid is a steroid metabolite and the drug dimer is further described by the formula (LII):

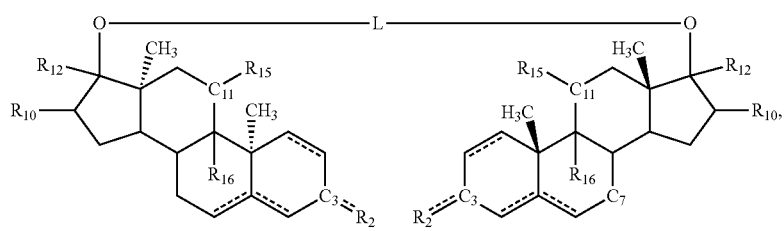

wherein the bond between $C_3$ and $R_2$, and $C_{11}$ and $R_{15}$ is a single or a double bond; $R_2$ represents OH or =O; $R_{10}$ represents H or OH; $R_{12}$ represents —C(=O)CH$_2$OH, —C(=O)OH, —C(=O)CH$_2$OH, or —C(=O)CH$_3$; $R_{15}$ represents H, OH, or =O; $R_{16}$ represents H or F; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LII) can be formed from tetrahydrotriamcinolone, cortienic acid, 17-hydroxypregnenolone, 17,21-dihydroxypregnenolone, or deoxycortisone.

In particular embodiments, the steroid is a steroid metabolite and the drug dimer is further described by the formula (LIII):

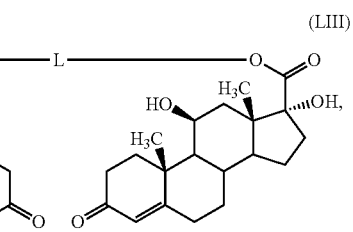

wherein L is —C(O)—(R$^A$)—C(O)—, —(R$^A$)—, or —C(O)—O—(R$^A$)—O—C(O)— and R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms; or L is —O—(R$^A$)—O— and R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from —O($CH_2CH_2O$)$_n$ $CH_2CH_2O$—, —O($CH_2CH_2CH_2CH_2O$)$_m$$CH_2CH_2$ $CH_2CH_2O$—, and —O($CH_2CH(CH_3)O$)$_p$$CH_2CH(CH_3)$ O—; and n, m, and p are integers from 1 to 10. The drug dimer of formula (LIII) can be formed from cortienic acid.

In particular embodiments, the steroid is a steroid metabolite and the drug dimer is further described by the formula (LIV):

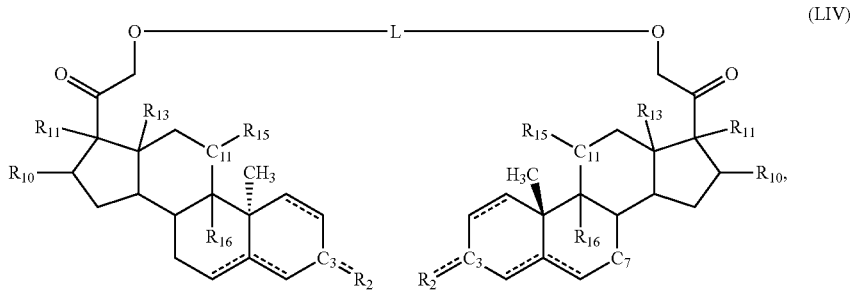

(LIV)

wherein the bond between $C_3$ and $R_2$, and $C_{11}$ and $R_{15}$ is a single or a double bond; $R_2$ represents OH or =O; $R_{10}$ represents H or OH; $R_{11}$ represents H or OH; $R_{13}$ represents H, —$CH_2OH$, or —$CH_3$; $R_{15}$ represents H, OH, or =O; $R_{16}$ represents H or F; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$ $CH_2CH_2O$—, —O($CH_2CH_2CH_2CH_2O$)$_m$$CH_2CH_2$ $CH_2$ $CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LIV) can be formed from tetrahydrotriamcinolone, 11-dehydrocorticosterone, 17,21-dihydroxypregnenolone, 18-hydroxycorticosterone, or 21-hydroxypregnenolone.

In particular embodiments, the steroid is a steroid metabolite and the drug dimer is further described by the formula (LV):

wherein the bond between $C_3$ and $R_2$ is a single or a double bond; $R_2$ represents OH or =O; $R_{10}$ represents H or OH; $R_{11}$ represents H or OH; $R_{12}$ represents —C(=O)$CH_2OH$, —C(=O)OH, —C(=O)$CH_2OH$, or —C(=O)$CH_3$; $R_{13}$ represents H, —$CH_2OH$, or —$CH_3$; $R_{16}$ represents H or F; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LV) can be formed from tetrahydrotriamcinolone, cortienic acid, 11-dehydrocorticosterone, 11β-hydroxypregnenolone, ketoprogesterone, 18-hydroxycorticosterone, or deoxycortisone.

In particular embodiments, the steroid is a steroid metabolite and the drug dimer is further described by the formula (LVI):

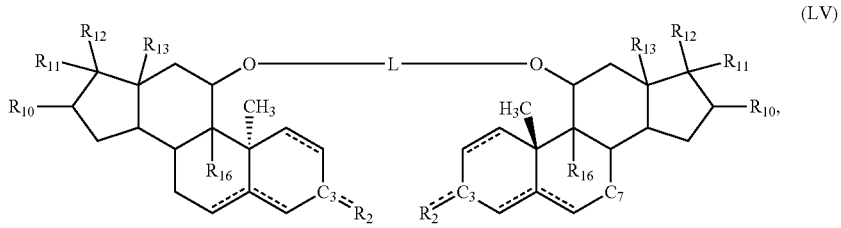

(LV)

(LVI)

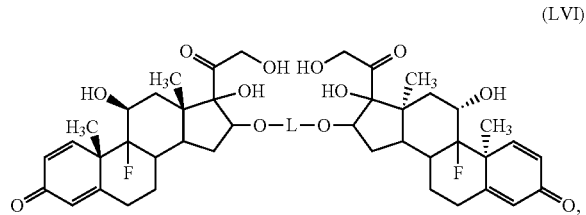

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LVI) can be formed from tetrahydrotriamcinolone.

In particular embodiments, the steroid is a steroid metabolite and the drug dimer is further described by the formula (LVII):

(LVII)

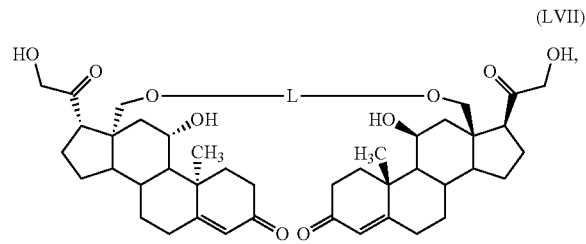

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LVII) can be formed from 18-hydroxycorticosterone.

In particular embodiments, the steroid is a cholesterol-derivative and the drug dimer is further described by the formula (LVIII):

(LVIII)

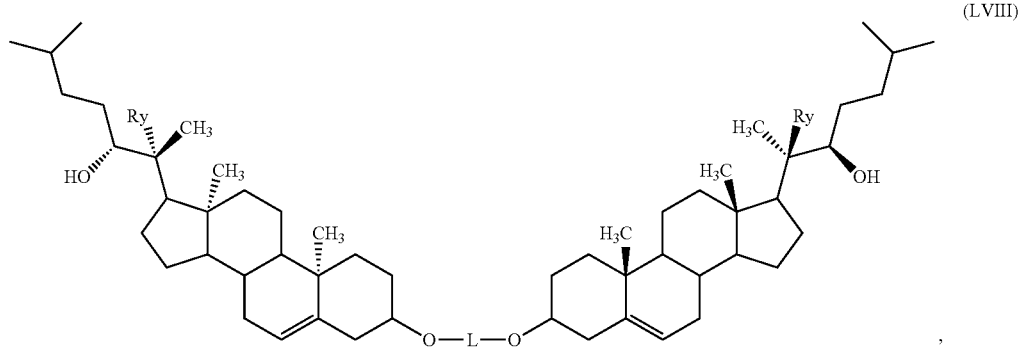

wherein Ry represents H or OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LVIII) can be formed from 22R-hydroxycholesterol or 20α-22R-dihydroxycholesterol.

In particular embodiments, the steroid is a cholesterol-derivative and the drug dimer is further described by the formula (LIX):

(LIX)

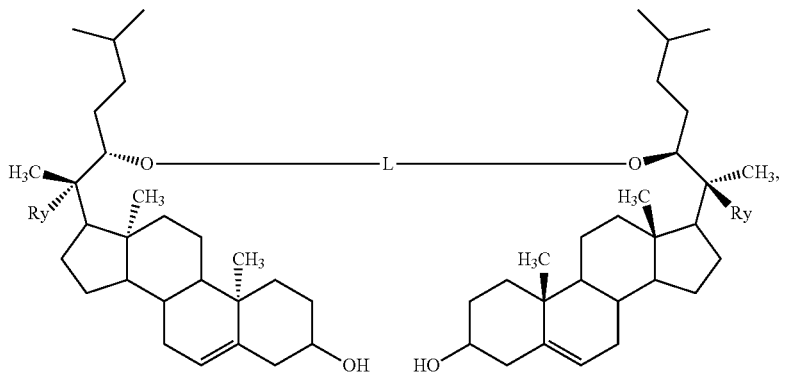

wherein Ry represents H or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2$O—, —O($CH_2CH_2CH_2CH_2O$)$_m$$CH_2CH_2CH_2CH_2$O—, or —O($CH_2CH(CH_3)O$)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LIX) can be formed from 22R-hydroxycholesterol or 20α-22R-dihydroxycholesterol.

In particular embodiments, the steroid is a cholesterol-derivative and the drug dimer is further described by the formula (LX):

(LX)

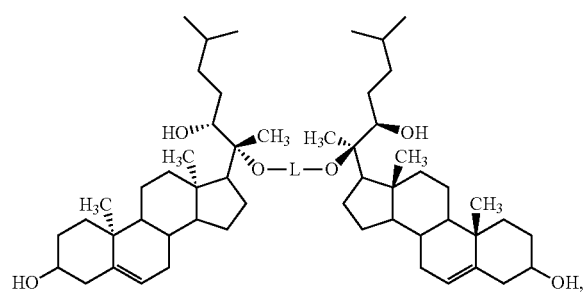

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2$O—, —O($CH_2CH_2CH_2CH_2O$)$_m$$CH_2CH_2CH_2CH_2$O—, or —O($CH_2CH(CH_3)O$)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LX) can be formed from 20α-22R-dihydroxycholesterol.

In particular embodiments, the steroid is a neurosteroid and the drug dimer is further described by the formula (LXI):

(LXI)

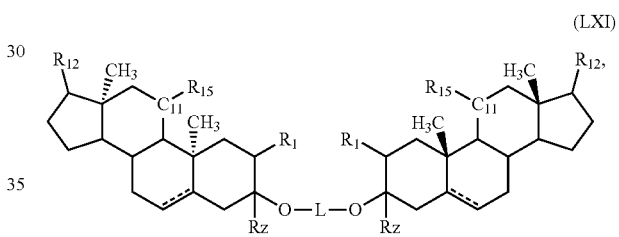

wherein the bond between $C_{11}$ and $R_{15}$ is a single or a double bond; Rz represents H or —$CH_3$; $R_1$ represents H or —$OCH_2CH_3$; $R_2$ represents OH or =O; $R_{12}$ represents —OH, —C(=O)$CH_3$, —C(=O)$CH_2$OH, or —CH($CH_3$)($CH_2$)$_2$CH(OH)CH($CH_3$)$_2$; $R_{15}$ represents H, —N($CH_3$)$_2$, or =O; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2$O—, —O($CH_2CH_2CH_2CH_2O$)$_m$$CH_2CH_2CH_2CH_2$O—, or —O($CH_2CH(CH_3)O$)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXI) can be formed from alphaxalone, alphadolone, hydroxydione, minaxolone, tetrahydrodeoxycorticosterone, allopregnanolone, pregnanolone, ganoxolone, 3α-androstanediol, epipregnanolone, isopregnanolone, or 24(S)-hydroxycholesterol.

In particular embodiments, the steroid is a neurosteroid and the drug dimer is further described by the formula (LXII):

(LXII)

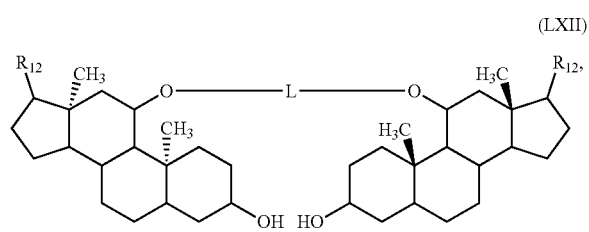

wherein $R_{12}$ represents —C(=O)CH$_3$, or —C(=O)CH$_2$OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LXII) can be formed from alphaxalone or alphadolone.

In particular embodiments, the steroid is a neurosteroid and the drug dimer is further described by the formula (LXIII):

(LXIII)

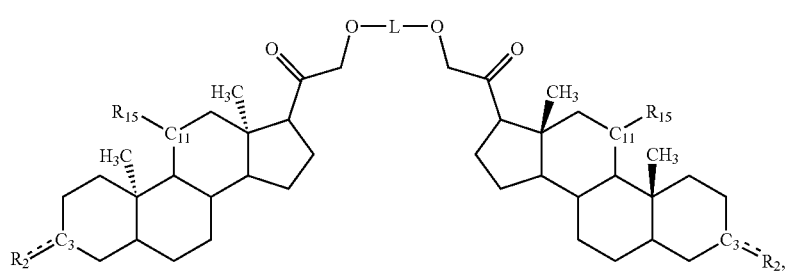

wherein the bond between C$_3$ and R$_2$, and C$_{11}$ and R$_{15}$ is a single or a double bond; R$_2$ represents OH or =O; R$_{15}$ represents H or =O; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LXIII) can be formed from alphadolone, hydroxydione, or tetrahydrodeoxycorticosterone.

In particular embodiments, the steroid is a neurosteroid and the drug dimer is further described by the formula (LXIV):

(LXIV)

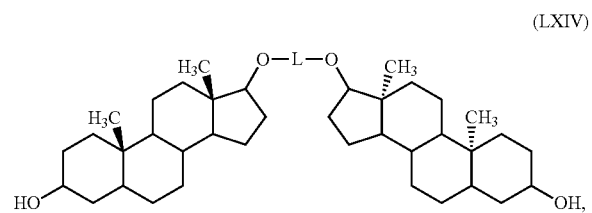

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LXIV) can be formed from 3α-androstanediol.

In particular embodiments, the steroid is a neurosteroid and the drug dimer is further described by the formula (LXV):

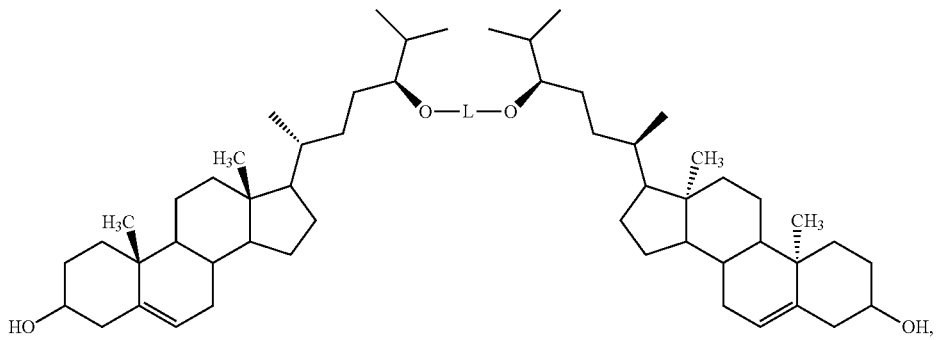

(LXV)

wherein L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXV) can be formed from 24(S)-hydroxycholesterol.

In particular embodiments, the steroid is a pheromone and the drug dimer is further described by the formula (LXVI):

(LXVI)

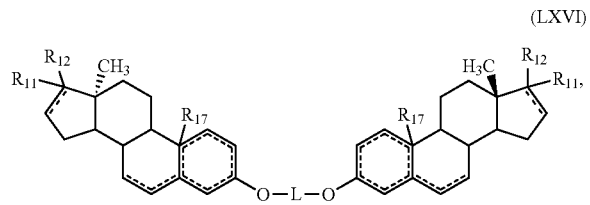

wherein $R_2$ represents OH or =O; $R_{11}$ represents H, —C(=O)CH$_3$, —OC(=O)(CH$_2$)$_4$CH$_3$, or is absent; $R_{12}$ represents H, —C(=O)CH$_3$, —OC(=O)(CH$_2$)$_4$CH$_3$, or is absent; $R_{17}$ represents CH$_3$ or is absent; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXVI) can be formed from androstadienol, androstadienone, androstenol, androstenone, estratetraenol, 5-dehydroprogesterone, 6-dehydro-retroprogesterone, allopregnanolone, or hydroxyprogesterone caproate.

In particular embodiments, the steroid is a progestin and the drug dimer is further described by the formula (LXVII):

(LXVII)

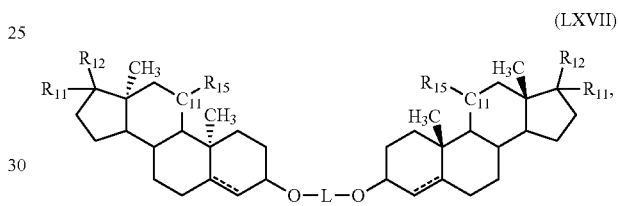

wherein the bond between $C_{11}$ and $R_{15}$ is a single or a double bond; $R_2$ represents OH or =O; $R_{11}$ represents H, OH, —CH(OH)CH$_3$, —C(=O)CH$_2$OH, —C(=O)CH$_3$, or —CH(OH)CH$_2$OH; $R_{12}$ represents H, OH, —CH(OH)CH$_3$, —C(=O)CH$_2$OH, —C(=O)CH$_3$, or —CH(OH)CH$_2$OH; $R_{15}$ represents H, =O, or OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXVII) can be formed from allopregnone-3α,20α-diol, allopregnone-3β,20β-diol, allopregnane-3β,21-diol-11,20-dione, allopregnane-3β,17α-diol-20-one, 3,20-allopregnanedione, 3β,11β,17α,20β,21-pentol, allopregnane-3β,17α,20β,21-tetrol, allopregnane-3α,11β,17α,21-tetrol-20-one, allopregnane-3β,11β,17α,21-tetrol-20-one, allopregnane-3β,17α,20β-triol, allopregnane-3β,17α,21-triol-11,20-dione, allopregnane-3β,11β,21-triol-20-one, allopregnane-3β,17α,21-triol-20-one, allopregnane-3α-ol-20-one; allopregnane-3β-ol-20-one, pregnanediol, 3,20-pregnanedione, 4-pregnene-20,21-diol-3,11-dione, 4-pregnene-11β,17α,20β,21-tetrol-3-one, 4-pregnene-17α,20β,21-triol-3,11-dione, 4-pregnene-17α,20β,21-triol-3-one, or pregnenolone.

In particular embodiments, the steroid is a progestin and the drug dimer is further described by the formula (LXVIII):

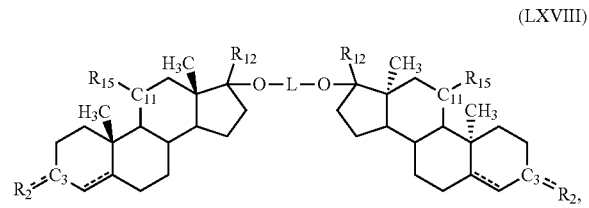

(LXVIII)

wherein the bond between $C_3$ and $R_2$, and $C_{11}$ and $R_{15}$ is a single or a double bond; $R_2$ represents OH or =O; $R_{12}$ represents H, OH, —CH(OH)CH$_3$, —C(=O)CH$_2$OH, —C(=O)CH$_3$, or —CH(OH)CH$_2$OH; $R_{15}$ represents H, =O, or OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LXVIII) can be formed from allopregnane-3β,17α-diol-20-one, 3,20-allopregnanedione,3β,11β,17α,20β,21-pentol, allopregnane-3β,17α,20β,21-tetrol, allopregnane-3α,11β,17α,21-tetrol-20-one, allopregnane-3β,11β,17α,21-tetrol-20-one, allopregnane-3β,17α,20β3-triol, allopregnane-3β,17α,21-triol-11,20-dione, allopregnane-3β,17α,21-triol-20-one, 4-pregnene-11β,17α,20β,21-tetrol-3-one, 4-pregnene-17α,20β,21-triol-3,11-dione, or 4-pregnene-17α,20β,21-triol-3-one.

In particular embodiments, the steroid is a progestin and the drug dimer is further described by the formula (LXIX):

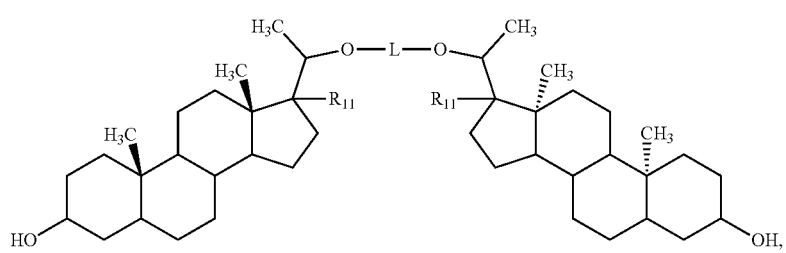

(LXIX)

wherein $R_{11}$ represents H, OH, —CH(OH)CH$_3$, —C(=O)CH$_2$OH, —C(=O)CH$_3$, or —CH(OH)CH$_2$OH; $R_{15}$ represents H or OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LXIX) can be formed from allopregnone-3α,20α-diol, allopregnone-3β,20β-diol or allopregnane-3,17α,20β-triol.

In particular embodiments, the steroid is a progestin and the drug dimer is further described by the formula (LXX):

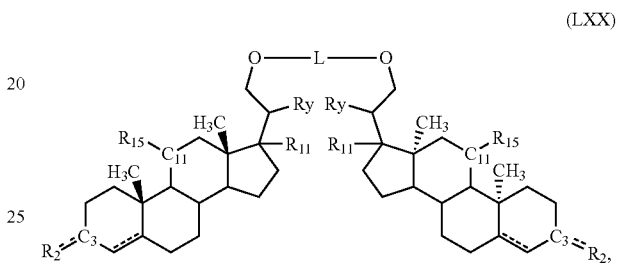

(LXX)

wherein the bond between O3 and $R_2$, and $C_{11}$ and $R_{15}$ is a single or a double bond; Ry represents OH or =O; $R_2$ represents OH or =O; $R_{11}$ represents H, OH, —CH(OH)CH$_3$, —C(=O)CH$_2$OH, —C(=O)CH$_3$, or —CH(OH)CH$_2$OH; $R_{12}$ represents H, OH, —CH(OH)CH$_3$, —C(=O)CH$_2$OH, —C(=O)CH$_3$, or —CH(OH)CH$_2$OH; $R_{15}$ represents H, =O, or OH; and L is —C(O)O—(R$^A$)—OC(O)—, —C(O)—OC(O)—(R$^A$)—C(O)O—C(O)—, or —C(O)—(R$^B$)—C(O)O—(R$^A$)—OC(O)—(R$^B$)—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each R$^B$ is independently selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms. The drug dimer of formula (LXX) can be formed from allopregnane-3β,21-diol-11,20-dione, 3,20-allopregnanedione,3β,11β,17α,20β,21-pentol, allopregnane-3β,17α,20β,21-tetrol, allopregnane-3α,11β,17α,21-tetrol-20-one, allopregnane-3β,11β,17α,21-tetrol-20-one, allopregnane-3β,17α,21-triol-11,20-dione, allopregnane-3β,11β,21-triol-20-one, allopregnane-3β,17α,21-triol-20-one, 4-pregnene-20,21-diol-3,11-dione, 4-pregnene-11β,17α,20β,21-tetrol-3-one, 4-pregnene-17α,20β,21-triol-3,11-dione, or 4-pregnene-17α,20β,21-triol-3-one.

In particular embodiments, the steroid is a progestin and the drug dimer is further described by the formula (LXXI):

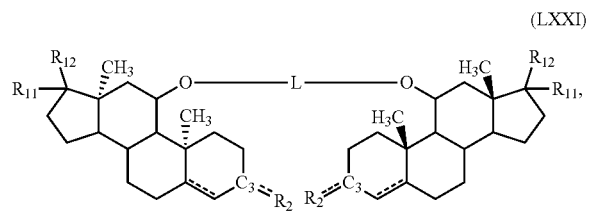

(LXXI)

wherein the bond between $C_3$ and $R_2$ is a single or a double bond; $R_2$ represents OH or =O; $R_{11}$ represents H, OH, —CH(OH)CH$_3$, —C(=O)CH$_2$OH, —C(=O)CH$_3$, or —CH(OH)CH$_2$OH; $R_{12}$ represents H, OH, —CH(OH)CH$_3$, —C(=O)CH$_2$OH, —C(=O)CH$_3$, or —CH(OH)CH$_2$OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXXI) can be formed from allopregnane-3β,21-diol-11,20-dione, 3,20-allopregnanedione,3β,11β,17α,20β,21-pentol, allopregnane-3α,11β,17α,21-tetrol-20-one, allopregnane-3β,11β,17α,21-tetrol-20-one, allopregnane-3β,17α,21-triol-11,20-dione, allopregnane-3β,11β,21-triol-20-one, 4-pregnene-20,21-diol-3,11-dione, 4-pregnene-11β,17α,20β,21-tetrol-3-one, or 4-pregnene-17α,20β,21-triol-3,11-dione.

In particular embodiments, the steroid is a progestin and the drug dimer is further described by the formula (LXXII)

wherein the bond between $C_3$ and $R_2$, and $C_{11}$ and $R_{15}$ is a single or a double bond; $R_2$ represents OH or =O; $R_{11}$ represents H or OH; $R_{15}$ represents H, =O, or OH; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXXII) can be formed from 3,20-allopregnanedione,3β,11β,17α,20β,21-pentol, allopregnane-3β,17α,2β,21-tetrol, 4-pregnene-20,21-diol-3,11-dione, 4-pregnene-11β,17α,20β,21-tetrol-3-one, 4-pregnene-17α,20β,21-triol-3,11-dione, or 4-pregnene-17α,20β,21-triol-3-one.

In particular embodiments, the steroid is other steroid and the drug dimer is further described by the formula (LXXIII):

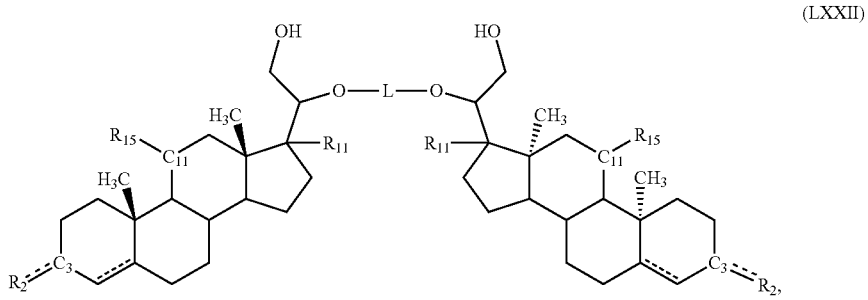

(LXXII)

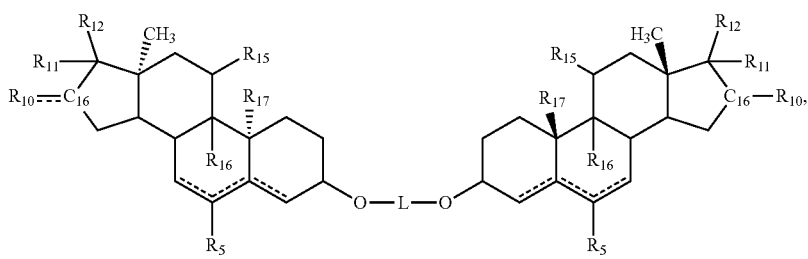

(LXXIII)

wherein the bond between $C_{16}$ and $R_{10}$ is a single or a double bond; $R_2$ represents OH or =O; $R_5$ represents H, $C_1$, or —$CH_3$; $R_{10}$ represents H or =$CH_2$; $R_{11}$ represents H, OH, —$CH_3$, —C(=O)$CH_3$, —C(=O)$CH_2$OC(=O)$CH_3$, or —OC(=O)$CH_3$; $R_{12}$ represents H, OH, —$CH_3$, —C(=O)$CH_3$, —C(=O)$CH_2$OC(=O)$CH_3$, or —OC(=O)$CH_3$; $R_{15}$ represents H or OH; $R_{16}$ represents F or H; $R_{17}$ represents H or —$CH_3$; and L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2$O—, —O($CH_2CH_2CH_2CH_2O$)$_m$$CH_2CH_2CH_2CH_2$O—, or —O($CH_2CH(CH_3)O$)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXXIII) can be formed from flugestone, prebediolone, chlormadinone acetate, medrogestone, or segesterone acetate.

In particular embodiments, the steroid is other steroid and the drug dimer is further described by the formula (LXXIV):

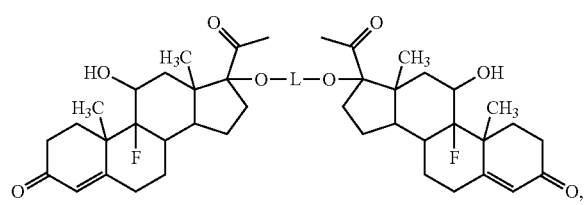

(LXXIV)

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2$O—, —O($CH_2CH_2CH_2CH_2O$)$_m$$CH_2CH_2CH_2CH_2$O—, or —O($CH_2CH(CH_3)O$)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXXIV) can be formed from flugestone.

In particular embodiments, the steroid is a other steroid and the drug dimer is further described by the formula (LXXV):

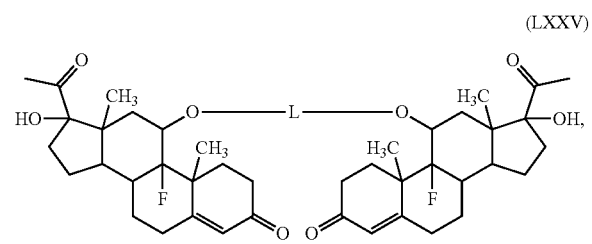

(LXXV)

wherein L is —C(O)O—($R^A$)—OC(O)—, —C(O)—OC(O)—($R^A$)—C(O)O—C(O)—, or —C(O)—($R^B$)—C(O)O—($R^A$)—OC(O)—($R^B$)—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2$O—, —O($CH_2CH_2CH_2CH_2O$)$_m$$CH_2CH_2CH_2CH_2$O—, or —O($CH_2CH(CH_3)O$)$_p$$CH_2CH(CH_3)$O—; n, m, and p are integers from 1 to 10; and each $R^B$ is independently selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms. The drug dimer of formula (LXXV) can be formed from flugestone.

Formulations

The pharmaceutical compositions of the disclosure can include an article in the form of fibers, fiber meshes, woven fabrics, non-woven fabrics, pellets, cylinders, hollow tubes, microparticles (e.g., microbeads), nanoparticles (e.g., nanobeads), or other shaped articles. In some embodiments, the pharmaceutical composition of the disclosure has a non-circular shape that affects, e.g., increases, the surface area (e.g., extruded through star-shaped dye or any other form shaping process with or without a dye mold). Suitable pharmaceutical compositions for use with this disclosure can be small regularly or irregularly shaped particles, which can be solid, porous, or hollow.

Different forms of pharmaceutical compositions of the present disclosure (e.g., fibers, fiber meshes, woven fabrics, non-woven fabrics, pellets, cylinders, hollow tubes, microparticles (e.g., microbeads), nanoparticles (e.g., nanobeads), or other shaped articles) can have the advantages of providing a controllable surface area, being easily injected, not requiring removal after completion of drug release, and allow for tailoring drug release rates required for a given indication. When used as an injectable drug delivery device, drug release rate and interaction with cells are strongly dependent on the size distribution of the pharmaceutical composition form.

Processing Methods

Articles of the disclosure can be formed using any number of the methods, for example, heat processing or solvent processing of the drug dimer of formula (I). Heat processing can include heat molding, injection molding, extrusion, 3D printing, melt electrospinning, fiber spinning, fiber extrusion, and/or blow molding. Solvent processing may include coating, micro printing, emulsion processing, dot printing, micropatterning, fiber spinning, solvent blow molding, electrospraying, and electrospinning.

Electrospraying Method

In some embodiments, the pharmaceutical compositions of the disclosure are dissolved in a solvent (e.g., acetone) at concentrations ranging from, e.g., 10-30% w/v, and are electrosprayed to form micro- and nanobeads. The solutions can be loaded into a syringe and can be injected at a particular rate, e.g., 0.5 mL/h, onto a stationary collection plate. Between the needle and collecting surface, a potential difference of, e.g., 18 kV, can be maintained. Exemplary concentration of 10% w/v is used to obtain nanoparticles. In other embodiments, a concentration of 30% w/v is used to obtain microbeads.

Fiber Spinning Methods

In some embodiments, the pharmaceutical compositions of the disclosure, e.g., fibrous meshes with aligned and unaligned morphologies are prepared by electrospinning. The pharmaceutical compositions of the disclosure are dissolved in a solvent (e.g., THF, or 1:1 ratio of DCM/THF). The solutions may be injected from a syringe at a particular rate, e.g., 0.5 mL/h, onto a cylindrical mandrel rotating at a particular rotational speed, e.g., 1150 rpm, to obtain aligned fibers, or onto a stationary collector surface to obtain unaligned fibers. A potential difference (e.g., 18 kV or 17 kV) can be maintained between the needle and collecting surface for aligned and random fibers.

In other embodiments, fibers are prepared either from the melt at elevated temperatures, the glassy state intermediate, or from solution by dissolving the pharmaceutical compositions of the disclosure in a solvent (e.g., DCM, THF, or chloroform). As used herein, melt spinning describes heat processing from the melt state, heat spinning describes heat processing from the glassy state, and wet, dry, and gel spinning describe solution processing.

The viscous melt, intermediate, or solution can be fed through a spinneret and fibers may be formed upon cooling (melt or heat spinning) or following solvent evaporation with warm air as the compound exits the spinneret (dry spinning). Wet spinning and gel spinning, performed according to methods known in the art, may also be used to produce the fibers of the disclosure. Heat spinning describes a process that is essentially the same as the melt spinning process, but performed with the glassy state intermediate and heated above the glass transition temperature (Tg) to get the viscous fluid to extrude/spin instead of the melt. Alternatively, tweezers may be dipped into melted material or concentrated solutions and retracted slowly in order to pull fibers. The rate of pulling and distance pulled may be varied to yield fibers and columnar structures of different thickness.

Emulsion Method

In some embodiments, micro-particles or nano-particles made from the pharmaceutical composition can be formed using an emulsion process. The pharmaceutical composition may be dissolved in an organic solvent (e.g. DCM, THF, etc.) and a surfactant (e.g. SDS, PVA, etc.) may be added to the solution/mixture at a low percentage (e.g. 1%). The resulting mixture may be stirred for the appropriate time at room temperature to form an emulsion. The emulsion may be subsequently added to Milli-Q water under stirring for an appropriate time (e.g. 1 h) to remove residual solvent. The resulting micro- or nano-particles may be collected by centrifugation and dried to obtain the desired form.

Extrusion Method

In some embodiments, injectable cylinders made from the pharmaceutical composition may be formed by heat extrusion. The pharmaceutical composition may be loaded into a hot melt extruder, heated to a temperature above the melting point (for crystalline compositions) or glass transition temperature (for pre-melted or amorphous compositions), and extruded using a light compressive force to push the material through the nozzle and a light tensile force to pull the material out of the extruder. The extrudate may be cut to the desired length for appropriate drug dosing for the indication of interest.

Bead Sizing and Milling

In some embodiments, a milling process may be used to reduce the size of an article of the disclosure to form sized particles, e.g., beads, in the micrometer (microbeads) to nanometer size range (nanobeads). The milling process may be performed using a mill or other suitable apparatus. Dry and wet milling processes such as jet milling, cryo-milling, ball milling, media milling, sonication, and homogenization are known and can be used in methods described herein. Generally, in a wet milling process, a suspension of the material to be used as the core is agitated with or without excipients to reduce particle size. Dry milling is a process wherein the material to be used as the article core is mixed with milling media with or without excipients to reduce particle size. In a cyro-milling process, a suspension of the material to be used as the core is mixed with milling media with or without excipients under cooled temperatures. In some embodiments, subsequent heating of the milled microparticle above the Tg is needed to achieve a spherical shape, or particles with non-spherical shapes can be used as milled.

Low Temperature Processing Using Intermediate Glassy State Articles

In certain embodiments, the prodrug dimer has a limited window (e.g., short timeframe of seconds to minutes) of thermal stability, whereby the purity of the dimer is minimally affected at elevated temperatures. In some embodiments, it is beneficial to make an intermediate glassy state form (e.g., film, pellet, micro-particles, or other shaped article). This can be accomplished by heat or solvent processing to remove or reduce the crystallinity of the material to form a glassy state composition. The glassy state composition is subsequently heat processed at a lower temperature (e.g., processing just above the glass transition temperature (Tg), and below the melt temperature (Tm)). This can provide a longer timeframe for heat processing the glassy state material into the final shaped article, while reducing the impact of processing conditions on the purity of the prodrug dimer in the article.

Exemplary processing details are provided in the Examples.

Drug Delivery

The pharmaceutical compositions of the disclosure provide optimal delivery of a drug as they release the drug from an article of the disclosure in a controlled manner, for example, by surface erosion. The surface erosion mechanism of drug release may allow the shaped article to maintain its physical form (shape), while gradually decreasing in size as the surface erodes (e.g., like a bar of soap), rather than bulk erosion that is characteristic of some polymer-based drug release vehicles (e.g., polylactic/glycolic acid). This may inhibit burst release and reduce the formation of inflammatory particulates (e.g., no crystalline particulates are formed when drug is released in the manner described herein). The drug can be controlled to be delivered over a desired period of time. A slower and steadier rate of delivery (e.g., release of less than 10% of D1 or D2 (as a percentage of the total drug, D1 or D2, present in the fiber in prodrug form) at 37° C. in 100% bovine serum over 5 days) may in turn result in a reduction in the frequency with which the pharmaceutical composition must be administered to a subject, and improve the safety profile of the drug. Drug release can also be tailored to avoid side effects of slower and longer release of the drug by engineering the article to provide steady release over a comparatively shorter period of time. Depending on the indication and the drug, the drug release can be tailored for dose and duration appropriate to the indication of interest.

The rate of release of a drug can depend on many factors, for example, the drug composition of the drug dimer. Drug release rate from the formed object of the drug dimer can be modulated by the cleavage of drug-linker bond through hydrolysis or enzymatic degradation. Therefore, the selection of linking moiety can affect drug release rate. Further, the drug release rate can be controlled by the selection of the functional group on the drug to conjugate through to the linker, for example, a primary vs. a secondary steroid hydroxyl group. The rate of release of a given drug from a drug dimer may also depend on the quantity of the loaded drug dimer as a percent of the final drug dimer formulation, e.g., by using a pharmaceutical excipient (e.g., bulking agent/excipient) or a second steroid drug (e.g., active or benign) as a homodimer mixture, or within the same molecule as a heterodimer that acts as a bulking agent. Another factor that can affect the release rate of a drug from, for example a microbead, is the microbead size. In some embodiments, drug release is tailored based on the solubility of drug dimer (e.g., through selection of appropriate drug and/or linker) that will influence the rate of surface erosion (e.g., dissolution/degradation) from the article. In other embodiments, drug release is affected by changes in surface area of the formulation, e.g., by changing the diameter of the microbeads. By adjusting the vide supra factors, dissolution, degradation, diffusion, and controlled release may be varied over wide ranges. For example, release may be designed to be initiated over minutes to hours, and may extend over the course of days, weeks, months, or years.

Uses and Pharmaceutical Compositions

In some embodiments, the drug dimers of the disclosure are used as a drug delivery device (or, e.g., a drug depot) with a minimal need for additives. This may achieve a local, sustained release and a local biological effect, while minimizing a systemic response. In some embodiments, when present, the additives are in small amounts and do not affect the physical or bulk properties. In some embodiments, when present, the additives do not alter the drug release properties from the pharmaceutical composition but rather act to improve processing of the prodrug dimer into the shaped article. In some embodiments, the pharmaceutical compositions contain additives such as a plasticizer (e.g., to reduce thermal transition temperatures), an antioxidant (e.g., to increase stability during heat processing), a binder (e.g., to add flexibility to the fibers), a bulking agent (e.g., to reduce total drug content), a lubricant, a radio-opaque agent, or mixtures thereof. The additives may be present at 30% (w/w), e.g., 20% (w/w), 10% (w/w), 7% (w/w), 5% (w/w), 3% (w/w), 1% (w/w), 0.5% (w/w), or 0.1% (w/w). Examples of plasticizers are polyols, e.g., glycerol, ethylene glycol, diethylene glycol, triethylene glycol, tetraethylene glycol, polyethylene glycol, propylene glycol, triacetin, sorbitol, mannitol, xylitol, fatty acids, monosaccharides (e.g., glucose, mannose, fructose, sucrose), ethanolamine, urea, triethanolamine, vegetable oils, lecithin, or waxes. Exemplary antioxidants are glutathione, ascorbic acid, cysteine, or tocopherol. The binders and bulking agents can be, e.g., polyvvinylpyrrolidone (PVP), starch paste, pregelatinized starch, hydroxypropyl methyl cellulose (HPMC), carboxymethyl cellulose (CMC), or polyethylene glycol (PEG) 6000.

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an agent even though such agent does not treat the cause of the pain).

Pharmaceutical compositions containing the drug dimers described herein may be administered to a subject via any route known in the art. These include, but are not limited to, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), buccal and inhalational administration. Desirably, the articles of the disclosure are administered parenterally as injections (intravenous, intramuscular, or subcutaneous), or locally as injections (intraocularly or into a joint space). The formulations are admixed under sterile conditions with a pharmaceutically acceptable carrier or suspension or resuspension agents (e.g., for micro- and nanoparticles) and any needed preservatives or buffers as may be required.

The articles of the disclosure described herein including a drug dimer may be administered to a subject to be delivered in an amount sufficient to deliver to a subject a therapeutically effective amount of an incorporated pharmaceutical agent as part of prophylactic or therapeutic treatment, or as a part of adjunctive therapy to avoid side-effects of another drug or therapy. In general, an effective amount of a pharmaceutical agent or component refers to the amount necessary to elicit the desired biological response. The desired concentration of pharmaceutical agent in the article of the disclosure will depend on numerous factors, including, but not limited to, absorption, inactivation, and excretion rates of the drug as well as the delivery rate of the compound from the subject compositions, the desired biological endpoint, the agent to be delivered, the target tissue, etc. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The concentration and/or amount of any pharmaceutical agent to be administered to a subject may be readily determined by one of ordinary skill in the art. Known methods are also available to assay local tissue concentrations, diffusion rates from drug dimers and local blood flow before and after administration of the therapeutic formulation.

Sterilization of Formulations

Generally, it is desired that a formulation is sterile before or upon administration to a subject. A sterile formulation is essentially free of pathogenic microorganisms, such as bacteria, microbes, fungi, viruses, spores, yeasts, molds, and others generally associated with infections. In some embodiments, articles of the disclosure may be subject to an aseptic process and/or other sterilization process. An aseptic process typically involves sterilizing the components of a formulation, final formulation, and/or container closure of a drug product through a process such as heat, gamma irradiation, ethylene oxide, or filtration and then combining in a sterile environment. In some cases, an aseptic process is preferred. In other embodiments, terminal sterilization is preferred.

Treatment Methods

The formulations of the disclosure may be used in the fields of ophthalmology, oncology, laryngology, endocrinology and metabolic diseases, rheumatology, urology, neurology, cardiology, dental medicine, dermatology, otology, post-surgical medicine, orthopedics, pain management, and gynecology.

The compound of the disclosure can be selected for the desired property, such as corticosteroid dimers for use in treating inflammatory diseases or conditions; the use of antibiotic steroid dimers for treating an infection; or the use of an anticancer steroid dimer for treating a proliferative disorder.

Ophthalmic Uses

In certain embodiments, the articles of the disclosure may be used prevent, treat or manage diseases or conditions at the back of the eye, such as at the retina, macula, choroid, sclera and/or uvea.

In some embodiments, the articles of the disclosure are used as injectable drug delivery devices for ophthalmology (e.g., intravitreal injection, coating on a minimally invasive glaucoma surgery (MIGS) devices, or implant in blebs). During an intravitreal injection a medication is placed directly into the space in the back of the eye called the vitreous cavity, which is filled with a jelly-like fluid called the vitreous humor gel. Intravitreal injections may be used to treat retinal diseases such as diabetic retinopathy, macular degeneration, macular edema, uveitis, and retinal vein occlusion.

In certain embodiments, the articles of the disclosure may be used to treat, prevent, or manage an ocular condition, i.e., a disease, ailment, or condition that affects or involves the eye or one or more of the parts or regions of the eye. In some embodiments, the articles of the disclosure may be used to treat, prevent, or manage an ocular condition at the front of the eye of a subject. A front of the eye ocular condition includes a disease, ailment or condition, such as for example, post-surgical inflammation; uveitis; infections; aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; corneal neovascularization; refractive disorders and strabismus. In some embodiments, articles of the disclosure may be used to treat, prevent, or manage an ocular condition at the back of the eye of a subject. A posterior ocular condition can include a disease, ailment, or condition, such as intraocular melanoma; acute macular neuroretinopathy; Behcet's disease; choroidal neovascularization; uveitis; diabetic uveitis; histoplasmosis; infections, such as fungal or viral-caused infections; macular degeneration, such as acute macular degeneration, non-exudative age related macular degeneration and exudative age related macular degeneration; edema, such as macular edema (e.g., cystoid macular edema (CME) and diabetic macular edema (DME)); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, retinoblastoma, and glaucoma. In some embodiments, the articles of the disclosure may be used to treat, prevent, or manage dry eye in a subject. In some embodiments, the articles of the disclosure may be used to treat, prevent, or manage inflammation in the eye of a subject (e.g., where the drug dimer is formed from one or more corticosteroids). Inflammation is associated with a variety of ocular disorders. Inflammation may also result from a number of ophthalmic surgical procedures, including cataract surgery. In some embodiments, the pharmaceutical agent that is delivered into the eye by the articles of the disclosure and/or methods described herein may be a corticosteroid. In certain embodiments, the pharmaceutical agent includes one or more of hydrocortisone, cortisone, tixocortol, prednisolone, methylprednisolone, prednisone, triamcinolone acetonide, mometasone, amcinonide, budesonide, desonide, fluocinonide, fluocinolone, halcinonide, betamethasone, dexamethasone, fluocortolone, hydrocortisone, aclometasone, prednicarbate, clobetasone, clobetasol, fluprednidene, glucocorticoid, mineralocorticoid, aldosterone, deoxycorticosterone, fludrocortisone, halobetasol, diflorasone, desoximetasone, fluticasone, flurandrenolide, alclometasone, diflucortolone, flunisolide, and beclomethasone. In some embodiments, the drug dimer of the disclosure are used as adjunctive therapy to reduce inflammation and fibrosis associated with devices (e.g., minimally invasive glaucoma surgery (MIGS) devices). In some embodiments, articles of the disclosure may be used to treat, prevent, or manage age-related macular degeneration (AMD) in a subject.

Osteoarthritis Treatment

In some embodiments, the articles of the disclosure are used for the treatment of osteoarthritis (OA). For OA of the knee, intraarticular (IA) injection (e.g., steroids) is preferred as the last non-operative modality, if other conservative treatment modalities are ineffective. Steroids may be used to reduce inflammation in tendons and ligaments in osteoarthritic joints. IA steroid injections provide short term reduction in OA pain and can be considered as an adjunct to core treatment for the relief of moderate to severe pain in people with OA. Exemplary steroids used in the treatment of OA are betamethasone, methylprednisolone, dexamethasone, and triamcinolone acetonide. In some embodiments, microspheres of the disclosure composed of the drug dimers are injected into a knee joint for the treatment of OA.

Surgical Procedures

In some embodiments, the articles of the disclosure are used in conjunction with a surgical procedure. For example, an article of the disclosure can be implanted at a surgical site to reduce the risk of infection, inflammation, or the recurrence of disease (such as a cancer) treated by the surgical procedure.

Examples

The following examples are put forth to provide those of ordinary skill in the art with a description of how the compositions and methods described herein may be used, made, and evaluated, and are intended to be purely exemplary of the disclosure and are not intended to limit the scope of what the inventors regard as their disclosure. Compounds 1-17 can be used in the methods, compositions, and articles of the disclosure.

TABLE 1

Compounds of the disclosure

| Compound | Dimer | Abbreviation |
|---|---|---|
| 1 | Dexamethasone-Triethylene Glycol-Dexamethasone | Dex-TEG-Dex |
| 2 | Hydrocortisone-Triethylene Glycol-Hydrocortisone | HC-TEG-HC |
| 3 | Triamcinolone Acetonide-Triethylene Glycol-Triamcinolone Acetonide | TA-TEG-TA |
| 4 | Dexamethasone-Triethylene Glycol-Hydrocortisone | Dex-TEG-HC |
| 5 | Dexamethasone-Hexane-Dexamethasone | Dex-HEX-Dex |
| 6 | Hydrocortisone-Succinate-Hydrocortisone | HC-SUCC-HC |
| 7 | Anecortave-Triethylene Glycol-Anecortave | Anec-TEG-Anec |
| 8 | Dexamethasone-Pentaethylene Glycol-Dexamethasone | Dex-EG5-Dex |
| 9 | Fusidic Acid-Triethylene Glycol-Fusidic Acid (carbonate ester) | FA-TEG-FA (CE) |
| 10 | Dexamethasone-Polyethylene Glycol (MW = 200)-Dexamethasone | Dex-PEG200-Dex |
| 11 | Dexamethasone-Heptaethylene Glycol-Dexamethasone | Dex-EG7-Dex |
| 12 | Dexamethasone-Nonaethylene Glycol-Dexamethasone | Dex-EG9-Dex |
| 13 | Dexamethasone-Polyethylene Glycol (MW = 300)-Dexamethasone | Dex-PEG300-Dex |
| 14 | Cholesterol-Triethylene Glycol-Cholesterol | CHS-TEG-CHS |
| 15 | Fusidic Acid-Triethylene Glycol-Fusidic Acid (ester) | FA-TEG-FA (E) |
| 16 | Ethinylestradiol-Triethylene Glycol-Ethinylestradiol | Ethin-TEG-Ethin |
| 17 | Prednisolone-Triethylene Glycol-Prednisolone | Pred-TEG-Pred |

Example 1. Compound 1 (Dex-TEG-Dex) can be Synthesized, Processed into Pellets in the Glassy State by Heat Molding, and Release Drug Through Surface Erosion from an Intact Pellet Dexamethasone (1 mol equivalent) was suspended in dichloromethane on an ice bath and triethylamine (2 mol equivalent) and triethylene glycol bis(chloroformate) (0.6 mol equivalent) were added to the mixture. The ice bath was allowed to warm to room temperature and the reaction was stirred overnight. The solvent was removed and the solid residue was purified by column chromatography. Product was recrystallized from acetonitrile twice to give Compound 1 (FIG. 1A) as an off-white crystalline solid.

Compound 1: HPLC (mobile phase: $H_2O$/TFA and MeCN/TFA) 31.7 min; Elemental analysis: Anal. Calcd for $C_{52}H_{68}F_2O_{16}$: C, 63.27; H, 6.94; N, 0.00; Cl, 0.00 Found: C, 62.62; H, 6.84; N, <0.50; Cl<100 ppm. $^1$H NMR (400 MHz, DMSO-$d_6$) δ (ppm) 0.80 (d, J=7 Hz, 6H, 2×C16 α-$CH_3$); 0.90 (s, 6H, 2×C18-$CH_3$); 1.08 (m, 2H, 2×C16-H); 1.35 (m, 2H, 2×C14-H); 1.49 (s, 6H, 2×C19-$CH_3$); 1.54 (q, J=13 Hz, 2H, 2×C13-H); 1.64 (q, J=11 Hz, 2H, 2×C15-$CH_2$); 1.77 (m, 2H, 2×C15-$CH_2$); 2.15 (m, 4H, 2×C6-$CH_2$); 2.32 (m, 4H, 2×C7-$CH_2$); 2.62 (m, 2H, 2×C12-$CH_2$); 2.89 (m, 2H, 2×C12-$CH_2$); 3.57 (s, 4H, 2×TEG O$CH_2$); 3.65 (m, 4H, 2×TEG O$CH_2$); 4.15 (m, 2H, 2×OCH); 4.22 (m, 4H, 2×TEG O$CH_2$); 4.79 (d, 2H, AB, J=18.5 Hz, 2H, C21-$CH_2$O—); 5.09 (d, 2H, AB, J=18.5 Hz, 2H, C21-$CH_2$O—); 5.18 (s, 2H, C17-OH); 5.40 (d, 2H, J=4.5 Hz, C11-OH); 6.01 (d, 2H, J=1.9 Hz, 2×alkene C4-CH); 6.23 (dd, 2H, J=10.1 and 1.9 Hz, CH, 2×alkene C2-CH); 7.29 (d, 2H, C1-CH 2×alkene CH, 10.1 Hz, 2H). MS (ESI+) m/z: [M+H]+ Calcd for $C_{52}H_{69}F_2O_{16}$ 987.46; Found 987.46.

Figure 1D:
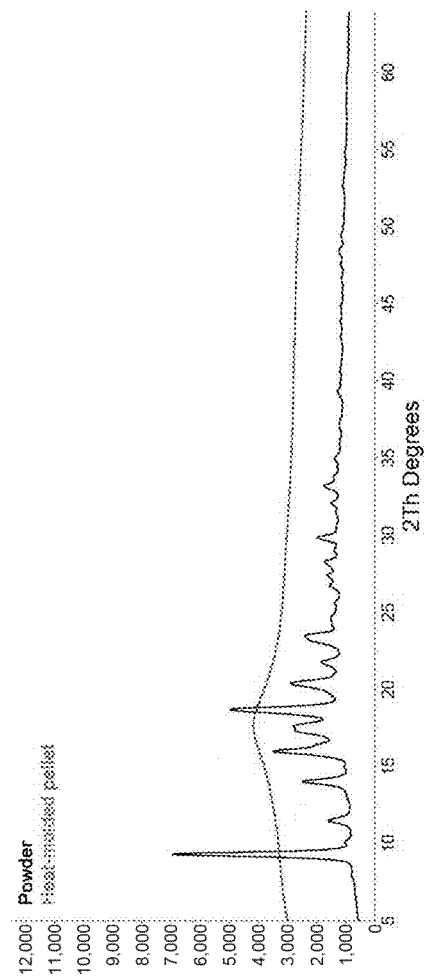
Figure 1A:
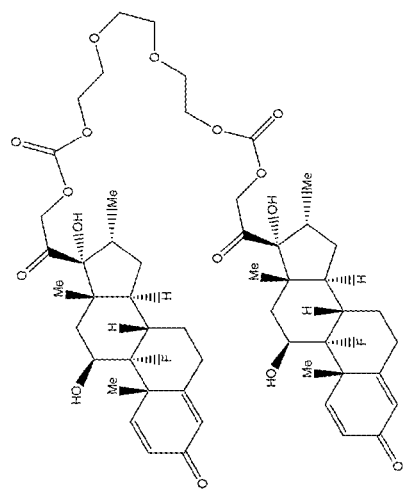
Figure 1B:
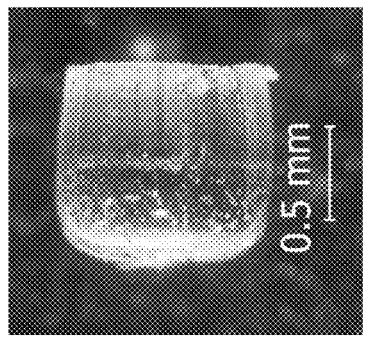

Compound 1 was formed into pellets in the glassy state by heat molding (FIG. 1B). Crystalline powder was melted at 185° C. and pellets were formed from 1 mm×1 mm cylindrical molds. The starting powder and heat-processed pellets were tested by differential scanning calimetry (DSC; FIG. 1C) and powder x-ray diffraction (PXRD; FIG. 1D) to confirm heat-processing converted compound 1 from the crystalline state to the glassy state.

Figure 1E:
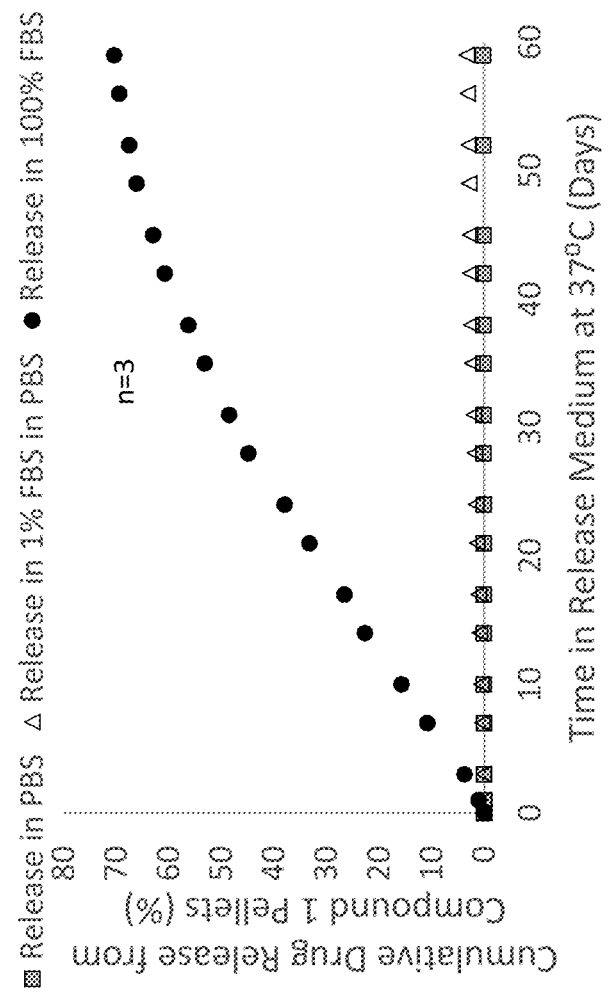
Figure 1F:
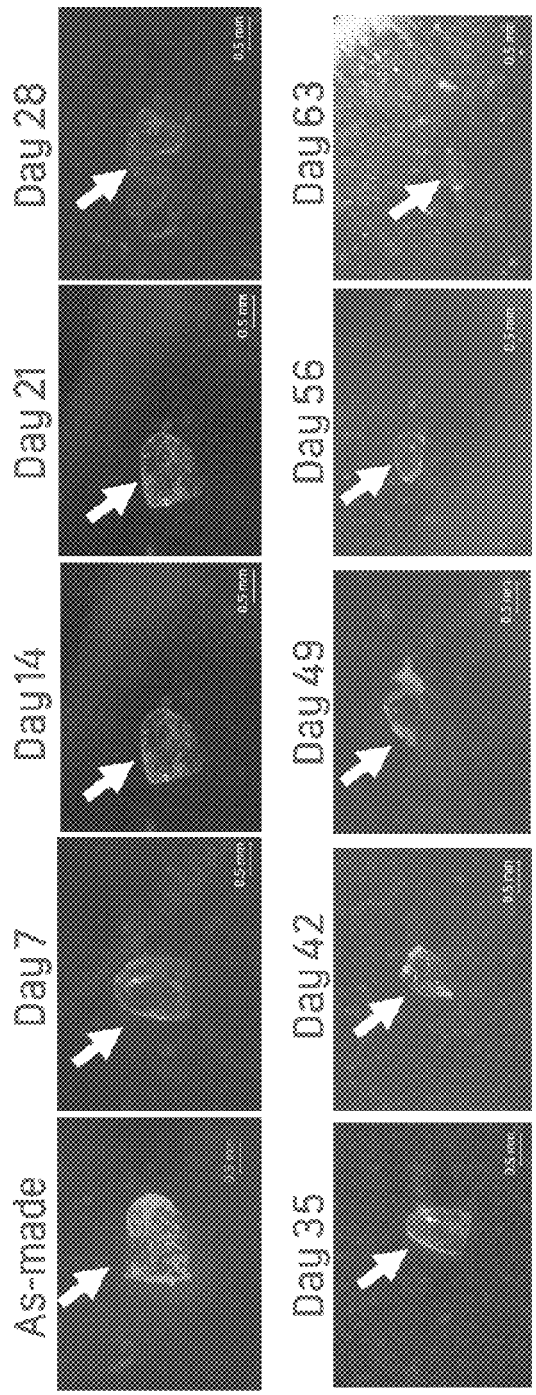

Heat-molded pellets from Compound 1 (1 mm×1 mm) were then placed in 20 mL glass vials and 2 mL of release buffer (either 100% phosphate buffered saline (PBS), 1% fetal bovine serum (FBS) in PBS, or 100% FBS) was added. Samples were incubated at 37° C. on a shaker rotating at 115 rpm. After 1 day, 3 days, 7 days, and subsequently in alternating 3 and 4 day intervals (i.e., 1, 3, 7, 10, 14 days etc.), release buffer was sampled directly (PBS) or syringe filtered, proteins were precipitated with acetonitrile, and drug release products were extracted. The samples were analyzed by high performance liquid chromatography (HPLC) to quantify drug products. Cumulative drug release was calculated and plotted as a percentage of the total drug in each pellet released over time (FIG. 1E). Representative images of the pellets confirm surface erosion over time in 100% FBS (FIG. 1F).

Example 2. Compound 1 (Dex-TEG-Dex) can be Processed into Different Forms in the Glassy State by Multiple Processing Methods from the Melt State Compound 1 was processed into different forms in the glassy state from the melt state. Heat-molded pellets (FIG. 2A) were prepared as described in Example 1 with a cylindrical mold (0.35 mm diameter and 0.8 mm length). Extruded cylinders (FIG. 2B) were prepared by adding Compound 1 as a crystalline powder into a micro-extruder with different nozzles to form extruded material of different diameters. The micro-extruder was heated to 185° C. to melt the powder and form the extrudate. FIG. 2C shows an extruded cylinder with a 23G diameter nozzle, cut, and loaded into a 23G needle. Glass droplets (FIG. 2D) were formed by dispersing Compound 1 as a powder on PTFE sheet and heating it to 185° C. Fibers of Compound 1 were prepared by heat extrusion at 185° C. using a small diameter nozzle (e.g. 30-32G) combined with a tensile force to pull the extrudate out of the nozzle. Fibers were also prepared by melting Compound 1 from a powder at 185° C. and by pulling the melted material at different rates to yield fibers of different diameters (FIG. 2E).

Figure 3B:
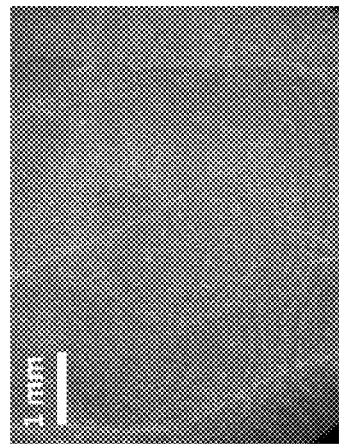
Figure 3A:
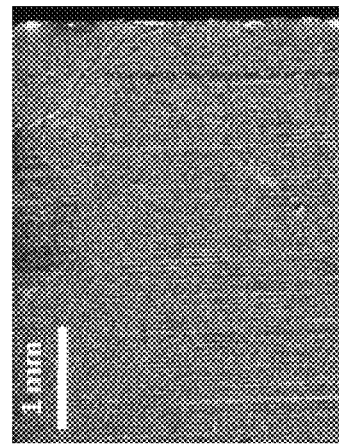

Example 3. Compound 1 (Dex-TEG-Dex) can be Processed into Different Forms in the Glassy State by Multiple Processing Methods from the Solution State Compound 1 was processed into different forms in the glassy state, including coatings, non-woven fibrous meshes, fibers, and micro- and nano-particles, from the solution state using organic solvents. Compound 1 was coated onto titanium (FIG. 3A) and poly(styrene-block-isobutylene-block-styrene) (SIBS) surfaces (FIG. 3B) from acetone by drop coating and can be coated using other common techniques (e.g., dip-coating, spray coating, electrospraying, etc.).

Figure 3D:
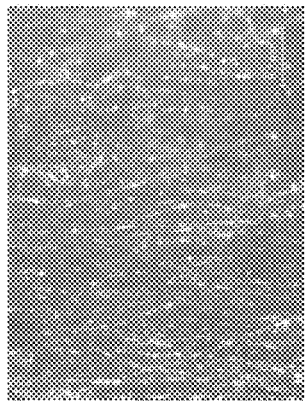
Figure 3C:
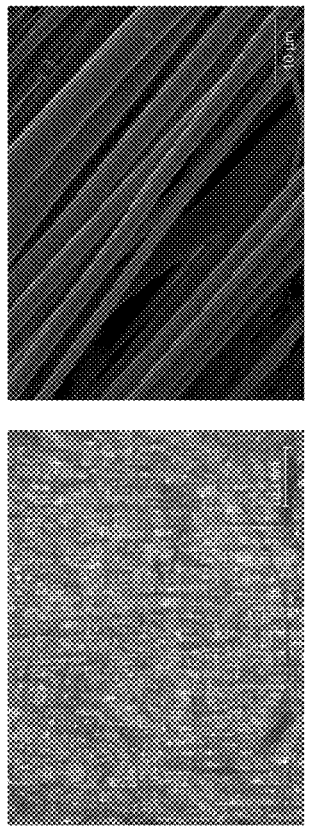
Figure 3F:
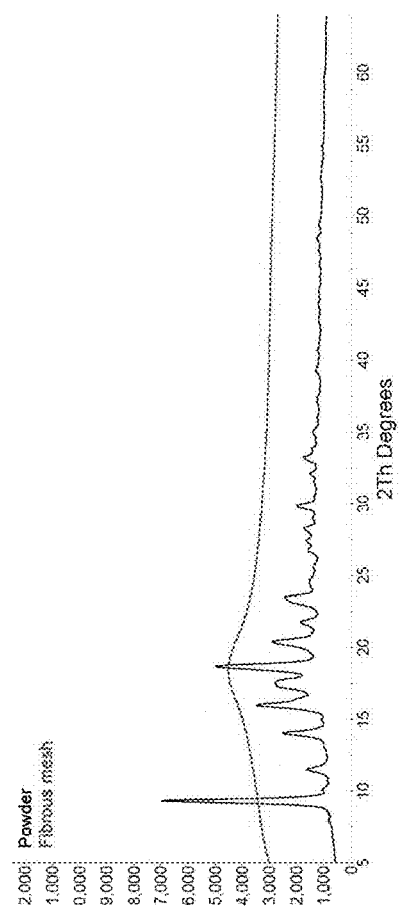
Figure 3E:
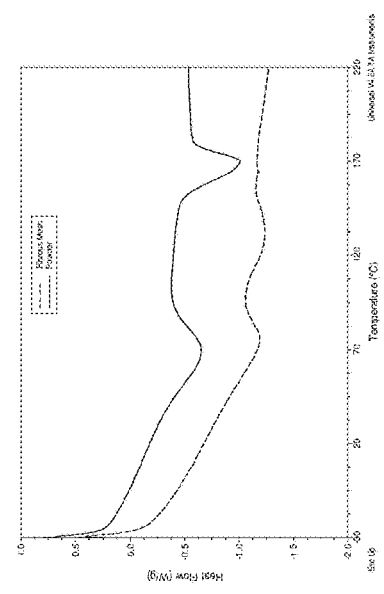

Non-woven fibrous meshes with aligned (FIG. 3C) and unaligned (FIG. 3D) morphologies were prepared by electrospinning. Compound 1 was dissolved in tetrahydrofuran (THF) and was electrosprayed onto a cylindrical rotating mandrel to obtain aligned fibers or onto a stationary collector surface to obtain unaligned fibers. Compound 1 as the starting powder and solvent-processed fibrous mesh were tested by DSC (FIG. 3E) and PXRD (FIG. 3F) to confirm the meshes were in the glassy state.

Fibers (FIG. 3G) were prepared by dissolving Compound 1 in dichloromethane (DCM), THF, or chloroform and by pulling Compound 1 from the solution. The rate of pulling and distance pulled were varied to yield fibers and columnar structures of different thickness.

Electrosprayed micro- and nano-particles were prepared by dissolving Compound 1 in acetone. A concentration of 10% w/v was used to electrospray Compound 1 into nanoparticles (FIG. 3H), while a concentration of 30% w/v was used to electrospray Compound 1 into microparticles (FIG. 3I).

Micro-particles of Compound 1 were prepared by emulsion from DCM using sodium dodecyl sulfate (FIG. 3J). The microparticles were analyzed by DSC (FIG. 3K) to confirm they were in the glassy state. Different preparation conditions (solvents, concentrations, surfactants, surfactant concentrations, mixing conditions, etc.) resulted in different particle sizes and distributions.

Figure 4:
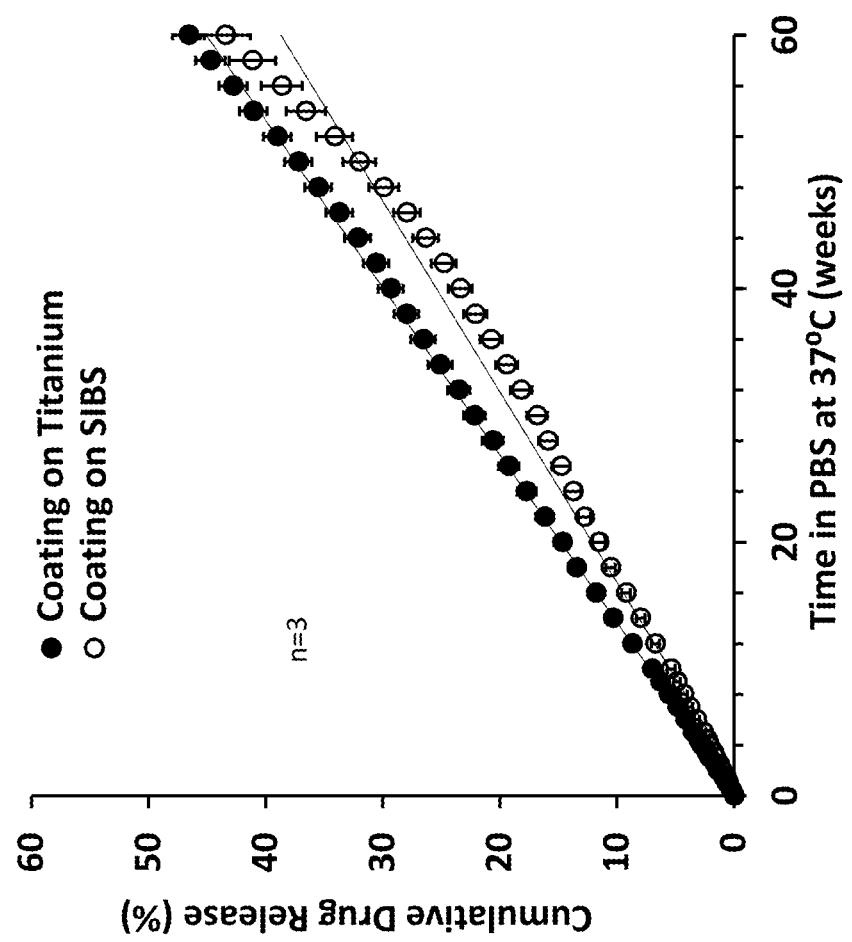
FIG. 4 is a graph showing cumulatie drug release from a coating of Compound 1 (Dex-TEG-Dex) from titanium and poly(styrene-block-isobutylene-block-styrene) (SIBS) over time.

Example 4: Drug Release from Compound 1 (Dex-TEG-Dex) Coated on Different Surfaces Compound 1 was coated onto titanium and SIBS as described in Example 3 above. Drug release from the coated material was carried out in PBS as described in Example 1 above. Cumulative drug release was calculated and plotted as a percentage of the total drug in each coated surface released over time (FIG. 4).

Figure 5:
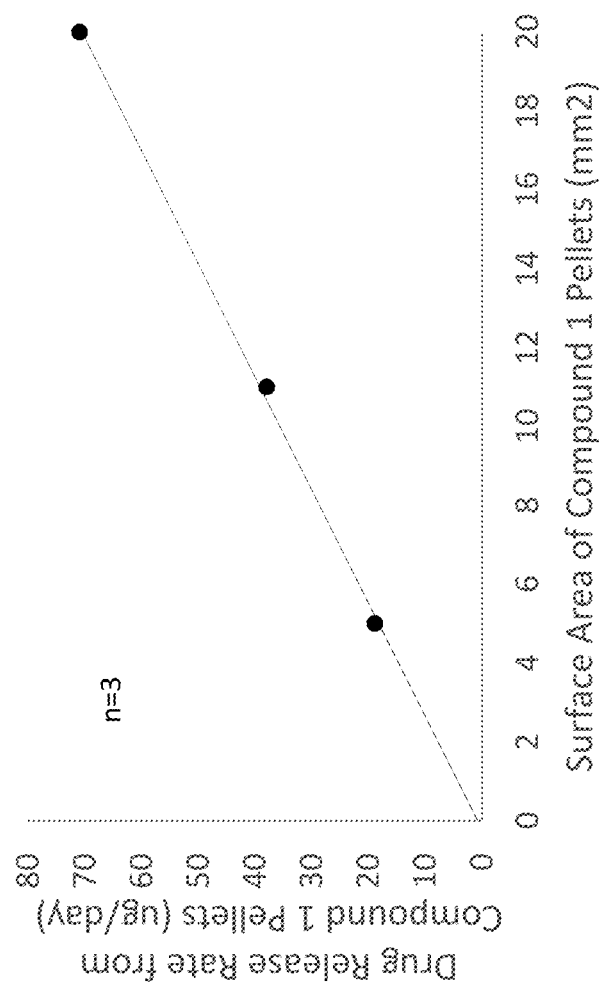
FIG. 5 is a graph showing rate of drug release of Compound 1 (Dex-TEG-Dex) pellets.

Example 5: Drug Release Properties from Heat-Molded Pellets of Compound 1 (Dex-TEG-Dex) can be Adjusted by Changing the Physical Properties of the Pellets Due to Surface Erosion Mechanism of Drug Release Compound 1 was heat-molded into pellets with 1 mm and 0.35 mm diameters using the conditions described in Example 1 and 2 above to get pellets with different masses of Compound 1 and different surface areas. Details of the samples are summarized in the table below. Drug release from the different samples was carried out in 100% FBS as described in Example 1 over a 7 day period. The change in drug release expected from different surface areas due to the surface erosion mechanism of drug release is exemplified in FIG. 5 as a plot of surface area vs. the average drug released per day taken from the linear release curves.

TABLE 2

Heat-Molded Pellets Formed From Compound 1. Different Masses and Surface Areas were Obtained by Changing the Number of Pellets of Given Dimensions.

| Sample Number | Pellet Dimensions (diameter × length) | Number of Pellets | Total Mass of Compound 1 | Total Surface Area |
| --- | --- | --- | --- | --- |
| 1 | ~1 mm × 1 mm | 1 | ~1 mg | ~5 mm$^2$ |
| 2 | ~0.35 mm × ~0.8 mm | 12 | ~1 mg | ~11 mm$^2$ |
| 3 | ~1 mm × 1 mm | 4 | ~4 mg | ~20 mm$^2$ |

Example 6: Mechanical Testing of Extruded Cylinders of Compound 1 (Dex-TEG-Dex) Using a 3 Point Bend Test (ASTM C1684-18)

Figure 6:
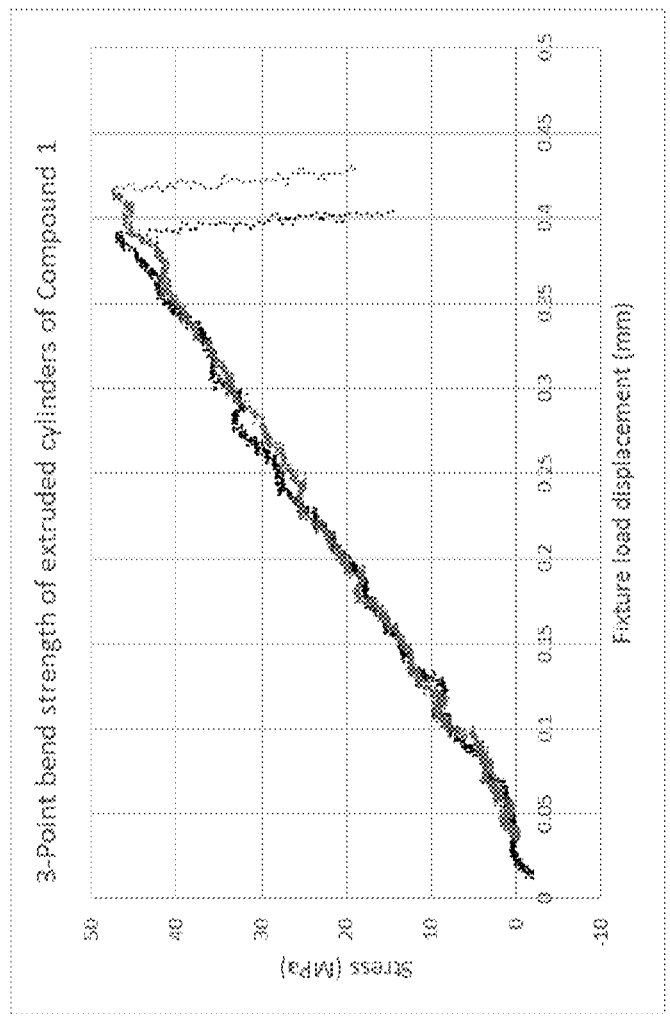
FIG. 6 is an image and a graph showing mechanical testing of extruded cylinders of Compound 1 (Dex-TEG-Dex) using a 3-point bend test.

The mechanical properties of extruded cylinders of Compound 1 were quantified with a 3-point bend test using ASTM C1684-18 (Standard test method of Flexural strength of advanced ceramics and ambient temperature—cylindrical rod strength). The ASTM C1684-18 was followed as closely as possible but modifications were necessary due to the small dimensions of the extruded cylinders. Representative fracture force data from the 3 point bend test of Compound 1 cylinders (0.25 mm×6 mm) are shown in FIG. 6.

Example 7: Ethylene Oxide Gas Sterilization of Heat Molded Pellets of Compound 1 (Dex-TEG-Dex)

Figure 7B:
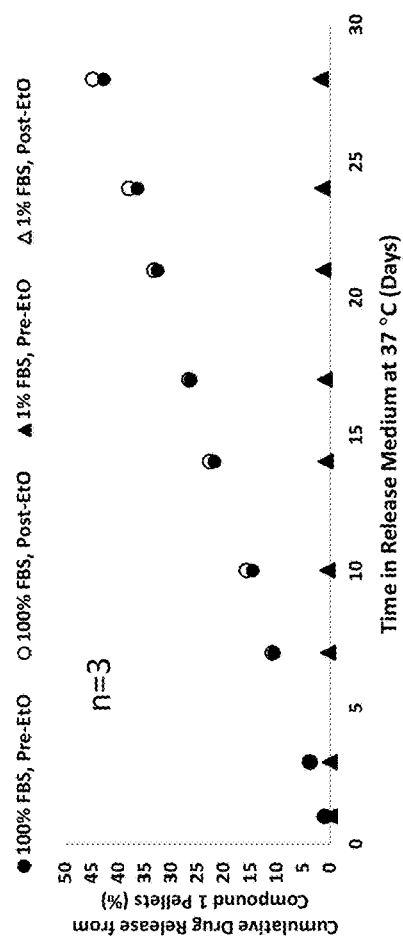
FIG. 7A and FIG. 7B are a series of graphs showing pre- and post-ETO sterilized pellets analyzed by HPLC to determine change in pellet purity, and drug release to identify changes in release properties due to the ETO sterilization process.
Figure 7A:
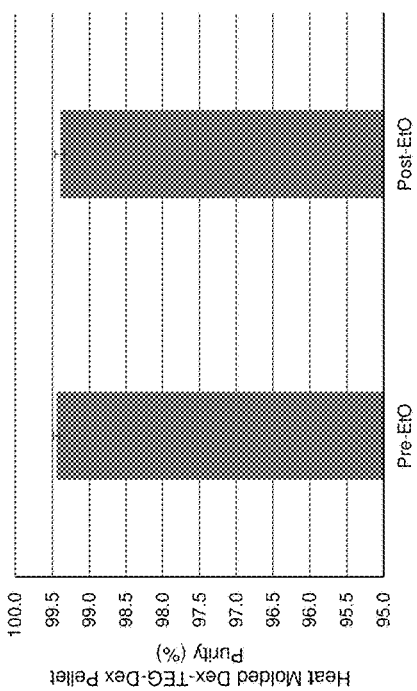

Heat-molded pellets from Compound 1 (1 mm in diameter) were sterilized by ethylene oxide (ETO) gas at a temperature of 55° C. Pre- and post-ETO sterilized pellets were analyzed by HPLC to demonstrate no changes in pellet (Compound 1) purity (FIG. 7A) and drug release (FIG. 7B) to demonstrate no changes in release properties due to the ETO sterilization process. Drug release was carried out in either 1% FBS in PBS or 100% FBS as described in Example 1.

Figure 8A:
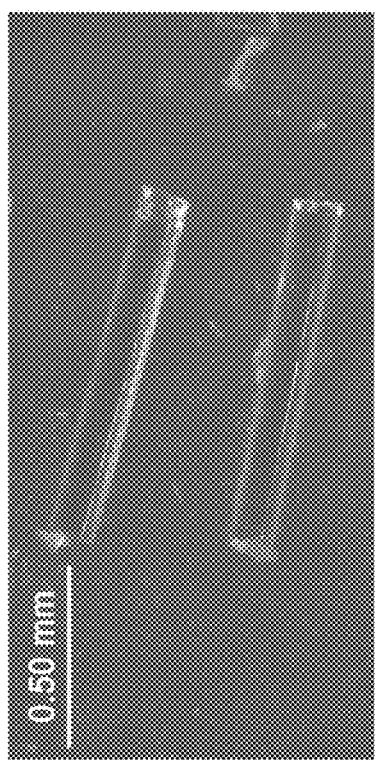
FIG. 8A to FIG. 8F are a series of images and graphs showing Compound 1 formed into heat extruded cylinders (FIGS. 8A-8D), purity of extrudate over time (FIG. 8E), and coating formed from Compound 1 (FIG. 8F).
Figure 8B:
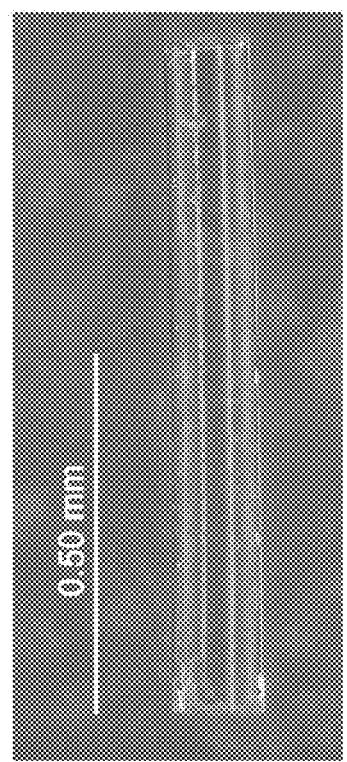
Figure 8C:
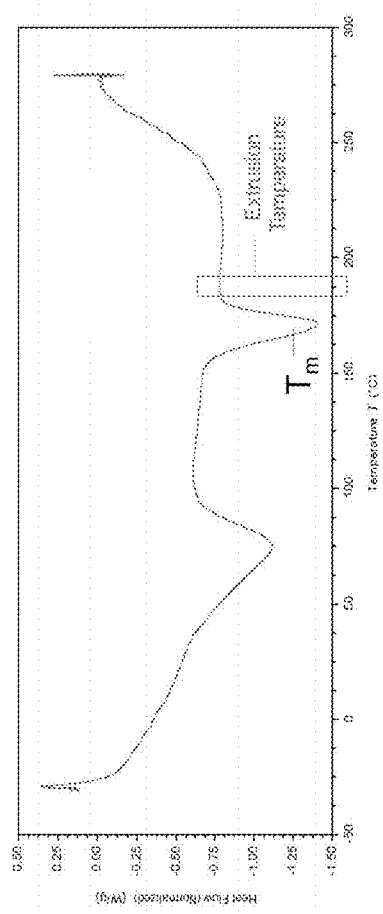
Figure 8D:
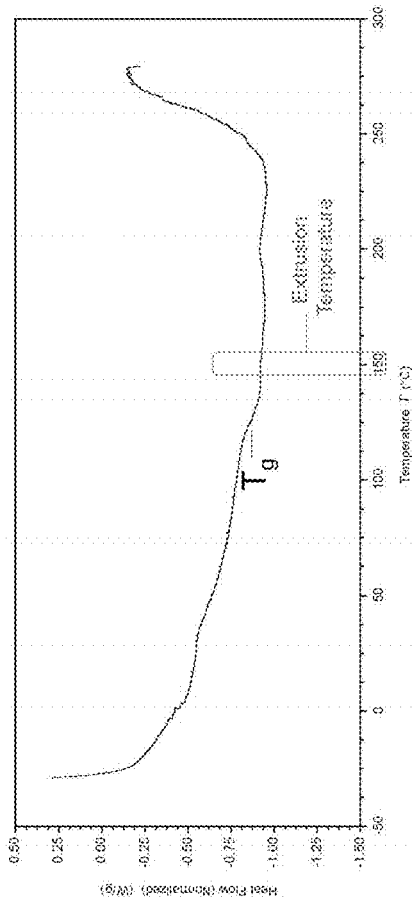
Figure 8E:
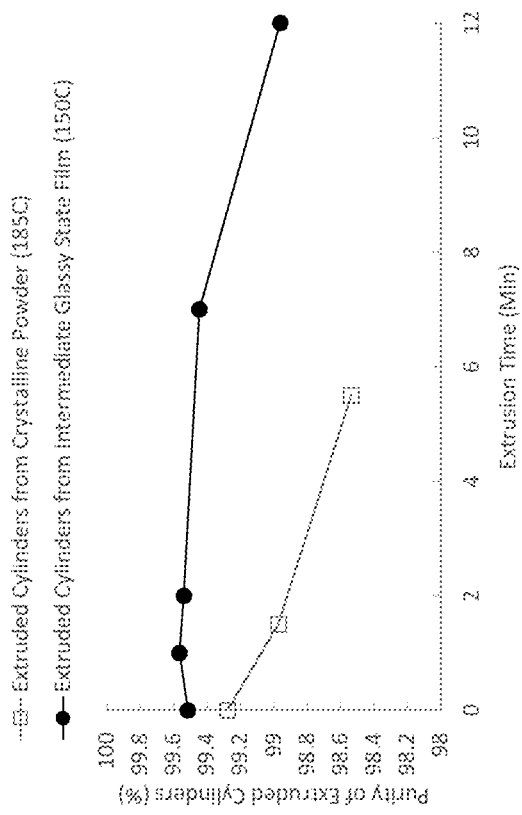

Example 8: Processing Compound 1 (Dex-TEG-Dex) into an Intermediate Glassy State to Manufacture the Final Article Compound 1 (Dex-TEG-Dex) was formed into heat extruded cylinders directly from the crystalline powder by heating above the melting point (185° C.), as shown in FIGS. 8A and 8B, using the methods described above in Example 2. Compound 1 was also formed into heat extruded cylinders by forming an intermediate glassy state form from the melt followed by heat extrusion above the glass transition temperature (150° C.) as shown in FIGS. 8C and 8D. Purity of the extrudate over time is shown in FIG. 8E and demonstrates longer extrusion run times using the intermediate glassy state before Compound 1 drops in purity when compared to extrusion from the melt state.

Figure 8F:
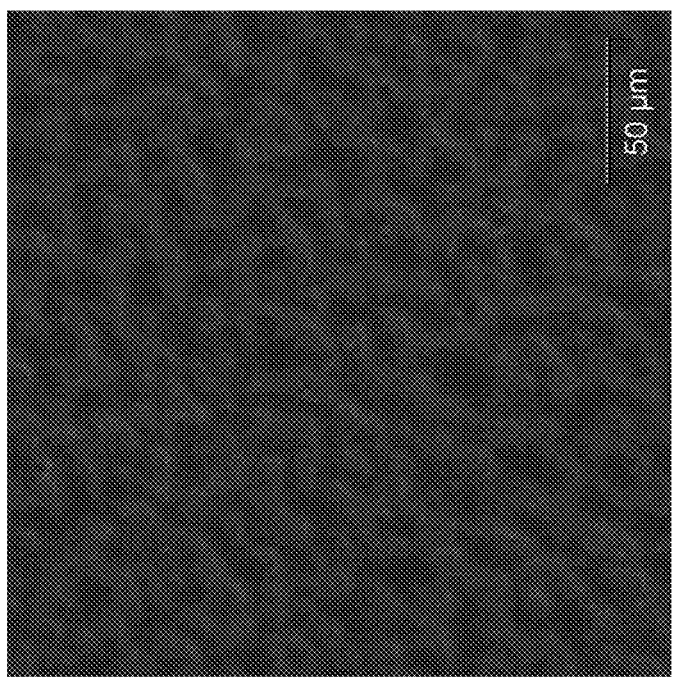

An intermediate glassy state was also formed from the solution state. Compound 1 was dissolved in acetone and was electrosprayed onto a polymer surface to form glassy state microparticles. The sprayed surface was heated to ~150° C. to obtain a coating as shown in FIG. 8F.

Example 9: Synthesis of Compounds

The compounds in Table 3, below, were synthesized using standard methods known in the art, similar to the synthesis of Compound 1 in Example 1 above. Details of the synthesized compounds are also shown in the table below. All compounds were synthesized to HPLC purity of >98% and structures were confirmed by $^1$H NMR and ESI MS. Melting points (Tm) and glass transition temperatures (Tg) were determined to establish processing temperatures needed to heat-process the compounds into pellets, fibers, and cylinders for further testing.

Example 10: Formation of Pellets, Fibers, and/or Cylinders in the Glassy State from Compounds 2-10 & 17 and Drug Release from Intact Glassy-State Pellets Compounds 2-10 & 17 were processed into heat molded pellets (1 mm×1 mm), fibers from the melt state, and/or heat extruded cylinders from the melt or intermediate glassy state as described in Examples 1, 2, and 7 above using the appropriate temperature for each compound (i.e. above the Tm or Tg as required). Processing Compounds 2-10 & 17 into the articles converted crystalline compounds into the glassy state and was confirmed for heat molded pellets by DSC. Drug release from heat molded pellets was carried out in PBS and/or 100% FBS, as described in Example 1, for different time periods. Cumulative drug release plotted over time demonstrated drug release from different compounds occurs mostly linearly at different rates from intact pellets in the timeframes tested, similar to drug release from Compound 1. Pellets of Compound 4, a heterodimer, released both dexamethasone and hydrocortisone. Figures corresponding to images of the pellets, fibers, and cylinders and drug release curves from pellets are shown in the table below.

TABLE 3

Structure of Compounds

Figure 9B:
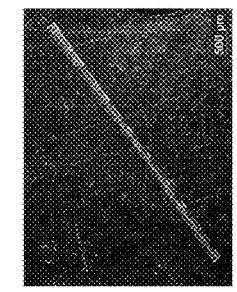
FIG. 9A to FIG. 9E are a series of images and a graph showing Compound 2 (Hydrocortisone-Triethylene Glycol-Hydrocortisone, HC-TEG-HC) formed into heat-molded pellets, fibers, and extruded cylinders, as well as drug release over time.
Figure 9C:
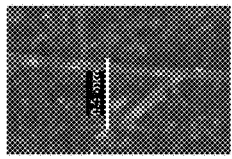
Figure 9D:
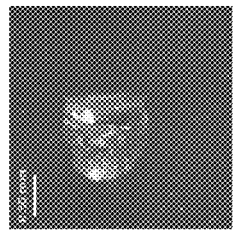
Figure 9E:
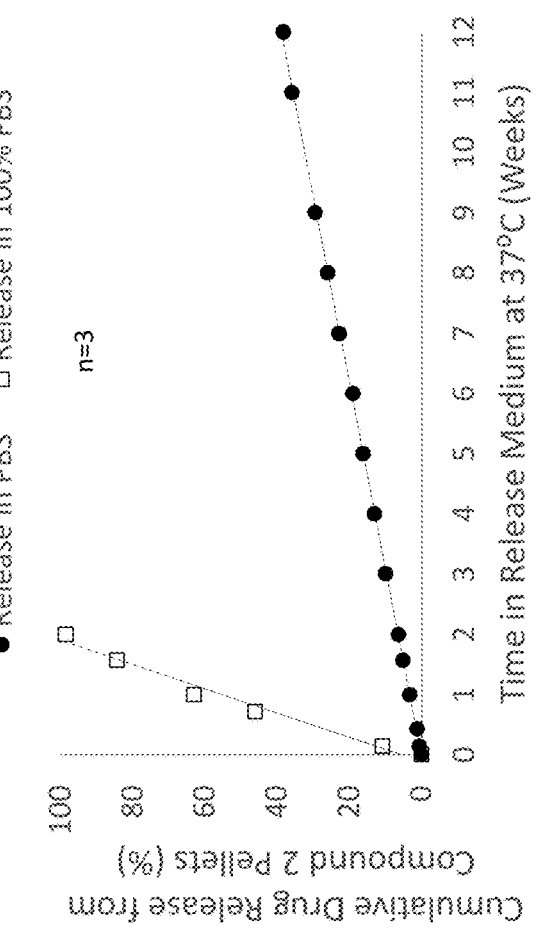
Figure 9A:
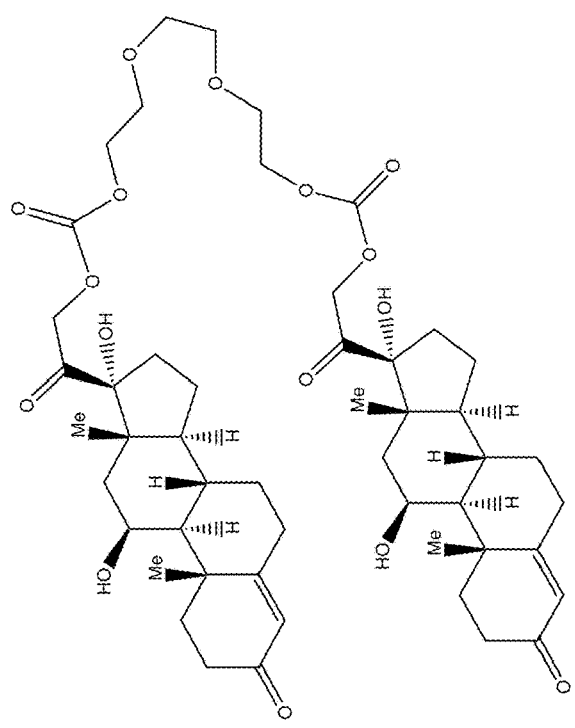
Figure 11B:
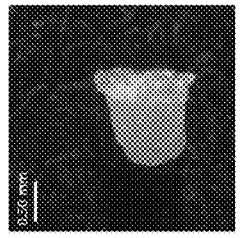
FIG. 11A to FIG. 11C are an image and a graph showing Compound 4 (Dexamethasone-Triethylene Glycol-Hydrocortisone, Dex-TEG-HC) formed into heat-molded pellets and drug release over time.
Figure 11C:
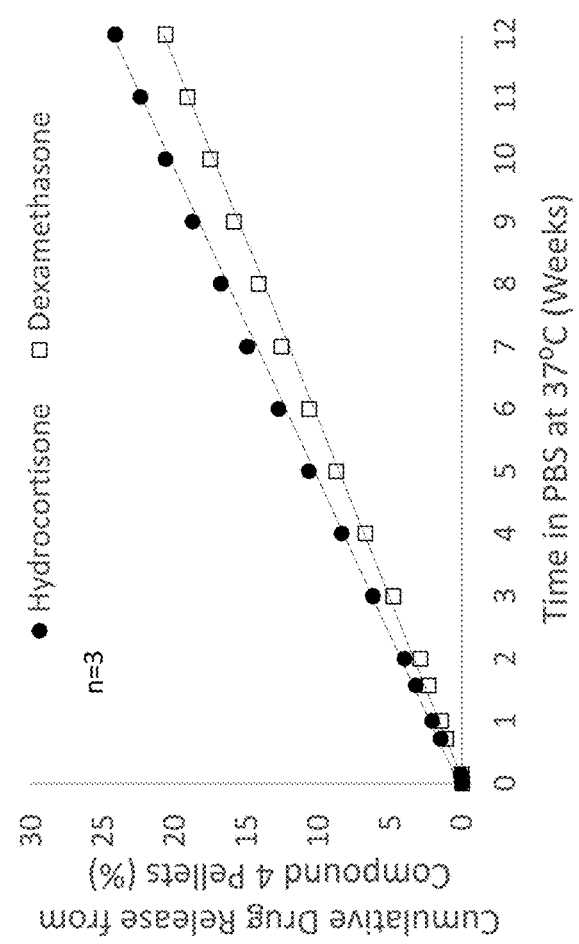
Figure 11A:
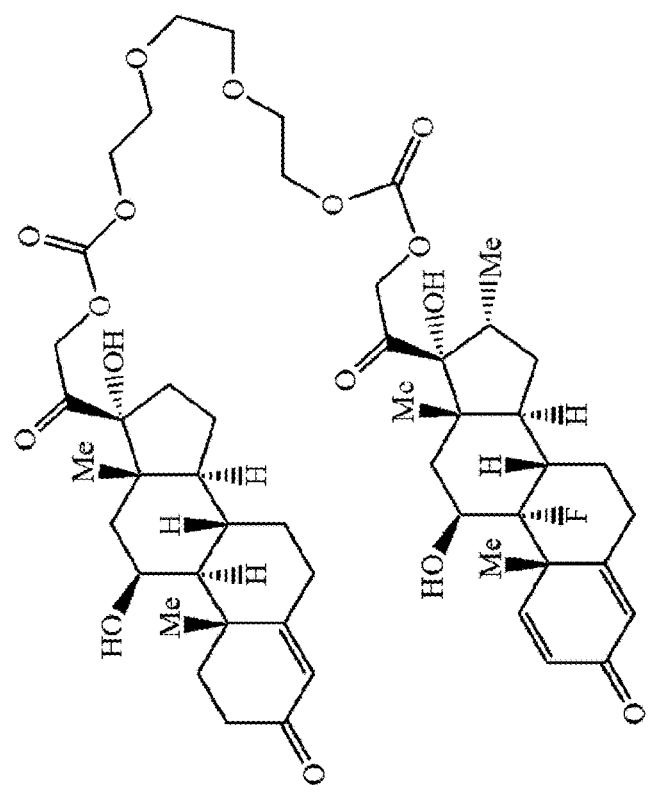
Figure 13A:
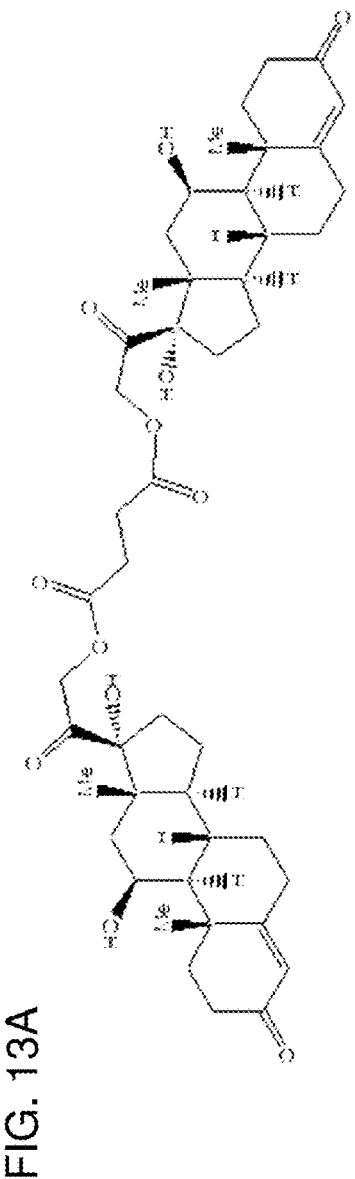
FIG. 13A to FIG. 13E are a series of images and a graph showing Compound 6 (Hydrocortisone-Succinate-Hydrocortisone, HC-SUCC-HC) formed into heat-molded pellets and fibers, as well as drug release over time.
Figure 15B:
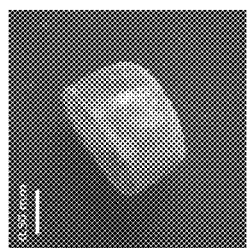
FIG. 15A to FIG. 15C are an image and a graph showing Compound 8 (Dexamethasone-Pentaethylene Glycol-Dexamethasone, Dex-EG5-Dex) formed into heat-molded pellets and drug release over time.
Figure 15C:
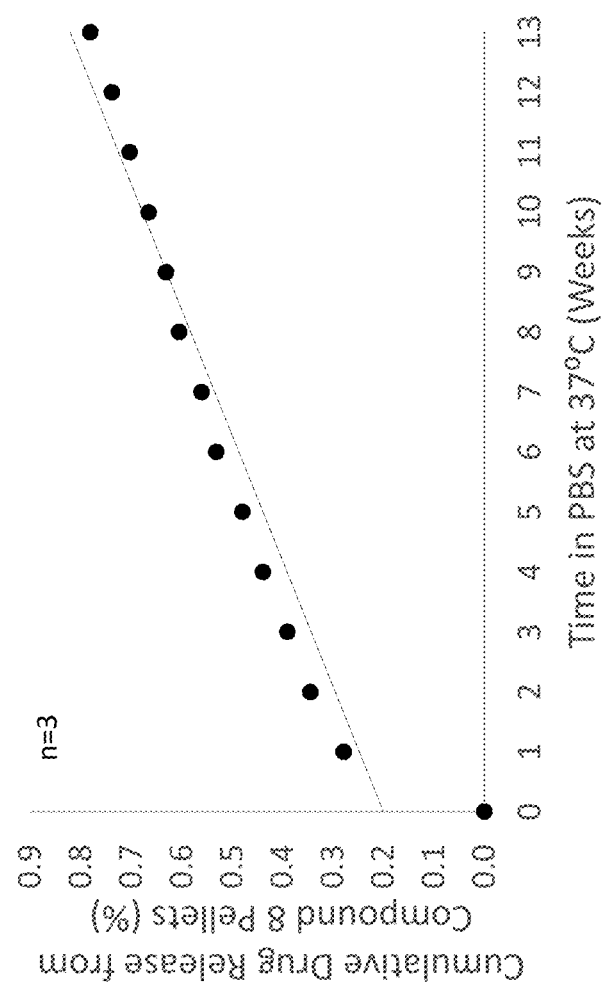
Figure 15A:
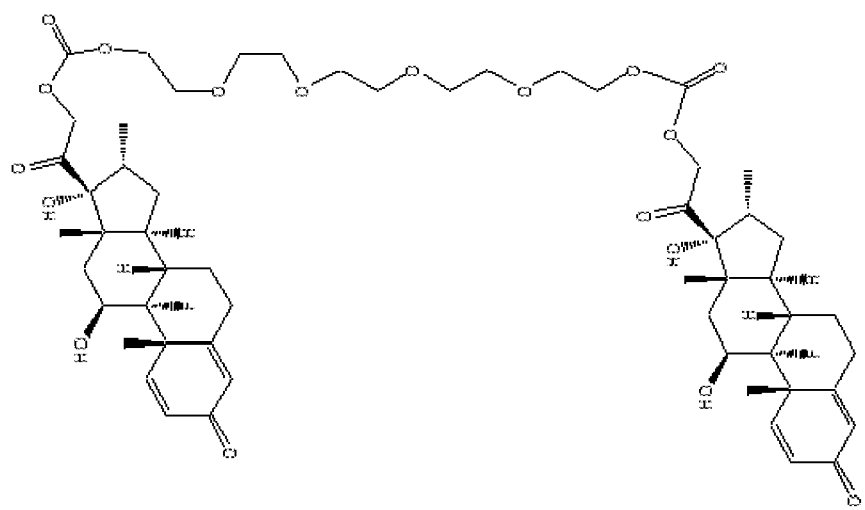
Figure 17A:
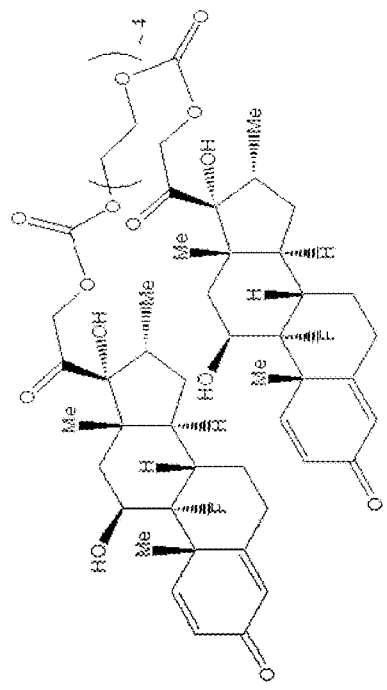
FIG. 17A to FIG. 17D are a series of images and a graph showing Compound 10 (Dexamethasone-Polyethylene Glycol (MW=200)-Dexamethasone, Dex-PEG200-Dex) formed into heat-molded pellets and extruded cylinders, as well as drug release over time.
Figure 24B:
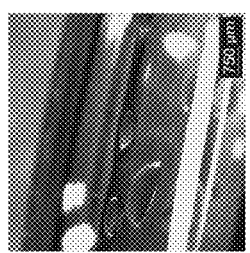
FIG. 24A to FIG. 24D are a series of images and a graph showing Compound 12 (Dexamethasone-Nonaethylene Glycol-Dexamethasone, Dex-EG9-Dex) formed into heat-molded pellets and extruded cylinders, and the extruded cylinders after two weeks in PBS at 37° C.
Figure 24C:
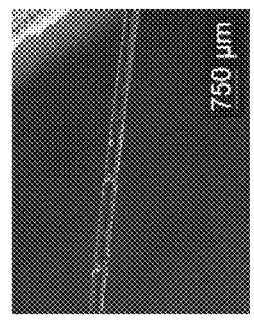
Figure 24D:
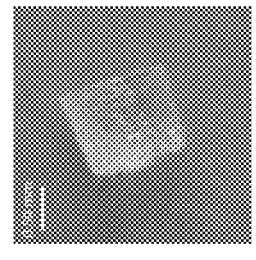
Figure 24A:
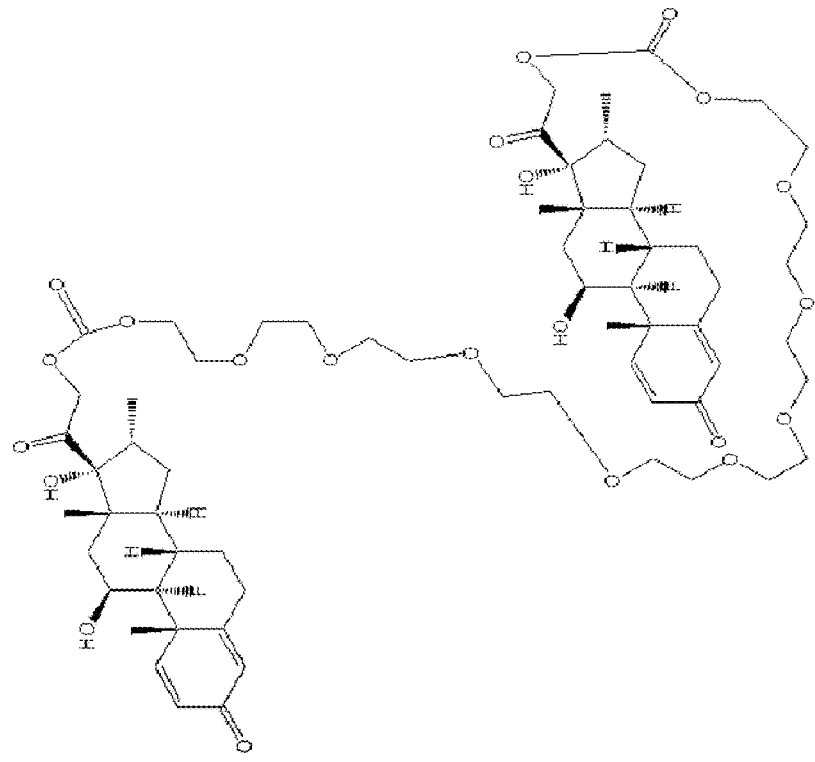
Figure 25A:
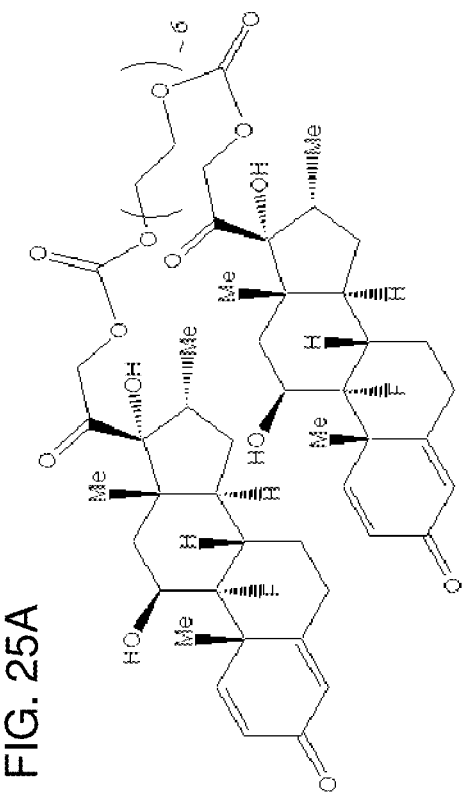
FIG. 25A to FIG. 25D are a series of images and a graph showing Compound 13 (Dexamethasone-Polyethylene Glycol (MW=300)-Dexamethasone, Dex-PEG300-Dex) formed into heat-molded pellets and extruded cylinders, and the extruded cylinders after two weeks in PBS at 37° C.
Figure 29B:
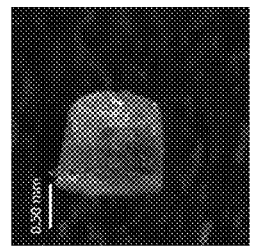
FIG. 29A and FIG. 29B is an image showing Compound 16 (Ethinylestradiol-Triethylene Glycol-Ethinylestradiol, Ethin-TEG-Ethin) formed into heat-molded pellets.
Figure 29A:
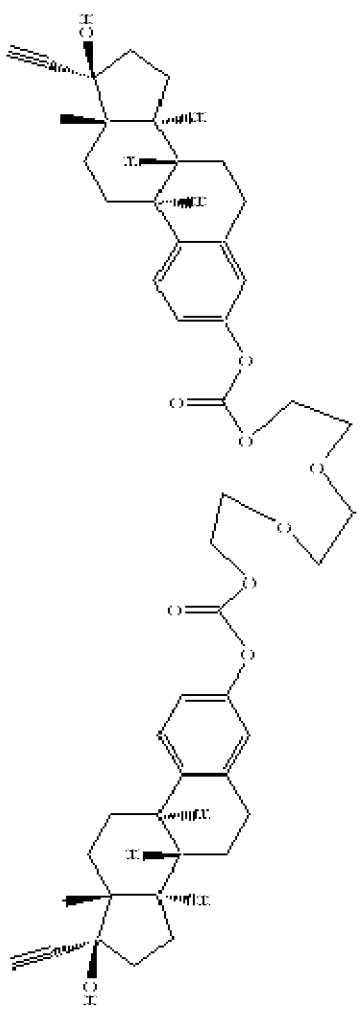

| Compound (Abbreviation) | Steroid | Linker | Linking Moiety | Structure | Tm & Tg (° C.) |
|---|---|---|---|---|---|
| 2 (HC-TEG-HC) | Hydrocortisone | Triethylene Glycol | Carbonate | FIG. 9A | 127 & 113 |
| 3 (TA-TEG-TA) | Triamcinolone Acetonide | Triethylene Glycol | Carbonate | FIG. 10A | 183 & 138 |
| 4 (Dex-TEG-HC) | Dexamethasone & Hydrocortisone | Triethylene Glycol | Carbonate | FIG. 11A | 143 & 120 |
| 5 (Dex-HEX-Dex) | Dexamethasone | Hexane Diol | Carbonate | FIG. 12A | 149 & 146 |
| 6 (HC-SUCC-HC) | Hydrocortisone | Succinic Acid | Ester | FIG. 13A | 157 & 144 |
| 7 (Anec-TEG-Anec) | Anecortave | Triethylene Glycol | Carbonate | FIG. 14A | 102 & 100 |
| 8 (Dex-EG5-Dex) | Dexamethasone | Pentaethylene Glycol | Carbonate | FIG. 15A | n.d.* & 66 |
| 9 (FA-TEG-FA (CE)) | Fusidic Acid | Triethylene Glycol | Carbonate Ester | FIG. 16A | 91 & 85 |
| 10 (Dex-PEG200-Dex) | Dexamethasone | Polyethylene Glycol (MW = 200) | Carbonate | FIG. 17A | n.d.* & 96 |
| 11 (Dex-EG7-Dex) | Dexamethasone | Heptaethylene Glycol | Carbonate | FIG. 23D | 51 & 47 |
| 12 (Dex-EG9-Dex) | Dexamethasone | Nonaethylene Glycol | Carbonate | FIG. 24A | 41 & 37 |
| 13 (Dex-PEG300-Dex) | Dexamethasone | Polyethylene Glycol (MW = 300) | Carbonate | FIG. 25A | 77 & 75 |
| 14 (CHS-TEG-CHS) | Cholesterol | Triethylene Glycol | Carbonate | FIG. 27A | 99 & 22 |
| 15 (FA-TEG-FA (E)) | Fusidic Acid | Triethylene Glycol | Ester | FIG. 28A | 87 & 84 |
| 16 (Ethin-TEG-Ethin) | Ethinylestradiol | Triethylene Glycol | Carbonate | FIG. 29A | 61 & 53 |
| 17 (Pred-TEG-Pred) | Prednisolone | Triethylene Glycol | Carbonate | FIG. 30A | 128 & 112 |

*n.d. = not determined

TABLE 4

Compounds processed in glassy state and drug release

Figure 13C:
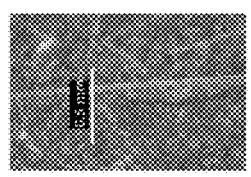
Figure 13B:
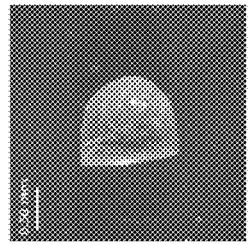
Figure 13D:
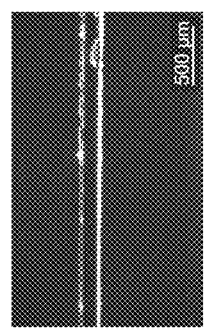
Figure 13E:
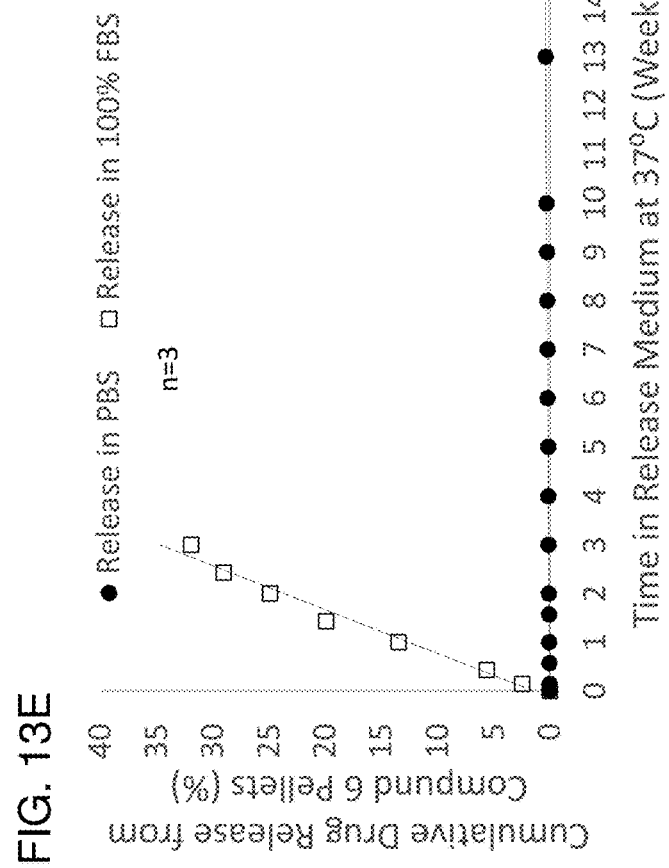
Figure 17B:
Figure 17C:
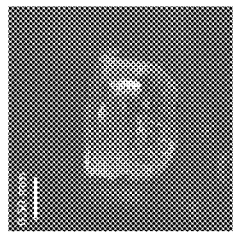
Figure 17D:
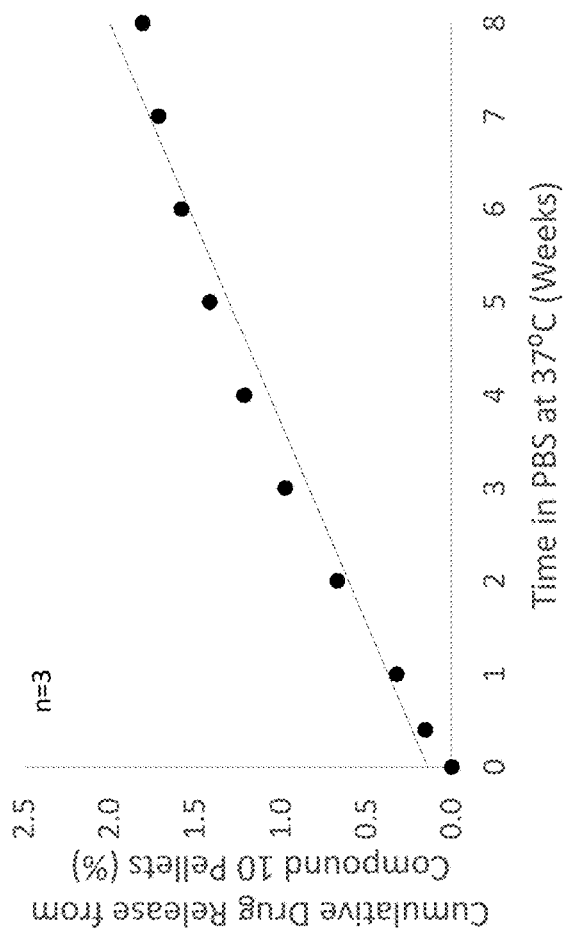

| Compound | Heat-Molded Pellets | Fibers | Extruded Cylinders | Drug Release |
|---|---|---|---|---|
| 2 (HC-TEG-HC) | FIG. 9B | FIG. 9C | FIG. 9D | FIG. 9E |
| 3 (TA-TEG-TA) | FIG. 10B | FIG. 10C | FIG. 10D | FIG. 10E |
| 4 (Dex-TEG-HC) | FIG. 11B | Not tested | Not tested | FIG. 11C |
| 5 (Dex-Hex-Dex) | FIG. 12B | FIG. 12C | FIG. 12D | FIG. 12E |
| 6 (HC-SUCC-HC) | FIG. 13B | FIG. 13C | FIG. 13D | FIG. 13E |
| 7 (Anec-TEG-Anec) | FIG. 14B | FIG. 14C | FIG. 14D | FIG. 14E |
| 8 (Dex-EG5-Dex) | FIG. 15B | Not tested | Not tested | FIG. 15C |
| 9 (FA-TEG-FA (CE)) | FIG. 16B | FIG. 16C | FIG. 16D | FIG. 16E |
| 10 (Dex-PEG200-Dex) | FIG. 17B | Not tested | FIG. 17C | FIG. 17D |
| 17 (Pred-TEG-Pred) | FIG. 30B | FIG. 30C | Not tested | Not tested |

Figure 18G:
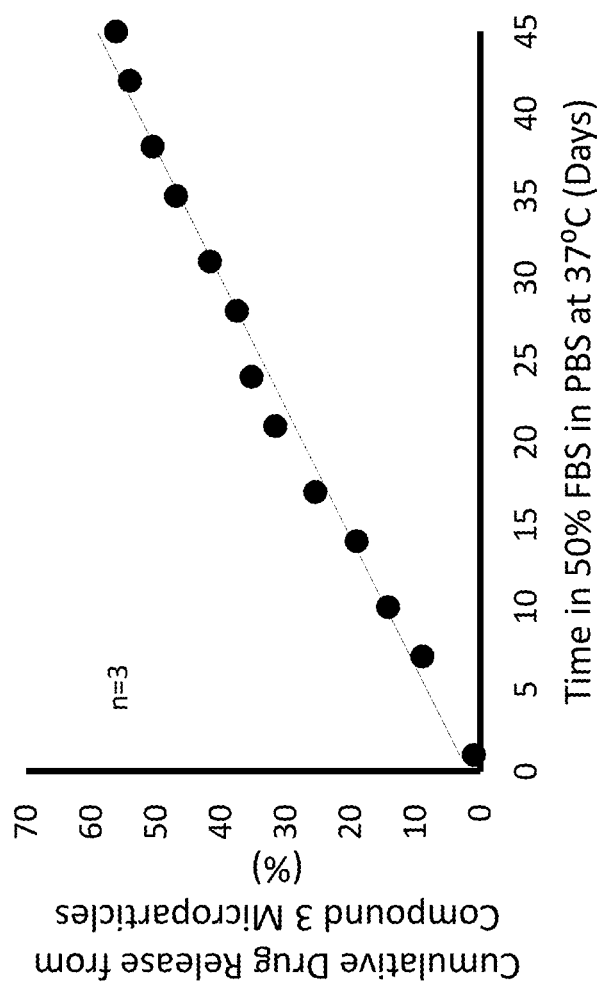

Example 11. Nano- and Micro-Particle Formation in the Glassy State from Compounds 3 (TA-TEG-TA) & 5 (Dex-HEX-Dex) Provide Sustained Release of Drug Electrospraying and emulsions were used to make nano- and microparticles from Compounds 3 (FIGS. 18A and 18B) and 5 (FIGS. 18C and 18D) using conditions similar to that described for Compound 1 in Example 3 above. Different preparation conditions, for example solvents, concentrations, surfactants, surfactant concentrations, mixing conditions, etc., resulted in different particle sizes and distributions. DSC was used to confirm the particles were in the glassy state. FIG. 18E shows an example DSC chromatogram and FIG. 18F shows particle size distribution for microparticles made by emulsion from Compound 3 in DCM using SDS as a surfactant. Drug release from microparticles of Compound 3 was carried out in 50% FBS in PBS, similar to that described in Example 1. Cumulative drug release was calculated and plotted as a percentage of the total drug released over time (FIG. 18G).

Example 12: Heat-Molded Pellets in the Glassy State can be Formed from Mixtures of Two Dimers and Drugs are Released from Both Compounds of the Intact Pellet Pellets in the glassy state were formed by heat molding a mixture of compounds as shown in the table below. The starting crystalline compounds were mixed together and were heat molded at a temperature above the higher melting point compound. Drug release from the pellets (1 mm×1 mm and 1 mg of total mixture) was carried out in PBS as described in Example 1. Cumulative drug release was calculated and plotted as a percentage of the total drug released over time. Linear drug release from intact pellets was observed for both compounds in the mixed pellets.

TABLE 4

Heat-molded pellets formed from mixtures of two compounds and drug release

Figure 19B:
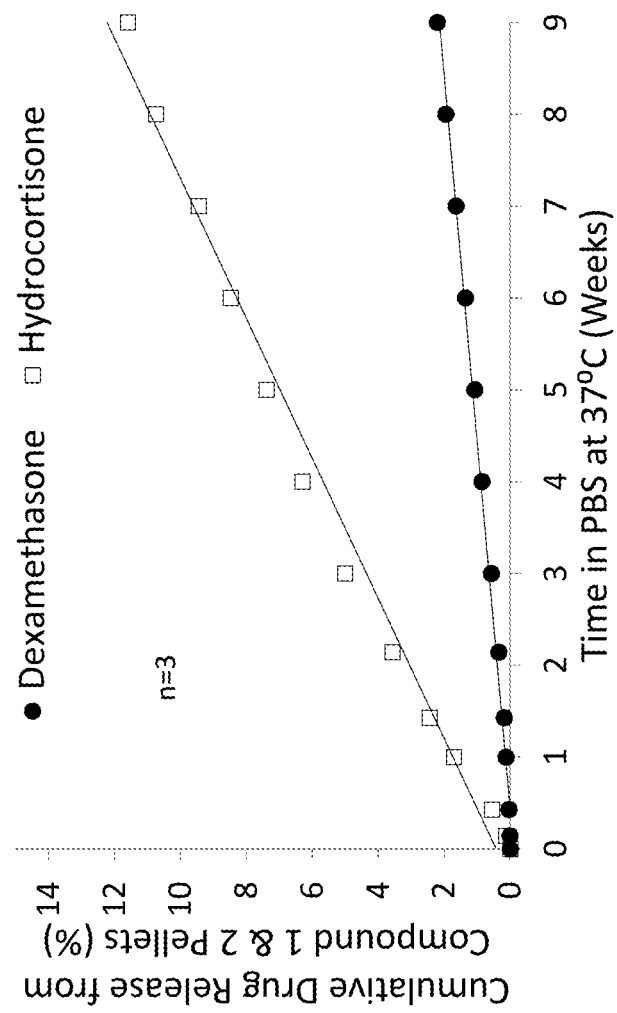
FIG. 19A and FIG. 19B are an image and a graph showing a mixture of Compounds 1 and 2 formed into heat-molded pellets and drug release over time.
Figure 19A:
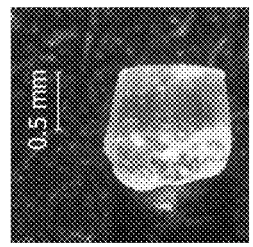
Figure 20B:
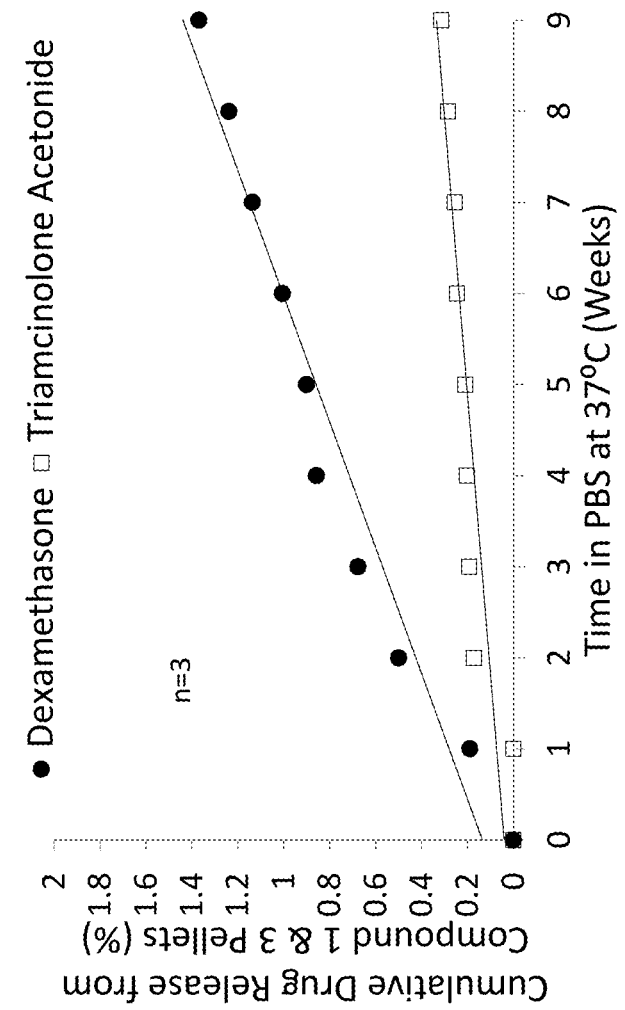
FIG. 20A and FIG. 20B are an image and a graph showing a mixture of Compounds 1 and 3 formed into heat-molded pellets and drug release over time.
Figure 20A:
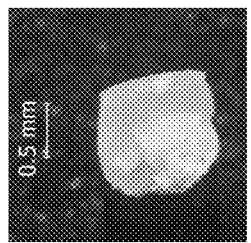

| Mixture | Components of Mixture | Ratio | Heat-Molded Pellet | Drug Release |
|---|---|---|---|---|
| A | Compound 1 (Dex-TEG-Dex) & Compound 2 (HC-TEG-HC) | 1:1 w/w | FIG. 19A | FIG. 19B |
| B | Compound 1 (Dex-TEG-Dex) & Compound 3 (TA-TEG-TA) | 1:1 w/w | FIG. 20A | FIG. 20B |
| C | Compound 2 (HC-TEG-HC) & Compound 3 (TA-TEG-TA) | 1:1 w/w | FIG. 21A | FIG. 21B |

Example 13: Methods to Adjust Release of Drug from Glassy State Articles

Figure 22A:
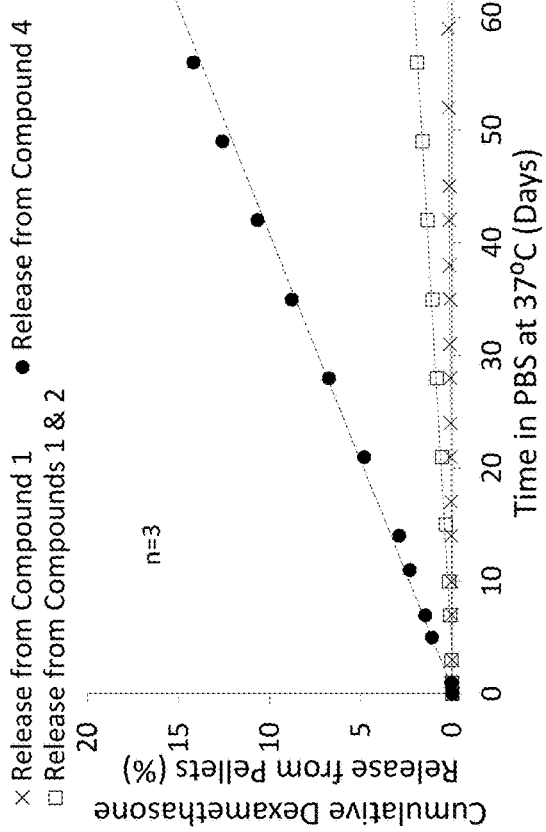
Figure 22B:
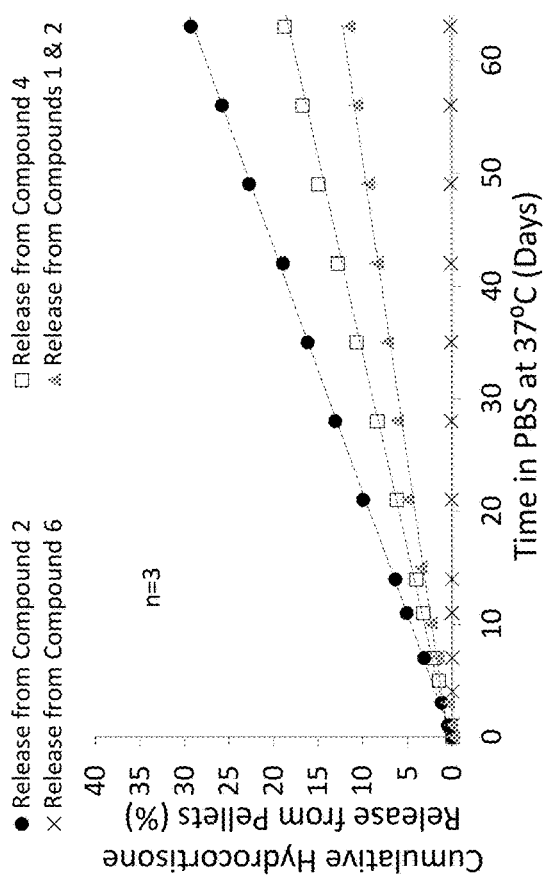

The release of drug from glassy state articles can be controlled in various ways for example by changing the environment the article is placed or by adjusting the physical properties of the article to take advantage of the surface erosion mechanism of drug release. In scenarios where the environment and physical properties of the article are fixed, other properties such as processing conditions, formulation, and/or compound structure via a change in linker can be adjusted to engineer the article to obtain the desired drug release properties for the application of interest. To exemplify this, FIG. 22A plots the release of hydrocortisone from heat molded pellets (1 mm×1 mm) in PBS at 37° C. from Compound 2 (HC-TEG-HC), Compound 4 (Dex-TEG-HC), and Compound 6 (HC-SUCC-HC) as shown in Example 9 above and from Mixture A (Compound 1 & 2 (1:1 w/w)) as shown in Example 10 above. Similarly, FIG. 22B plots the release of dexamethasone from heat molded pellets (1 mm×1 mm) in PBS at 37° C. from Compound 1 (Dex-TEG-Dex) and Compound 4 (Dex-TEG-HC) as shown in Examples 1 and 9 above and from Mixture A (Compound 1 & 2 (1:1 w/w)) as shown in Example 10 above. Linear drug release from intact pellets was observed for all pellets but differences in the rate of drug release was varied using different linkers, using a second steroid dimer as an excipient, or by using a second steroid in the form of a heterodimer. Dexamethasone release from heat molded pellets (1 mm×1 mm) of Compound 1 (Dex-TEG-Dex) and Compound 5 (Dex-Hex-Dex) in 100% FBS as shown in FIG. 22C further exemplifies how linker affects the drug release rates.

Example 14: Compounds 11 (Dex-EG7-Dex), 12 (Dex-EG9-Dex), and 13 (Dex-PEG300-Dex) can be Formed into Heat Molded Pellets and Extruded Cylinders in the Glassy State but Undergo Physical Form (Shape) and Drug Release Changes Over Time in Release Medium at 37° C.

Compounds 11, 12, and 13 were processed into heat molded pellets (1 mm×1 mm) and heat extruded cylinders as described in Examples 1, 2, and 7 above using the appropriate temperature for the compound and are shown in the table below. The heat-processed articles from Compounds 11. 12, and 13 were in the glassy state as confirmed by DSC. Drug release from heat molded pellets were carried out in PBS and 100% FBS, as described in Example 1, for Compounds 11 and 12. Physical form (shape) and drug release changes occurred for both compounds in PBS and 100%

Figure 26A:
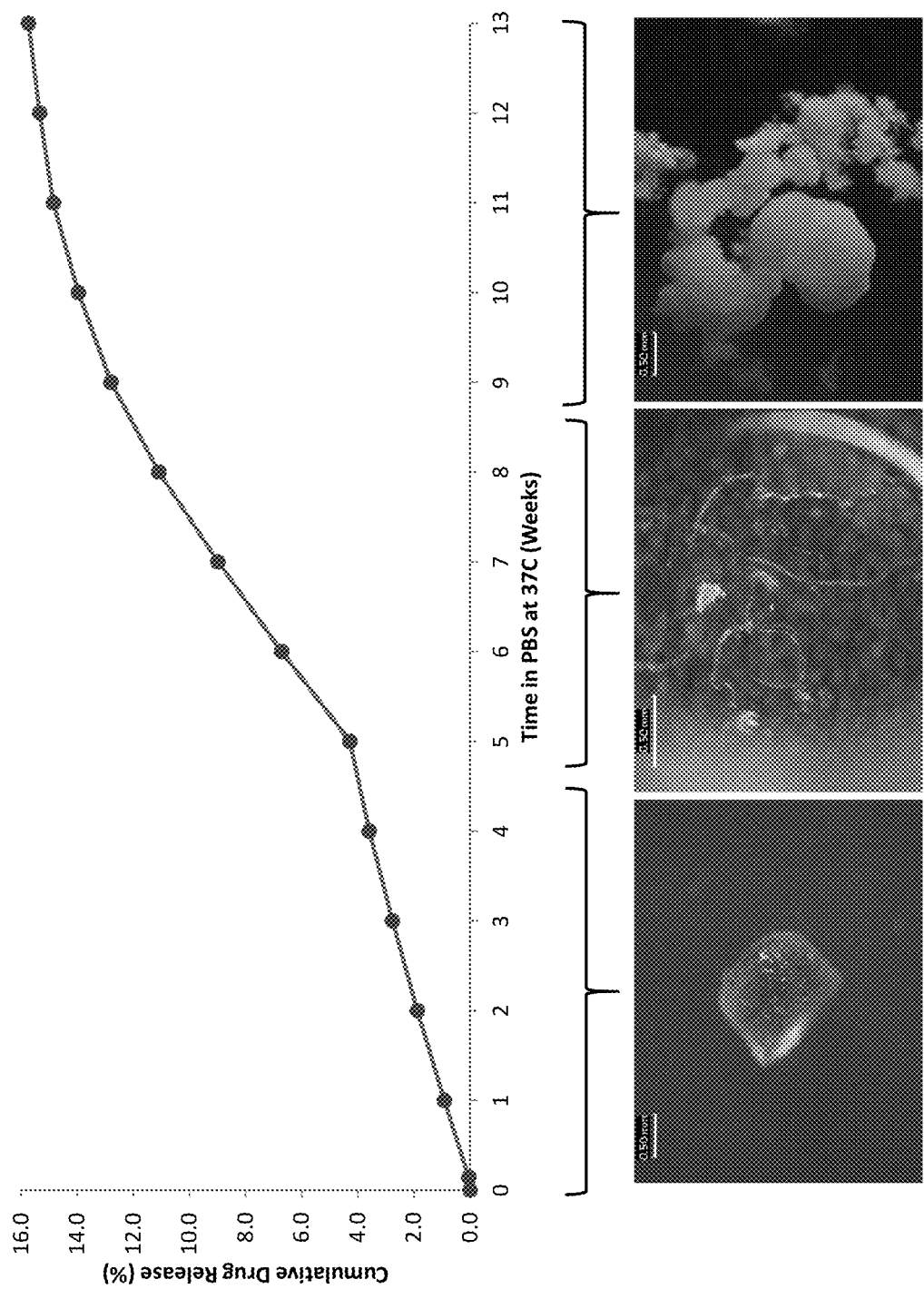
FIG. 26A and FIG. 26B are a series of images and graphs showing physical form (geometric shape) changes and drug release from heat-molded pellets for Compounds 11 and 12 over time.
Figure 26B:
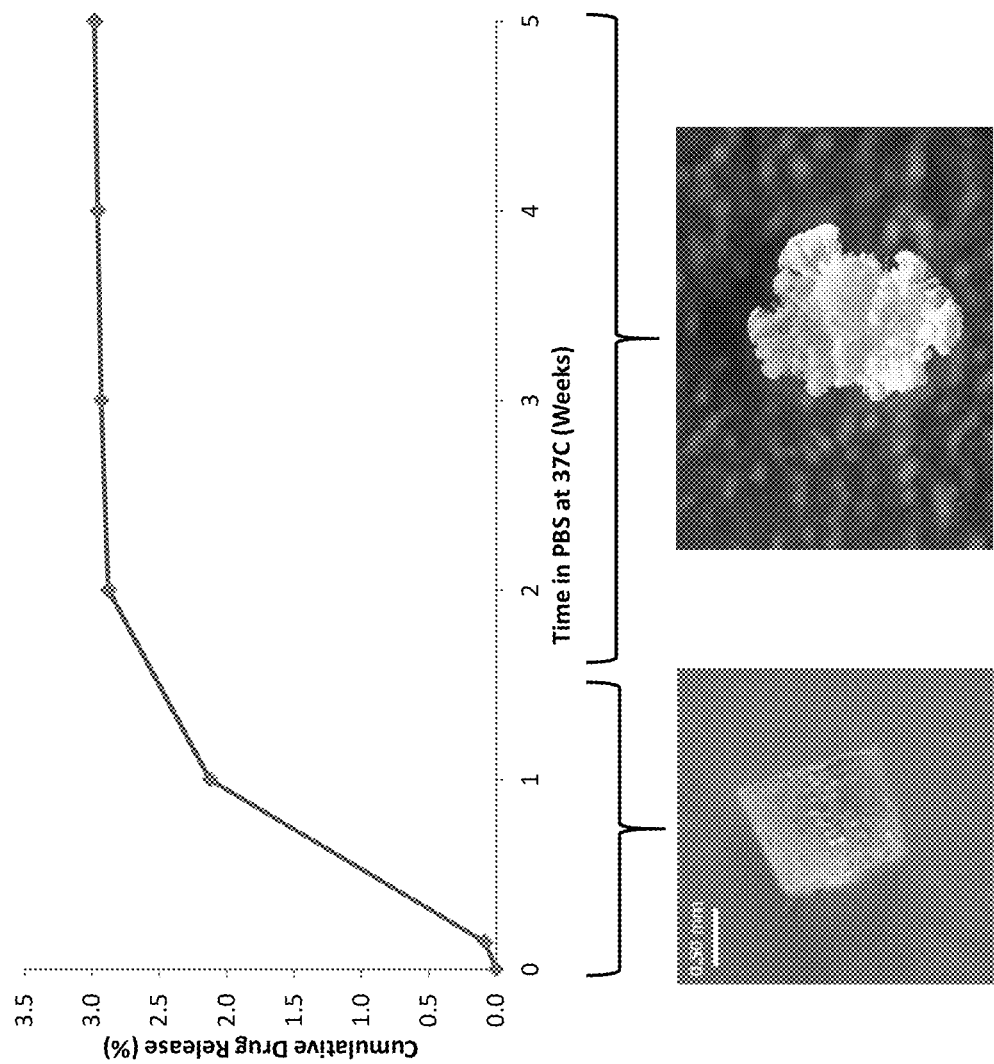

FBS and is exemplified in FIGS. 26A and 26B for pellets of Compounds 11 and 12, respectively, in PBS at 37° C. The drug release changes corresponded to the changes in physical form (geometric shape) with the pellets. Similar changes in physical form (shape) were observed for extruded cylinders for Compounds 11, 12, and 13 where they formed into droplets on the bottom of the vial in less than 2 weeks in PBS at 37° C. as shown in the table below.

TABLE 5

Compounds 11, 12, and 13 processed in glassy state

Figure 25D:
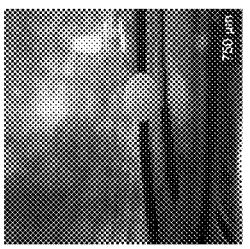
Figure 25C:
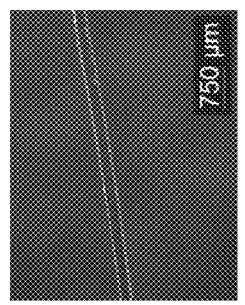
Figure 25B:
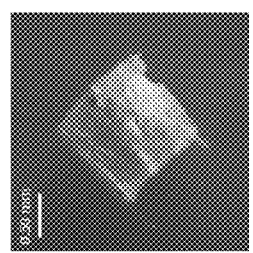

| Compound | Processed Compounds in Glassy State | | Extruded Cylinder |
|---|---|---|---|
| | Heat Molded Pellets | Extruded Cylinders | after 2 weeks in PBS at 37° C. |
| 11 (Dex-EG7-Dex) | FIG. 23B | FIG. 23C | FIG. 23D |
| 12 (Dex-EG9-Dex) | FIG. 24B | FIG. 24C | FIG. 24D |
| 13 (Dex-PEG300-Dex) | FIG. 25B | FIG. 25C | FIG. 25D |

Example 15: Compound 14 (CHS-TEG-CHS) can be Formed into Pellets and Fibers but have Residual Crystallinity and Pellets Fail to Release Drug in Release Medium at 37° C.

Compound 14 was processed into heat molded pellets (1 mm×1 mm) and fibers as described in Examples 1 and 2 above and are shown in the table below. The heat-processed pellets had residual crystallinity as confirmed by DSC. Drug release from heat molded pellets was carried out in PBS and 100% FBS, as described in Example 1, but no drug was released from the pellets in either release medium.

TABLE 6

Compound 7 processed in glassy state

| Compound | Processed Compounds in Glassy State | |
|---|---|---|
| | Heat Molded Pellets | Fibers |
| 14 (CHS-TEG-CHS) | FIG. 27B | FIG. 27C |

Example 16: Compound 15 (FA-TEG-FA (E)) and 16 (Ethin-TEG-Ethin) can be Formed into Pellets and Fibers in the Glassy State but Fail to Release Drug in Release Medium at 37° C.

Compounds 15 and 16 were processed into heat molded pellets (1 mm×1 mm) and fibers as described in Examples 1 and 2 above and are shown in the table below. The heat-processed articles were in the glassy state as confirmed by DSC. Drug release from heat molded pellets was carried out in PBS and 100% FBS, as described in Example 1, but no drug was released from the pellets in either release medium.

TABLE 7

Compounds 15 and 16 processed in glassy state

| Compound | Processed Compounds in Glassy State | |
|---|---|---|
| | Heat Molded Pellets | Fibers |
| 15 (FA-TEG-FA (E)) | FIG. 28B | FIG. 28C |
| 16 (Ethin-TEG-Ethin) | FIG. 29B | Not tested |

Example 17. Microparticles and Nanoparticles for Treating Local Inflammation

Microparticles and nanoparticles are formed from Compound 1 according to the methods described in above. The micro- and nanoparticles are then injected into the joint of a subject suffering from inflammation, e.g., arthritis, and releases dexamethasone into the subject at a steady rate over three months. Local inflammation in the joint of the subject is reduced. Similarly, the other compounds of the disclosure can likewise be used to form micro- and nanoparticles and injected into the joint of a subject for the purposes of treating, e.g., inflammation, and the drug is released at a steady rate over several months (e.g., three months).

Example 18. Drug Dimers

Compounds 18-20, described below, can by prepared using method analogous to those described herein. The compounds can be processed as described herein to produce articles capable of producing an extended release profile following implantation into a subject, and can be used in the methods, compositions, and articles of the disclosure.

| Compound | Dimer | Abbreviation |
|---|---|---|
| 18 | Dexamethasone-glycerol-Dexamethasone | Dex-Gly-Dex |
| 19 | Hydrocortisone-Hexane-Hydrocortisone | HC-Hex-HC |
| 20 | Prednisolone-TEG-Abiraterone | Pred-TEG-Abir |

Example 19. Effect of Compound on Article Stability and Drug Release Profiles

Each of compounds 1, 4, 5, 8, and 10-13 differ in modest changes to the linker covalently tethering two dexamethasone radicals into a dimer. All of the compounds were observed to be capable of being processed into articles (e.g., glassy amorphous solids). However, articles formed from different compounds were observed to exhibit dramatically different stability (under physiologically relevant conditions) and dramatically different dexamethasone release profiles.

Articles formed from Compounds 11, 12, and 13 with dexamethasone and longer PEG linkers appear to undergo physical form (shape) changes, while articles formed from Compound 1 and 8 with dexamethasone and shorter PEG linkers do not. As evidenced in FIGS. 23D, 24D, and 25D, Compounds 11, 12, and 13 form into spherical droplets after two weeks in PBS. On the other hand, FIG. 1F shows pellets formed from Compound 1 maintaining their shape as they gradually get smaller due to surface erosion.

Articles formed from different compounds were also observed to exhibit dramatically different dexamethasone release profiles. As a result of these physical form (shape)

changes to the articles of Compounds 11, 12, and 13, the drug release mechanism is not via surface erosion and is therefore not linear or predictable (see FIGS. 26A and 26B). The physical form (shape) changes observed with the articles correspond to the changes in release rates. Further, as shown in FIG. 26B, drug release ends up stopping completely. It was unexpected that the longer length of the PEG linker would lead to the articles failing to show the beneficial properties of the shorter-length compounds. On the other hand, the dexamethasone release profiles from articles formed from compounds 1, 5, 8, and 10 were observed to be generally linear over the course of 12 weeks or more (see, e.g., FIGS. 1E, 12E, 15C, and 17D). In contrast, the dexamethasone release profiles from articles formed from compounds 11 and 12 were observed to be non-linear (see FIGS. 26A and 26B). Surprisingly, in articles formed from compound 12 the dexamethasone release stops at only ca. 3% cumulative release after just 2 weeks in PBS.

The dexamethasone release profiles from heat molded pellets (1 mm×1 mm) of Compound 1 (Dex-TEG-Dex) and Compound 5 (Dex-Hex-Dex) in 100% FBS as shown in FIG. 22C exemplifies how linker affects the drug release rates. The difference in these release profiles show that articles formed from Compound 1 might be preferred for use (e.g., for a pellet of 1 mm×1 mm in 100% FBS) where dexamethasone release is only needed for 1 or 2 months, while articles formed from Compound 5 might be preferred for use where dexamethasone release is needed for 6 months or more.

Furthermore, the drug itself (i.e., D1 and/or D2) can affect the release rate of a compound. For instance, Compounds 9 (FA-TEG-FA (CE)) and 2 release very quickly in 100% FBS but in a controlled manner, as evidenced in FIGS. 16E and 9E respectively, compared to other drug dimers that similarly include a triethylene glycol linker, such as Compounds 1, 3, and 7 (FIGS. 1E, 10E, and 14E, respectively). It was also observed that Compounds 14-16 showed no release after several weeks in 100% FBS at 37° C., each of which also has a triethylene glycol linker but is formed from a different drug or includes a different linking moiety (i.e., Compounds 9 and 15). The differences in these release profiles suggest that even when the drug dimers share the same linker, the drug itself may affect the release profile.

While all of the compounds can be processed into different articles in the glassy/amorphous state, the differences between the compounds become apparent once they are put in an aqueous or biological environment.

Some embodiments of the disclosure provided herein can be defined according to the following numbered items:

1. An article comprising a compound of formula (A-VIII):

D1-L-D2        (A-VIII)

or a pharmaceutically acceptable salt thereof, wherein
 (i) each of D1 and D2 is, independently, a radical formed from a steroid; and L is a linker covalently linking D1 to D2,
 (ii) at least 90% (w/w) of the article is the compound of formula (A-VIII),
 (iii) the article is free of controlled release excipient, and
 (iv) D1 and D2 is released from the article at 37° C. in 100% bovine serum or at 37° C. in PBS at a rate such that $t_{10}$ is greater than or equal to $\frac{1}{10}$ of $t_{50}$.

2. An article comprising a compound of formula (A-VIII):

D1-L-D2        (A-VIII)

or a pharmaceutically acceptable salt thereof, wherein
 (i) each of D1 and D2 is, independently, a radical formed from a steroid; and L is a linker covalently linking D1 to D2,
 (ii) at least 90% (w/w) of the article is the compound of formula (A-VIII),
 (iii) the article is a fiber, fiber mesh, woven fabric, non-woven fabric, pellet, cylinder, hollow tube, microparticle, nanoparticle, or shaped article, and
 (iv) the article is free of controlled release excipient.

3. The article of item 1 or 2, wherein the compound, D1, or D2 are released from the article through surface erosion.

4. An article comprising a compound of formula (A-VIII):

D1-L-D2        (A-VIII)

or a pharmaceutically acceptable salt thereof, wherein the article is formed by a process comprising the steps of:
 (a) heating the compound, or a pharmaceutically acceptable salt thereof, to form a melt; and
 (b) heat molding the melt to form the article,
wherein each of D1 and D2 is, independently, a radical formed from a steroid; and L is a linker covalently linking D1 to D2.

5. An article comprising a compound of formula (A-VIII):

D1-L-D2        (A-VIII)

or a pharmaceutically acceptable salt thereof, wherein the article is formed by a process comprising the steps of:
 (a) heating the compound, or a pharmaceutically acceptable salt thereof, to form a melt; and
 (b) injection molding the melt to form the article,
wherein each of D1 and D2 is, independently, a radical formed from a steroid; and L is a linker covalently linking D1 to D2.

6. An article comprising a compound of formula (A-VIII):

D1-L-D2        (A-VIII)

or a pharmaceutically acceptable salt thereof, wherein the article is formed by a process comprising the steps of:
 (a) heating the compound, or a pharmaceutically acceptable salt thereof, to form a melt; and
 (b) blow molding the melt to form the article,
wherein each of D1 and D2 is, independently, a radical formed from a steroid; and L is a linker covalently linking D1 to D2.

7. An article comprising a compound of formula (A-VIII):

D1-L-D2        (A-VIII)

or a pharmaceutically acceptable salt thereof, wherein the article is formed by a process comprising the steps of:
 (a) dissolving the compound, or a pharmaceutically acceptable salt thereof, to form a solution; and
 (b) evaporating the solvent to form the article,
wherein each of D1 and D2 is, independently, a radical formed from a steroid; and L is a linker covalently linking D1 to D2.

8. The article of item 7, wherein step (b) comprises solvent casting to form a film or a fiber.

9. An article comprising a compound of formula (A-VIII):

D1-L-D2        (A-VIII)

or a pharmaceutically acceptable salt thereof, wherein the article is formed by a process comprising the steps of:
 (a) dissolving the compound, or a pharmaceutically acceptable salt thereof, to form a solution; and
 (b) electrospinning or electrospraying the solution to form the article,
wherein each of D1 and D2 is, independently, a radical formed from a steroid; and L is a linker covalently linking D1 to D2.

10. An article comprising a compound of formula (A-VIII):

D1-L-D2    (A-VIII)

or a pharmaceutically acceptable salt thereof, wherein the article is formed by a process comprising the steps of:
(a) heating the compound, or a pharmaceutically acceptable salt thereof, to form a melt; and
(b) electrospinning or electrospraying the melt to form the article,
wherein each of D1 and D2 is, independently, a radical formed from a steroid; and L is a linker covalently linking D1 to D2.

11. An article comprising a compound of formula (A-VIII):

D1-L-D2    (A-VIII)

or a pharmaceutically acceptable salt thereof, wherein the article is formed by a process comprising the steps of:
(a) heating the compound, or a pharmaceutically acceptable salt thereof, to form a melt;
(b) extruding the melt to form the article,
wherein each of D1 and D2 is, independently, a radical formed from a steroid; and L is a linker covalently linking D1 to D2.

12. The article of one of items 1-11, wherein L has a molecular weight of from 80 to 800 Da.

13. The article of any one of items 1-12, wherein L is covalently linked to D1 and to D2 via one or more ester, carbonate, carbonate ester, or anhydride linkages.

14. The article of item 13, wherein L is covalently linked to D1 and to D2 via one or more carbonate linkages.

15. The article of any one of items 1-14, wherein
L comprises the radical —C(O)—($R^A$)—C(O)— or —O—($R^A$)—O—;
$R^A$ is a radical of a polyol and includes at least one free hydroxyl group or $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—; and
q, r, and s are integers from 1 to 10.

16. An article formed from the compound of any one of items 84-102, 108, and 110.

17. The article of any one of items 1-16, wherein each of D1 and D2 is selected from an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid.

18. The article of any one of items 1-17, wherein the compound is further described by one of formulas (II)-(LXXV).

19. The article of any one of items 1-18, wherein D1 and D2 are formed from the same steroid, or wherein D1 and D2 are formed from different steroids.

20. The article of item 19, wherein the article comprises a mixture of two or more compounds of formula (A-VIII).

21. The article of any one of items 1-20, wherein at least 70% (w/w) of the article is the compound of formula (A-VIII).

22. The article of any one of items 1-21, wherein at least 90% (w/w) of the article is the compound of formula (A-VIII).

23. The article of any one of items 1-22, wherein the compound, D1, or D2 are released from the article through surface erosion.

24. The article of item 23, wherein the surface erosion releases less than 10% of D1 or D2, as a percentage of the total drug, D1 or D2, present in the article in prodrug form, at 37° C. in 100% bovine serum over 5 days; or the surface erosion releases less than 2% of D1 or D2, as a percentage of the total drug, D1 or D2, present in the article in prodrug form, at 37° C. in PBS over 5 days; or the surface erosion releases greater than 20% of D1 or D2, as a percentage of the total drug, D1 or D2, present in the article in prodrug form, at 37° C. in 100% bovine serum over not fewer than 6 days; or the surface erosion releases greater than 5.0% of D1 or D2, as a percentage of the total drug, D1 or D2, present in the article in prodrug form, at 37° C. in PBS over not fewer than 6 days; or D1 and/or D2 is released from the article at a rate such that $t_{10}$ is greater than or equal to $\frac{1}{10}$ of $t_{50}$.

25. The article of any one of items 1-24, wherein the article further comprises from 0.1% to 10% (w/w) of one or more additives, wherein the one or more additives are selected from plasticizers, antioxidants, binders, lubricants, radio-opaque agents, and mixtures thereof.

26. The article of any one of items 1-25, wherein the article is a fiber, fiber mesh, woven fabric, non-woven fabric, pellet, cylinder, hollow tube, microparticle, nanoparticle, or shaped article.

27. The article of any one of items 1-26, wherein the article is free of controlled release excipient, free of a crystallization inhibiting excipient, free of a mechanical integrity enhancing excipient, and/or free of a binding excipient; or the article optionally has a glassy state.

28. A fiber formed from the compound of any one of items 84-102, 108, and 110.

29. A fiber formed from a compound of formula (A-VIII):

D1-L-D2    (A-VIII)

or a pharmaceutically acceptable salt thereof, wherein the fiber is prepared by a process comprising the steps of:
(a) dissolving the compound, or a pharmaceutically acceptable salt thereof, in a solvent to form a solution; and
(b) electrospinning, dry spinning, wet spinning, or gel spinning the solution to form the fiber,
wherein each of D1 and D2 is, independently, a radical formed from a steroid; and L is a linker covalently linking D1 to D2.

30. A fiber formed from a compound of formula (A-VIII):

D1-L-D2    (A-VIII)

or a pharmaceutically acceptable salt thereof, wherein the fiber is prepared by a process comprising the steps of:
(a) heating the compound, or a pharmaceutically acceptable salt thereof, to form a melt; and
(b) extruding the melt to form the fiber,
wherein each of D1 and D2 is, independently, a radical formed from a steroid; and L is a linker covalently linking D1 to D2.

31. A fiber formed from a compound of formula (A-VIII):

D1-L-D2    (A-VIII)

or a pharmaceutically acceptable salt thereof, wherein the fiber is prepared by a process comprising the steps of:
(a) heating the compound, or a pharmaceutically acceptable salt thereof, to form a melt; and (b) electrospinning the melt to form the fiber, wherein each of D1 and D2 is, independently, a radical formed from a steroid; and L is a linker covalently linking D1 to D2.

32. The fiber of any one of items 29-31, wherein L has a molecular weight of from 80 to 800 Da.

33. The fiber of any one of items 29-32, wherein L is covalently linked to D1 and to D2 via one or more ester, carbonate, carbonate ester, or anhydride linkages.

34. The fiber of any one of items 29-33, wherein

L comprises the radical —C(O)—($R^4$)—C(O)— or —O—($R^4$)—O—;

$R^4$ is a radical of a polyol and includes at least one free hydroxyl group or $R^4$ is selected from $C_1$-20 alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$—, or —(CH$_2$CH(CH$_3$)O)$_s$CH$_2$CH(CH$_3$)—; and q, r, and s are integers from 1 to 10.

35. The fiber of any one of items 29-34, wherein each of D1 and D2 is selected from an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid.

36. The fiber of any one of items 29-34, wherein the compound is further described by one of formulas (II)-(LXXV).

37. The fiber of any one of items 28-36, wherein D1 and D2 are formed from the same steroid, or wherein D1 and D2 are formed from different steroids.

38. The fiber of item 37, wherein the fiber comprises a mixture of two or more compounds of formula (A-VIII).

39. The fiber of any one of items 28-38, wherein at least 70% (w/w) of the fiber is the compound of formula (A-VIII).

40. The fiber of any one of items 28-38, wherein at least 90% (w/w) of the fiber is the compound of formula (A-VIII).

41. The fiber of any one of items 28-40, wherein the compound, D1, or D2 are released from the fiber through surface erosion.

42. The fiber of item 41, wherein the surface erosion releases less than 10% of D1 or D2, as a percentage of the total drug, D1 or D2, present in the fiber in prodrug form, at 37° C. in 100% bovine serum over 5 days; or the surface erosion releases less than 2% of D1 or D2, as a percentage of the total drug, D1 or D2, present in the fiber in prodrug form, at 37° C. in PBS over 5 days; or the surface erosion releases greater than 20% of D1 or D2, as a percentage of the total drug, D1 or D2, present in the fiber in prodrug form, at 37° C. in 100% bovine serum over not fewer than 6 days; or the surface erosion releases greater than 5.0% of D1 or D2, as a percentage of the total drug, D1 or D2, present in the fiber in prodrug form, at 37° C. in PBS over not fewer than 6 days; or D1 and/or D2 is released from the fiber at a rate such that $t_{10}$ is greater than or equal to $\frac{1}{10}$ of $t_{50}$.

43. The fiber of any one of items 28-42, wherein the fiber further comprises from 0.1% to 10% (w/w) of one or more additives, wherein the one or more additives are selected from plasticizers, antioxidants, binders, lubricants, radio-opaque agents, and mixtures thereof.

44. The fiber of any one of items 28-43, wherein the fiber is free of controlled release excipient, free of a crystallization inhibiting excipient, free of a mechanical integrity enhancing excipient, and/or free of a binding excipient; or the fiber optionally has a glassy state.

45. A fiber mesh or woven fabric formed from the fiber of any one of items 28-44.

46. A non-woven fabric formed from the fiber of any one of items 28-44.

47. A glassy state composition formed from a compound of any one of items 84-102, 108, and 110.

48. A glassy state composition formed from a compound of formula (A-VIII):

$$D1\text{-}L\text{-}D2 \qquad\qquad \text{(A-VIII)}$$

or a pharmaceutically acceptable salt thereof, wherein the composition is prepared by a process comprising the steps of:

(a) heating the compound, or a pharmaceutically acceptable salt thereof, to form a melt; and (b) cooling the melt to form the composition, wherein each of D1 and D2 is, independently, a radical formed from a steroid; and L is a linker covalently linking D1 to D2.

49. The glassy state composition of item 47 or 48, wherein L has a molecular weight of from 80 to 800 Da.

50. The glassy state composition of any one of items 47-49, wherein L is covalently linked to D1 and to D2 via one or more ester, carbonate, carbonate ester, or anhydride linkages.

51. The glassy state composition of any one of items 47-50, wherein

L comprises the radical —C(O)—($R^4$)—C(O)— or —O—($R^4$)—O—;

$R^4$ is a radical of a polyol and includes at least one free hydroxyl group or $R^4$ is selected from $C_1$-20 alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$—, or —(CH$_2$CH(CH$_3$)O)$_s$CH$_2$CH(CH$_3$)—; and q, r, and s are integers from 1 to 10.

52. The glassy state composition of any one of items 47-51, wherein each of D1 and D2 is selected from an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid.

53. The glassy state composition of any one of items 47-52, wherein the compound is further described by one of formulas (II)-(LXXV).

54. The glassy state composition of any one of items 47-53, wherein D1 and D2 are formed from the same steroid, or wherein D1 and D2 are formed from different steroids.

55. The glassy state composition of item 54, wherein the glassy state composition comprises a mixture of two or more compounds of formula (A-VIII).

56. The glassy state composition of any one of items 47-55, wherein at least 70% (w/w) of the glassy state composition is the compound of formula (A-VIII).

57. The glassy state composition of any one of items 47-56, wherein at least 90% (w/w) of the glassy state composition is the compound of formula (A-VIII).

58. The glassy state composition of any one of items 47-57, wherein the compound, D1, or D2 are released from the glassy state composition through surface erosion.

59. The glassy state composition of item 58, wherein the surface erosion releases less than 10% of D1 or D2, as a percentage of the total drug, D1 or D2, present in the glassy state composition in prodrug form, at 37° C. in 100% bovine serum over 5 days; or the surface erosion releases less than 2% of D1 or D2, as a percentage of the total drug, D1 or D2, present in the glassy state composition in prodrug form, at 37° C. in PBS over 5 days; or the surface erosion releases greater than 20% of D1 or D2, as a percentage of the total drug, D1 or D2, present in the glassy state composition in prodrug form, at 37° C. in 100% bovine serum over not fewer than 6 days; or the surface erosion releases greater than 5.0% of D1 or D2, as a percentage of the total drug, D1 or D2, present in the glassy state composition in prodrug form, at 37° C. in PBS over not fewer than 6 days; or D1 and/or D2 is released from the glassy state composition at a rate such that $t_{10}$ is greater than or equal to $\frac{1}{10}$ of $t_{50}$.

60. The glassy state composition of any one of items 47-59, wherein the glassy state composition further comprises from 0.1% to 10% (w/w) of one or more additives, wherein the one or more additives are selected from plasticizers, antioxidants, binders, lubricants, radio-opaque agents, and mixtures thereof.

61. The glassy state composition of any one of items 47-60, wherein the glassy state composition is formed by machining, molding, fiber spinning, electrospinning, electrospraying, blow molding, or extruding.

62. The glassy state composition of any one of items 47-61, wherein the glassy state composition is a fiber, fiber mesh, woven fabric, non-woven fabric, pellet, cylinder, hollow tube, microparticle, nanoparticle, or shaped article in the shape of a cylinder, a cube, a sheet, a star, a toroid, a pyramid, a sphere, an irregular polygon, or a regular polygon.

63. The glassy state composition of item 62, wherein the glassy state composition is a shaped article in the form of:
  (i) fibers having a mean diameter of from about 0.01 to 1 mm;
  (ii) pellets having a mean diameter of from about 0.2 to 5 mm;
  (iii) cylinders of from about 0.01 to 1 mm in diameter and 0.5 to 20 mm in length;
  (iv) microparticles having a mean diameter of from about 1 to 1000 µm; or
  (v) nanoparticles having a mean diameter of from about 0.01 to 1 µm.

64. The glassy state composition of any one of items 47-63, wherein the glassy state composition is free of controlled release excipient, free of a crystallization inhibiting excipient, free of a mechanical integrity enhancing excipient, and/or free of a binding excipient.

65. A substrate comprising a coating formed from a compound of formula (A-VIII):

D1-L-D2        (A-VIII).

wherein
  (i) each of D1 and D2 is, independently, a radical formed from a steroid; and L is a linker covalently linking D1 to D2 via one or more carbonate or carbonate ester linkages,
  (ii) at least 90% (w/w) of the article is the compound of formula (A-VIII), and
  (iii) the article is free of controlled release excipient.

66. The substrate of item 65, wherein L has a molecular weight of from 80 to 800 Da.

67. The substrate of item 65 or 66, wherein L is covalently linked to D1 and to D2 via one or more carbonate linkages.

68. The substrate of any one of items 65-67, wherein each of D1 and D2 is selected from an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid.

69. The substrate of any one of items 65-68, wherein the compound is further described by one of formulas (II)-(LXXV).

70. The substrate of any one of items 65-69, wherein D1 and D2 are formed from the same steroid, or wherein D1 and D2 are formed from different steroids.

71. The substrate of item 70, wherein the coating comprises a mixture of two or more compounds of formula (A-VIII).

72. The substrate of any one of items 65-71, wherein at least 70% (w/w) of the coating is the compound of formula (A-VIII).

73. The substrate of any one of items 65-72, wherein at least 90% (w/w) of the coating is the compound of formula (A-VIII).

74. The substrate of any one of items 65-73, wherein the compound, D1, or D2 are released from the coating through surface erosion.

75. The substrate of item 74, wherein the surface erosion releases less than 10% of D1 or D2, as a percentage of the total drug, D1 or D2, present in the coating in prodrug form, at 37° C. in 100% bovine serum over 5 days; or the surface erosion releases less than 2% of D1 or D2, as a percentage of the total drug, D1 or D2, present in the coating in prodrug form, at 37° C. in PBS over 5 days; or the surface erosion releases greater than 20% of D1 or D2, as a percentage of the total drug, D1 or D2, present in the coating in prodrug form, at 37° C. in 100% bovine serum over not fewer than 6 days; or the surface erosion releases greater than 5.0% of D1 or D2, as a percentage of the total drug, D1 or D2, present in the coating in prodrug form, at 37° C. in PBS over not fewer than 6 days; or D1 and/or D2 is released from the coating at a rate such that or $t_{10}$ is greater than or equal to $\frac{1}{10}$ of $t_{50}$.

76. The substrate of any one of items 65-75, wherein the article further comprises from 0.1% to 10% (w/w) of one or more additives, wherein the one or more additives are selected from plasticizers, antioxidants, binders, lubricants, radio-opaque agents, and mixtures thereof.

77. The substrate of any one of items 65-76, wherein the coating is free of controlled release excipient, free of a crystallization inhibiting excipient, free of a mechanical integrity enhancing excipient; or the coating optionally has a glassy state.

78. A substrate comprising a coating formed from the compound of any one of items 84-102, 108, and 110.

79. The substrate of item 78, wherein at least 70% (w/w) of the coating is the compound.

80. The substrate of item 78, wherein at least 90% (w/w) of the coating is the compound.

81. The substrate of any one of items 78-80, wherein the coating has a glassy state and is formed from the compound of any one of items 84-102, 108, and 110.

82. A coating having a glassy state formed from the compound of any one of items 84-102, 108, and 110.

83. An implantable medical device comprising the substrate of any one of items 65-82, wherein the coating resides on the surface of the implantable medical device.

84. A compound described by the formula (A-I):

$$D1\text{-}O\text{-}L\text{-}O\text{-}D2 \qquad a(A\text{-}I),$$

or a pharmaceutically acceptable salt thereof, wherein
each of D1-O and D2-O is, independently, a radical formed from a steroid;
L is —C(O)—OC(O)—($R^B$)—C(O)O—C(O)—; and
$R^B$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms,
wherein the steroid is an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, or a corticosteroid.

85. A compound described by the formula (A-III):

$$D1\text{-}O\text{-}L\text{-}O\text{-}D2 \qquad (A\text{-}III),$$

or a pharmaceutically acceptable salt thereof, wherein
each of D1-O and D2-O is, independently, a radical formed from a steroid;
L is —C(O)O—($R^A$)—OC(O)—;
wherein O—($R^A$)—O is a radical of a polyol and comprises at least one free hydroxyl group,
wherein the steroid is an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, or a corticosteroid.

86. A compound described by the formula (A-III):

$$D1\text{-}O\text{-}L\text{-}O\text{-}D2 \qquad (A\text{-}III),$$

or a pharmaceutically acceptable salt thereof, wherein
each of D1-O and D2-O is, independently, a radical formed from a steroid;
L is —C(O)O—($R^A$)—OC(O)—, —C(O)—($R^B$)—C(O)—, or —C(O)—OC(O)—($R^B$)—C(O)O—C(O)—;
$R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and comprises at least one free hydroxyl group or is selected from:

O(CH$_2$CH$_2$O)$_n$CH$_2$CH$_2$O—,
O(CH$_2$CH$_2$CH$_2$CH$_2$O)$_m$CH$_2$CH$_2$CH$_2$CH$_2$O—, or
O(CH$_2$CH(CH$_3$)O)$_p$CH$_2$CH(CH$_3$)O—;

n, m, and p are integers from 1 to 10; and
$R^B$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms,
wherein the steroid is an anabolic steroid, an androgenic steroid, a progestin steroid, an estrogen steroid, a cancer treatment steroid, an antibiotic steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, or a benign steroid.

87. A compound described by the formula (A-IV):

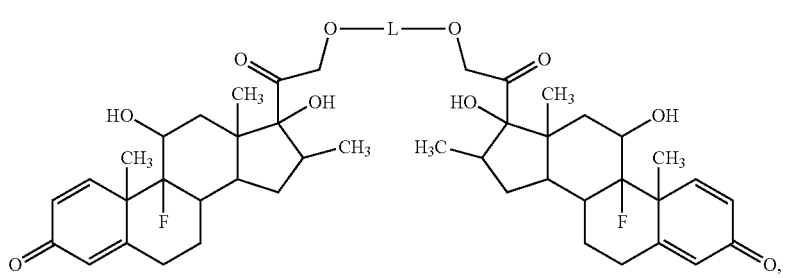

(A-IV)

or a pharmaceutically acceptable salt thereof, wherein
L is —C(O)O—($R^A$)—OC(O)—;
$R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and comprises at least one free hydroxyl group or O—($R^A$)—O is selected from:

O(CH$_2$CH$_2$O)$_n$CH$_2$CH$_2$O—,
O(CH$_2$CH$_2$CH$_2$CH$_2$O)$_m$CH$_2$CH$_2$CH$_2$CH$_2$O—, or
O(CH$_2$CH(CH$_3$)O)$_p$CH$_2$CH(CH$_3$)O—;

n, m, and p are integers from 1 to 10; and

88. The compound of one of items 85-87, wherein O—($R^A$)—O is a radical of a polyol formed from a cyclitol, a sugar alcohol, or glycerin.

89. The compound of item 86 or 87, wherein O—($R^A$)—O is a radical formed from an alkane diol, diethylene glycol, triethylene glycol, tetraethylene glycol, or pentaethylene glycol.

90. The compound of any one of items 84-85, 88, and 89, wherein each of D1-O and D2-O is, independently, described by any one of formulas (I-a) to (1-sss).

91. The compound of item 90, wherein at least one of D1-O and D2-O is formed from:
(i) an anabolic steroid selected from androisoxazole, androstenediol, bolandiol, bolasterone, clostebol, ethylestrenol, formyldienolone, 4-hydroxy-19-nortestosterone, methandriol, methenolone, methyltrienolone, nandrolone, norbolethone, oxymesterone, stenbolone, and trenbolone;
(ii) an androgenic steroid selected from boldenone, fluoxymesterone, mestanolone, mesterolone, methandrostenolone, 17-methyltestosterone, 17-α-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate tiomesterone dehydroepiandrosterone (DHEA), androstenedione, androstenediol, androsterone, dihydrotestosterone (DHT), and androstanolone;

(iii) a progestin steroid selected from norethisterone, norethisterone acetate, gestodene, levonorgestrel, allylestrenol, anagestone, desogestrel, dimethisterone, dydrogesterone, ethisterone, ethynodiol, ethynodiol diacetate, etonogestrel, gestodene, ethinylestradiol, haloprogesterone, 17-hydroxy-16-methylene-progesterone, 17 alpha-hydroxyprogesterone, lynestrenol, medroxyprogesterone, melengestrol, norethindrone, norethynodrel, norgesterone, gestonorone, norethisterone, norgestimate, norgestrel, levonorgestrel, norgestrienone, norvinisterone, pentagestrone, MENT (7-methyl-19-testosterone); norelgestromin, and trimigestone drospirenone, tibolone, and megestrol;

(iv) an estrogen steroid selected from estrogen, eguilenin, equilin, 17β-estradiol, estradiol benzoate, estriol, ethinyl estradiol, mestranol, moxestrol, mytatrienediol, quinestradiol, and quinestrol;

(v) a glucocorticoid selected from medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, loprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6α-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol;

(vi) a steroid selected from abiraterone, cyproterone acetate, dutasteride, enzalutamide, finasteride, galeterone, fusidic acid, cholesterol, 11-deoxycortisol, 11-deoxycorticosterone, pregnenolone, cholic acid, chenodeoxycholic acid, ursodeoxycholic acid, obeticholic acid, tetrahydrocortisone, tetrahydrodeoxycortisol, tetrahydrocorticosterone, 5α-dihydrocorticosterone, and 5α-dihydropregesterone;

(vii) an anti-angiogenic steroid or an intraocular pressure (IOP) lowering steroid selected from anecortave acetate, anecortave, 11-epicortisol, 17α-hydroxyprogesterone, tetrahydrocortexolone, and tetrahydrocortisol;

(viii) a cholic acid-related bile acid steroid selected from deoxycholic acid, apocholic acid, dehydrocholic acid, glycochenodeoxycholic acid, glycocholic acid, glycodeoxycholic acid, hyodeoxycholic acid, lithocholic acid, α-muricholic acid, β-muricholic acid, γ-muricholic acid, ω-muricholic acid, taurochenodeoxycholic acid, taurocholic acid, taurodeoxycholic acid, taurolithocholic acid, and tauroursodeoxycholic acid;

(ix) a neurosteroid selected from alphaxalone, alphadolone, hydroxydione, minaxolone, tetrahydrodeoxycorticosterone, allopregnanolone, pregnanolone, ganoxolone, 3α-androstanediol, epipregnanolone, isopregnanolone, and 24(S)-hydroxycholesterol;

(x) other steroid selected from flugestone, prebediolone, chlormadinone acetate, medrogestone, and segesterone acetate; (xi) a pheromone including androstadienol, androstadienone, androstenol, androstenone, estratetraenol, 5-dehydroprogesterone, 6-dehydro-retroprogesterone, allopregnanolone, and hydroxyprogesterone caproate;

(xii) a steroid metabolite selected from tetrahydrotriamcinolone, cortienic acid, 11-dehydrocorticosterone, 11β-hydroxypregnenolone, ketoprogesterone, 17-hydroxypregnenolone, 17,21-dihydroxypregnenolone, 18-hydroxycorticosterone, deoxycortisone, 21-hydroxypregnenolone, and progesterone; or (xiii) a progestin including allopregnone-3α,20α-diol, allopregnone-3β,20β-diol, allopregnane-3β,21-diol-11,20-dione, allopregnane-3β,17α-diol-20-one, 3,20-allopregnanedione,3β,11β,17α,20β,21-pentol, allopregnane-3β, 17α,20β,21-tetrol, allopregnane-3α,11β,17α,21-tetrol-20-one, allopregnane-3β,11β,17α,21-tetrol-20-one, allopregnane-3β,17α,20-triol, allopregnane-3β,17α,21-triol-11,20-dione, allopregnane-3β,1β,21-triol-20-one, allopregnane-3β,17α,21-triol-20-one, allopregnane-3α-ol-20-one, allopregnane-3β-ol-20-one, pregnanediol, 3,20-pregnanedione, 4-pregnene-20,21-diol-3,11-dione, 4-pregnene-1β,17α,20β, 21-tetrol-3-one, 4-pregnene-17α,20β,21-triol-3,11-dione, 4-pregnene-17α,20β,21-triol-3-one, and pregnenolone.

92. A compound described by the formula (A-VI):

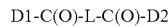 (A-VI), or a pharmaceutically acceptable salt thereof, wherein
each of D1-C(O) and D2-C(O) is, independently, a radical formed from a steroid;
L is —O—(R$^A$)—O— or —OC(O)—O—(R$^A$)—O—C(O)O—;
R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and comprises at least one free hydroxyl group or O—(R$^A$)—O is selected from:

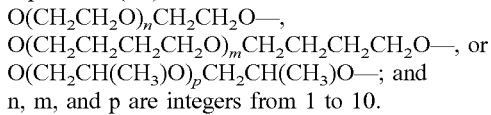

n, m, and p are integers from 1 to 10.

93. The compound of item 92, wherein O—(R$^A$)—O is a radical of a polyol formed from a cyclitol, a sugar alcohol, or glycerin.

94. The compound of item 92, wherein O—(R$^A$)—O is a radical formed from an alkane diol, diethylene glycol, triethylene glycol, tetraethylene glycol, or pentaethylene glycol.

95. A compound described by the formula (A-VII):

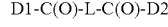 (A-VII), or a pharmaceutically acceptable salt thereof, wherein
each of D1-C(O) and D2-C(O) is, independently, a radical formed from a steroid;
L is —O—C(O)—O—(R$^A$)—O—C(O)—O—; and
R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms.

96. The compound of any one of items 92-95, wherein at least one of D1-C(O) and D2-C(O) is formed from fusidic acid, cholic acid, chenodeoxycholic acid, ursodeoxycholic acid, or obeticholic acid.

97. The compound of any one of items 84-96, wherein D1-O and D2-O are formed from the same steroid, or wherein D1-C(O) and D2-C(O) are formed from the same steroid.

98. The compound of any one of items 84-96, wherein D1-O and D2-O are formed from different steroids, or wherein D1-C(O) and D2-C(O) are formed from different steroids.

99. The compound of any one of items 84-98, wherein $R^A$ is a $C_{1-10}$ alkylene.

100. The compound of any one of items 84-86 and 88-99, wherein upon hydrolysis D1 and D2 form corticosteroids selected from alclometasone, beclomethasone, betamethasone, betamethasone valerate, budesonide, chloroprednisone, cloprednol, corticosterone, cortisone, desonide, desoximerasone, dexamethasone, diflorasone, diflucortolone, enoxolone, flucloronide, flumethasone, flunisolide, fluocinolone acetonide, fluocortolone, fluprednisolone, flurandrenolide, halometasone, hydrocortisone, hydrocortisone butyrate, meprednisone, methylprednicolone, paramethasone, prednisolone, prednisone, prednival, prednylidene, triamcinolone, and triamcinolone acetonide.

101. The compound of any one of items 84-100, wherein the compound is further described by one of formulas (II)-(LXXV).

102. The compound of item 101, wherein $R^A$ comprises —$(CH_2CH_2O)_qCH_2CH_2$—, q is an integer of 1 to 10, and upon hydrolysis each of D1 and D2, independently, form dexamethasone, triamcinolone, betamethasone, prednisolone, prednisone, fluocinolone, fluocinolone acetonide, mometosone, mometosone furoate, anecoratve, hydrocortisone, triamcinolone acetonide, abiraterone, fusidic acid, or cholesterol.

103. A method of forming an article comprising a compound of formula (A-VIII):

D1-L-D2 (A-VIII)

or a pharmaceutically acceptable salt thereof, wherein each of D1 and D2 is, independently, a radical formed from a steroid; and L is a linker covalently linking D1 to D2, and wherein the article is formed by a process comprising the steps of:

(a) heating the compound, or a pharmaceutically acceptable salt thereof, to form a melt;

(b) cooling the melt to form a glassy state composition; and (c) heating the glassy state composition to a temperature above the glass transition temperature of the glassy state composition and shaping the glassy state composition to form a shaped article.

104. A method of forming an article comprising a compound of formula (A-VIII):

D1-L-D2 (A-VIII)

or a pharmaceutically acceptable salt thereof, wherein each of D1 and D2 is, independently, a radical formed from a steroid; and L is a linker covalently linking D1 to D2, and wherein the article is formed by a process comprising the steps of:

(a) dissolving the compound, or a pharmaceutically acceptable salt thereof, in a solvent to form a solution;

(b) evaporating the solvent to form a glassy state composition; and (c) heating the glassy state composition to a temperature above the glass transition temperature of the glassy state composition and shaping the glassy state composition to form a shaped article.

105. The method of item 103 or 104, wherein step (c) comprises extruding, molding, blow molding, heat spinning, electrospinning or electrospraying the glassy state composition to form the shaped article.

106. A method of forming an article comprising a compound of formula (A-VIII):

D1-L-D2 (A-VIII)

or a pharmaceutically acceptable salt thereof, wherein each of D1 and D2 is, independently, a radical formed from a steroid; and L is a linker covalently linking D1 to D2, and wherein the article is formed by a process comprising the steps of:

(a) dissolving the compound, or a pharmaceutically acceptable salt thereof, in a solvent to form a solution;

(b) electrospraying or electrospinning the solution to form a glassy state composition; and (c) heating the glassy state composition to a temperature above the glass transition temperature of the glassy state composition and shaping the glassy state composition to form a coating.

107. The method of any one of items 103-106, wherein the method produces an article free of controlled release excipient, free of a crystallization inhibiting excipient, free of a mechanical integrity enhancing excipient, and/or free of a binding excipient; or the method produces an article that optionally has a glassy state.

108. Compound 3.

109. A pharmaceutical composition comprising Compound 3 and a pharmaceutically acceptable excipient.

110. Compound 17.

111. A pharmaceutical composition comprising Compound 17 and a pharmaceutically acceptable excipient.

The invention claimed is:

1. An article comprising a compound of formula (A-VIII):

D1-L-D2 (A-VIII)

or a pharmaceutically acceptable salt thereof, wherein
(i) each of D1 and D2 is, independently, a radical formed from a steroid; and L is a linker covalently linking D1 to D2,
(ii) at least 70% (w/w) of the article is the compound of formula (A-VIII),
(iii) the article is free of controlled release polymer and comprises the compound in amorphous form, and
(iv) the article is a fiber, pellet, cylinder, hollow tube, microparticle, or a nanoparticle.

2. The article of claim 1, wherein the compound, D1, and/or D2 is released from the article through surface erosion.

3. The article of claim 1, wherein the article is formed by a process comprising the steps of: (a) heating the compound, or a pharmaceutically acceptable salt thereof, to form a melt; and (b) heat molding, injection molding, the melt to form the article.

4. The article of claim 1, wherein the article is formed by a process comprising the steps of: (a) dissolving the compound, or a pharmaceutically acceptable salt thereof, in a solvent to form a solution; and (b) evaporating the solvent to form the article.

5. The article of claim 4, wherein step (b) comprises solvent casting to form a film or a fiber.

6. The article of claim 1, wherein the article is formed by a process comprising the steps of: (a) dissolving the compound, or a pharmaceutically acceptable salt thereof, in a solvent to form a solution; and (b) electrospinning or electrospraying the solution to form the article.

7. The article of claim 1, wherein the article is formed by a process comprising the steps of: (a) dissolving the compound, or a pharmaceutically acceptable salt thereof, in an organic solvent containing a surfactant to form an emulsion; and (b) removing organic solvent from the emulsion to form the in the shape of a nanoparticle or microparticle.

8. The article of claim 1, wherein the article is formed by a process comprising the steps of: (a) heating the compound, or a pharmaceutically acceptable salt thereof, to form an intermediate glassy state material; and (b) heat extruding the intermediate glassy state material to form the article.

9. The article of claim 1, wherein L has a molecular weight of from 80 to 800 Da.

10. The article of claim 1, wherein L is covalently linked to D1 and to D2 via one or more ester, carbonate, carbonate ester, or anhydride linkages.

11. The article of claim 10, wherein L is covalently linked to D1 and to D2 via one or more carbonate linkages.

12. The article of claim 1, wherein
L comprises the radical —C(O)—($R^A$)—C(O)— or —O—($R^A$)—O—;
$R^A$ is a radical of a polyol and includes at least one free hydroxyl group or $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —$(CH_2CH_2O)_qCH_2CH_2$—, —$(CH_2CH_2CH_2CH_2O)_rCH_2CH_2CH_2CH_2$—, or —$(CH_2CH(CH_3)O)_sCH_2CH(CH_3)$—; and
q, r, and s are integers from 1 to 10.

13. The article of claim 1, wherein each of D1 and D2 is selected from an anabolic steroid, an androgenic steroid, a progestin steroid, an estrogen steroid, a cancer treatment steroid, an antibiotic steroid, a glucocorticoid steroid, a benign steroid, an anti-angiogenic steroid, an intraocular pressure (IOP) lowering steroid, a cholic acid-related bile acid steroid, a cholesterol-derivative, other steroid, a pheromone, a steroid metabolite, a progestin, a neurosteroid, and a corticosteroid.

14. The article of claim 1, wherein the compound is further described by one of formulas (II)-(LXXV).

15. The article of claim 1, wherein D1 and D2 are formed from the same steroid.

16. The article of claim 1, wherein D1 and D2 are formed from different steroids.

17. The article of claim 1, wherein the article comprises a mixture of two or more compounds of formula (A-VIII).

18. The article of claim 1, wherein at least 90% (w/w) of the article is the compound of formula (A-VIII).

19. The article of claim 1, wherein at least 95% (w/w) of the article is the compound of formula (A-VIII).

20. The article of claim 1, wherein the article further comprises from 0.1% to 10% (w/w) of one or more additives, wherein the one or more additives are selected from plasticizers, antioxidants, binders, lubricants, radio-opaque agents, and mixtures thereof.

21. The article of claim 1, wherein the article has a glassy state.

22. The article of claim 1, wherein each of D1 and D2 is released from the article at 37° C. in 100% bovine serum or at 37° C. in phosphate buffered saline (PBS) at a rate such that $t_{10}$ is greater than or equal to $\frac{1}{10}$ of $t_{50}$.

23. A method of treating an inflammatory disease or condition in a subject in need thereof, the method comprising administering to the subject an article in an amount sufficient to treat the inflammatory disease or disorder in the subject, wherein the article comprises a compound of formula (A-VIII):

$$D1\text{-}L\text{-}D2 \qquad \text{(A-VIII)}$$

or a pharmaceutically acceptable salt thereof, wherein
(i) each of D1 and D2 is, independently, a radical formed from a steroid; and L is a linker covalently linking D1 to D2,
(ii) at least 70% (w/w) of the article is the compound of formula (A-VIII),
(iii) the article is free of controlled release polymer, and comprises the compound in amorphous form.

24. The method of claim 23, wherein the article is a fiber, pellet, cylinder, hollow tube, microparticle, or a nanoparticle.

25. The method of claim 23, wherein the article is administered locally.

26. The method of claim 25, wherein the article is administered intraocularly.

27. The method of claim 25, wherein the article is administered into a joint space.

28. The method of claim 25, wherein the inflammatory disease or condition is osteoarthritis.

29. A method of reducing inflammation at a location in a subject, the method comprising locally administering to the subject the article of claim 1 in an amount sufficient to reduce the inflammation in the subject at the location.

* * * * *